US009588046B2

(12) United States Patent
Ishihara et al.

(10) Patent No.: US 9,588,046 B2
(45) Date of Patent: Mar. 7, 2017

(54) FLUORESCENCE OBSERVATION APPARATUS

(71) Applicants: OLYMPUS CORPORATION, Tokyo (JP); OLYMPUS MEDICAL SYSTEMS CORP., Tokyo (JP)

(72) Inventors: Yasushige Ishihara, Tokyo (JP); Hiromi Shida, Tokyo (JP); Kei Kubo, Tokyo (JP); Satoshi Takekoshi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 409 days.

(21) Appl. No.: 14/198,671

(22) Filed: Mar. 6, 2014

(65) Prior Publication Data

US 2014/0184769 A1 Jul. 3, 2014

Related U.S. Application Data

(63) Continuation of application No. PCT/JP2012/072610, filed on Sep. 5, 2012.

(30) Foreign Application Priority Data

Sep. 7, 2011 (JP) ................. 2011-195341

(51) Int. Cl.
*G01N 21/64* (2006.01)
*A61B 1/00* (2006.01)
(Continued)

(52) U.S. Cl.
CPC ......... *G01N 21/64* (2013.01); *A61B 1/00009* (2013.01); *A61B 1/043* (2013.01);
(Continued)

(58) Field of Classification Search
CPC ... A61B 1/00009; A61B 1/0005; A61B 1/043; G01N 21/64; G01N 21/6456; G06T 2207/20216; G06T 5/50
(Continued)

(56) References Cited

U.S. PATENT DOCUMENTS 5,703,714 A * 12/1997 Kojima ................. G02B 21/06
250/201.3
5,749,830 A 5/1998 Kaneko et al.
(Continued)

FOREIGN PATENT DOCUMENTS

| CN | 1367455 A | 9/2002 |
| EP | 0920831 A1 | 6/1999 |

(Continued)

OTHER PUBLICATIONS

Bolte, S. and Cordelieres, F.P., "A guided tour into subcellular colocalization analysis in light microscopy", Journal of Microscopy, vol. 224, Pt 3, Dec. 2006, pp. 213-232.
(Continued)

*Primary Examiner* — Thai Tran
*Assistant Examiner* — Stephen Smith
(74) *Attorney, Agent, or Firm* — Scully, Scott, Murphy & Presser, PC

(57) ABSTRACT

Provided is a fluorescence observation apparatus including: a fluorescence image acquisition section and a reference image acquisition section that acquire a fluorescence image and a reference image of a subject, respectively; a division image generation section that generates a division image by dividing an image based on the fluorescence image by an image based on the reference image; a display section that displays a corrected fluorescence image based on the division image; a correction processing section that applies correction processing to at least one of the reference image
(Continued)

| OBSERVATION CONDITION (OBSERVATION SITE) | PREPROCESSING | | | POST-PROCESSING | | |
|---|---|---|---|---|---|---|
| | FIRST PREPROCESSING MODE | SECOND PREPROCESSING MODE | THIRD PREPROCESSING MODE | FIRST POST-PROCESSING MODE | SECOND POST-PROCESSING MODE | THIRD POST-PROCESSING MODE |
| LOCAL VIEW (DOUGLAS' POUCH, STOMACH, URINARY TRACT, RECTUM) | ○ | ○ | | | ○ | |
| OVERHEAD VIEW (GREATER OMENTUM, SUBPHRENIC AREA, INTESTINAL MEMBRANE) | ○ | ○ | | | | |
| PERSPECTIVE LARGE (DOUGLAS' POUCH, STOMACH) | | | | ○ | | ○ |
| PERSPECTIVE SMALL (GREATER OMENTUM, INTESTINAL MEMBRANE, URINARY TRACT) | | | | ○ | | ○ |
| MULTI-COLOR (GREATER OMENTUM, STOMACH) | | | ○ | | | |
| SINGLE-COLOR | | | | | | |
| IRREGULAR (GREATER OMENTUM, INTESTINAL MEMBRANE, STOMACH, RECTUM) | | | | ○ | | ○ |
| FLAT (SUBPHRENIC AREA, PART OTHER THAN LARGE INTESTINE WALL) | | | | ○ | | ○ |
| HIGH FAT (STOMACH, URINARY TRACT) | ○ | | | | | |
| LOW FAT | | | | | | | and the fluorescence image and/or to the division image prior to the generation of the division image or prior to the display of the corrected fluorescence image; an observation condition determination section that determines observation conditions of the subject; and a correction condition setting section that sets parameters regarding the correction processing according to the observation conditions.

17 Claims, 97 Drawing Sheets

(51) Int. Cl.
    *A61B 1/04*         (2006.01)
    *G06T 5/50*         (2006.01)

(52) U.S. Cl.
    CPC ............ *G01N 21/6456* (2013.01); *G06T 5/50* (2013.01); *A61B 1/0005* (2013.01); *G06T 2207/20216* (2013.01)

(58) Field of Classification Search
    USPC ........ 348/64, 65, 68, 77, 135; 600/109, 118, 600/160, 178, 310, 476, 477; 382/128, 382/274; 250/458.1
    See application file for complete search history.

(56) References Cited

U.S. PATENT DOCUMENTS

| | | | |
|---|---|---|---|
| 6,240,312 B1 | 5/2001 | Alfano et al. | |
| 6,364,829 B1* | 4/2002 | Fulghum | A61B 1/00009 600/160 |
| 6,529,768 B1* | 3/2003 | Hakamata | A61B 1/00009 600/310 |
| 6,537,211 B1 | 3/2003 | Wang et al. | |
| 6,563,122 B1* | 5/2003 | Ludeker | G01N 21/6456 250/458.1 |
| 7,260,248 B2 | 8/2007 | Kaufman et al. | |
| 8,031,938 B2 | 10/2011 | Edge | |
| 8,442,347 B2 | 5/2013 | Sakagami et al. | |
| 8,818,062 B2* | 8/2014 | Ishihara | A61B 1/00009 382/128 |
| 2001/0045506 A1 | 11/2001 | Masuyama | |
| 2001/0056238 A1 | 12/2001 | Tsujita | |
| 2002/0085753 A1 | 7/2002 | Sendai | |
| 2002/0105505 A1 | 8/2002 | Sendai | |
| 2002/0146734 A1 | 10/2002 | Ortyn et al. | |
| 2002/0161282 A1* | 10/2002 | Fulghum | A61B 1/00009 600/160 |
| 2002/0168096 A1 | 11/2002 | Hakamata et al. | |
| 2003/0001104 A1 | 1/2003 | Sendai et al. | |
| 2003/0013937 A1 | 1/2003 | Tsujita et al. | |
| 2003/0016301 A1 | 1/2003 | Aizaki et al. | |
| 2003/0078477 A1* | 4/2003 | Kang | A61B 1/042 600/178 |
| 2003/0117491 A1 | 6/2003 | Avni et al. | |
| 2003/0144585 A1 | 7/2003 | Kaufman et al. | |
| 2003/0218137 A1 | 11/2003 | Sendai | |
| 2004/0064016 A1 | 4/2004 | Kobayashi et al. | |
| 2004/0143157 A1* | 7/2004 | Doguchi | A61B 1/00059 600/109 |
| 2004/0148141 A1* | 7/2004 | Tsujita | A61B 1/00009 702/190 |
| 2004/0189798 A1 | 9/2004 | Hakamata | |
| 2004/0196457 A1 | 10/2004 | Aono et al. | |
| 2004/0196550 A1 | 10/2004 | Shimizu et al. | |
| 2004/0210138 A1 | 10/2004 | Murashita et al. | |
| 2004/0240716 A1 | 12/2004 | de Josselin de Jong et al. | |
| 2004/0257438 A1 | 12/2004 | Doguchi et al. | |
| 2005/0002091 A1 | 1/2005 | Amano | |
| 2005/0010081 A1 | 1/2005 | Doguchi et al. | |
| 2005/0027166 A1* | 2/2005 | Matsumoto | A61B 1/041 600/162 |
| 2005/0154227 A1 | 7/2005 | Stroefer et al. | |
| 2006/0017913 A1 | 1/2006 | Kawamata et al. | |
| 2006/0024756 A1 | 2/2006 | Tibbe et al. | |
| 2006/0025692 A1 | 2/2006 | Ishihara | |
| 2006/0082646 A1 | 4/2006 | Abe et al. | |
| 2006/0209185 A1 | 9/2006 | Yokoi | |
| 2007/0177153 A1 | 8/2007 | Takahashi | |
| 2007/0197874 A1 | 8/2007 | Ishihara | |
| 2008/0015446 A1* | 1/2008 | Mahmood | A61B 1/00009 600/476 |
| 2008/0247624 A1 | 10/2008 | Scholz | |
| 2008/0255426 A1 | 10/2008 | Iketani | |
| 2008/0255460 A1 | 10/2008 | Voegele et al. | |
| 2008/0296511 A1 | 12/2008 | Kawamata et al. | |
| 2009/0036743 A1 | 2/2009 | Yabe et al. | |
| 2009/0216085 A1 | 8/2009 | Yamazaki | |
| 2009/0263328 A1* | 10/2009 | Nakajima | G01N 21/6456 424/9.6 |
| 2009/0296203 A1* | 12/2009 | Kojima | G02B 21/365 359/363 |
| 2010/0016669 A1 | 1/2010 | Takaoka et al. | |
| 2010/0020163 A1 | 1/2010 | Watanabe et al. | |
| 2010/0049058 A1 | 2/2010 | Ishihara | |
| 2010/0059690 A1 | 3/2010 | Ishihara | |
| 2010/0080459 A1 | 4/2010 | Dai et al. | |
| 2010/0103250 A1 | 4/2010 | Ishihara | |
| 2010/0210903 A1 | 8/2010 | Ishihara | |
| 2010/0245550 A1 | 9/2010 | Ishihara | |
| 2010/0245551 A1 | 9/2010 | Morita | |
| 2010/0245619 A1 | 9/2010 | Watanabe et al. | |
| 2010/0292543 A1 | 11/2010 | Levitt et al. | |
| 2011/0001061 A1 | 1/2011 | Ishihara | |
| 2011/0009702 A1 | 1/2011 | Morishita et al. | |
| 2011/0012025 A1 | 1/2011 | Takei | |
| 2011/0017923 A1 | 1/2011 | Kubo et al. | |
| 2011/0044527 A1 | 2/2011 | Tibbe et al. | |
| 2011/0068278 A1 | 3/2011 | Morishita et al. | |
| 2011/0077462 A1* | 3/2011 | Saitou | A61B 1/0638 600/109 |
| 2011/0121200 A1 | 5/2011 | Watanabe | |
| 2011/0211741 A1* | 9/2011 | Nakano | G01N 15/1434 382/128 |
| 2011/0213252 A1 | 9/2011 | Fulghum | |
| 2011/0267458 A1 | 11/2011 | Kubo et al. | |
| 2011/0267493 A1 | 11/2011 | Kubo et al. | |
| 2012/0057743 A1* | 3/2012 | Priore | G01J 3/02 382/100 |
| 2012/0123205 A1* | 5/2012 | Nie | A61B 1/00174 600/109 |
| 2012/0150043 A1* | 6/2012 | Mahmood | A61B 1/00009 600/476 |
| 2013/0028501 A1 | 1/2013 | Ishihara | |
| 2013/0113907 A1 | 5/2013 | Ono | |
| 2013/0307952 A1 | 11/2013 | Ishihara | |
| 2014/0078279 A1 | 3/2014 | Shida | |
| 2014/0184769 A1 | 7/2014 | Ishihara et al. | |
| 2014/0213871 A1 | 7/2014 | Watanabe | |
| 2014/0301617 A1 | 10/2014 | Shida et al. | |

FOREIGN PATENT DOCUMENTS

| | | |
|---|---|---|
| EP | 1 006 386 A1 | 6/2000 |
| EP | 1099405 A1 | 5/2001 |
| EP | 2095758 A1 | 9/2009 |
| EP | 2105082 A1 | 9/2009 |
| EP | 2108300 A1 | 10/2009 |
| EP | 2123213 A2 | 11/2009 |
| EP | 2679136 A1 | 1/2014 |
| EP | 2679137 A1 | 1/2014 |
| JP | 62247232 A | 10/1987 |
| JP | 62247332 A | 10/1987 |
| JP | 03058279 A | 3/1991 |
| JP | 358729 B2 | 9/1991 |
| JP | 07222712 A | 8/1995 |
| JP | H07-246184 A | 9/1995 |
| JP | 08201464 A | 8/1996 |
| JP | 08317915 A | 12/1996 |
| JP | 10262160 A | 9/1998 |

(56) References Cited

FOREIGN PATENT DOCUMENTS

| | | | |
|---|---|---|---|
| JP | 11122540 A | 4/1999 | |
| JP | 2004024497 A | 1/2001 | |
| JP | 2001137173 A | 5/2001 | |
| JP | 2001137175 A | 5/2001 | |
| JP | 2001169999 A | 6/2001 | |
| JP | 2001314366 A * | 11/2001 | |
| JP | 2002172082 A | 6/2002 | |
| JP | 2002233492 A | 8/2002 | |
| JP | 2003000528 A | 1/2003 | |
| JP | 2003036436 A | 2/2003 | |
| JP | 2003079568 A | 3/2003 | |
| JP | 2003102672 A | 4/2003 | |
| JP | 2003111716 A | 4/2003 | |
| JP | 2004024496 A | 1/2004 | |
| JP | 2004535878 A | 12/2004 | |
| JP | 2005013279 A | 1/2005 | |
| JP | 2005185452 A | 7/2005 | |
| JP | 2005261974 A | 9/2005 | |
| JP | 2006025802 A | 2/2006 | |
| JP | 2006043196 A | 2/2006 | |
| JP | 2006061399 A | 3/2006 | |
| JP | 2006061683 A | 3/2006 | |
| JP | 2006115964 A | 5/2006 | |
| JP | 2006175052 A | 7/2006 | |
| JP | 2006524097 A | 10/2006 | |
| JP | 2007020775 A | 2/2007 | |
| JP | 2007029453 A | 2/2007 | |
| JP | 2007068597 A | 3/2007 | |
| JP | 2007222381 A | 9/2007 | |
| JP | 2008093254 A | 4/2008 | |
| JP | 2008154846 A | 7/2008 | |
| JP | 2008183349 A | 8/2008 | |
| JP | 2008-229025 A | 10/2008 | |
| JP | 2009034224 A | 2/2009 | |
| JP | 2007215927 A | 8/2009 | |
| JP | 4343594 B2 | 10/2009 | |
| JP | 2009279171 A | 12/2009 | |
| JP | 2009279172 A | 12/2009 | |
| JP | 2010036017 A | 2/2010 | |
| JP | 2010162123 A | 7/2010 | |
| JP | 2010220892 A | 10/2010 | |
| JP | 2010220893 A | 10/2010 | |
| JP | 2010220894 A | 10/2010 | |
| JP | 2010227253 A | 10/2010 | |
| JP | 2010263949 A | 11/2010 | |
| JP | 2011024726 A | 2/2011 | |
| JP | 2011244952 A | 12/2011 | |
| WO | 0042910 A1 | 7/2000 | |
| WO | 03009739 A2 | 2/2003 | |
| WO | 03069421 A2 | 8/2003 | |
| WO | 2004082472 A1 | 9/2004 | |
| WO | 2006101128 A1 | 9/2006 | |
| WO | 2008/008231 A1 | 1/2008 | |
| WO | WO 2008008231 A2 * | 1/2008 | ......... A61B 1/00009 |
| WO | 2008072579 A1 | 6/2008 | |
| WO | 2008143246 A1 | 11/2008 | |
| WO | 2009139203 A1 | 11/2009 | |
| WO | 2010110138 A1 | 9/2010 | |
| WO | 2011099363 A1 | 8/2011 | |
| WO | 2012176285 A1 | 12/2012 | |
| WO | 2013035738 A1 | 3/2013 | |

OTHER PUBLICATIONS

Office Action dated Jan. 11, 2016 received in related U.S. Appl. No. 13/565,440.
Extended European Supplementary Search Report dated Mar. 13, 2014 from related European Application No. 11 86 8025.5.
Office Action dated Nov. 20, 2015 received in related U.S. Appl. No. 14/100,422.
U.S. Non-Final Office Action dated Dec. 30, 2014 received in related U.S. Appl. No. 13/599,372.
Office Action dated Feb. 22, 2016 received in related U.S. Appl. No. 13/950,376.
Abstract Only of JP 2005-013279 (which corresponds to JP 4343594).
Office Action dated Mar. 12, 2014 received in parent U.S. Appl. No. 13/565,440.
Extended Supplementary European Search Report dated Apr. 30, 2015 from related European Application No. 12 81 6953.9.
U.S. Office Action dated May 27, 2015 received in related U.S. Appl. No. 13/565,440.
Office Action dated Apr. 8, 2016 received in related U.S. Appl. No. 14/154,241.

* cited by examiner

4 × 4 BINNING
SENSITIVITY PRIORITIZED/LOW RESOLUTION

2 × 2 BINNING

BINNING DISABLED
HIGH RESOLUTION

| NUMBER OF PIXELS FOR BINNING AND SUMMING | INCIDENT LIGHT LEVEL (photon/$\mu m^2$) |
|---|---|
| 1×1 | 100~ |
| 2×2 | 35~100 |
| 4×4 | 15~35 |
| 6×6 | 8.5~15 |
| 8×8 | 6.5~8.5 |
| 10×10 | ~6.5 |

FIG. 19

| NUMBER OF PIXELS FOR BINNING AND SUMMING | IMAGING-SURFACE ILLUMINANCE (photon/sec/$\mu m^2$) | | | | |
|---|---|---|---|---|---|
| | EXPOSURE TIME (msec) | | | | |
| | 8 | 16 | 24 | 50 | 100 |
| 1×1 | 13000~ | 6500~ 13000 | 4330~ 6500 | | |
| 2×2 | | | 1458~ 4300 | | |
| 4×4 | | | 625~ 1458 | | |
| 6×6 | | | 375~625 | | |
| 8×8 | | | 250~375 | | |
| 10×10 | | | 208~250 | 100~208 | ~100 |

| | INCIDENT LIGHT LEVEL (photon/$\mu m^2$) | | |
|---|---|---|---|
| THRESHOLD<br>NUMBER OF PIXELS<br>FOR BINNING AND SUMMING | 6 | 10 | 15 |
| 1×1 | 46~ | 100~ | 206~ |
| 2×2 | 18~46 | 35~100 | 64~206 |
| 4×4 | 8~18 | 15~35 | 24~64 |
| 6×6 | 5~8 | 8.5~15 | 15~24 |
| 8×8 | 3.6~5 | 6.5~8.5 | 10~15 |
| 10×10 | ~3.6 | ~6.5 | ~10 |

| CONTRAST T/C | SN RATIO THRESHOLD $S^3$ |
|---|---|
| ~1.5 | 15 |
| 1.5~3 | 10 |
| 3~ | 6 |

| LUMINANCE REPRESENTATIVE VALUE OF GRADATION VALUE D / EXPOSURE TIME t | SN RATIO THRESHOLD S/N |
|---|---|
| ~100000 | 15 |
| 100000~300000 | 10 |
| 300000~ | 6 |

M<M1

| NUMBER OF PIXELS FOR BINNING AND SUMMING | IMAGING-SURFACE ILLUMINANCE (photon/sec/$\mu m^2$) | | | | |
|---|---|---|---|---|---|
| | EXPOSURE TIME (msec) | | | | |
| | 8 | 16 | 24 | 50 | 100 |
| 1×1 | 13000~ | 6500~13000 | 4330~6500 | | |
| 2×2 | | | 1458~4330 | | |
| 4×4 | | | 625~1458 | | |
| 6×6 | | | 375~625 | 180~375 | 100~180 |
| 8×8 | | | | | 70~100 |
| 10×10 | | | | | ~70 |

M<M2

| NUMBER OF PIXELS FOR BINNING AND SUMMING | IMAGING-SURFACE ILLUMINANCE (photon/sec/$\mu m^2$) | | | | |
|---|---|---|---|---|---|
| | EXPOSURE TIME (msec) | | | | |
| | 8 | 16 | 24 | 50 | 100 |
| 1×1 | 13000~ | 6500~13000 | | | |
| 2×2 | | 2200~6500 | | | |
| 4×4 | | 875~2200 | | | |
| 6×6 | | 560~875 | | | |
| 8×8 | | 380~560 | | | |
| 10×10 | | 310~380 | 208~310 | 100~208 | ~100 |

| NUMBER OF PIXELS FOR BINNING AND SUMMING | IMAGING-SURFACE ILLUMINANCE (photon/sec/$\mu m^2$) | | | | |
|---|---|---|---|---|---|
| | EXPOSURE TIME (msec) | | | | |
| | 8 | 16 | 24 | 50 | 100 |
| 1×1 | 13000~ | 6500~ 13000 | 4330~ 6500 | 2080~ 4330 | 1040~ 2080 |
| 2×2 | | | | | 270~ 1040 |
| 4×4 | | | | | 150~270 |
| 6×6 | | | | | 100~150 |
| 8×8 | | | | | 70~100 |
| 10×10 | | | | | ~70 |

I2<I

| NUMBER OF PIXELS FOR BINNING AND SUMMING | IMAGING-SURFACE ILLUMINANCE (photon/sec/$\mu m^2$) | | | | |
|---|---|---|---|---|---|
| | EXPOSURE TIME (msec) | | | | |
| | 8 | 16 | 24 | 50 | 100 |
| 1×1 | 13000~ | 6500~13000 | | | |
| 2×2 | | 2200~6500 | | | |
| 4×4 | | 875~2200 | | | |
| 6×6 | | 560~875 | 375~560 | | |
| 8×8 | | | 250~375 | | |
| 10×10 | | | 208~250 | 100~208 | ~100 |

| CONTRAST | FIRST THRESHOLD | SECOND THRESHOLD |
|----------|-----------------|------------------|
| ~1.5 | 15 | 25 |
| 1.5~3 | 10 | 20 |
| 3~ | 6 | 10 |

| LUMINANCE REPRESENTATIVE VALUE OF GRADATION VALUES / EXPOSURE TIME sec | FIRST THRESHOLD | SECOND THRESHOLD |
|---|---|---|
| ~100000 | 15 | 25 |
| 100000~300000 | 10 | 20 |
| 300000~ | 6 | 10 |

| CORRECTED FLUORESCENCE IMAGE LUMINANCE VALUE | FLUORESCENCE CONCENTRATION (nM) |
|---|---|
| 0 | 0 |
| 1 | 1 |
| ⋮ | ⋮ |
| 4095 | 1000 |

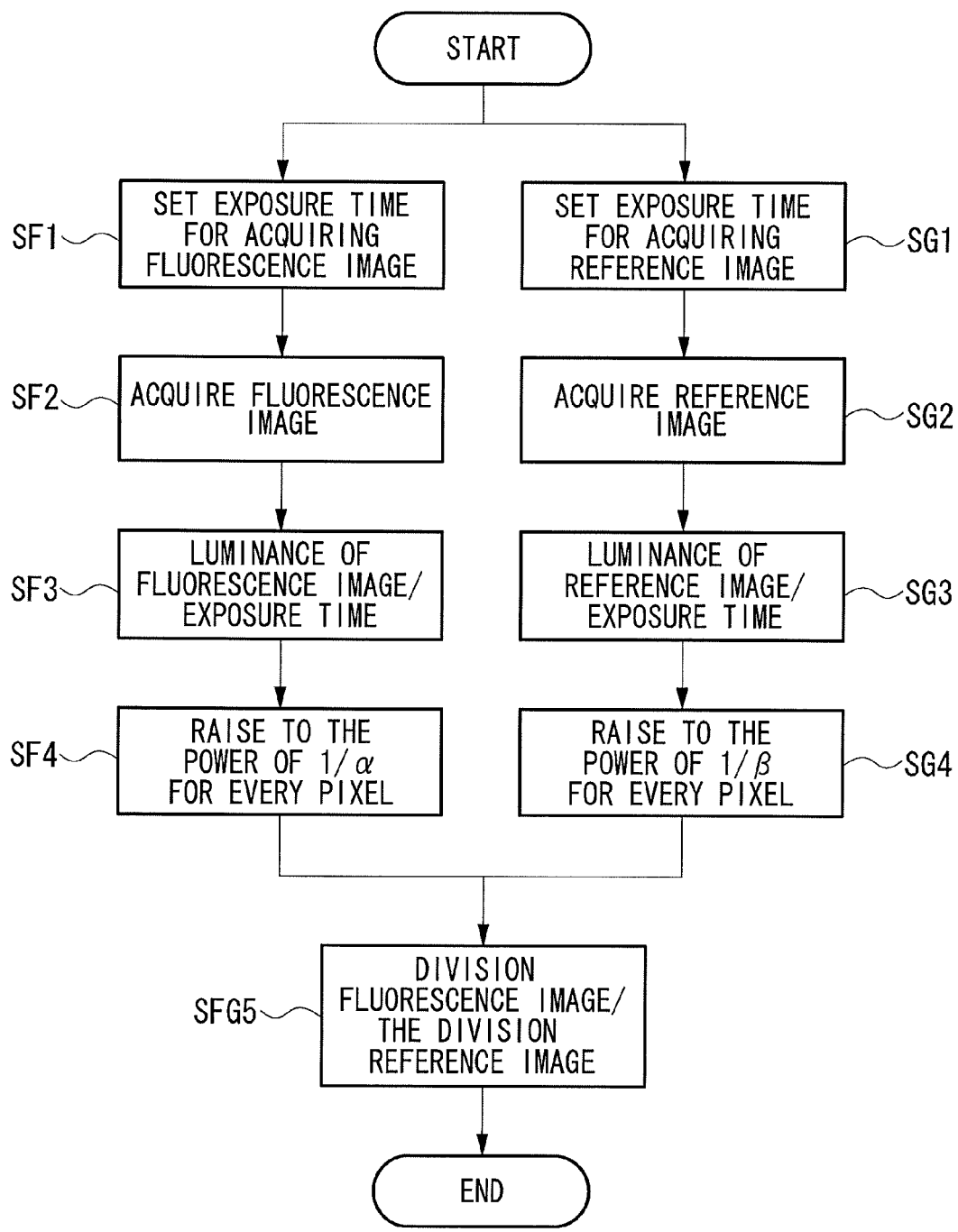

| GAIN VALUE | GAIN MULTIPLICATION FACTOR (FG) |
|---|---|
| 0 | 1 |
| 1 | 2 |
| ⋮ | ⋮ |
| 8 | 50 |

387

| LIGHT-ADJUSTMENT LEVEL | EXCITATION LIGHT INTENSITY |
|---|---|
| 0 | 1 |
| 1 | 2 |
| ⋮ | ⋮ |
| 8 | 50 |

FIG. 77

| BOUNDARY VALUE | NORMALIZED FLUORESCENCE SIGNAL INTENSITY | | | | NORMALIZED REFERENCE SIGNAL INTENSITY | | | |
|---|---|---|---|---|---|---|---|---|
| | BOUNDARY VALUE OR LESS | | BOUNDARY VALUE OR MORE | | BOUNDARY VALUE OR LESS | | BOUNDARY VALUE OR MORE | |
| | INDEX $\alpha_1$ | DETERMINED COEFFICIENT $R^2$ | INDEX $\alpha_2$ | DETERMINED COEFFICIENT $R^2$ | INDEX $\beta_1$ | DETERMINED COEFFICIENT $R^2$ | INDEX $\beta_2$ | DETERMINED COEFFICIENT $R^2$ |
| D(3) | -0.577 | 0.9786 | -1.37 | 0.9853 | -0.868 | 0.9804 | -1.69 | 0.9972 |
| D(4) | -0.639 | 0.9778 | -1.45 | 0.9951 | -0.979 | 0.9746 | -1.73 | 0.9986 |
| ... | ... | ... | ... | ... | ... | ... | ... | ... |
| D(5) | -0.94 | 0.9672 | -1.66 | 0.9981 | -1.30 | 0.9721 | -1.84 | 0.9998 |

FIG. 83

| | | | | | |
|---|---|---|---|---|---|
| OBSERVATION DISTANCE | 200 | ... | 120 | ... | 25 | 10 |
| REFERENCE IMAGE | 331 | ... | 294 | ... | 4617 | 14000 |
| FLUORESCENCE IMAGE | 5031 | ... | 5893 | ... | 53126 | 27000 |
| REFLECTED LIGHT GAIN | 1 | ... | 1 | ... | 1 | 1 |
| FLUORESCENCE GAIN | 150 | ... | 150 | ... | 100 | 30 |
| REFLECTED LIGHT EXPOSURE TIME | 20 | ... | 15 | ... | 10 | 7 |
| FLUORESCENCE EXPOSURE TIME | 100 | ... | 100 | ... | 70 | 30 |
| NORMALIZED REFERENCE IMAGE | 16.6 | ... | 37.5 | ... | 461.7 | 2000 |
| NORMALIZED FLUORESCENCE IMAGE | 33.5 | ... | 72.2 | ... | 758.9 | 3000 |
| FLUORESCENCE/REFLECTED LIGHT | 2.024 | ... | 1.923 | ... | 1.644 | 1.500 |

FIG. 84

| NORMALIZED REFERENCE IMAGE | 16.6 | ... | 37.5 | ... | 461.7 | ... | 2000 |
|---|---|---|---|---|---|---|---|
| COEFFICIENT | 2.024 | ... | 1.923 | ... | 1.644 | ... | 1.500 |

FIG. 117

| OBSERVATION CONDITION (OBSERVATION SITE) | PREPROCESSING | | | POST-PROCESSING | | |
|---|---|---|---|---|---|---|
| | FIRST PREPROCESSING MODE | SECOND PREPROCESSING MODE | THIRD PREPROCESSING MODE | FIRST POST-PROCESSING MODE | SECOND POST-PROCESSING MODE | THIRD POST-PROCESSING MODE |
| LOCAL VIEW (DOUGLAS' POUCH, STOMACH, URINARY TRACT, RECTUM) | ○ | ○ | | | | |
| OVERHEAD VIEW (GREATER OMENTUM, SUBPHRENIC AREA, INTESTINAL MEMBRANE) | ○ | ○ | | | | |
| PERSPECTIVE LARGE (DOUGLAS' POUCH, STOMACH) | | | | ○ | | ○ |
| PERSPECTIVE SMALL (GREATER OMENTUM, INTESTINAL MEMBRANE, URINARY TRACT) | | | | ○ | | ○ |
| MULTI-COLOR | | | ○ | | | |
| SINGLE-COLOR | | | | | | |
| IRREGULAR (GREATER OMENTUM, INTESTINAL MEMBRANE, STOMACH, RECTUM) | | | | ○ | | ○ |
| FLAT (SUBPHRENIC AREA, PART OTHER THAN LARGE INTESTINE WALL) | | | | ○ | | ○ |
| HIGH FAT (STOMACH, URINARY TRACT) | ○ | | | | | |
| LOW FAT | | | | | | |

FLUORESCENCE OBSERVATION APPARATUS

CROSS-REFERENCE TO RELATED APPLICATIONS

This is a continuation of International Application PCT/JP2012/072610, with an international filing date of Sep. 5, 2012, which is hereby incorporated by reference herein in its entirety. This application claims the benefit of Japanese Patent Application No. 2011-195341, filed on Sep. 7, 2011, the content of which is incorporated herein by reference.

TECHNICAL FIELD

The present invention relates to a fluorescence observation apparatus.

BACKGROUND ART

There has conventionally been known a method for correcting brightness variations in fluorescence images caused by observation distance and by dividing a fluorescence image by a reflected light image (see, for example, PTL 1 to PTL 3).

CITATION LIST

Patent Literature

{PTL 1}
Japanese Unexamined Patent Application, Publication No. Sho 62-247332
{PTL 2}
Japanese Examined Patent Application, Publication No. Hei 3-58729
{PTL 3}
Japanese Unexamined Patent Application, Publication No. 2006-175052

SUMMARY OF INVENTION

The present invention provides a fluorescence observation apparatus comprising: an illumination section comprising a light source that radiates excitation light and illumination light to a subject; a fluorescence image acquisition section that acquires a fluorescence image by capturing fluorescence generated in the subject by the radiation of the excitation light from the light source; a reference image acquisition section that acquires a reference image by capturing reflected light returned from the subject by the radiation of the illumination light from the light source; a division image generation section that generates a division image by dividing an image based on the fluorescence image by an image based on the reference image; a display section that displays a corrected fluorescence image based on the division image generated by the division image generation section; a correction processing unit that applies correction processing to at least one of the reference image and the fluorescence image and/or to the division image prior to the generation of the division image by the division image generation section or prior to the display of the corrected fluorescence image by the display section; an observation condition determination section that determines observation conditions of the subject; and a correction condition setting section that sets parameters regarding the correction processing by the correction processing section according to the observation conditions determined by the observation condition determination section.

BRIEF DESCRIPTION OF DRAWINGS

FIG. 19 is a diagram showing a table of a relationship between the image surface illuminance and the number of pixels for binning summing, as well as exposure time, created based on the graph of FIG. 18.

FIG. 32 is a diagram showing a table of a correspondence relationship between the imaging surface illuminance and the number of pixels for binning summing when the luminance of the reference image is small, the table stored in the sensitivity setting circuit of the preprocessing section of FIG. 21.

FIG. 53 is a flowchart of image processing in the image processing section including the processing section of FIG. 48.

FIG. 77 is a diagram showing a database obtained as a result of power approximation in FIG. 76.

FIG. 83 is a diagram showing an example of a table view of an association between a gradation value, gain, and exposure time of images as well as normalized images for deriving a coefficient used in the preprocessing section of FIG. 82 and a coefficient derived from them.

FIG. 84 is a diagram showing an example of a table view of an association between a gradation value and a coefficient of the normalized reference image derived from FIG. 83.

FIG. 104 is a block diagram showing a configuration of the post-processing section and the correction condition setting section that execute a third post-processing mode.

FIG. 105 is a flowchart showing a processing method in the third post-processing mode.

FIG. 106 is a diagram showing a state that the insertion portion is arranged to face an observation target site.

FIG. 107A is a diagram showing an example of the fluorescence image.

FIG. 107B is a histogram showing a relationship between the gradation values of the pixels in the fluorescence image of FIG. 107A and the frequency of each of the gradation values occupying the entire image.

FIG. 108A is a diagram showing an example of the division image.

FIG. 108B is a histogram showing a relationship between the gradation values of the pixels in the division image of FIG. 108A and the frequency of each of the gradation values occupying the entire image.

FIG. 109A is a diagram showing an example of the corrected fluorescence image with the background removed.

FIG. 109B is a histogram showing a relationship between the gradation values of the pixels in the corrected fluorescence image of FIG. 109A and the frequency of each of the gradation values occupying the entire image.

FIG. 110 is a diagram showing an example of the corrected fluorescence image.

FIG. 111 is a partial block diagram of the fluorescence observation apparatus that executes a first modification of the third post-processing mode.

FIG. 112 is a schematic configuration diagram of the fluorescence observation apparatus according to the modification of FIG. 111.

Figure 112:
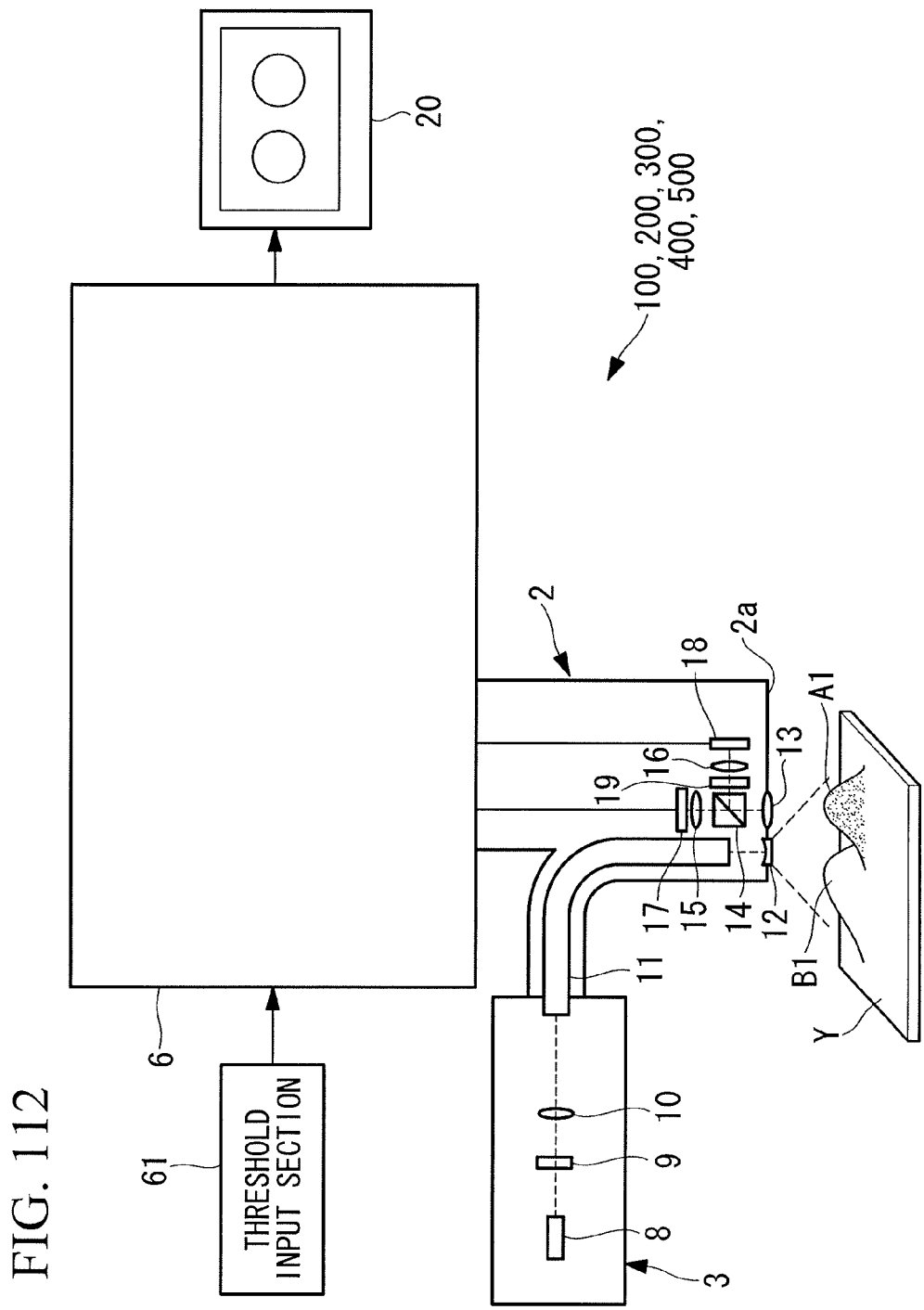
Figure 113:
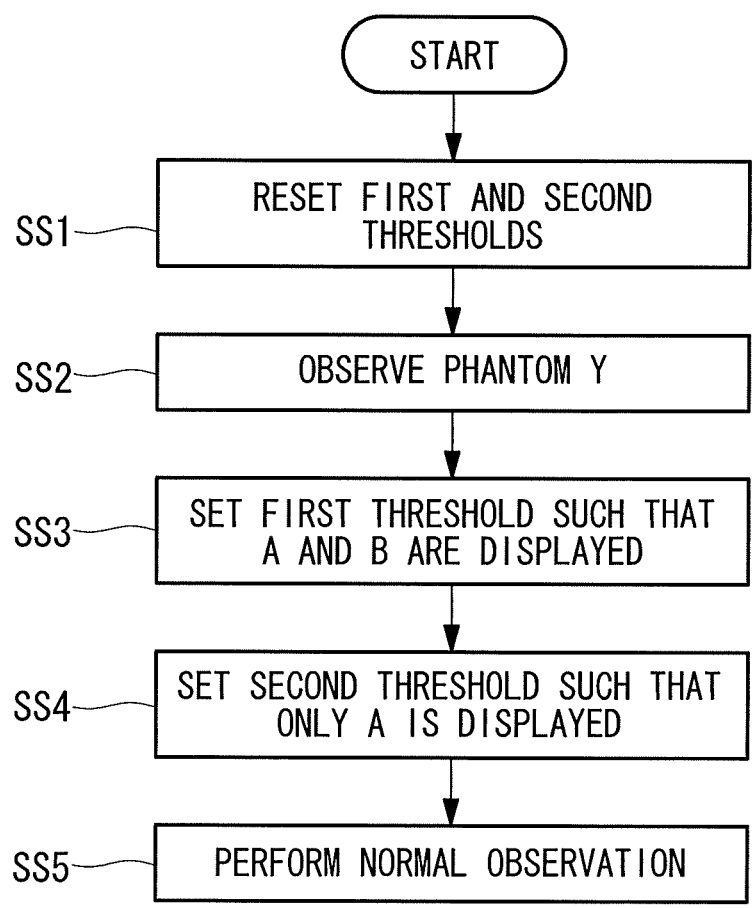

FIG. 113 is a flowchart showing operation of the fluorescence observation apparatus of FIG. 112.

Figure 114:
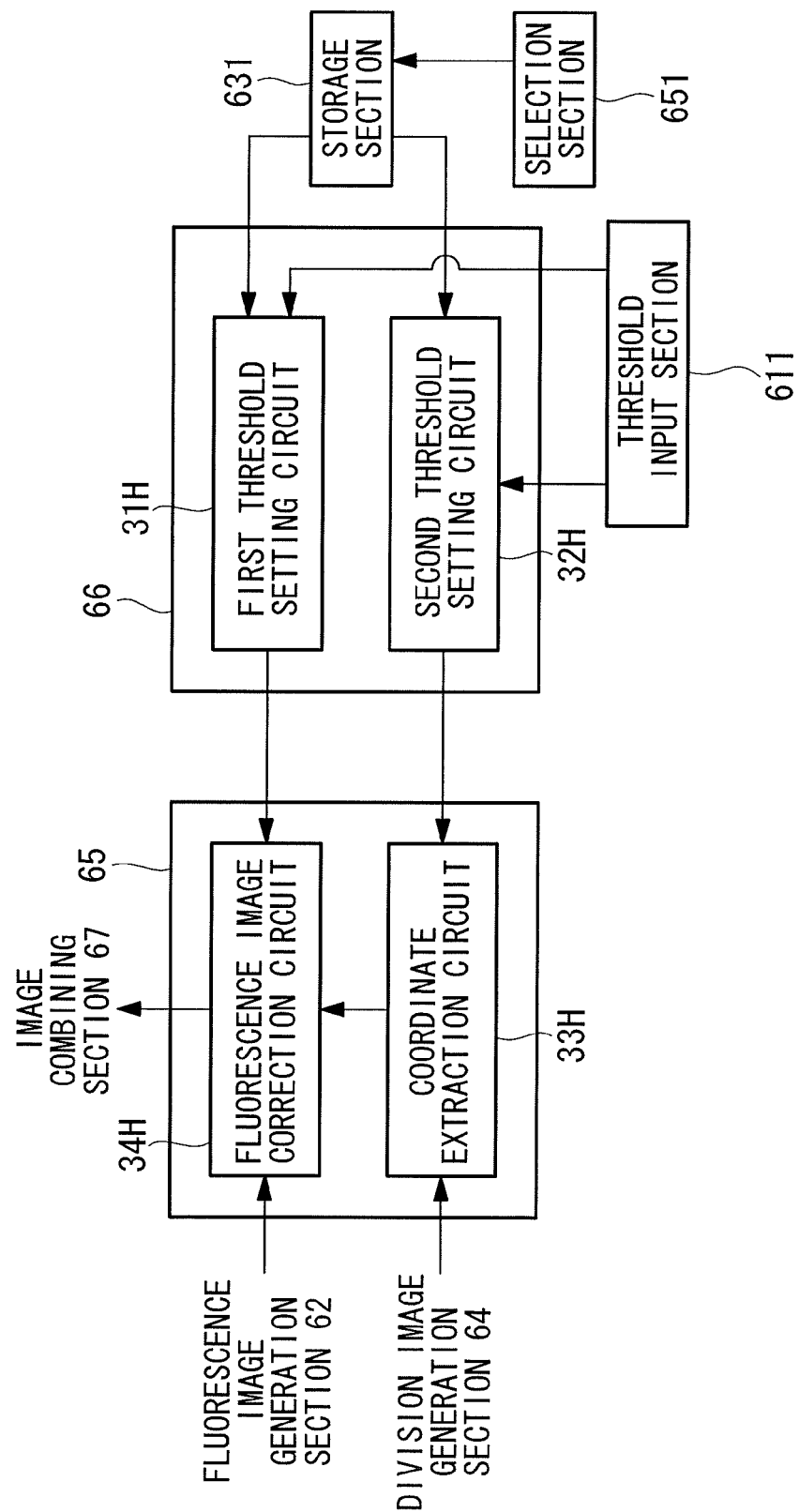

FIG. 114 is a partial block diagram of the fluorescence observation apparatus according to the modification of FIG. 112.

Figure 115:
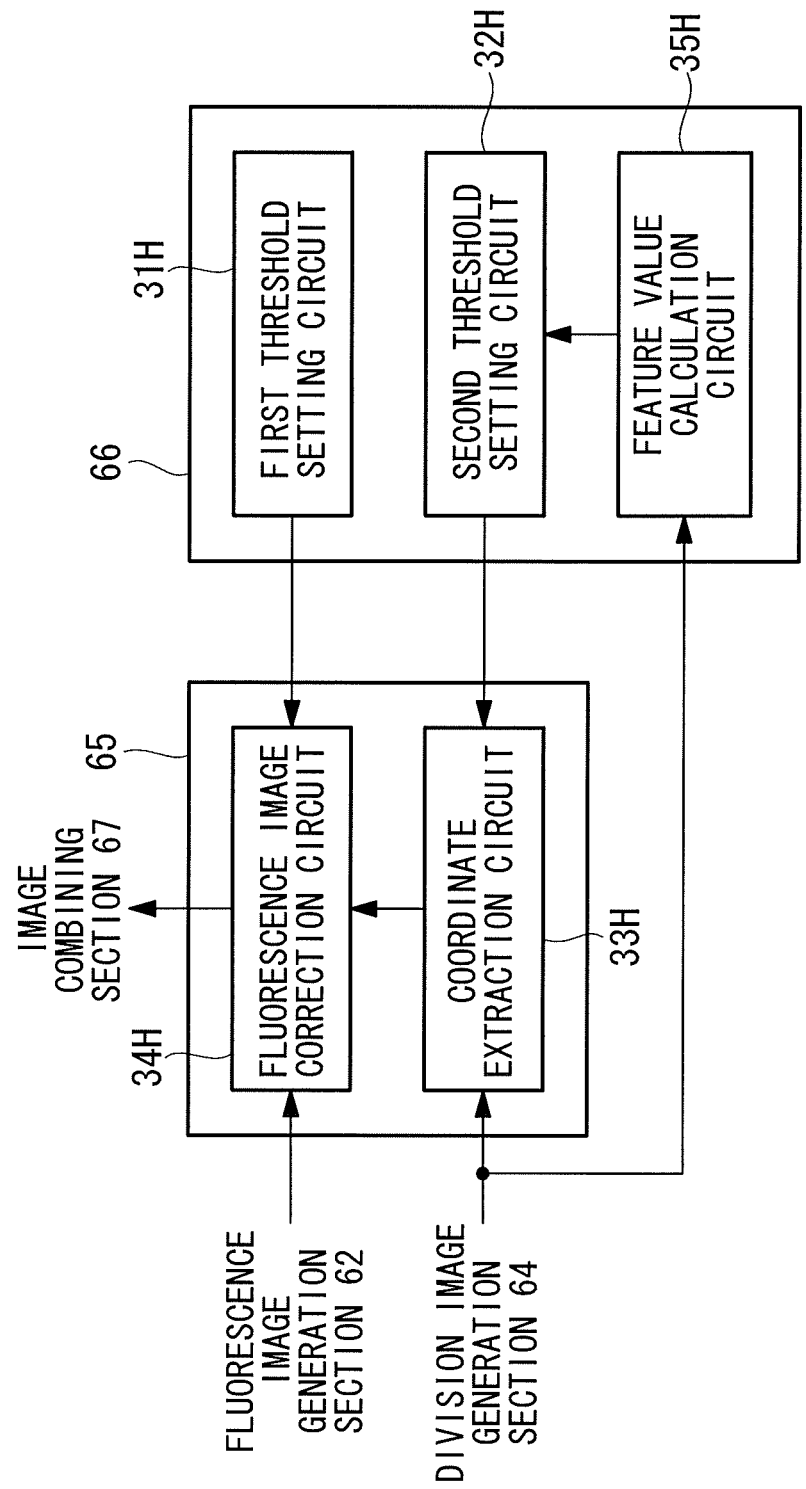

FIG. 115 is a partial block diagram of the fluorescence observation apparatus that executes a third modification of the third post-processing mode, which is a modification of the fluorescence observation apparatus of FIGS. 1 to 5.

Figure 116:
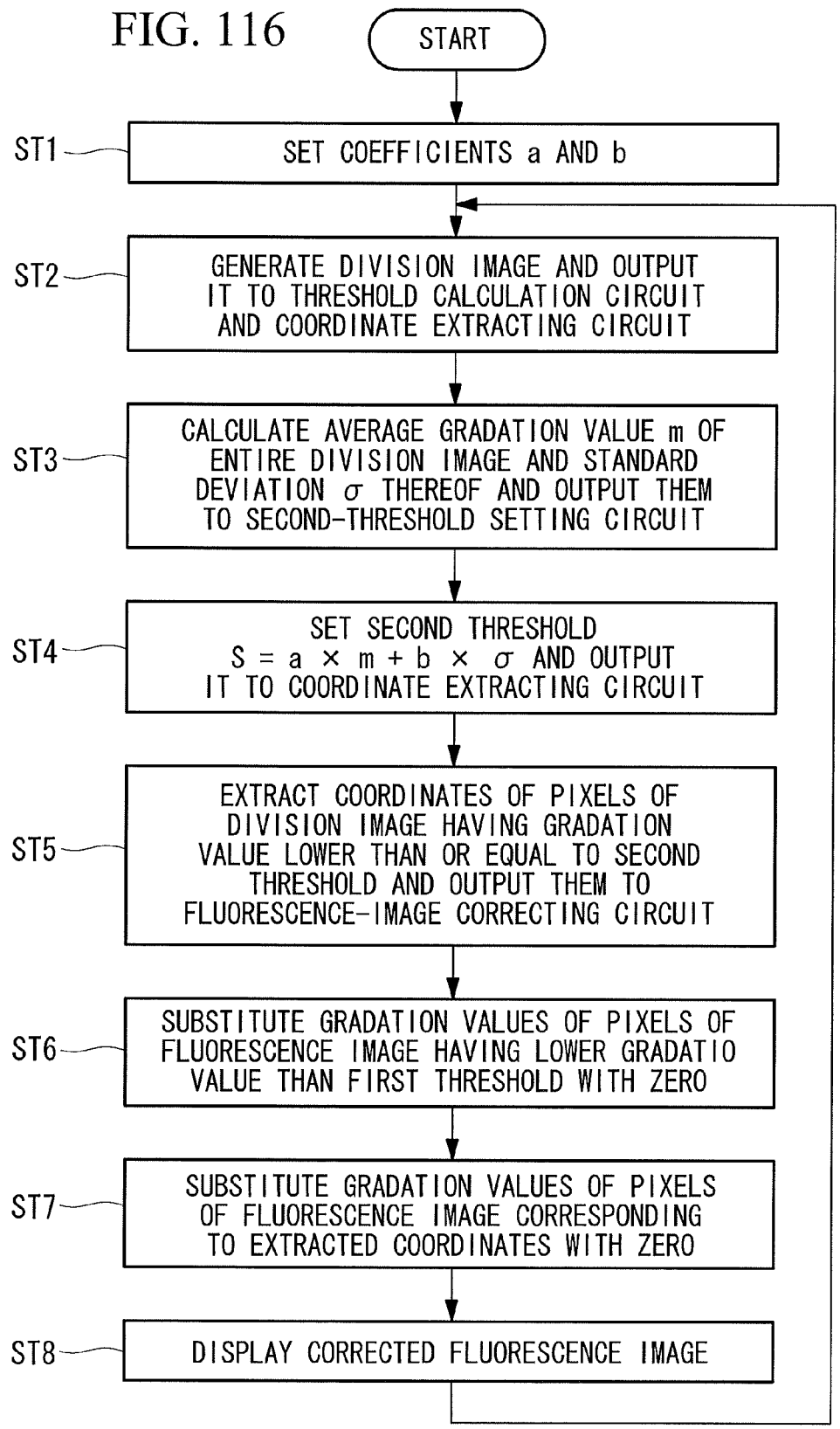

FIG. 116 is a flowchart showing operation of the fluorescence observation apparatus of FIG. 115.

FIG. 117 is a chart showing a correspondence between observation conditions as well as observation sites of an observation condition determination section and the post-processing modes as well as the preprocessing modes of the correction condition setting section.

DESCRIPTION OF EMBODIMENTS

Hereinafter, fluorescence observation apparatuses 100, 200, 300, 400, and 500 according to first to fifth embodiments of the present invention will be described with reference to the drawings. Note that an outline of the configuration and operation of the fluorescence observation apparatuses 100, 200, 300, 400, and 500 according to the first to fifth embodiments will be described first, and details of image processing by a preprocessing section 63 and a post-processing section 65 included in each of the fluorescence observation apparatuses 100, 200, 300, 400, and 500 will be described in detail after the description of the outline.

First Embodiment

The fluorescence observation apparatus 100 according to the first embodiment of the present invention will be described below with reference to FIG. 1.

Figure 1:
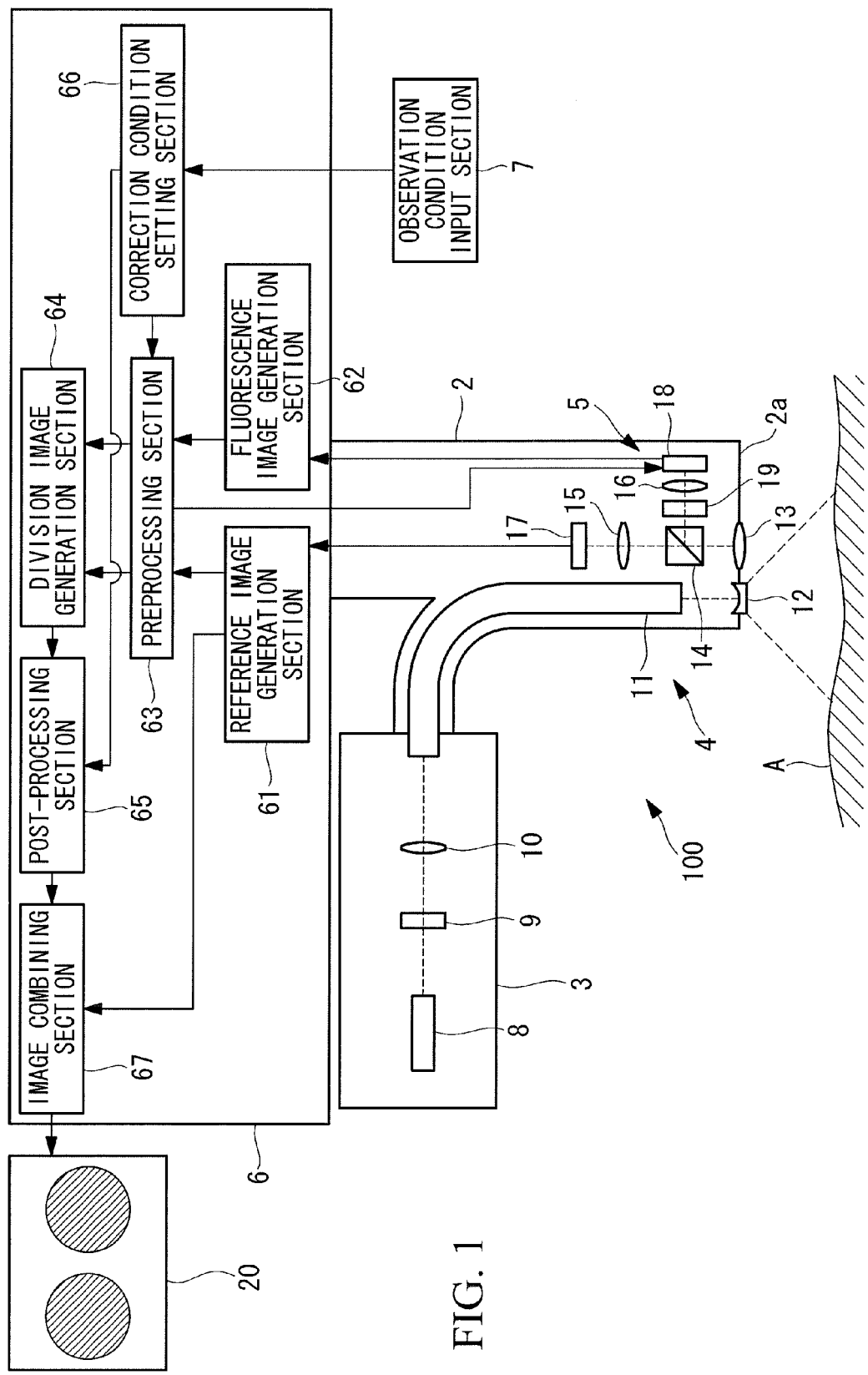
FIG. 1 is an overall configuration diagram of a fluorescence observation apparatus according to a first embodiment of the present invention.

The fluorescence observation apparatus 100 according to the present embodiment is an endoscope apparatus, and as shown in FIG. 1, includes: an elongated insertion portion 2 inserted to the body; a light source (illumination section) 3; an illumination unit (illumination section) 4 that radiates illumination light and excitation light from the light source 3 to an observation target (examination target) A from a tip of the insertion portion 2; an image capturing unit 5 that is arranged on the tip of the insertion portion 2 and that acquires image information of body tissue which is the observation target A; an image processing section 6 that is arranged on the base end side of the insertion portion 2 and that processes the image information acquired by the image capturing unit 5; an observation condition input section (observation condition determination section) 7 that inputs observation conditions of the observation target A to the image processing section 6; and a monitor (display section) 20 that displays an image processed by the image processing section 6.

The light source 3 includes: a xenon lamp 8; a filter 9 that cuts out excitation light and illumination light (wavelength band of 400 nm to 740 nm) from illumination light emitted from the xenon lamp 8; and a coupling lens 10 that focuses the excitation light and the illumination light cut out by the filter 9.

The illumination unit 4 includes: a light guide fiber 11 that is arranged substantially through the entire length in a longitudinal direction of the insertion portion 2 and that guides the excitation light and the illumination light focused by the coupling lens 10; and an illumination optical system 12 that is arranged at the tip of the insertion portion 2 and that diffuses the excitation light and the illumination light guided by the light guide fiber 11 to radiate the observation target A facing a tip surface 2a of the insertion portion 2.

The image capturing unit 5 includes: an objective lens 13 that focuses taken light returned from a predetermined observation range of the observation target A; a dichroic mirror (branch section) 14 that reflects light equal to or higher than the excitation wavelength (excitation light and fluorescence) in the reflected light focused by the objective lens 13 and that transmits illumination light at a wavelength shorter than the excitation wavelength; two focusing lenses (image capturing optical systems) 15 and 16 that focus the reflected light of the illumination light transmitted through the dichroic mirror 14 and the fluorescence reflected by the dichroic mirror 14, respectively; and two image capturing elements (reference image acquisition section and fluorescence image acquisition section) 17 and 18, such as CMOSs, that capture the reflected light of the fluorescence and the illumination light focused by the focusing lenses 15 and 16.

In FIG. 1, reference sign 19 denotes an excitation light cut filter that blocks the excitation light from the light reflected by the dichroic mirror 14.

The image processing section 6 includes: a reference image generation section 61 that generates a reference image from reference image information acquired by the image capturing element 17; a fluorescence image generation section 62 that generates a fluorescence image from fluorescence image information acquired by the image capturing element 18; a preprocessing section (correction processing section) 63 that generates a division reference image and a division fluorescence image by applying preprocessing to the reference image and the fluorescence image generated by the reference image generation section 61 and the fluorescence image generation section 62, respectively; a division image generation section 64 that divides the division fluorescence image generated by the preprocessing section 63 by the division reference image; a post-processing section (correction processing section) 65 that generates a corrected fluorescence image by applying post-processing to the division image generated in the division image generation section 64; a correction condition setting section 66 that sets processing conditions of the preprocessing section 63 and the post-processing section 65 based on input from the observation condition input section 7; and an image combining section 67 that generates a combined image from the corrected fluorescence image and the reference image generated by the post-processing section 65.

The preprocessing section 63 is provided with at least one preprocessing mode for applying pre-correction processing to the reference image and the fluorescence image as described in detail later. The preprocessing section 63 generates the division reference image and the division fluorescence image by applying the pre-correction processing to the reference image and the fluorescence image according to preprocessing parameter values (parameters) regarding the preprocessing mode set by the correction condition setting section 66 and outputs the images to the division image generation section 64.

The division image generation section 64 generates the division image by applying a division process to each pixel of the division fluorescence image based on the division reference image.

As described later in detail, the post-processing section 65 is provided with at least one post-processing mode (processing mode) for applying post-correction processing to the division image. The post-processing section 65 generates the corrected fluorescence image by applying the post-correction processing to the division image according to post-processing parameter values (parameters) regarding the post-processing mode set by the correction condition setting section 66.

The correction condition setting section 66 stores processing condition data associating the observation conditions (described later) set to the observation condition input section 7, the preprocessing parameter values regarding the preprocessing mode by the preprocessing section 63, and the post-processing parameter values regarding the post-processing mode by the post-processing section 65. The correction condition setting section 66 sets the parameter values regarding the preprocessing mode and the post-processing mode based on the observation conditions input from the observation condition input section 7 and outputs signals for commanding the execution of the correction processing based on the set parameter values to the preprocessing section 63 and the post-processing section 65.

The image combining section 67, for example, arranges the reference image and the corrected fluorescence image in parallel to create a combined image to display the images on the monitor 20 at the same time and outputs the combined image to the monitor 20.

The observation condition input section 7 stores first to fifth items described later, and observation conditions for at least one of the items is selected and input by operation of the operator. For the observation condition input section 7, an input device, such as a mouse, is used to input the observation conditions from a list displayed on a panel not shown, for example. The observation condition input section 7 outputs the input observation conditions to the correction condition setting section 66.

Next, the first to fifth items stored in the observation condition input section 7 will be described. Note that the observation condition setting section 7 may store all of the five items or may store only part of the five items.

The first item relates to the observation distance, and "local view" or "overhead view" is determined as the observation condition. More specifically, the "local view" denotes local observation of part of the observation target A by moving the tip surface 2a of the insertion portion 2 close to the observation target A, and the "overhead view" denotes overhead observation of the entire observation target A by moving the tip surface 2a of the insertion portion 2 away from the observation target A. The observation distance affects the brightness of the reference image and the fluorescence image.

The second item relates to the size of the length of perspective of the observation target A, and "perspective large" or "perspective small" is determined as the observation condition. More specifically, "perspective large" denotes observation of the observation target A with a large depth and a large length of perspective, such as a lumen, and "perspective small" denotes observation of the observation target A with a small depth and a small length of perspective, such as a membrane.

The third item relates to the hue of the observation target A, and "multi-color" or "single-color" is determined as the observation condition. More specifically, "multi-color" denotes observation of the observation target A with mixed organs and tissues in different hues, and "single-color" denotes observation of the observation target A with only organs and tissues in a similar hue.

The fourth item relates to the surface shape of the observation target A, and "irregular" or "flat" is determined as the observation condition. More specifically, "irregular" denotes observation of the observation target A having a surface shape with many irregularities, and "flat" denotes observation of the observation target A having a smooth surface shape with few irregularities.

The fifth item relates to the amount of fat in the observation target, and "high fat" or "low fat" is determined as the observation condition. More specifically, "high fat" denotes observation of the observation target A such as an organ and tissue with the surface covered by fat, and "low fat" denotes observation of the observation target A with no fat or only a small amount of fat.

Next, operation of the fluorescence observation apparatus 100 according to the present embodiment with the configuration will be described.

According to the fluorescence observation apparatus 100 of the present embodiment, the illumination light and the excitation light from the light source 3 is radiated from the tip surface 2a of the insertion portion 2 to the observation target A through the illumination unit 4. The image capturing element 17 acquires the reflected light on the surface of the observation target A, and the reference image generation section 61 generates the reference image. Meanwhile, the image capturing element 18 acquires the fluorescence generated inside of the observation target A by the radiation of the excitation light, and the fluorescence image generation section 62 generates the fluorescence image.

In this case, the operator inputs the observation conditions corresponding to the observation target A to be observed to the observation condition input section 7. By doing so, the correction condition setting section 66 sets the parameter values regarding the processing modes executed by the preprocessing section 63 and the post-processing section 65.

By doing so, the preprocessing section 63 applies the preprocessing to the reference image and the fluorescence image to generate the division reference image and the division fluorescence image. The generated division reference image and division fluorescence image are input to the division image generation section 64, and the division fluorescence image is divided by the division reference image to generate the division image. The post-processing section 65 applies the post-processing to the generated division image to generate the corrected fluorescence image. The image combining section 67 combines the generated corrected fluorescence image and reference image and displays the images on the monitor 20 in parallel.

In this way, according to the fluorescence observation apparatus 100 of the present embodiment, the dependency of distance and angle is canceled by dividing the division fluorescence image based on the fluorescence image by the division reference image based on the reference image. In this case, the dependency of distance and angle is caused by a plurality of observation conditions, such as properties of shape, structure, color, and the like of the observation target A and observation distance. According to the present embodiment, the parameter values used in the preprocessing of the fluorescence image and the reference image and in the post-processing of the division image are set according to the observation conditions input to the observation condition input section 7. By doing so, suitable correction processing is executed for the dependency of distance and angle based on a plurality of factors, and there is an advantage that the dependency of distance and angle between the corrected fluorescence image and the reference image can be removed with high precision.

Second Embodiment

Next, the fluorescence observation apparatus 200 according to the second embodiment of the present invention will be described below with reference to FIG. 2. In the description of the present embodiment, configurations common to the first embodiment are designated with the same reference numerals, and the description will not be repeated.

Figure 2:
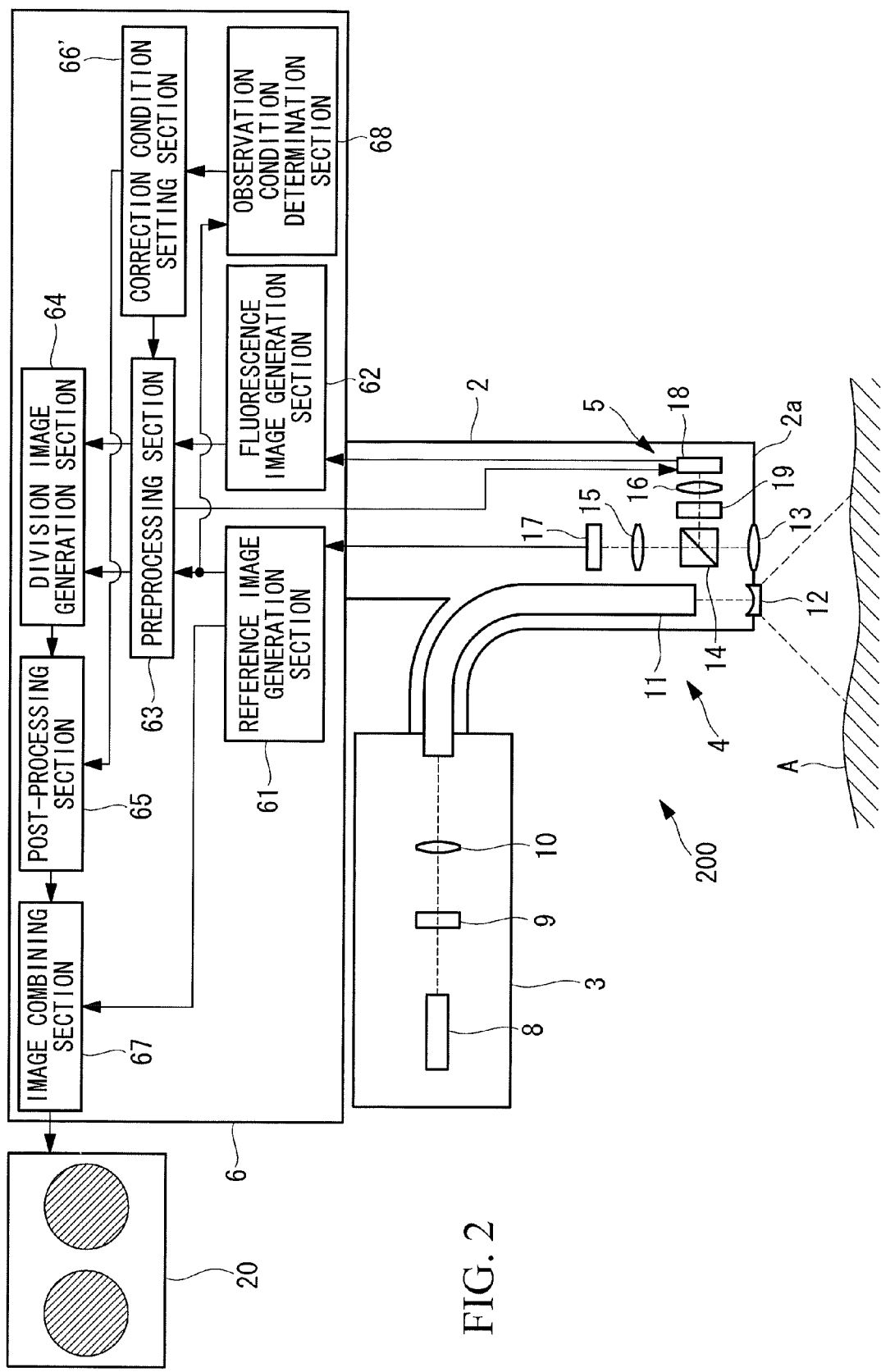
FIG. 2 is an overall configuration diagram of a fluorescence observation apparatus according to a second embodiment of the present invention.

As shown in FIG. 2, the fluorescence observation apparatus 200 according to the present embodiment is mainly different from the first embodiment in that the image processing section 6 includes, in place of the observation condition input section 7, an observation condition determination section 68 that determines the observation conditions based on the features of the reference image input from the reference image generation section 61.

The observation condition determination section 68 determines the observation conditions for at least one of the first to fifth items.

For the first item (observation distance), the observation condition determination section 68 detects an average value of normalized gradation values of the reference image and compares the average value with a predetermined threshold. The observation condition determination section 68 determines "local view" if the average value is equal to or higher than the predetermined threshold and determines "overhead view" if the average value is smaller than the predetermined threshold. The reference image is bright in the local view in which the tip surface 2a of the insertion portion 2 is moved close to the observation target A, and the reference image is dark in the overhead view in which the tip surface 2a of the insertion portion 2 is moved away from the observation target A.

For the second item (size of the length of perspective of the observation target), the observation condition determination section 68 detects a standard deviation of gradation values from the gradation values of all pixels of the reference image. The observation condition determination section 68 determines "perspective large" if the standard deviation is equal to or higher than a predetermined threshold and determines "perspective small" if the standard deviation is smaller than the threshold. If the observation target A has a deep structure, such as a lumen, the site close to the tip surface 2a of the insertion portion 2 is bright, and the site away from the tip surface 2a is dark. Therefore, the gradation values are distributed in a large range, and the standard deviation becomes large. On the other hand, if the observation target A has a flat structure, such as a membrane, variations in the distance at positions between the tip surface 2a of the insertion portion 2 and the observation target A are few. Therefore, the gradation values are concentrated in part of the range, and the standard deviation becomes small.

For the third item (hue of the observation target), the observation condition determination section 68 detects a distribution of a plurality of predetermined hues from RGB signals of all pixels of the reference image and determines "multi-color" or "single-color" based on the distribution of the detected hues.

For the fourth item (surface shape of the observation target), the observation condition determination section 68 detects a shade area from the reference image. The observation condition determination section 68 determines "irregular" if the proportion of the detected shade area in the entire reference image is equal to or higher than a predetermined threshold and determines "flat" if the proportion of the shade area in the entire reference image is smaller than the predetermined threshold. A known method, such as edge enhancement and differential of luminance value, is used as the detection method of the shade area.

For the fifth item (amount of fat), the observation condition determination section 68 detects a degree of yellow corresponding to the color of fat from the RGB signals of the pixels of the reference image. The observation condition determination section 68 determines "high fat" if the degree of yellow is equal to or higher than a predetermined threshold and determines "low fat" if the degree of yellow is less than the predetermined threshold.

A correction condition setting section 66' sets the parameter values of the processing modes by the preprocessing section and the post-processing section as in the first embodiment, based on the observation conditions of the items determined by the observation condition determination section 68.

According to the fluorescence observation apparatus 200 of the present embodiment with the configuration, the observation condition determination section 68 determines the observation conditions corresponding to the observation target A based on the reference image, and the need for the operation by the operator can be eliminated. In addition, when the observation target A changes along with the movement of the insertion portion 2, the preprocessing mode and the post-processing mode also switch according to the change in the observation target A. Therefore, it is suitable to move the insertion portion 2 in the body to continuously observe a plurality of observation targets A.

Third Embodiment

Next, the fluorescence observation apparatus 300 according to the third embodiment of the present invention will be described below with reference to FIG. 3. In the description of the present embodiment, configurations common to the first embodiment are designated with the same reference signs, and the description will not be repeated.

Figure 3:
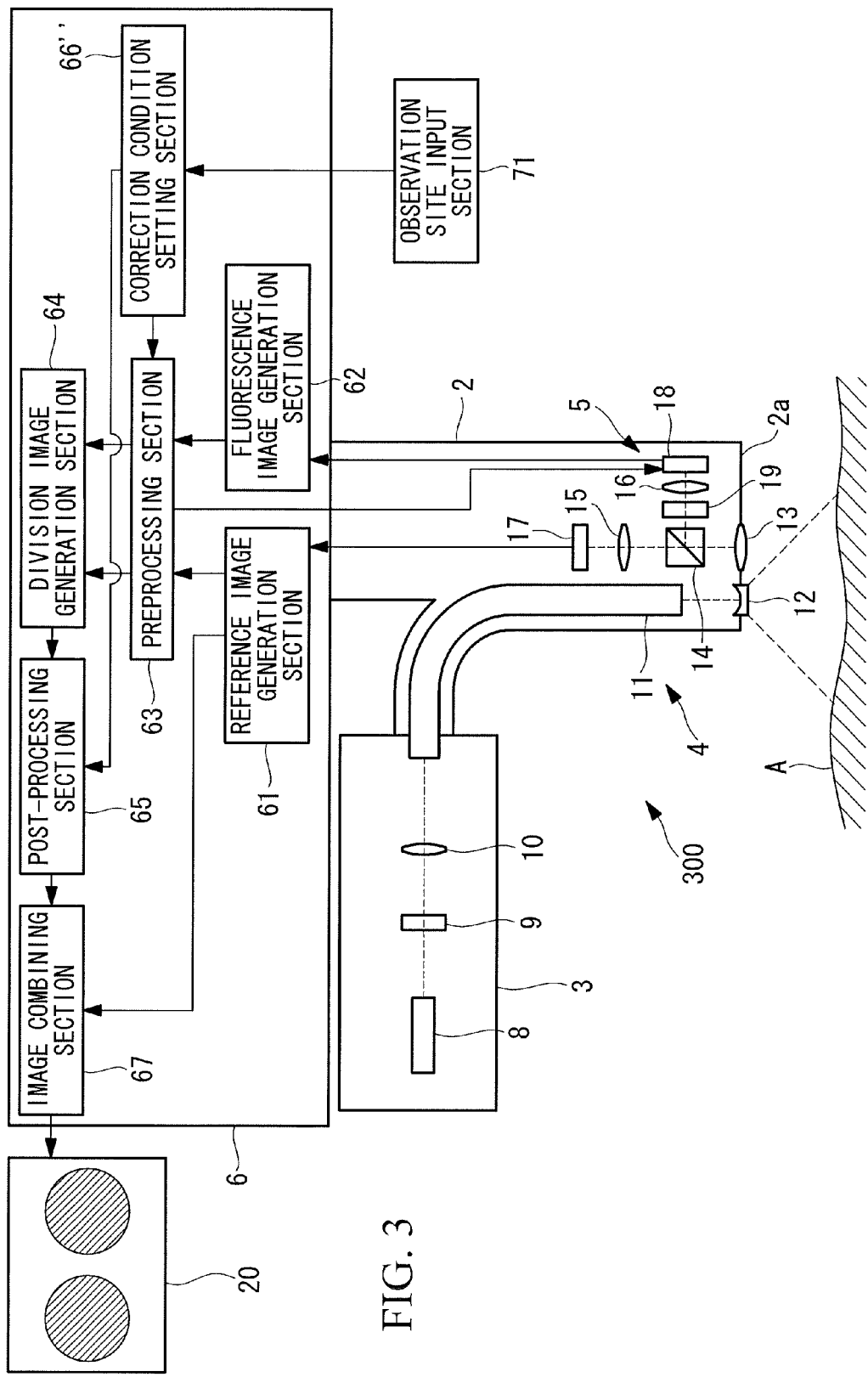
FIG. 3 is an overall configuration diagram of a fluorescence observation apparatus according to a third embodiment of the present invention.

As shown in FIG. 3, the fluorescence observation apparatus 300 according to the present embodiment is mainly different from the first embodiment in that an observation site input section 71, to which the operator inputs an observation site of the observation target A, is included in place of the observation condition input section 7.

One of a plurality of predetermined observation sites is input to the observation site input section 71 by the operation of the operator. The observation site input section 71 includes, for example, a foot switch not shown. If an insertion path of the insertion portion 2 is predetermined, the observation site input section 71 stores the observation sites in the order of observation and outputs the next observation site to a correction condition setting section 66" when the operator operates the foot switch.

In the present embodiment, the correction condition setting section 66" stores processing condition data associating the observation sites, the preprocessing modes by the preprocessing section 63 as well as the preprocessing parameter values, and the post-processing modes by the post-processing section 65 as well as the post-processing parameter values. The correction condition setting section 66" first sets the parameter values based on the observation site input from the observation site input section 71 and the processing modes including the preprocessing modes and the post-processing modes associated in the processing condition data and outputs signals for commanding execution of the correction processing based on the set parameter values to the preprocessing section 63 and the post-processing section 65.

According to the fluorescence observation apparatus 300 of the present embodiment with the configuration, the operator inputs the observation site, and the correction condition setting section 66" sets the parameter values of the correction processing by the preprocessing section 63 and the post-processing 65 based on the properties, such as shape, structure, and color, of the input observation site. By doing so, suitable correction processing is executed for the dependency of distance and angle based on a plurality of factors, and there is an advantage that the dependency of distance and angle between the corrected fluorescence image and the reference image can be removed with high precision.

Fourth Embodiment

Next, the fluorescence observation apparatus 400 according to the fourth embodiment of the present invention will be described below with reference to FIG. 4. In the description of the present embodiment, configurations common to the first embodiment are designated with the same reference signs, and the description will not be repeated.

Figure 4:
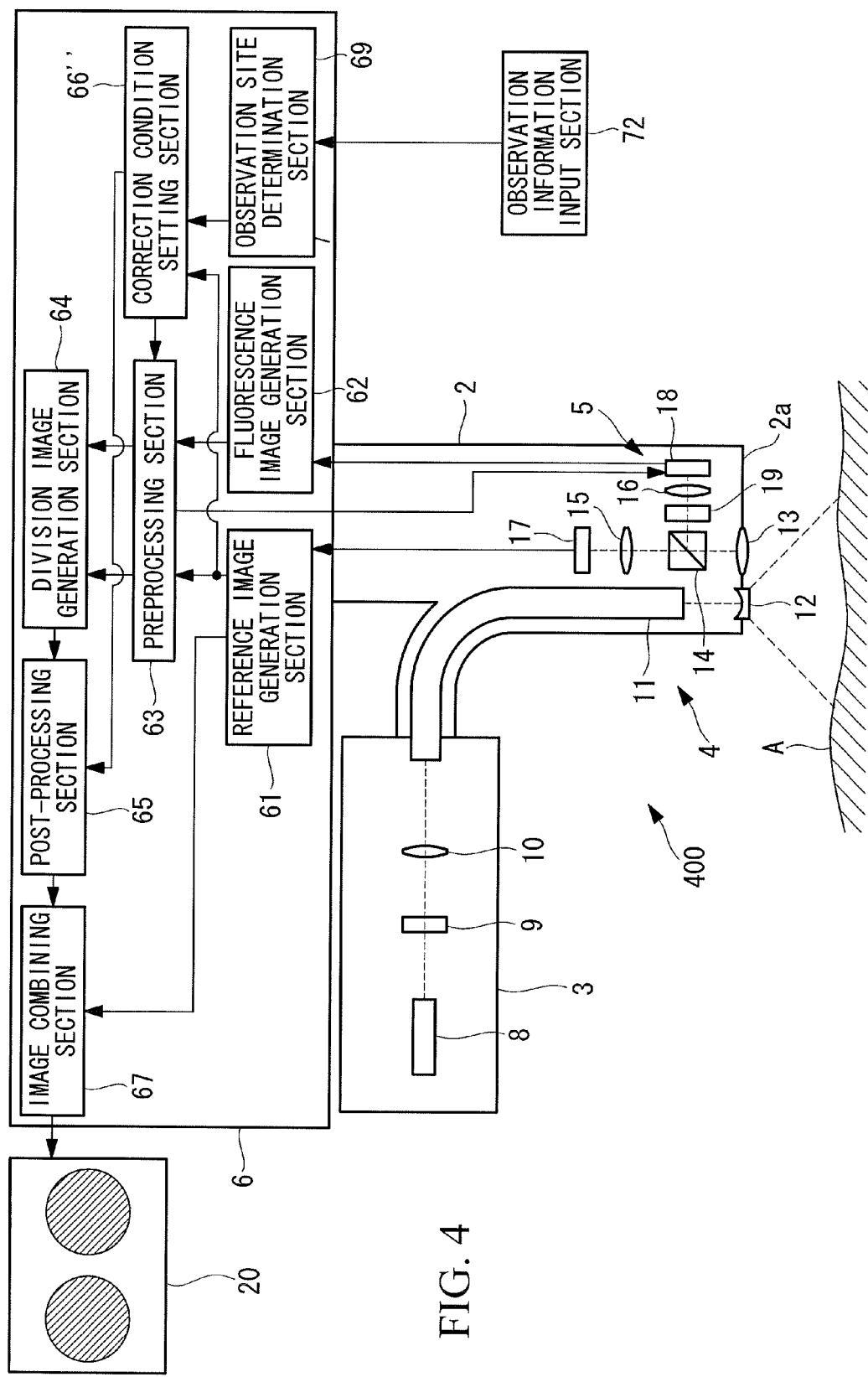
FIG. 4 is an overall configuration diagram of a fluorescence observation apparatus according to a fourth embodiment of the present invention.

As shown in FIG. 4, the fluorescence observation apparatus 400 according to the present embodiment is mainly different from the first embodiment in that the fluorescence observation apparatus 400 includes, in place of the observation condition input section: an observation information input section 72, to which information related to the observation is input by the operator; and an observation site determination section 69 that determines observation conditions based on the information related to the observation input to the observation information input section 72 and the reference image.

In the observation information input section 72, for example, the examination name, the organ name, and the like of the observation target A are set as the information related to the observation. The operator selects one or more pieces of the set information related to the observation and inputs the information to the observation information input section 72.

The observation site determination section 69 determines the observation site based on the information related to the observation set to the observation information input section 72 and features detected from the reference image. The observation site determination section 69 associates and stores, for example, the examination names, the observation sites, and the features of the observation sites. The observation site determination section 69 first selects part of the observation sites among all of the stored observation sites based on the examination name input from the observation information input section 72. Next, the observation site determination section 69 selects one of the selected part of the observation sites based on the features detected from the reference image to determine the observation site and outputs the determination result to the correction condition setting section 66".

The process by the correction condition setting section 66" is the same as the process by the correction condition setting section 66" in the third embodiment, and the description will not be repeated.

In an endoscope apparatus with limited usage, the observation conditions, such as the observation site and the observation method, are limited, and the observation conditions suitable for each observation site can be relatively easily determined. On the other hand, in a general-purpose endoscope apparatus, although it is desirable to include as many processing modes as possible to adapt to the observation targets A in various structures and the observation methods, it is difficult to ensure the determination accuracy because the choices of the parameter values in the processing modes by the correction condition setting section 66" increase. Whereas, according to the fluorescence observation apparatus 400 of the present embodiment, the observation site can be accurately determined based on the features of the reference image by narrowing down the observation sites to some level, from the information related to the observation input to the observation information input section 72.

In this way, according to the fluorescence observation apparatus 400 of the present embodiment, the observation site is determined based on the information related to the observation input by the operator, and the correction condition setting section 66" sets the parameter values in the correction processing by the preprocessing section 63 and the post-processing 65 appropriate for the observation site. By doing so, suitable correction processing is performed for the dependency of distance and angle based on a plurality of factors, and there is an advantage that the dependency of distance and angle between the corrected fluorescence image and the reference image can be removed with high precision.

Fifth Embodiment

Next, the fluorescence observation apparatus 500 according to the fifth embodiment of the present invention will be described below with reference to FIG. 5. In the description of the present embodiment, configurations common to the first embodiment are designated with the same reference signs, and the description will not be repeated.

Figure 5:
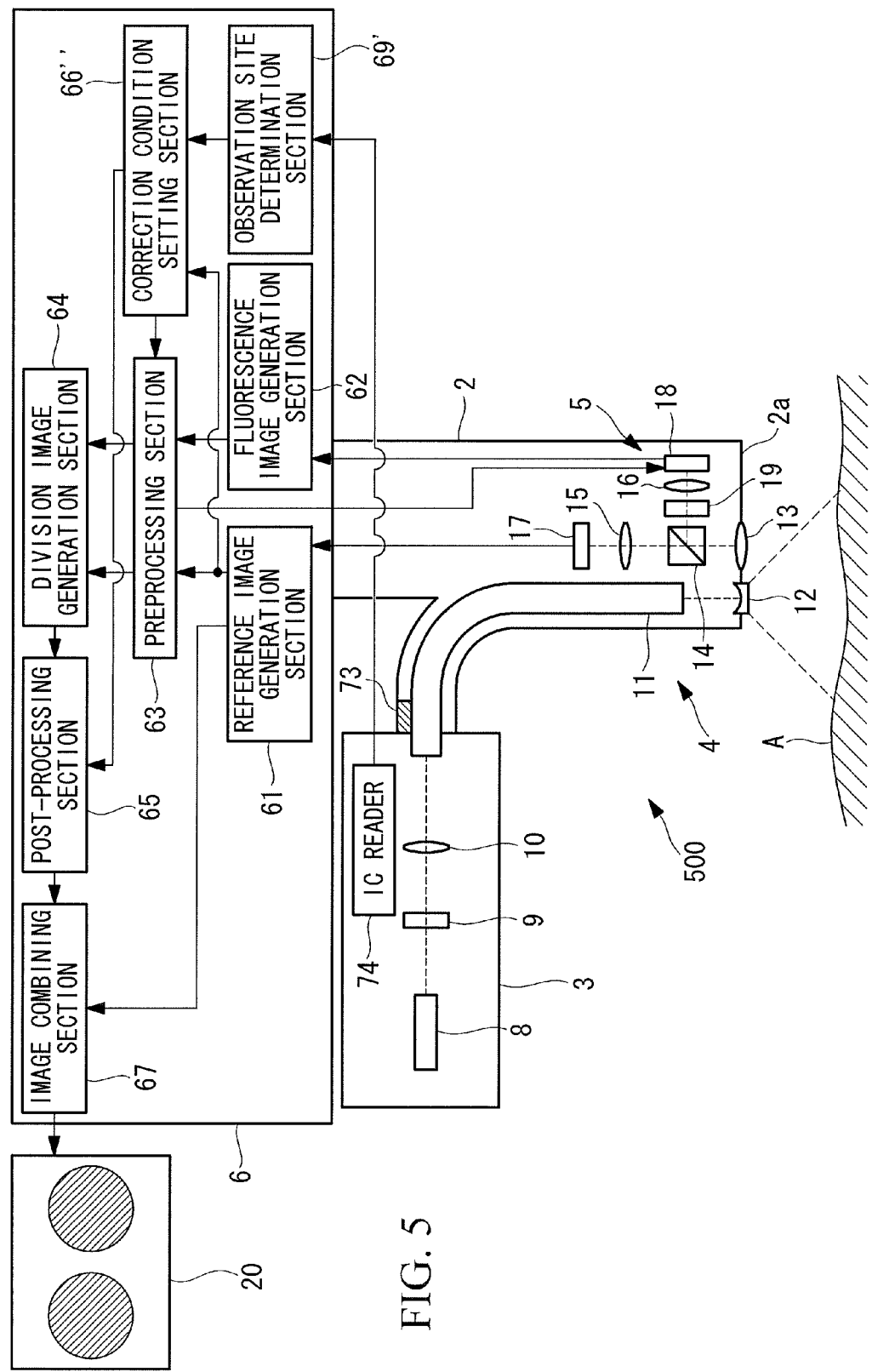
FIG. 5 is an overall configuration diagram of a fluorescence observation apparatus according to a fifth embodiment of the present invention.

As illustrated in FIG. 5, the fluorescence observation apparatus 500 according to the present embodiment is mainly different from the first embodiment in that the fluorescence observation apparatus 500 includes: an IC chip 73 attached to the insertion portion 2; an IC reader 74 arranged on the light source 3; and an observation site determination section 69' arranged on the image processing section 6.

The IC chip 73 stores identification information of the insertion portion 2, such as information related to the type of the insertion portion 2. The type of the insertion portion 2 is different according to the observation conditions, such as the observation site and the observation method. When the insertion portion 2 connected to the light source 3 is exchanged to change the observation conditions, the IC reader 74 reads the identification information stored in the IC chip 73 arranged on the insertion portion 2, and the identification information is transmitted to the observation site determination section 69'.

The observation site determination section 69' associates and stores the types of the insertion portion 2, the observation sites, and the features of the observation sites. The observation site determination section 69' first selects part of the observation sites among all of the stored observation sites based on the type of the insertion portion 2 input from the IC reader 74. Next, the observation site determination section 69' selects one of the selected part of the observation sites based on the features detected from the reference image to determine the observation site.

The subsequent processes by the observation site determination section 69' and the correction condition setting section 66'' are the same as those of the third embodiment, and the description will not be repeated.

In this way, according to the fluorescence observation apparatus 500 of the present embodiment, the choices of the observation sites are narrowed down based on the type of the insertion portion 2, and one observation site is further determined from the features of the reference image. The preprocessing section and the post-processing section execute the correction processing based on the parameter values in the processing modes determined according to the observation site determined by the observation site determination section 69'. By doing so, suitable correction processing is executed for the dependency of distance and angle based on a plurality of factors, and there is an advantage that the dependency of distance and angle between the corrected fluorescence image and the reference image can be removed with high precision.

Next, first to third preprocessing modes by the preprocessing section 63 and first to third post-processing modes by the post-processing section 65 included in the fluorescence observation apparatuses 1, 100, 200, 300, 400, and 500 according to the first to fifth embodiments will be described with reference to a correspondence table of the observation conditions and the processing modes shown in FIG. 117. In each embodiment, the preprocessing section 63 and the post-processing section 65 may include all processing modes described later or may include only part of the processing modes.

{Preprocessing Modes}
{First Preprocessing Mode}

The first preprocessing mode by the preprocessing section 63 included in the fluorescence observation apparatuses 100, 200, 300, 400, and 500 according to the first to fifth embodiments will be described. The first preprocessing mode is a processing mode of adjusting the brightness of the entire reference image and/or fluorescence image by adjusting the sensitivity of an image capturing element based on the number of pixels for binning summing and/or the exposure time of the image capturing element.

The first preprocessing mode is suitable for removing the dependency of observation distance and observation angle remained in the division image caused by attenuation of the fluorescence intensity due to the observation distance from the tip surface 2a of the insertion portion 2 to the observation target A and due to the fat covering the tissue. More specifically, the correction condition setting sections 66 and 66' of the fluorescence observation apparatuses 100 and 200 according to the first and second embodiments set the preprocessing parameter values of the first preprocessing mode when "local view", "overhead view", "high fat", or "low fat" is input or determined as the observation condition. The correction condition setting section 66'' of the fluorescence observation apparatuses 300, 400, and 500 according to the third to fifth embodiments sets the preprocessing parameter values of the first preprocessing mode when locally observed "Douglas' pouch" or the like, "greater omentum", "subphrenic area", "intestinal membrane", or the like for overhead observation, or "stomach", "urinary tract", or the like with the surface covered by fat is input or determined.

Here, the correction condition setting sections 66, 66', and 66'' set the preprocessing parameter values to reduce the sensitivity of the image capturing element in the first preprocessing mode described later when the observation conditions correspond to the local observation in which the light level of the reflected light and the fluorescence tends to be high. On the other hand, the correction condition setting sections 66, 66' and 66'' set the preprocessing parameter values to increase the sensitivity of the image capturing element when the observation conditions correspond to the overhead observation in which the light level of the reflected light and the fluorescence tends to be low. Hereinafter, a setting method of the preprocessing parameter values according to the first preprocessing mode will be described in detail.

Figure 6:
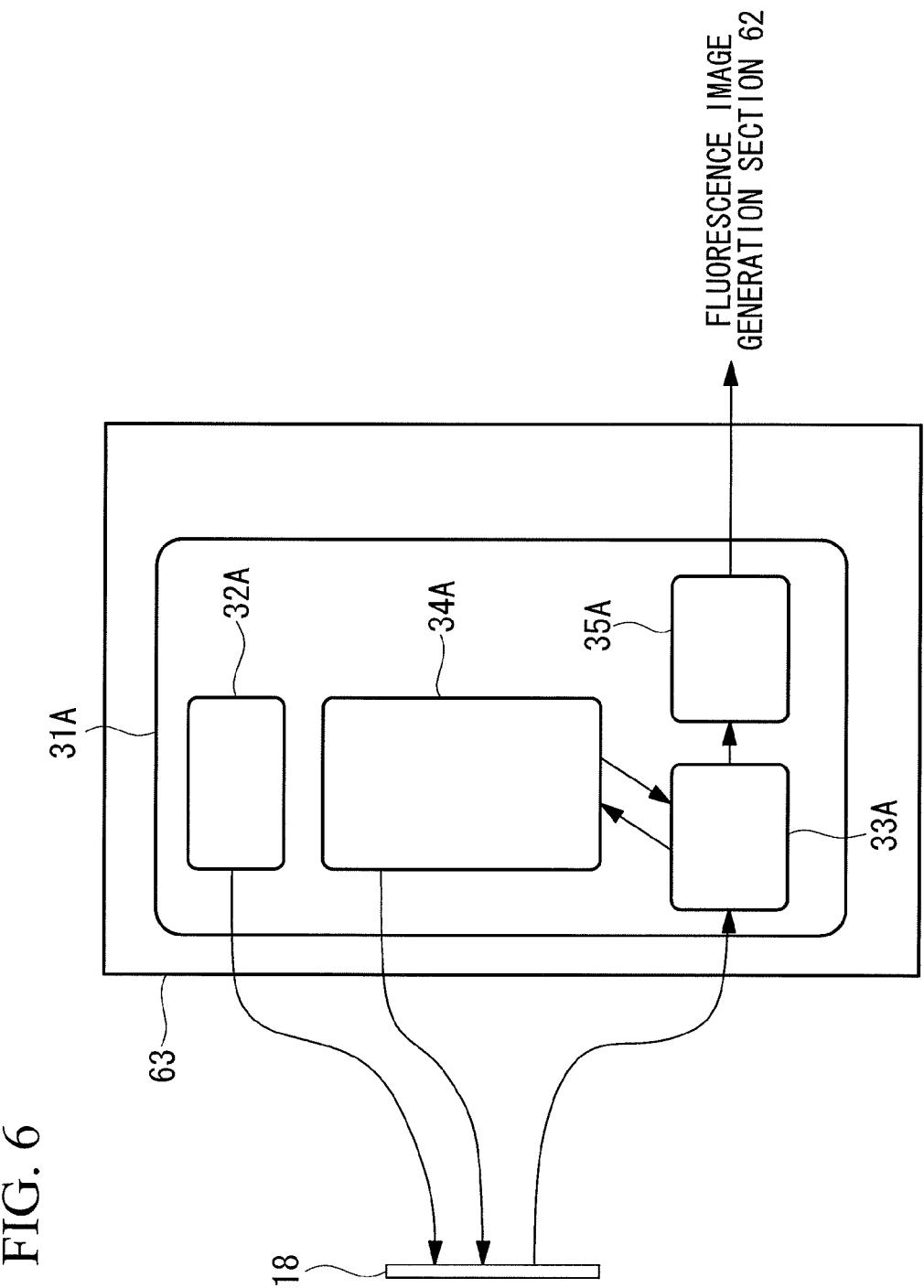
FIG. 6 is a block diagram showing a configuration of a preprocessing section that executes a first preprocessing mode.

As shown in FIG. 6, a control circuit 31A included in the preprocessing section 63 executes the first preprocessing mode. The control circuit 31A controls the generation of the fluorescence image information based on the electrical signal acquired by the image capturing element 18 and the sensitivity of the image capturing element 18.

Specifically, the control circuit 31A includes: an image capturing element driving circuit 32A that drives the image capturing element 18; a signal reading circuit 33A that reads an electrical signal from the image capturing element 18; a sensitivity control circuit 34A that controls the sensitivity of the image capturing element 18 based on the electrical signal read by the signal reading circuit 33A; and an image information construction circuit 35A that constructs fluorescence image information based on an electrical signal from the signal reading circuit 33A.

The sensitivity control circuit 34A is configured to control the sensitivity of the image capturing element 18, that is, control the binning setting, based on intensity thresholds (preprocessing parameters) S1 and S2 set by the correction condition setting sections 66, 66', and 66". Here, the correction condition setting sections 66, 66', and 66" set larger intensity thresholds S1 and S2 when the observation condition corresponds to "local observation" or "low fat" and set smaller intensity thresholds S1 and S2 when the observation condition corresponds to "overhead observation" or "high fat".

In addition, when the binning setting of the image capturing element 18 is disabled, the sensitivity control circuit 34A is configured to control the signal reading circuit 33A to output the electrical signal acquired by the image capturing element 18 that has disabled the binning setting of the image capturing element 18 to the image information construction circuit 35A. By doing so, the image information construction circuit 35A is configured to receive the electrical signal from the signal reading circuit 33A to construct the fluorescence image information. In addition, the image information construction circuit 35A is configured to output the constructed fluorescence image information to the fluorescence image generation section 62.

Operation of the first preprocessing mode by the preprocessing section 63 and the image processing section 6 including the preprocessing section 63 with the configuration will be described with reference to FIGS. 7A to 7C and 8.

Figure 7A:
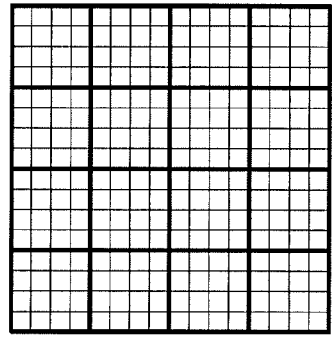
FIG. 7A is a diagram showing a state that binning setting of a CCD of FIG. 6 is set to 4×4.

First, with the start of the operation of the image capturing element driving circuit 32A, the binning setting of the image capturing element 18 is set to binning 4×4 as shown in FIG. 7A (step SA1). Then, a timer of the image processing section 6 is operated to insert the insertion portion 2 into the examination target, and the image capturing element 18 captures a fluorescence image (step SA2). The image capturing element 18 converts the fluorescence to an electrical signal.

In this case, since the binning setting of the image capturing element 18 is set to binning 4×4, electrical signals of a set of pixels including 4×4=16 pixels are summed to acquire an electrical signal of one pixel. Therefore, even if the fluorescence detected from each pixel is weak, the electrical signal from the set of pixels, representing the sum of 16 pixels, is relatively intense and is detected without fail, so that the presence or absence of fluorescence can be easily detected.

The electrical signals acquired by the image capturing element 18 are output to the control circuit 31A and read by the signal reading circuit 33A, and whether there is a set of pixels exceeding the intensity threshold S1 is determined by the operation of the sensitivity control circuit 34A (step SA3). As a result, if it is determined that there is no set of pixels exceeding the intensity threshold S1, the process returns to step SA2 (step SA3 "NO"), and the operation of step SA2 and step SA3 is repeated until a set of pixels exceeding the intensity threshold S1 is found.

Figure 7B:
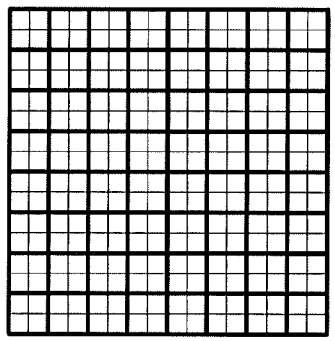
FIG. 7B is a diagram showing a state that the binning setting of the CCD of FIG. 6 is set to 2×2.

On the other hand, if it is determined that there is a set of pixels exceeding the intensity threshold S1 (step SA3 "YES"), the sensitivity control circuit 34A sets the binning setting of the image capturing element 18 to binning 2×2 as shown in FIG. 7B (step SA4). Then, an observation site that is substantially the same as the site captured in step SA2 is captured by the operation of the image capturing element 18 set to binning 2×2 (step SA5).

In this case, the image capturing element 18 is set to binning 2×2, and electrical signals of a set of pixels including 2×2=4 pixels are summed and acquired. Therefore, the sensitivity can be reduced to increase the resolution, and an image around the site where the fluorescence exists can be obtained, in which the image is sharper than the last time.

The electrical signals from the sets of pixels acquired by the image capturing element 18 set to binning 2×2 are read by the signal reading circuit 33A of the control circuit 31A, and whether there is a set of pixels exceeding the predetermined intensity threshold S2 is determined by the operation of the sensitivity control circuit 34A (step SA6).

If it is determined that there is no set of pixels exceeding the intensity threshold S2, the process returns to step SA1 by the operation of the sensitivity control circuit 34A (step SA6 "NO"), and the binning setting of the image capturing element 18 is set to binning 4×4 that is the same as the initial setting. Then, the operation of steps SA1 to SA6 is repeated until a set of pixels exceeding the intensity threshold S2 is found.

Figure 7C:
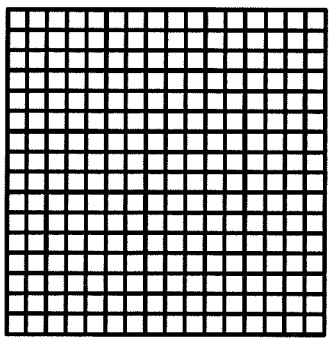
FIG. 7C is a diagram showing a state that the binning setting of the CCD of FIG. 6 is disabled.
Figure 8:
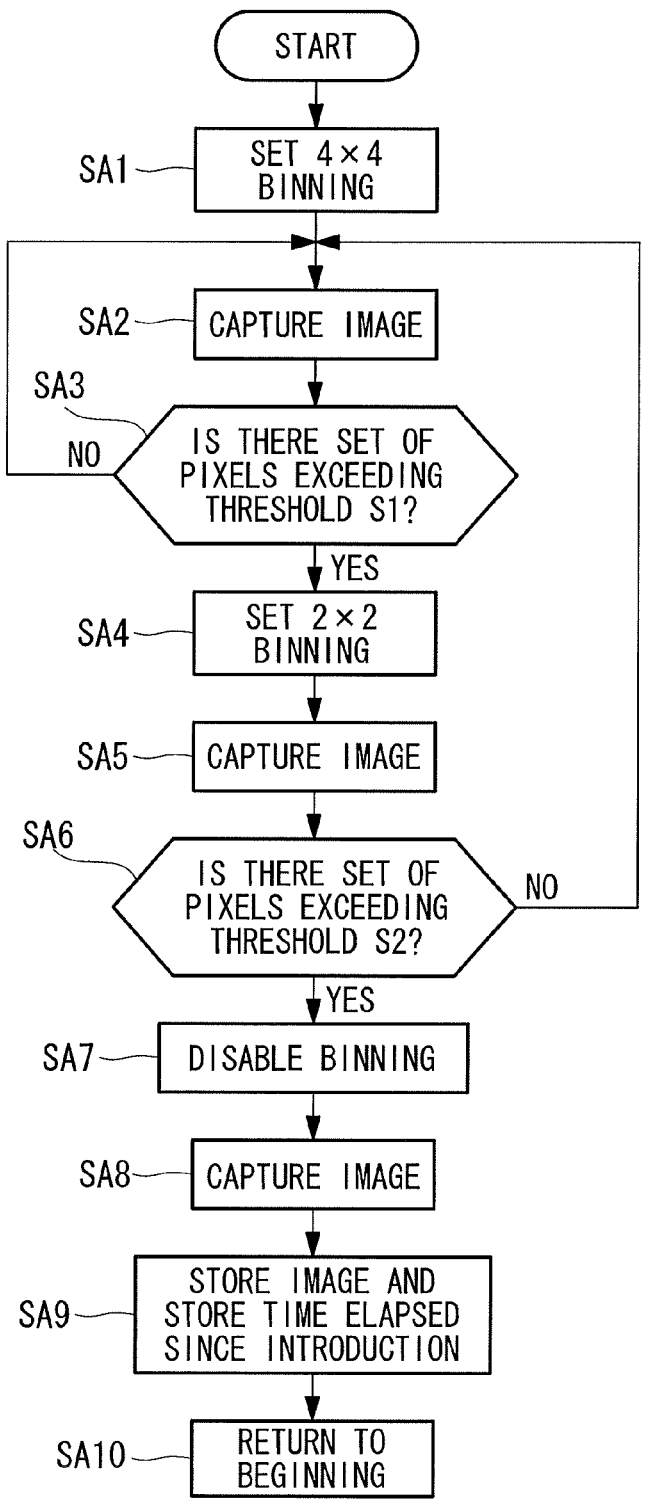
FIG. 8 is a flowchart describing a first preprocessing mode by the preprocessing section of FIG. 6.

On the other hand, if it is determined that there is a set of pixels exceeding the intensity threshold S2 (step SA6 "YES"), the sensitivity control circuit 34A disables the binning setting of the image capturing element 18 as shown in FIG. 7C (step SA7). Then, an observation site substantially the same as the site captured in step SA5 is captured by the operation of the image capturing element 18 in which the binning setting is disabled (step SA8).

In this case, since the binning setting of the image capturing element 18 is disabled, an electrical signal is acquired from each pixel. Therefore, an image can be captured at the highest resolution. By doing so, a sharper image of the observation target A including an area where the fluorescence intensity exceeds the intensity threshold S2 can be acquired.

In this case, the electrical signals acquired by the image capturing element 18 are output from the signal reading circuit 33A to the image information construction circuit 35A by the operation of the sensitivity control circuit 34A, and fluorescence image information is constructed. The fluorescence image information constructed in the image information construction circuit 35A is transmitted to the fluorescence image generation section 62 of the image processing section 6. The fluorescence image generation section 62 outputs a fluorescence image generated from the input fluorescence image information to the preprocessing section 63.

As described, according to the first preprocessing mode, the binning of the image capturing element 18 is controlled to capture an image. Therefore, the possibility of missing out the diseased region can be reduced, and not only the presence or absence of the diseased region, but also the shape and the size of the diseased region can be sharply captured. In addition, since the acquired image is associated with the elapsed time, the position of the diseased region can be detected.

Next, a modification of the first preprocessing mode will be described.

The first preprocessing mode of the present modification is mainly different from the first preprocessing mode described above in that a sensitivity control circuit 34A' controls the exposure time of the image capturing element 18.

Figure 9:
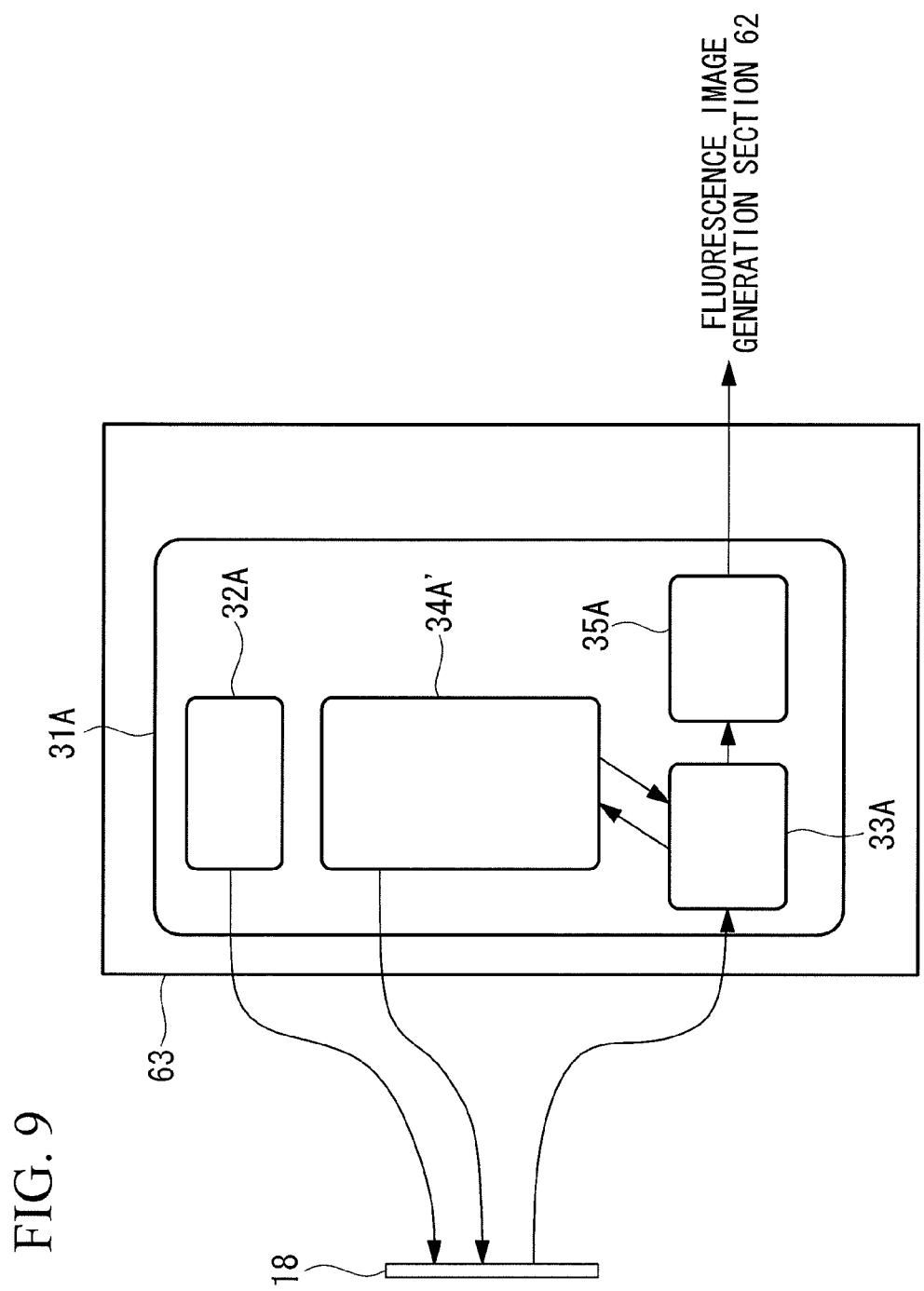
FIG. 9 is a block diagram showing a configuration of the preprocessing section that executes a modification of the first preprocessing mode.

In the present first preprocessing mode, the sensitivity control circuit 34A' is configured to switch the exposure time of the image capturing element 18 to an exposure time T1 for importing an appropriate light level and to an exposure time T0 longer than the exposure time T1 as shown in FIG. 9. In addition, when the exposure time T1 is set, the sensitivity control circuit 34' is configured to control the signal reading circuit 33A to output a read electrical signal to the image information construction circuit 35A.

Figure 10:
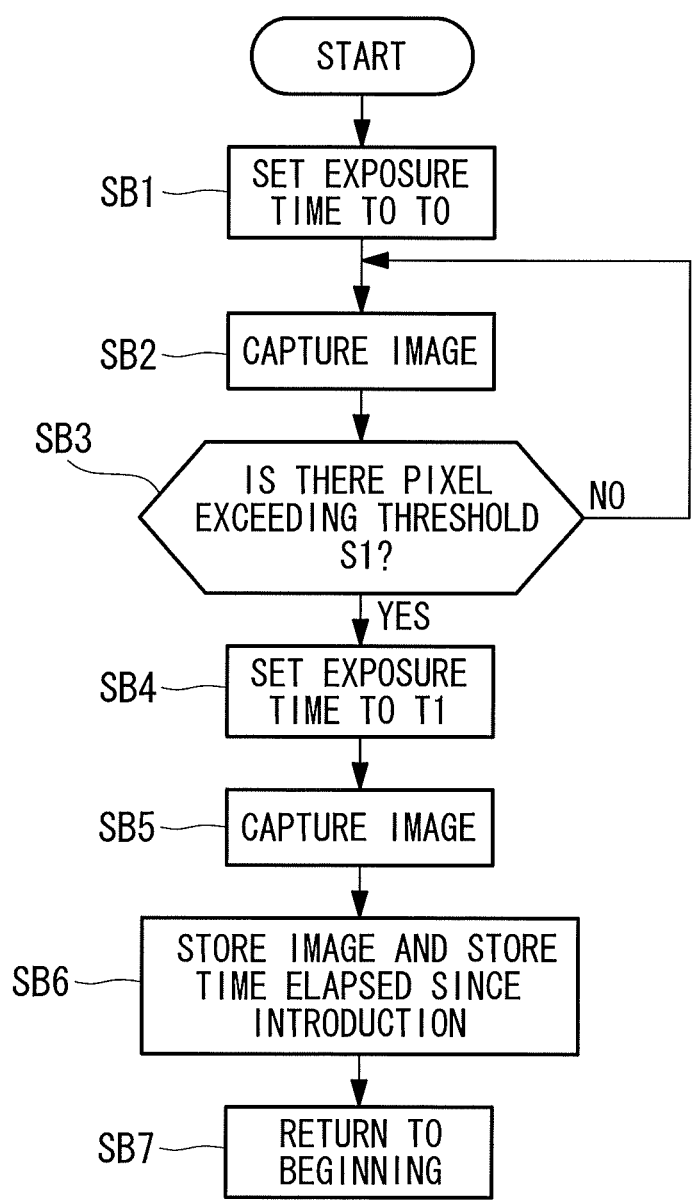
FIG. 10 is a flowchart showing operation of the preprocessing section of FIG. 9.

The preprocessing section 63 with the configuration first sets the exposure time of the image capturing element 18 to T0 in the initial setting as shown in FIG. 10 (step SB1). When the insertion portion 2 is inserted into the examination target, the fluorescence is detected from each pixel of the image capturing element 18 to capture an image (step SB2). In this case, since the exposure time of the image capturing element 18 is set to T0, the exposure time is long, and the light level imported from each pixel can be increased greater than an appropriate level, instead of sacrificing the frame rate. Therefore, even if the fluorescence is weak, the electrical signal acquired from each pixel is relatively large so that the fluorescence is not missed out, and the presence or absence of fluorescence can be easily detected.

Next, if it is determined that there is no pixel exceeding the predetermined intensity threshold S1 by the operation of the sensitivity control circuit 34A', the process returns to step SB2 (step SB3 "NO"), and the operation of step SB2 and step SB3 is repeated until a pixel exceeding the intensity threshold S1 is found.

On the other hand, if it is determined that there is a pixel exceeding the intensity threshold S1 (step SB3 "YES"), the sensitivity control circuit 34A' sets the exposure time of the image capturing element 18 to the exposure time T1 (step SB4). Then, a site of a body cavity inner wall 4 that is substantially the same as the site captured in step SB2 is captured at the exposure time T1 (step SB5). In this case, since the image capturing element 18 is set to the exposure time T1 for importing an appropriate light level, the frame rate can be improved, and the influence of blurring can be reduced. An image around the site where the fluorescence exists can be obtained, in which the image is sharper than the last time.

As described, according to the present first preprocessing mode, the exposure time of the image capturing element 18 is controlled to capture an image. Therefore, the possibility of missing out the diseased region can be reduced, and not only the presence or absence of the diseased region, but also the shape and the size of the diseased region can be sharply captured.

The first preprocessing mode can be modified as follows.

Figure 11:
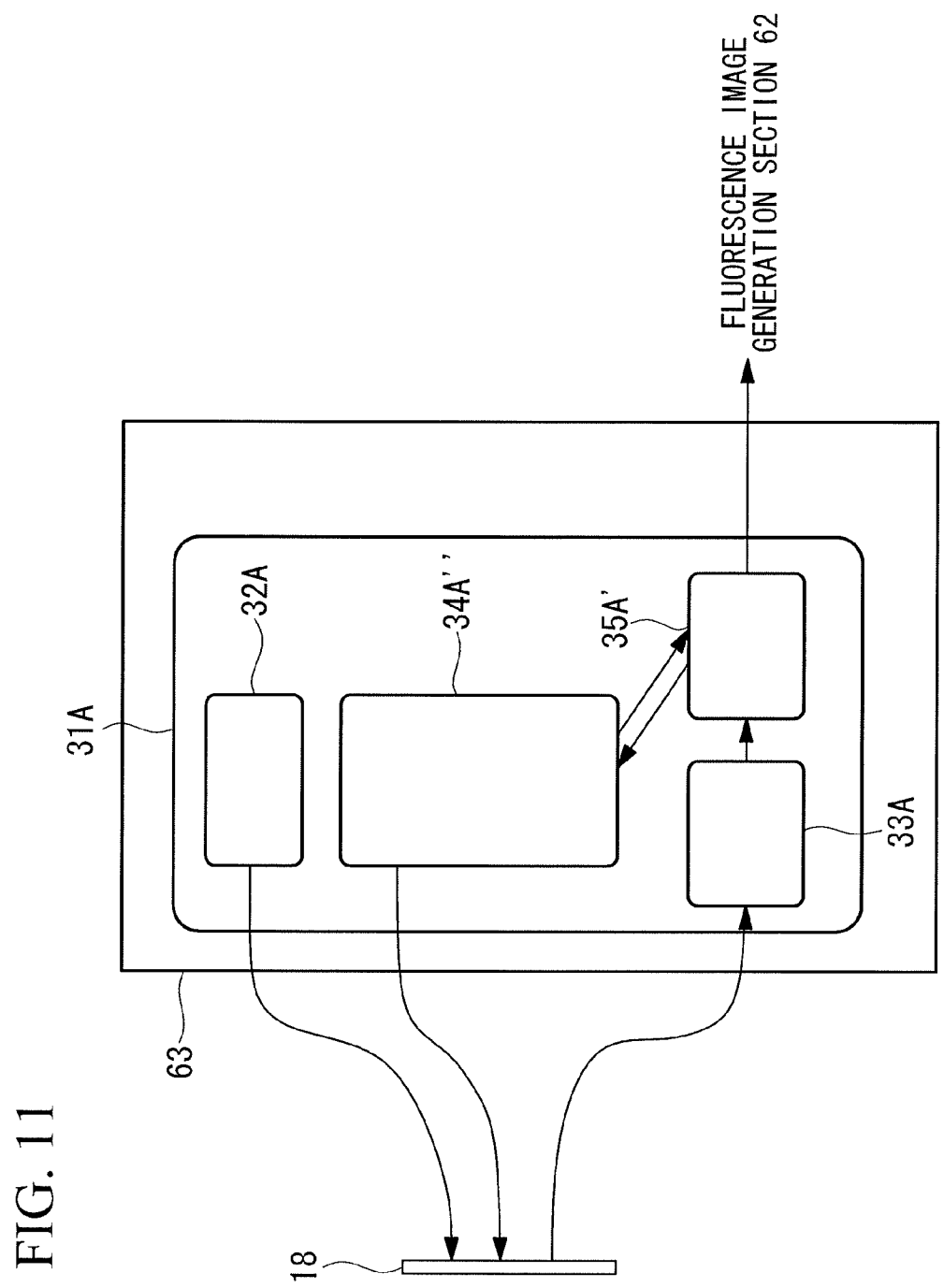
FIG. 11 is a block diagram showing a configuration of the preprocessing section according to another modification of the first preprocessing mode.

In the first preprocessing mode described above, the sensitivity control circuit 34A' controls the exposure time of the image capturing element 18, and when there is a high-luminance area of fluorescence, the sensitivity control circuit 34A' reduces the exposure time to acquire sharp fluorescence image information. Instead of this, a sensitivity control circuit 34A" may switch the number of times of an averaging process (that is, average processing). For example, as shown in FIG. 11, an image information construction circuit 35A' sequentially constructs the fluorescence image information and averages the fluorescence image information of multiple times. When there is a high-luminance area of fluorescence, the sensitivity control circuit 34A" can reduce the number of times of averaging.

Figure 12:
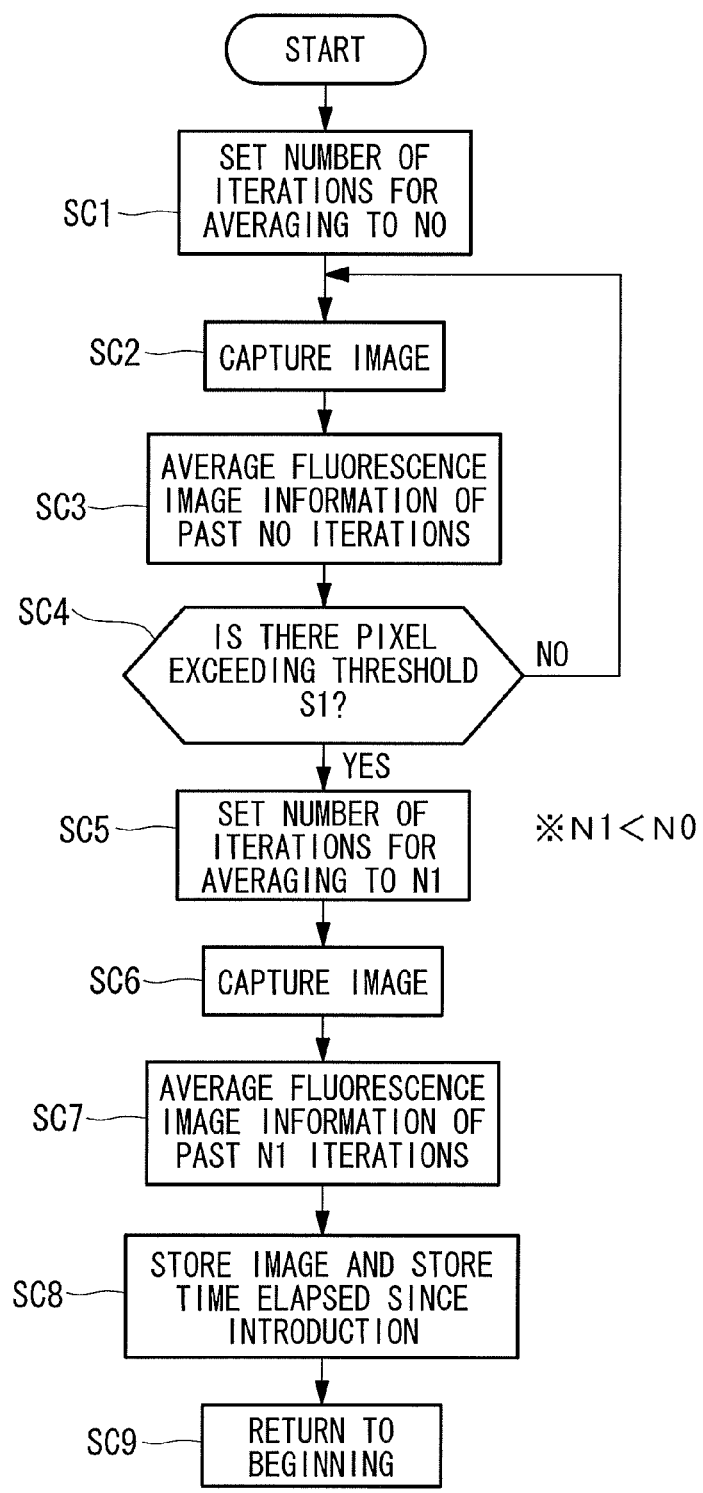
FIG. 12 is a flowchart showing operation of the preprocessing section of FIG. 11.

Specifically, as shown in FIG. 12, the number of times of averaging N0 for a large number of times of construction is set as initial setting (step SC1). The fluorescence is detected from each pixel of the image capturing element 18 to capture an image (step SC2), and the acquired electrical signals are transmitted to the image information construction circuit 35A' through the signal reading circuit 33A. The image information construction circuit 35A' constructs fluorescence image information based on the transmitted electrical signals and applies the averaging process to the fluorescence image information of the last N0 times (step SC3). The averaging process of the fluorescence image information for a large number of times of construction can reduce the level of noise randomly included in the fluorescence image information while retaining the luminance of the pixels where the fluorescence exists. More specifically, of all pixels, the pixels where the fluorescence exits can be emphasized, and the fluorescence can be easily detected.

Next, if the sensitivity control circuit 34A" determines that there is no pixel exceeding the predetermined intensity threshold S1 (step SC4 "NO"), the process returns to step SC2, and the operation of steps SC2 to SC4 is repeated until a pixel exceeding the intensity threshold S1 is found.

On the other hand, if it is determined that there is a pixel exceeding the intensity threshold S1 (step SC4 "YES"), the sensitivity control circuit 34A" sets the number of times of averaging N1 for the number of times of construction less than the number of times of averaging N0 (step SC5). Then, a site of the body cavity inner wall 4 that is substantially the same as the site captured in step SC2 is captured (step SC6), and the image information construction circuit 35A' applies the averaging process to the fluorescence image information of the last N1 times of the constructed fluorescence image information (step SC7). In this case, since the number of times of averaging is set to N1 that is less than N0, the influence of blurring can be reduced, and an image around the site where the fluorescence exists can be obtained, in which the image is sharper than the last time.

Note that although the sensitivity control circuit 34" switches the number of times of averaging N0 to the number of times of averaging N1 in the present modification, if, for example, it is determined that there is a pixel exceeding the luminance of the predetermined intensity threshold S1 based on the number of times of averaging N0, the averaging process may be disabled, and the image information construction circuit 35A' may transmit the most recently constructed fluorescence image information to the fluorescence image generation section 62.

In addition, although the image information construction circuit 35A' executes the averaging process of the fluorescence image information in the present modification, the fluorescence image information may be simply summed to detect the presence or absence of fluorescence based on a predetermined intensity threshold that is set according to this.

Next, a first modification of the first preprocessing mode will be described.

Figure 13:
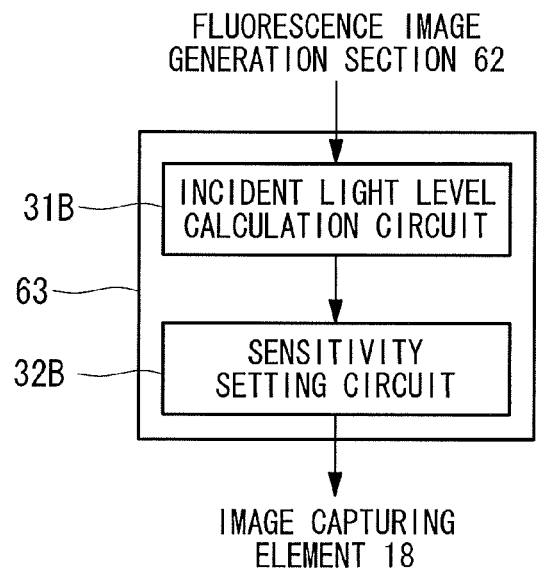
FIG. 13 is a block diagram showing a configuration of the preprocessing section that executes a first modification of the first preprocessing mode.

The preprocessing mode according to the present modification is executed by an incident light level calculation circuit 31B and a sensitivity setting circuit 323 included in the preprocessing section 63 as shown in FIG. 13.

The incident light level calculation circuit 31B calculates an incident light level $P_{in}$ of the image capturing element 18 based on the luminance information of the fluorescence image.

As described in detail later, the sensitivity setting circuit 32B (storage section) stores a table indicating a correspondence relationship between a lowest number of pixels B for binning summing and the incident light level $p_{in}$ required for an SN ratio S/N to be equal to or higher than a predetermined SN threshold (preprocessing parameter). Here, the table stores a correspondence relationship between at least two patterns of incident light level $S_3$ and the number of pixels B for binning summing which are set for different SN thresholds. The correction condition setting sections 66, 66', and 66" instruct the sensitivity setting circuit 32B to select a table with a pattern that is set for a smaller SN threshold when the observation condition corresponds to "local observation" or "low fat" and to select a table with a pattern that is set for a larger SN threshold when the observation condition corresponds to "overhead observation" or "high fat".

In the preprocessing section 63, the sensitivity setting circuit 32B is configured to search, from the table, the number of pixels B for binning summing corresponding to the incident light level $p_{in}$ calculated by the incident light level calculation circuit 31B and set the number of pixels B for binning summing to the image capturing element 18.

Here, a calculation method of the incident light level $p_{in}$ by the incident light level calculation circuit 31B will be described.

When light is incident on the imaging surface of the image capturing element 18, the image capturing element 18 converts the incident light to charge according to quantum efficiency (photon/charge conversion efficiency), and an amplifier converts the charge to voltage according to the charge/voltage conversion coefficient. The voltage value is converted to a digital signal according to an A/D conversion coefficient of an A/D converter.

Therefore, a gradation value (luminance information) V, which is a representative value of the pixels of the fluorescence image, is obtained by Expression (1). An average value or a median value of the luminance of all pixels, an average value of the luminance of the area of interest, or an average value of the luminance of the top several percent of the histogram is used as the representative value.

$$V = p_{in} SB\eta C_{I-V} C_{A-D} \quad (1)$$

Here, $p_{in}$ denotes an incident light level (photon/μm²), S denotes a captured pixel area (μm²/pixel), B denotes the number of pixels for binning summing (pixel), η denotes quantum efficiency (charge/photon), $C_{I-V}$ denotes a charge/voltage conversion coefficient (mV/charge), and $C_{A-D}$ denotes an AD conversion coefficient.

From Expression (1), the incident light level $p_{in}$ can be calculated by Expression (2).

$$p_{in} = V/(SB\eta C_{I-V} C_{A-D}) \quad (2)$$

Next, the relationship between the incident light level $p_{in}$ and the SN ratio S/N will be described. The SN ratio S/N also depends on noise characteristics of the image capturing element 18.

When a CMOS is used as the image capturing element 18, the SN ratio S/N is obtained by Expression (3).

$$S/N = (S\eta p_{in})/\sqrt{((S\eta p_{in} + N_d t + N_r^2)/B)} \quad (3)$$

Here, $N_d$ denotes a dark current per unit time per pixel (charge/sec/pixel), $N_r$ denotes readout noise (charge rms), t denotes exposure time (sec), and B denotes the number of pixels for binning summing.

Figure 14:
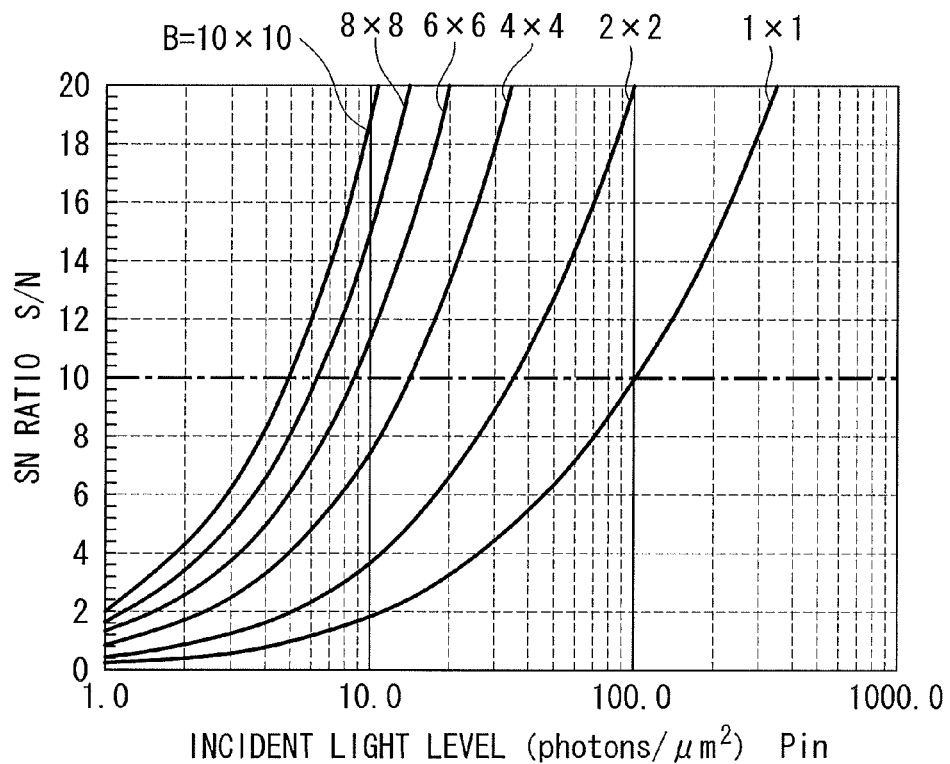
FIG. 14 is a diagram showing a graph of a relationship between an SN ratio and an incident light level of a fluorescence image processed by the preprocessing section of FIG. 13.

From Expression (3), FIG. 14 illustrates the number of pixels B for binning summing based on the relationship between the incident light level $p_{in}$ and the SN ratio S/N. In FIG. 14, examples of no binning (1×1) to 10×10 are illustrated as the number of pixels B for binning summing. In addition, S ti 3.0 μm²/pixel, η≈0.4, Nd≈50 charge/sec/pixel, and Nr≈5.4 charge rms are used in the present embodiment, for example. The values can be appropriately changed depending on the used image capturing element or the like.

Figures 15, 16:
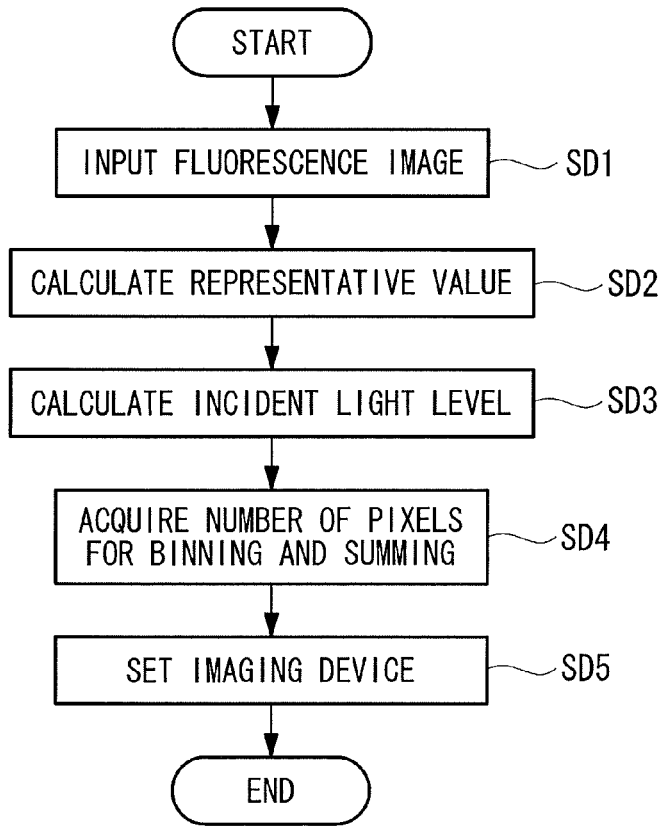
FIG. 15 is a diagram showing a table of a relationship between the incident light level and the number of pixels for binning summing created based on the graph of FIG. 14.
FIG. 16 is a flowchart showing a sensitivity setting procedure of an image capturing element by the preprocessing section of FIG. 13.

As shown in FIG. 15, the table stored in the sensitivity setting circuit 32B of the preprocessing section 63 indicates a correspondence relationship between the lowest number of pixels B for binning summing required for the SN ratio S/N to be equal to or higher than 10 and the incident light level $p_{in}$ in the graph of FIG. 14. In the table, the exposure time t is fixed to 0.024 sec (24 msec), for example.

According to the first preprocessing mode by the preprocessing section with the configuration, the generated fluorescence image is transmitted to the preprocessing section 63 (step SD1), and the representative value is obtained (step SD2), as shown in FIG. 16. Then, the obtained representative value is input to the incident light level calculation circuit 31B and assigned to Expression (2) to calculate the incident light level $p_{in}$ (step SD3). The calculated incident light level $p_{in}$ is input to the sensitivity setting circuit 32B, and the number of pixels B for binning summing corresponding to the incident light level $p_{in}$ is output from the sensitivity setting circuit 32B (step SD4) and set to the image capturing element 18 (step SD5).

By doing so, the image capturing element 18 provided with the new number of pixels B for binning summing acquires new fluorescence image information, and the fluorescence image generation section 22 outputs the generated fluorescence image to the division image generation section 64 as a division fluorescence image.

In this case, according to the first modification of the first preprocessing mode, the number of pixels B for binning summing is obtained from the table stored in the sensitivity setting circuit 32B according to the incident light level $p_{in}$ obtained from the luminance information of the fluorescence image. Therefore, the lowest number of pixels B for binning summing can be set to the image capturing element 18 so that the SN ratio S/N is equal to or greater than the SN threshold, and there is an advantage that the resolution can be improved while preventing the reduction of the image quality.

More specifically, since the incident light level $p_{in}$, that is, the number of incident photons per unit area, is used as a reference, the signal value for calculating the SN ratio S/N does not change even if the number of pixels B for binning summing is changed. When the sensitivity adjustment is performed based on the brightness of the image as in the past, the signal value may change even if the brightness of the image is the same, and a suitable SN threshold may not be able to be set. However, according to the present modification, a suitable SN threshold can be set without being affected by the number of pixels B for binning summing.

Note that in the first modification of the first processing mode, the SN ratio S/N is lower than 10 when the incident light level $p_{in}$ calculated by the incident light level calculation circuit 31B is less than 5 photons/μm² even after the number of pixels B for binning summing is set to the highest (10×10). In such a case, a warning may be displayed on the monitor 20. In this case, an improvement, such as reducing the observation distance, can be made to perform observation in which the SN ratio S/N is equal to or higher than 10.

In addition, the highest number of pixels B for binning summing is not limited to 10×10, and it may be higher or lower.

In addition, the SN threshold of the SN ratio S/N may be set to a number other than 10 according to the performance of the used fluorescent agent or the like. For example, when a fluorescent agent, which has a high disease specificity and in which the difference in the generated amount of fluorescence is large compared to normal tissue, is used, a relatively low SN threshold may be set. By doing so, fluorescence observation can be performed at higher resolution and higher sensitivity.

The first modification of the first processing mode can be further modified as follows. More specifically, in a modification of the first modification of the first preprocessing mode, the preprocessing section 63 may adjust not only the number of pixels B for binning summing, but also the exposure time t.

Figure 17:
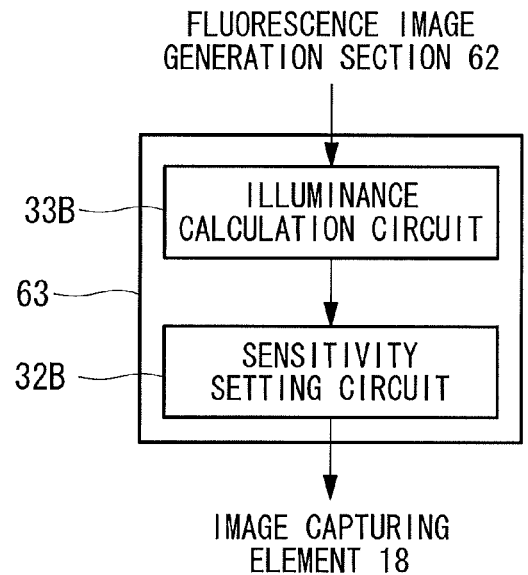
FIG. 17 is a block diagram showing a configuration of the preprocessing section that executes the first modification of the first preprocessing mode.

In this case, as shown in FIG. 17, the preprocessing section 63 includes: an illuminance calculation circuit 33B that calculates an imaging surface illuminance $E_{in}$ on the imaging surface of the image capturing element 18 based on the luminance information of the fluorescence image; and a sensitivity setting circuit 32B that stores a table indicating a correspondence relationship between the imaging surface illuminance $E_{in}$, the number of pixels B for binning summing, and the exposure time t.

The imaging surface illuminance $E_{in}$ is an incidence light level per unit time on the imaging surface and can be calculated by Expression (4).

$$E_{in}=V/(tSB\eta C_{I\text{-}V}C_{A\text{-}D}) \quad (4)$$

Accordingly, the sensitivity setting circuit 32B is configured to search, from the table, the number of pixels B for binning summing and the exposure time t corresponding to the imaging surface illuminance $E_{in}$ calculated by the illuminance calculation circuit 31 to set them to the image capturing element 18.

Here, since $$p_{in}=E_{in}t \quad (5),$$

the relationship between the SN ratio S/N and the imaging surface illuminance $E_{in}$ is as in Expression (6), based on Expression (3) and Expression (5).

$$S/N=S\eta E_{in}t/\sqrt{((S\eta E_{in}t+N_d t+B_r^2)/B)} \quad (6)$$

Figure 18:
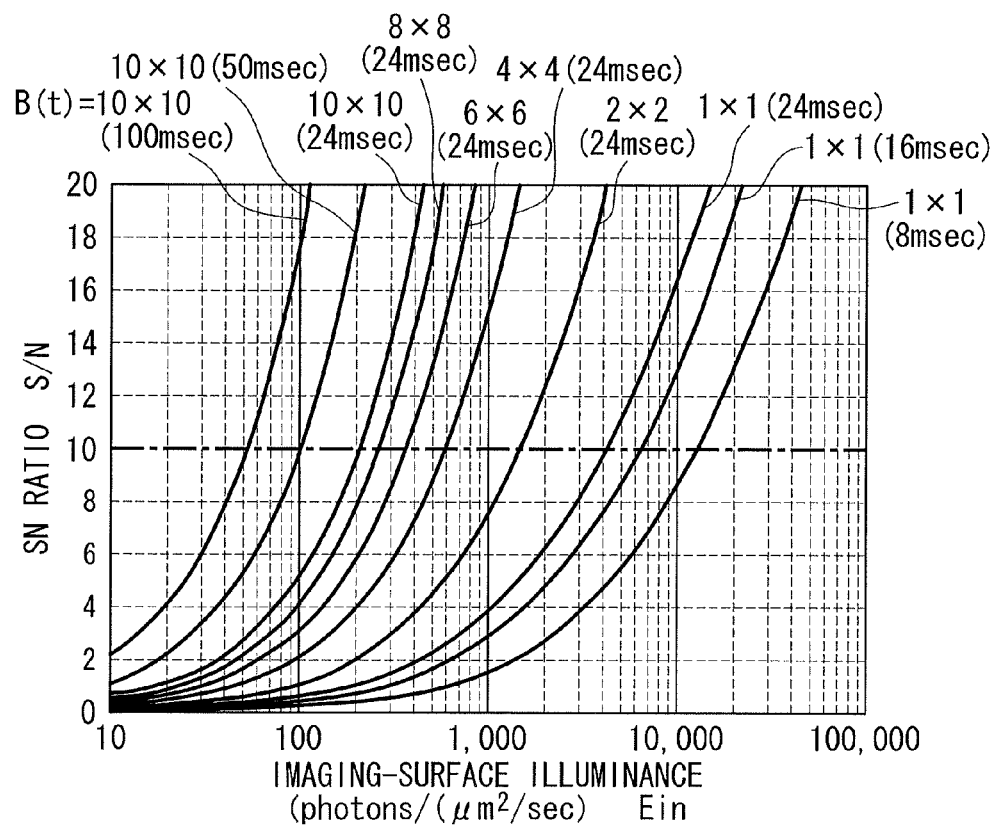
FIG. 18 is a diagram showing a relationship between the SN ratio and an imaging surface illuminance of the fluorescence image processed by the preprocessing section of FIG. 17.

Specifically, as shown in FIG. 18, the SN ratio S/N can be expressed as a function of the imaging surface illuminance $E_{in}$ that includes the number of pixels B for binning summing and the exposure time t as parameters.

Then, in the table for deriving the number of pixels B for binning summing and the exposure time t from the imaging surface illuminance $E_{in}$, the number of pixels B for binning summing is adjusted based on the exposure time 24 msec in the table shown in FIG. 19, and the exposure time t is increased or decreased when the number of pixels B for binning summing becomes the highest or the lowest. Note that the same values as those of the first modification are used for S, η, Nd, and $N_r$.

Figure 20:
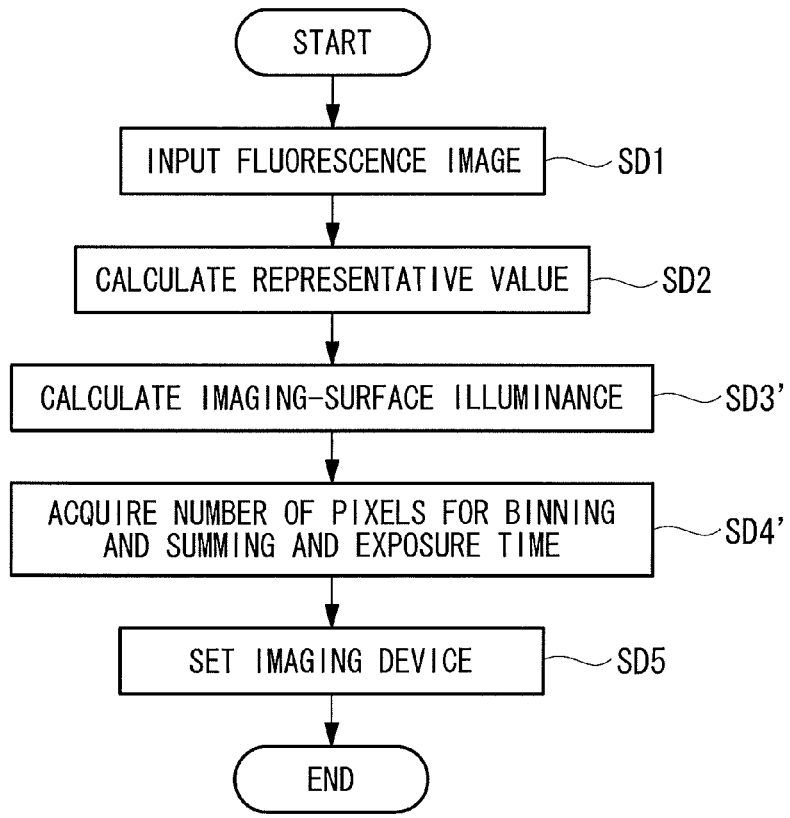
FIG. 20 is a flowchart showing a sensitivity setting procedure of the image capturing element by the preprocessing section of FIG. 17.

According to the modification of the first preprocessing mode, as shown in FIG. 20, the image surface illuminance $E_{in}$ is obtained from the luminance information of the fluorescence image (step SD3'), and the number of pixels B for binning summing and the exposure time t are obtained from the table stored in the sensitivity setting circuit 32B according to the imaging surface illumination $E_{in}$ (step SD4'). When the imaging surface illuminance $E_{in}$ is 100 photons/sec/μm² to 250 photons/sec/μm², 100 msec to 24 msec is selected for the exposure time t, with the number of pixels B for binning summing fixed to 10×10.

In addition, when the imaging surface illuminance $E_{in}$ is 208 photons/sec/μm² to 4330 photons/sec/μm², 10×10 to 1×1 is selected as the number of pixels B for binning summing, with the exposure time t fixed at 24 msec. Furthermore, when the imaging surface illuminance $E_{in}$ is equal to or higher than 6500 photons/sec/μm², 24 msec to 8 msec is selected as the exposure time t, with the number of pixels B for binning summing fixed to 1×1.

By doing so, even if weak fluorescence in which the incident light level $P_{in}$ is less than 5 photons/μm² is observed, the exposure time t can be increased to ensure the SN ratio S/N of equal to or higher than 10. Furthermore, in an area with a large imaging surface illuminance $E_{in}$ (equal to or higher than 4330 photons/sec/μm²), although a sufficiently high SN ratio S/N is obtained even if the number of pixels B for binning summing is set to the lowest 1×1, there is an advantage of increasing the effect of suppressing the image blur by setting a shorter exposure time t with an increase in the imaging surface illuminance $E_{in}$.

Figure 21:
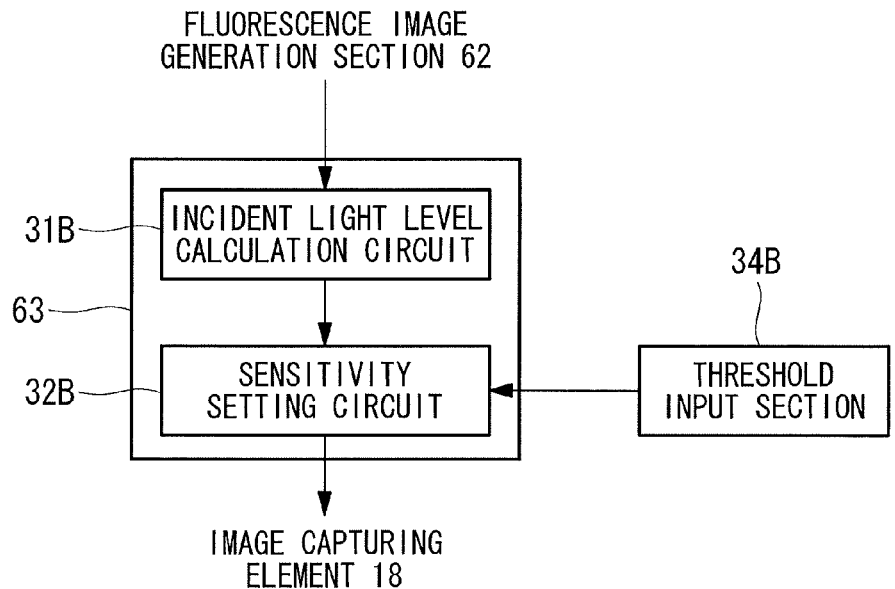
FIG. 21 is a block diagram showing a configuration of the preprocessing section that executes a modification of the first modification of the first preprocessing mode.

The fluorescence observation apparatuses 100, 200, 300, 400, and 500 in which the preprocessing section 63 is provided with the first preprocessing mode may include, as shown in FIG. 21, a threshold input section 34B for inputting, from the outside, an SN threshold $S_3$ in obtaining the number of pixels B for binning summing in the sensitivity setting circuit 32B. The threshold input section 34B is, for example, a switch, a button, and the like, and one of 6, 10, and 15 can be selected as the SN threshold $S_3$ of the SN ratio S/N.

Figures 22, 23:
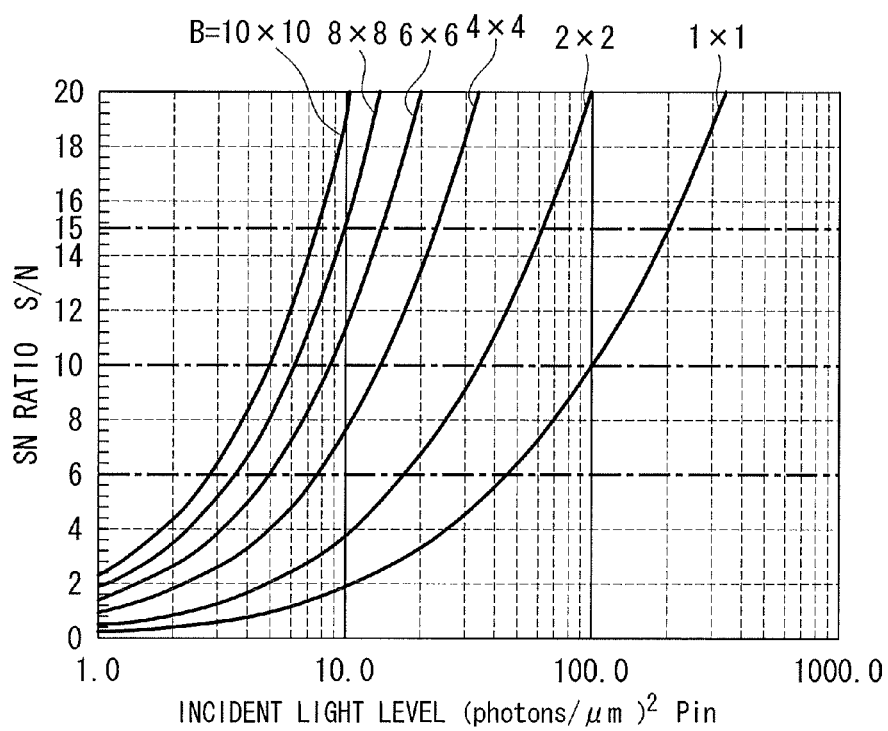
FIG. 22 is a diagram showing an example of a table included in a sensitivity setting circuit of the preprocessing section of FIG. 21.
FIG. 23 is a diagram showing an example of a graph included in the sensitivity setting circuit of the preprocessing section of FIG. 21.

In this configuration, the sensitivity setting circuit 32B stores a table shown in FIG. 22. The sensitivity setting circuit 32B is configured to select the number of pixels B for binning summing from the table based on the SN threshold $S_3$ input from the threshold input section 34B and the incident light level $p_{in}$ calculated by the incident light level calculation circuit 31B and to set the number of pixels B for binning summing to the image capturing element 18.

According to the fluorescence observation apparatuses 100, 200, 300, 400, and 500 with the configuration, a suitable SN threshold $S_3$ of the SN ratio S/N can be set according to the performance of the agent or the application. For example, when a fluorescent agent with a high contrast is used, the SN ratio S/N obtained by the image capturing element 18 can be low. Therefore, a small SN threshold $S_3$ can be set to set a small number of pixels B for binning summing even if the incident light level $p_{in}$ is low, and the reduction in the resolution and the influence of the image blur can be minimized.

In contrast, in an application in which the observation distance is assumed to be large, such as observation in the abdominal cavity by a rigid scope and observation in the stomach by a flexible scope, the observation site may be relatively small, and the visibility may be reduced. Therefore, there is an advantage that sensitivity which ensures the visibility can be obtained by increasing the SN threshold of the SN ratio S/N.

Note that in the fluorescence observation apparatuses 100, 200, 300, 400, and 500 with the configuration, instead of selecting the number of pixels B for binning summing stored in the table according to the SN threshold $S_3$ input from the threshold input section 343, the sensitivity setting circuit 32B may store a graph shown in FIG. 23 indicating the relationship between the incident light level $p_{in}$ and the SN ratio S/N of each number of pixels B for binning summing. When the SN threshold $S_3$ is input, the input SN threshold $S_3$ may be used each time to create, from the stored graph, a table selecting the smallest number of pixels B for binning summing that can achieve the SN ratio S/N equal to or higher than the SN threshold $S_3$. In FIG. 23, lines indicating 6, 10, and 15 are depicted as examples of the SN threshold $S_3$ of the SN ratio S/N.

By doing so, the SN threshold $S_3$ of the SN ratio S/N can be freely set independent of the values stored in advance, and there is an advantage that a finer sensitivity adjustment can be performed.

Furthermore, although the input SN threshold $S_3$ is used to select, from the stored table or graph, the smallest number of pixels B for binning summing that can achieve the SN ratio S/N equal to or higher than the SN threshold $S_3$, in addition to this, the number of pixels B for binning summing and the exposure time t may be adjusted as in the modification of the first modification. Furthermore, the SN threshold $S_3$ of the SN ratio S/N may be input by the operator before the start of the observation according to the usage or may be input according to the circumstances during the observation.

Figures 24, 25:
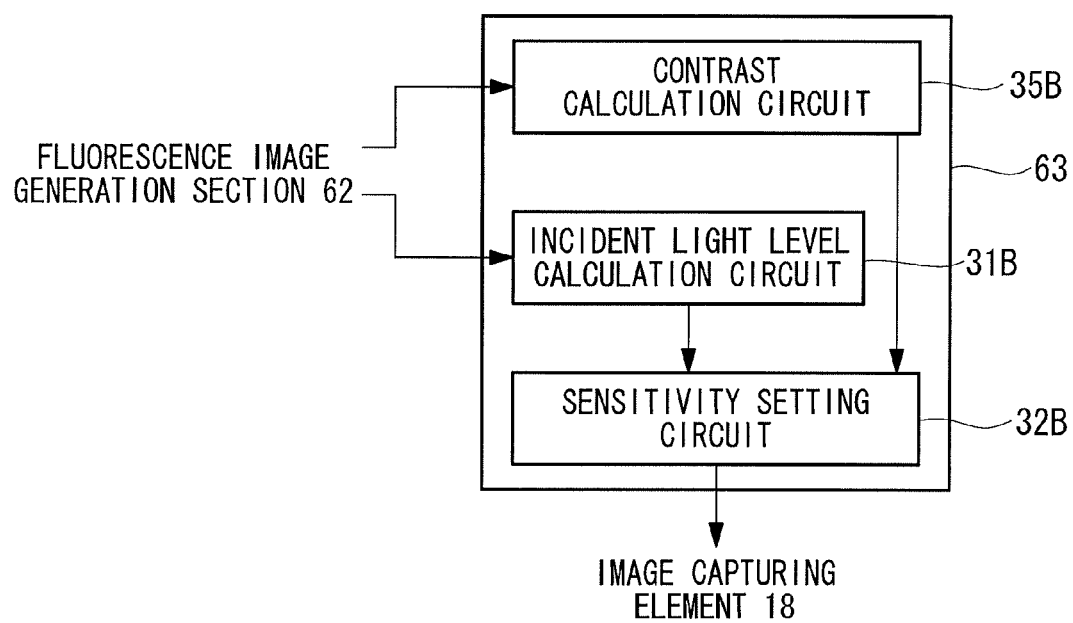
FIG. 24 is a configuration diagram showing a first modification of the preprocessing section of FIG. 21.
FIG. 25 is a diagram showing a table of a correspondence relationship between a contrast and a threshold of the SN ratio stored in the sensitivity setting circuit of the preprocessing section of FIG. 24.

In addition, although the SN threshold $S_3$ input from the threshold input section 34B is used in the present modification, instead of this, a contrast calculation circuit 35B that calculates the contrast of the image from the fluorescence image generated by the fluorescence image generation section may be arranged as shown in FIG. 24, and the SN threshold $S_3$ of the SN ratio S/N may be set based on a contrast T/C calculated by the contrast calculation circuit 35B.

In this case, a table associating the contrast T/C and the SN threshold $S_3$ can be stored in the sensitivity setting circuit 32B.

The contrast calculation circuit 35B can, for example, generate a histogram of the fluorescence image and calculate, as the contrast, the ratio T/C of an average value C of all gradation values and an average value T of the top 5% of the histogram.

It is preferable that in the table, as shown in FIG. 25, the SN threshold $S_3$ of the SN ratio S/N be set low when the contrast T/C of the used fluorescent agent is high, and the SN threshold of the SN ratio S/N be set high when the contrast T/C is low. Since the SN threshold $S_3$ of the SN ratio S/N is set based on the actually obtained fluorescence image, a more suitable SN threshold can be set compared to when the SN threshold is manually input.

Note that although the average value T of the top 5% of the histogram is used as the contrast T/C, the average value T is not limited to this. For example, in an application in which the observed diseased region is large, such as in an observation of colorectal polyps or the like, the proportion of the high-luminance area in the fluorescence image is likely to be high. Therefore, for example, an average value T of the top 10% of the histogram may be used.

Furthermore, instead of setting the SN threshold $S_3$ of the SN ratio S/N from the contrast T/C of the fluorescence image, the SN threshold $S_3$ of the SN ratio S/N may be set from the luminance value of the reference image.

Figures 26, 27:
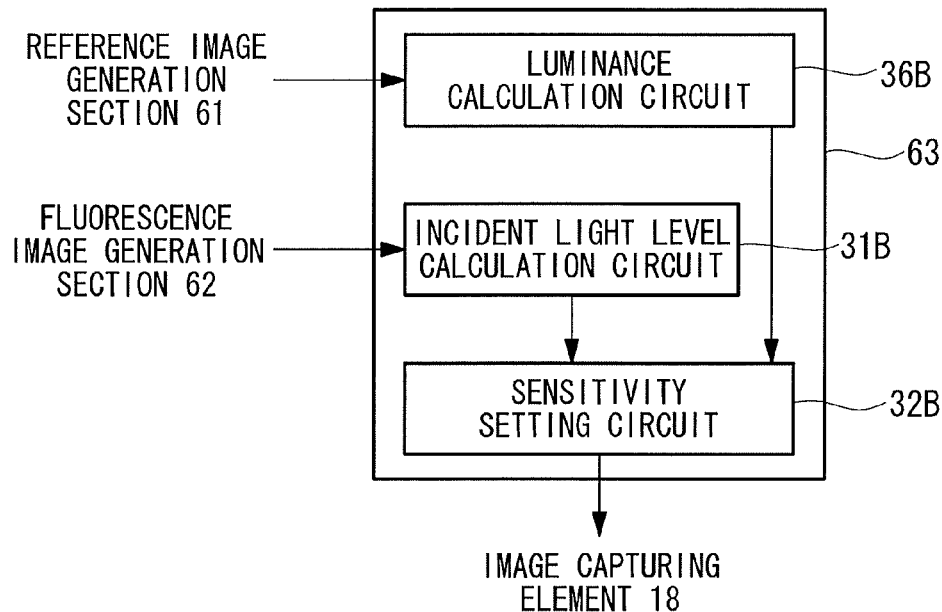
FIG. 26 is a configuration diagram showing a second modification of the preprocessing section of FIG. 21.
FIG. 27 is a diagram showing a table of a correspondence relationship between the luminance of a reference image and the threshold of the SN ratio stored in the sensitivity setting circuit of the preprocessing section of FIG. 26.

In this case, as shown in FIG. 26, a luminance calculation circuit 36B that calculates a luminance D/t of the reference image by dividing a representative value D, such as an average value of the luminance values of the reference image generated by the reference image generation section 61, by the exposure time t can be arranged, and a table associating the luminance D/t of the reference image and the SN threshold $S_3$ can be stored in the sensitivity setting circuit 32B.

In the table, as shown in FIG. 27, it is preferable to set a higher SN threshold $S_3$ of the SN ratio S/N to improve the visibility of the observation target A in an application in which the observation distance is large, that is, when the luminance D/t of the reference image is low. In an application in which the observation distance is small, that is, when the luminance D/t of the reference image is high, a lower SN threshold $S_3$ of the SN ratio S/N can be set in the table.

In contrast, since the observation site is largely displayed when the observation distance is small, reduction in the resolution and generation of image blur are tolerated to some extent. In this case, a higher SN threshold $S_3$ of the SN ratio S/N may be set to provide a higher number of pixels B for binning summing.

In addition, since the observation site is displayed small when the observation distance is large, the reduction in the resolution and the image blur tend to have a large influence. Accordingly, in this case, a lower SN threshold $S_3$ of the SN ratio S/N may be set to prevent the exposure time t from becoming too long or to prevent the number of pixels B for binning from becoming too large.

The values of the luminance D/t in FIG. 27 indicate examples of values expressing the luminance value by 12 bit gradation and expressing the exposure time by a unit sec. More specifically, if D/t is 100000 when the exposure time is 24 msec, the gradation value is 2400.

Figures 28, 29:
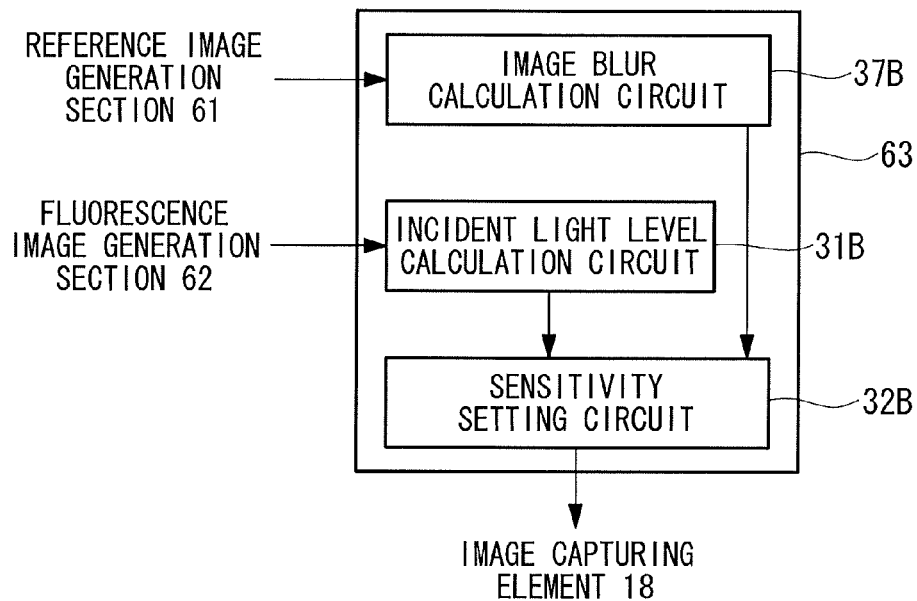
FIG. 28 is a configuration diagram showing a third embodiment of the preprocessing section of FIG. 21.
FIG. 29 is a diagram showing a table of a correspondence relationship between the imaging surface illuminance and the number of pixels for binning summing when an image blur is small, the table stored in the sensitivity setting circuit of the preprocessing section of FIG. 28.

In addition, as shown in FIG. 28, an image blur calculation circuit 37B that calculates an image blur M from the reference image generated by the reference image generation section 61 may be arranged, and the sensitivity setting circuit 32B may select a table associating the exposure time t as well as the number of pixels B for binning summing with the imaging surface illuminance $E_{in}$ according to the size of the calculated image blur M. The image blur M can be calculated by, for example, using a known technique to calculate a blur level and using the blur level to convert the blur level into a numeric value.

The sensitivity setting circuit 32B compares the image blur M transmitted from the image blur calculation circuit 37B with predetermined thresholds M1 and M2 and separately selects a table for three cases, M<M1, M1<M<M2, and M2<M. An example of the table in the case of M<M1 is as shown in FIG. 29. An example of the table in the case of M1<M<M2 is as shown in FIG. 19. An example of the table in the case of M2<M is as shown in FIG. 30.

The table of FIG. 29 indicates a case in which the image blur M is the smallest, and increasing the exposure time t while keeping the number of pixels B for binning summing small is prioritized to perform observation at a high resolution. The table of FIG. 19 indicates a case in which the image blur M is medium, and the exposure time t is set to the standard value of 24 msec to change the number of pixels B for binning summing. The table of FIG. 30 indicates a case in which the image blur M is the largest, and reducing the exposure time t is prioritized to suppress the image blur M to improve the visibility. By doing so, sensitivity adjustment more appropriate for the observation situation can be performed.

Figures 30, 31:
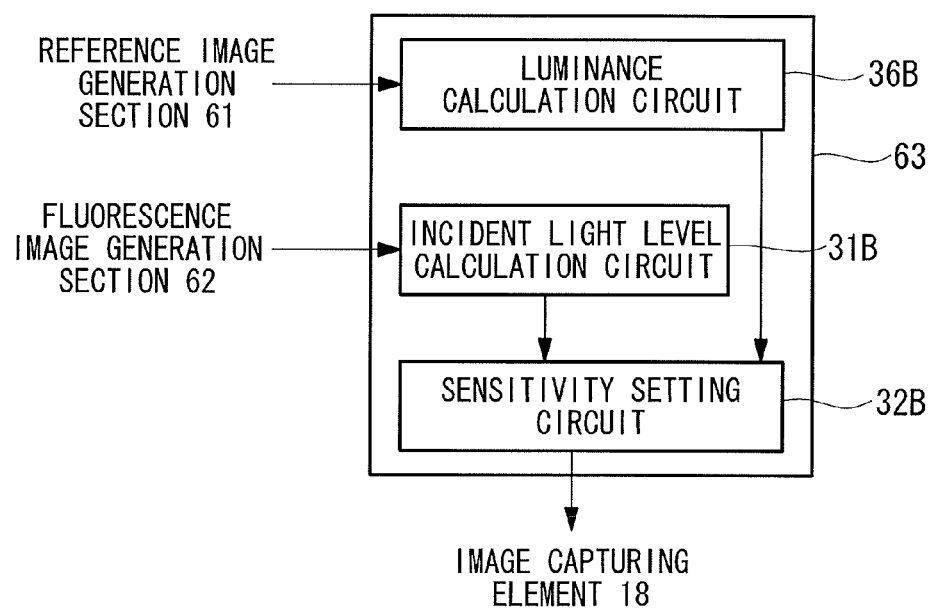
FIG. 30 is a diagram showing a table of a correspondence relationship between the imaging surface illuminance and the number of pixels for binning summing when the image blur is large, the table stored in the sensitivity setting circuit of the preprocessing section of FIG. 28.
FIG. 31 is a configuration diagram showing a fourth modification of the preprocessing section of FIG. 21.

Furthermore, in place of the image blur calculation circuit 37B, the luminance calculation circuit 36B that calculates a luminance I of the reference image generated by the reference image generation section 61 may be arranged as shown in FIG. 31, and the sensitivity setting circuit 32B may select a table associating the exposure time t as well as the number of pixels B for binning summing with the imaging surface illuminance $E_{in}$ according to the size of the calculated luminance I of the reference image.

Figures 33, 34:
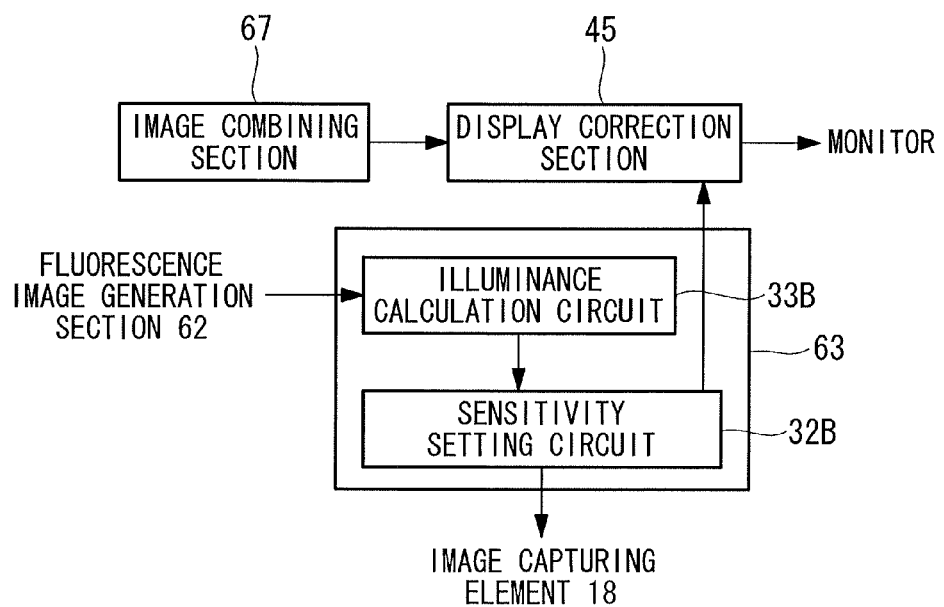
FIG. 33 is a diagram showing a table of a correspondence relationship between the imaging surface illuminance and the number of pixels for binning summing when the luminance of the reference image is large, the table stored in the sensitivity setting circuit of the preprocessing section of FIG. 28.
FIG. 34 is a configuration diagram showing a modification of the preprocessing section of FIG. 17.

The sensitivity setting circuit 32B compares the luminance I of the reference image transmitted from the luminance calculation circuit 36B with predetermined thresholds I1 and I2 and separately selects a table for three cases, I<I1, I1<I<I2, and I2<I. An example of the table in the case of I<I1 is as shown in FIG. 32. An example of the table in the case of I1<I<I2 is as shown in FIG. 19. An example of the table in the case of I2<I is as shown in FIG. 33.

The table of FIG. 32 indicates a case in which the luminance I of the reference image is the smallest, and increasing the exposure time t while keeping the number of pixels B for binning summing small is prioritized to perform observation at a high resolution. The table of FIG. 19 indicates a case in which the luminance I is medium, and the exposure time t is set to the standard value of 24 msec to change the number of pixel B for binning summing. The table of FIG. 33 indicates a case in which the luminance I is the largest, and reducing the exposure time t is prioritized to suppress the image blur to improve the visibility.

By doing so, sensitivity adjustment more appropriate for the observation situation can be performed. The fact that the luminance I is small means that the observation distance is large, and high-resolution imaging is needed because the size of the diseased region in the image is small. Therefore, this is an effective method for usage that requires a high resolution, particularly in the usage in which the observation distance is relatively large such as in an abdominal cavity endoscope and observation in the stomach, or when a small diseased region such as peritoneal dissemination metastatic foci is observed.

In addition, since the number of pixels B for binning summing and the exposure time T are adjusted based on the SN ratio S/N in the first modification, the brightness of the division fluorescence image may fluctuate.

Accordingly, as shown in FIG. 34, a display correction section 45 that performs correction by multiplying the gradation value of the fluorescence image generated by the fluorescence image generation section 22 by a conversion coefficient $C_{raw\text{-}display}$ of the following Expression (7) may be arranged.

$$C_{raw\text{-}display} = B_{max} t_{max} / Bt \quad (7)$$

In this case, $B_{max}$ denotes an upper limit value of the number of pixels B for binning summing, and $t_{max}$ denotes an upper limit value of the exposure time t.

By doing so, the display on the monitor 20 at a brightness different from the actual brightness of fluorescence caused by adjustment of the sensitivity can be avoided, and there is an advantage that quantitative information can be provided to the operator while maintaining the sensitivity.

In addition, when the preprocessing section 63 included in the fluorescence observation apparatus 500 according to the fifth embodiment shown in FIG. 5 is provided with the first modification of the first preprocessing mode, information indicating a correspondence relationship between the incident light level $P_{in}$ (or imaging surface illuminance) and the suitable number of pixels B for binning summing as well as exposure time t may be stored in the sensitivity setting circuit 32B, for each type of information of the insertion portion 2.

By doing so, when the insertion portion 2 is exchanged, identification information in an IC chip 73 arranged on the insertion portion 2 is read by the IC reader 74 and transmitted to the sensitivity setting circuit 32B. Since the sensitivity setting circuit 32B automatically selects the number of pixels B for binning summing and/or the exposure time t corresponding to the identification information of the insertion portion 2, observation can be performed at a sensitivity appropriate for the observation conditions.

In addition, when CCDs are used as the image capturing elements 17 and 18 in place of the CMOSs, Expression (8) can be used in place of Expression (3)

$$S/N = S\eta p_{in} / \sqrt{((S\eta p_{in} + N_d t + N_r^2 / B) / B)} \quad (8)$$

Next, a second modification of the first preprocessing mode will be described.

Figure 35:
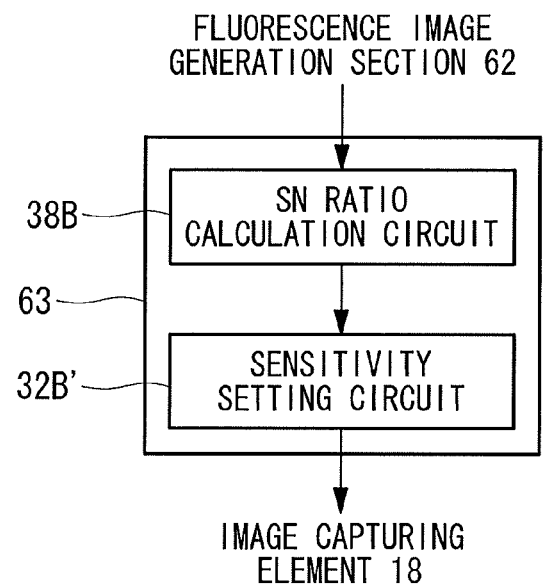
FIG. 35 is a block diagram showing a configuration of the preprocessing section that executes a second modification of the first preprocessing mode.

The second modification of the first preprocessing mode is executed by an SN ratio calculation circuit (image quality evaluation section) 38B and a sensitivity setting circuit 32B' included in the preprocessing section 63 as shown in FIG. 35. The SN ratio calculation circuit 38B calculates an SN ratio SNR based on the luminance information of the fluorescence image. The sensitivity setting circuit 32B' sets the sensitivity of the image capturing element 18 based on the SN ratio SNR calculated by the SN ratio calculation circuit 38B.

Figure 36:
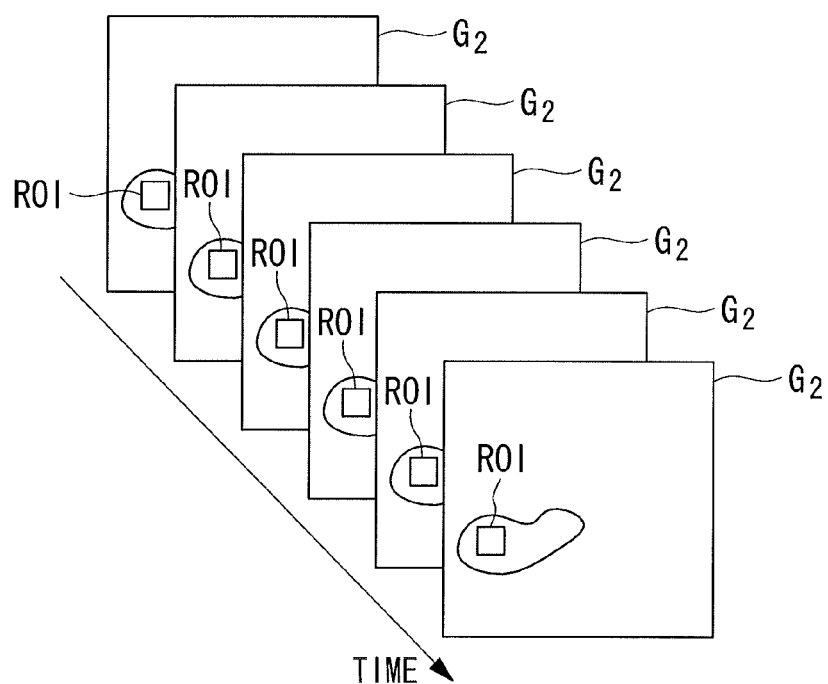
FIG. 36 is a diagram showing an example of fluorescence images and an area of interest acquired at different times by the preprocessing section of FIG. 35.

As shown in FIG. 36, the SN ratio calculation circuit 38B is configured to set an area of interest ROI in the fluorescence image and to calculate, by Equations 1 and 2, temporal average values and fluctuations (standard deviations) from gradation values of the pixels in the ROI of a plurality of fluorescence images acquired at different time points transmitted from the fluorescence image generation section 22.

$$V^*(x, y) = \frac{1}{n} \sum_{j=1}^{n} V(x, y, j) \quad \{\text{Equation 1}\}$$

$$S(x, y) = \sqrt{\frac{1}{n-1} \sum_{j=1}^{n} (V(x, y, j) - V^*(x, y))^2} \quad \{\text{Equation 2}\}$$

In this case,

V (x, y, j) denotes a gradation value of a pixel of coordinates (x, y) in the ROI of the fluorescence image acquired at a j-th time point, V* (x, y) denotes an average value of first to n-th gradation values V (x, y, j), n denotes a predetermined number of fluorescence images, and S (x, y) denotes a temporal fluctuation of first to n-th gradation values V (x, y, j).

The SN ratio SNR is calculated by Equation 3 by using the average values V* (x, y) and the fluctuations S (x, y) calculated for all pixels in the ROI based on Equation 1 and Equation 2. In equation 3, the average values V* (x, y) are divided by the fluctuations S (x, y), and the values are averaged and calculated for all pixels in the ROI.

$$SNR = \frac{1}{\text{total number of pixels in } ROI} \sum_{x,y \in \text{entire } ROI} \frac{V^*(x, y)}{S(x, y)} \quad \{\text{Equation 3}\}$$

Figure 37:
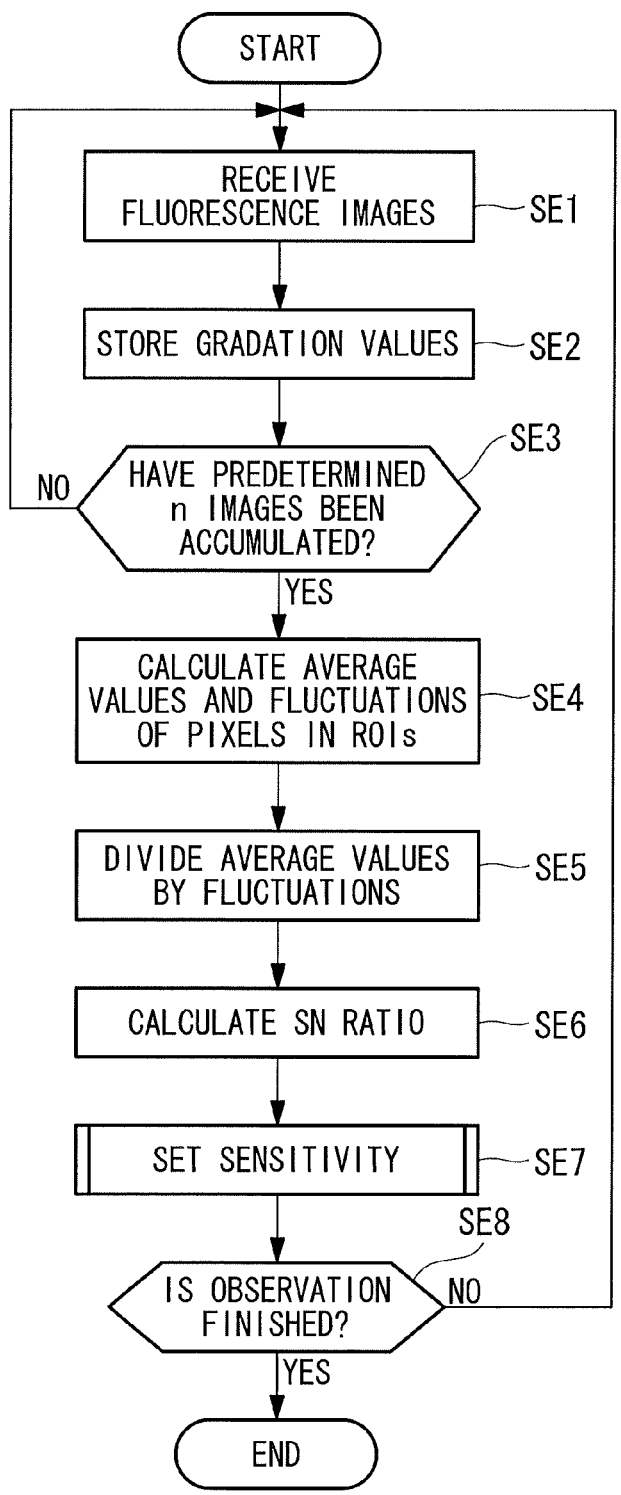
FIG. 37 is a flowchart describing a process of the sensitivity setting circuit of the preprocessing section of FIG. 35.

More specifically, as shown in FIG. 37, the SN ratio calculation circuit 383 stores the gradation values of all pixels in the ROI every time the fluorescence image is transmitted from the fluorescence image generation section 62. The SN ratio calculation circuit 38B calculates the average values V* (x, y) and the fluctuations S (x, y) for all pixels in the ROI when a predetermined n-th fluorescence image is transmitted and divides the average values V* (x, y) by the fluctuations S (x, y). Then, when the division of the average values V* (x, y) by the fluctuations S (x, y) for all pixels in the ROI is finished, the values are summed and averaged to calculate the SN ratio SNR.

The sensitivity setting circuit 32B' is configured to store a first SN threshold and a second SN threshold input from the correction condition setting sections 66, 66', and 66" and to adjust, based on the number of pixels B for binning summing and the exposure time t, the sensitivity of the image capturing element 18 to set the SN ratio SNR calculated by the SN ratio calculation circuit 38B between the two SN thresholds. In this case, the correction condition setting sections 66, 66', and 66" set smaller values for the first and second SN thresholds (preprocessing parameters) when the observation condition corresponds to "local observation" or "low fat" and set larger values when the observation condition corresponds to "overhead observation" or "high fat".

Figure 38:
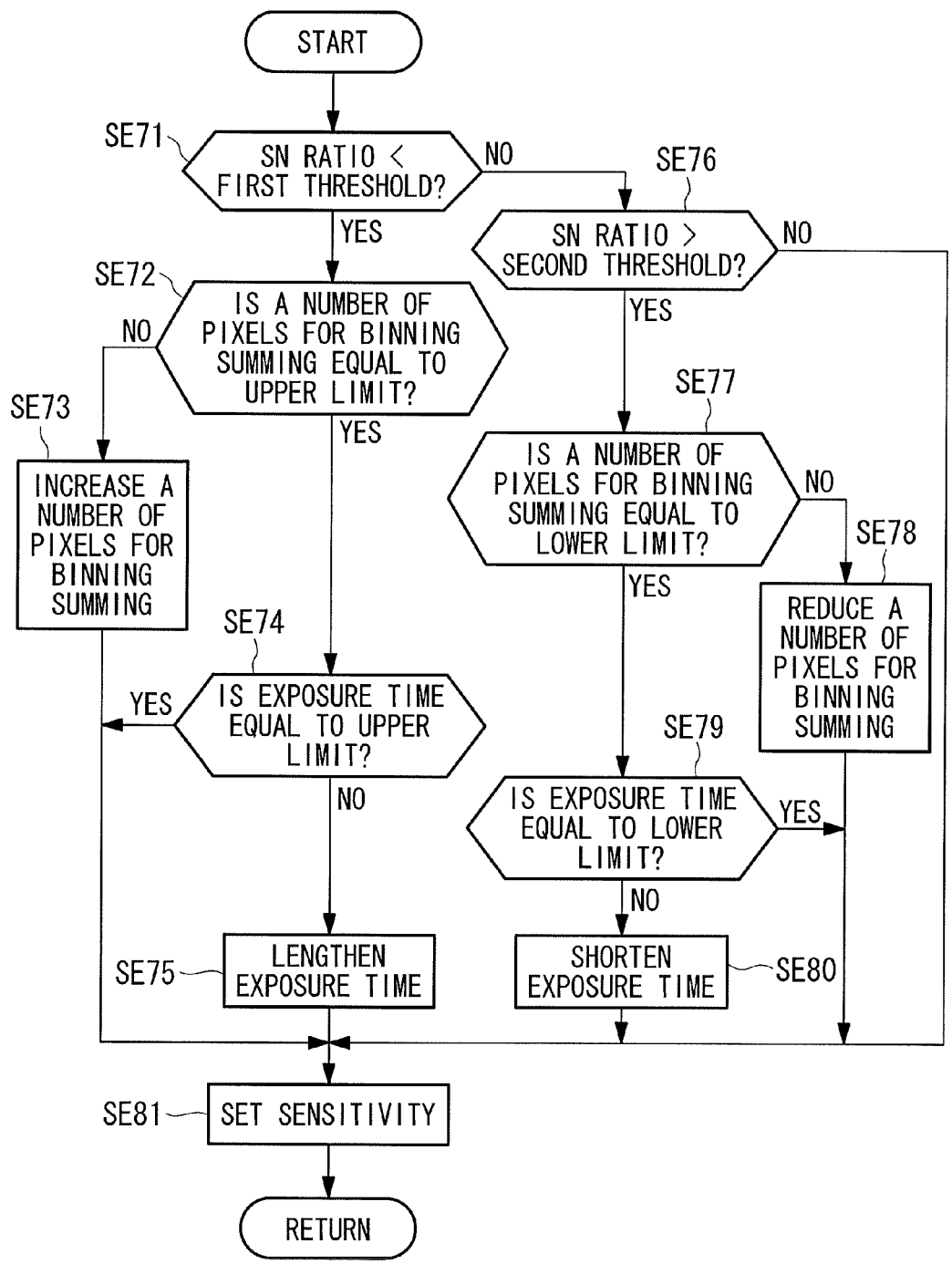
FIG. 38 is a flowchart describing a process of the sensitivity setting circuit of the preprocessing section of FIG. 35.

Specifically, as shown in FIG. 38, the SN ratio SNR calculated by the SN ratio calculation circuit 38B and the first SN threshold are compared (step SE71). If the SN ratio SNR is smaller than the first SN threshold, whether the number of pixels B for binning summing is the upper limit is determined (step SE72). If the number of pixels B for binning summing is not the upper limit, the number of pixels B for binning summing is increased (step SE73).

If the number of pixels B for binning summing is the upper limit in step SE72, whether the exposure time t is the upper limit is determined (step SE74). If the exposure time t is not the upper limit, the exposure time t is lengthened (step SE75). Then, the new number of pixels B for binning summing and/or exposure time t is set to the image capturing element 18 (step SE81).

If the exposure time t is the upper limit in step SE74, the process is not executed, and the process flow returns to the next sensitivity setting.

In addition, if the SN ratio SNR is equal to or higher than the first SN threshold, the SN ratio SNR and the second SN threshold are compared (step SE76). If the SN ratio SNR is larger than the second SN threshold, whether the number of pixels B for binning summing is the lower limit is determined (step SE77). If the number of pixels B for binning summing is not the lower limit, the number of pixels B for binning summing is reduced (step SE78).

If the number of pixels B for binning summing is the lower limit in step SE777, whether the exposure time t is the lower limit is determined (step SE79). If the exposure time t is not the lower limit, the exposure time is shortened (step SE80). Then, the new number of pixels B for binning summing and/or exposure time t is set to the image capturing element 18 (step SE81). If the exposure time t is the lower limit in step SE79, the process is not executed, and the process flow returns to the next sensitivity setting.

According to the first preprocessing mode by the preprocessing section 63 with the configuration, as shown in FIG. 37, a plurality of fluorescence images acquired and generated at different time points are transmitted to the preprocessing section 63 (step SE1) and stored in the SN ratio calculation circuit 38B (step SE2). Next, whether predetermined n fluorescence images are accumulated is determined (step SE3). If predetermined n fluorescence images are accumulated, the SN ratio calculation circuit 38B calculates the average values of the gradation values and the fluctuations based on the gradation values of the pixels in the predetermined ROI of the fluorescence images (step SE4) and the average value is divided by the fluctuation for each pixel (step SE5). Furthermore, an average value of the values obtained by dividing the average values by the fluctuations for all pixels in the ROI is calculated as the SN ratio SNR (step SE6) and transmitted to the sensitivity setting circuit 32B' (step SE7).

The sensitivity setting circuit 32B' compares the transmitted SN ratio SNR and the first SN threshold (step SE71). If the SN ratio SNR is smaller than the first SN threshold, whether the set number of pixels B for binning summing is the upper limit value is determined (step SE 72). If the number of pixels B for binning summing is not the upper limit value, the number of pixels B for binning summing is increased by a predetermined increment (step SE73) and set to the image capturing element 18 (step SE81).

On the other hand, if the number of pixels B for binning summing is the upper limit, whether the exposure time t is the upper limit value is determined (step SE74). If the exposure time t is not the limit value, the exposure time t is increased by a predetermined increment and set to the image capturing element 18 (step SE81). If the exposure time t is the upper limit value, the sensitivity setting process ends without changing the sensitivity.

In addition, if the SN ratio SNR is equal to or higher than the first SN threshold as a result of the comparison in step SE71, the SN ratio SNR is compared with the second SN threshold (step SE76). If the SN ratio SNR is larger than the second SN threshold, whether the set number of pixels B for binning summing is the lower limit value is determined (step SE77). If the SN ratio SNR is not the lower limit value, the number of pixels B for binning summing is reduced by a predetermined decrement (step SE78) and set to the image capturing element 18 (step SE81).

On the other hand, if the number of pixels B for binning summing is the lower limit value in step SE77, whether the exposure time t is the lower limit value is determined (step SE79). If the exposure time t is not the lower limit value, the exposure time t is reduced by a predetermined decrement (step SE80) and set to the image capturing element 18 (step SE81). If the exposure time t is the lower limit value, the sensitivity setting process ends without changing the sensitivity. After the end of the sensitivity setting process, the process from step SE1 is repeated until the observation is finished (step SE8).

Then, in this way, the image capturing element 18 provided with the new number of pixels B for binning summing and/or exposure time t acquires the fluorescence image information, and the fluorescence image generated in the fluorescence image generation section 62 is output to the division image generation section 64 as a division fluorescence image.

In this way, the number of pixels B for binning summing and/or the exposure time t can be set to the image capturing element 18 so that the SN ratio SNR obtained from the luminance information of the fluorescence image is equal to or higher than the first SN threshold, allowing the fluorescence observation while ensuring the minimum image quality. In addition, the number of pixels B for binning summing and/or the exposure time t can be set to the image capturing element 18 so that the SN ratio SNR is equal to or lower than the second SN threshold, allowing the fluorescence observation while minimizing the influence of the image blur.

In this case, since the SN ratio SNR is calculated by using the luminance information of the actually acquired fluorescence image, there is an advantage that sensitivity adjustment appropriate for the circumstances can be performed. In addition, since the SN ratio SNR is calculated by using the luminance information of the actually acquired fluorescence image, suitable sensitivity adjustment can be always performed without being affected by individual differences and errors of the insertion portion 2 and the like exchanged according to the observation conditions.

Note that in the second modification of the first preprocessing mode, although the exposure time t is adjusted when adjustment cannot be performed any more after the adjustment of the number of pixels B for binning summing, the adjustment may be performed in reverse order or alternately.

In addition, although the number of pixels B for binning summing and/or the exposure time t is adjusted based on two SN thresholds, instead of this, the adjustment may be performed by a single SN threshold.

In addition, although the SN ratio calculation circuit 38B calculates the temporal average values and fluctuations in the second modification of the first preprocessing mode, instead of this, the SN ratio SNR may be calculated based on spatial average values and fluctuations.

In this case, the SN ratio calculation circuit 38B is configured to calculate, by Equations 4 and 5, average values and fluctuations (standard deviations) of the gradation values of the pixels in a plurality of areas of interest ROIs set in the fluorescence images transmitted from the fluorescence image generation section 62.

$$V^*(j) = \frac{1}{n(j)} \sum_{x,y \in ROIj} V(x,y) \quad \{\text{Equation 4}\}$$

$$S(j) = \sqrt{\frac{1}{n(j)-1} \sum_{x,y \in ROIj} (V(x,y) - V^*(j))^2} \quad \{\text{Equation 5}\}$$

In this case,

V (x, y) denotes a gradation value of a pixel of coordinates (x, y) in the ROI of the fluorescence image, n (j) denotes the number of pixels in a j-th ROI, V* (j) denotes an average value of the gradation value V (x, y) in the j-th ROI, and S (j) denotes a spatial fluctuation of the gradation value V (x, y) in the j-th ROI.

Then, from the calculated average values and fluctuations in the plurality of ROIs, the average value of the values obtained by dividing the average values by the fluctuations is calculated for all ROIs based on Equation 6.

$$SNR = \frac{1}{\text{number of } ROIs} \sum_j \frac{V^*(j)}{S(j)} \quad \{\text{Equation 6}\}$$

According to the first preprocessing mode, for example, in the usage of largely moving the viewing range, the SN ratio SNR can be more accurately calculated by calculating the SN ratio SNR from a single fluorescence image than by accumulating a plurality of fluorescence images to calculate the SN ratio SNR, and there is an advantage that suitable sensitivity adjustment can be performed.

In the modification of the first preprocessing mode, although the two predetermined SN thresholds are set in the sensitivity setting circuit 32B', instead of this, the SN threshold may be variable according to the performance of the agent or the application.

Figure 39:
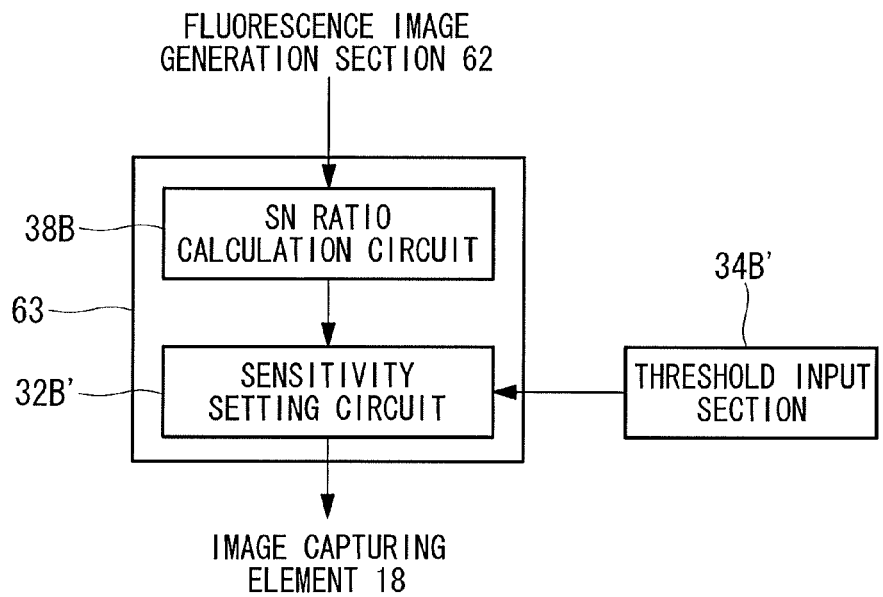
FIG. 39 is a block diagram showing a first modification of the preprocessing section of FIG. 35.

For example, as illustrated in FIG. 39, a threshold input section 34B' for inputting the SN threshold $S_3$ from the outside when the sensitivity setting circuit 32B' obtains the number of pixels B for binning summing may be included.

The threshold input section 34B' is, for example, a switch, a button, and the like, and the SN threshold $S_3$ of the SN ratio SNR can be selected.

Figure 40:
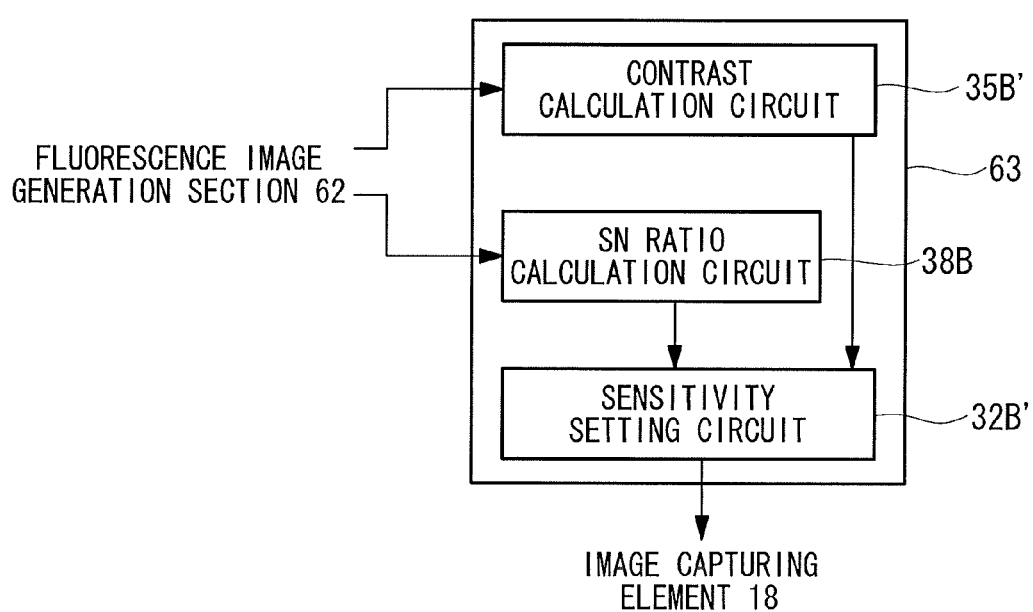
FIG. 40 is a block diagram showing a second modification of the preprocessing section of FIG. 35.

Furthermore, instead of using the SN threshold S3 input from the threshold input section 343', as illustrated in FIG. 40, a contrast calculation circuit 353' that calculates the contrast T/C of the image from the fluorescence image generated by the fluorescence image generation section 62 may be arranged, and the SN threshold $S_3$ of the SN ratio SNR may be set based on the contrast T/C calculated by the contrast calculation circuit 35B'.

Figures 41, 42:
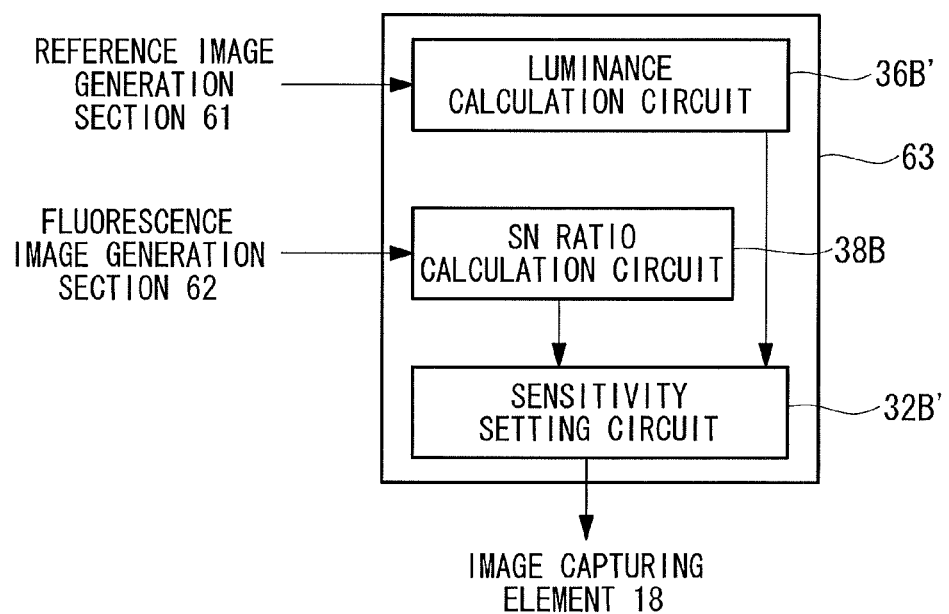
FIG. 41 is a diagram showing a table of a correspondence relationship between the contrast and the threshold of the SN ratio stored in the sensitivity setting circuit of the preprocessing section of FIG. 40.
FIG. 42 is a block diagram showing a third modification of the preprocessing section of FIG. 35.

In this case, a table associating the contrast T/C and the SN threshold as shown in FIG. 41 can be stored in the sensitivity setting circuit 32B'.

The contrast calculation circuit 35B' can, for example, generate a histogram of the fluorescence image and calculate, as the contrast, a ratio T/C of an average value C of all gradation values and an average value T of the top 5% of the histogram.

In the table, it is preferable that a low SN threshold of the SN ratio SNR be set if the contrast T/C of the used fluorescent agent is high and that a high SN threshold of the SN ratio SNR be set if the contrast T/C is low. By doing so, since the SN threshold of the SN ratio SNR is set based on the actually obtained fluorescence image, a more suitable SN threshold can be set compared to when the SN threshold is manually input.

Note that although the average value T of the top 5% of the histogram is used as the contrast T/C, the value is not limited to this. For example, in an application in which the observed diseased region is large, such as in observation of colorectal polyps or the like, the proportion of the high-luminance area in the fluorescence image is likely to be high. Therefore, for example, the average value T of the top 10% of the histogram may be used.

Furthermore, instead of setting the SN threshold of the SN ratio SNR from the contrast T/C of the fluorescence image, the SN threshold of the SN ratio SNR may be set from the luminance values of the reference image.

In this case, as shown in FIG. 42, a luminance calculation section 36B' that calculates a luminance D/t of the reference image by dividing a representative value D, such as an average value of the luminance values of the reference image generated by the reference image generation section 61, by the exposure time t can be arranged, and a table associating the luminance D/t of the reference image and the SN threshold can be stored in the sensitivity setting circuit 32B'.

Figures 43, 44:
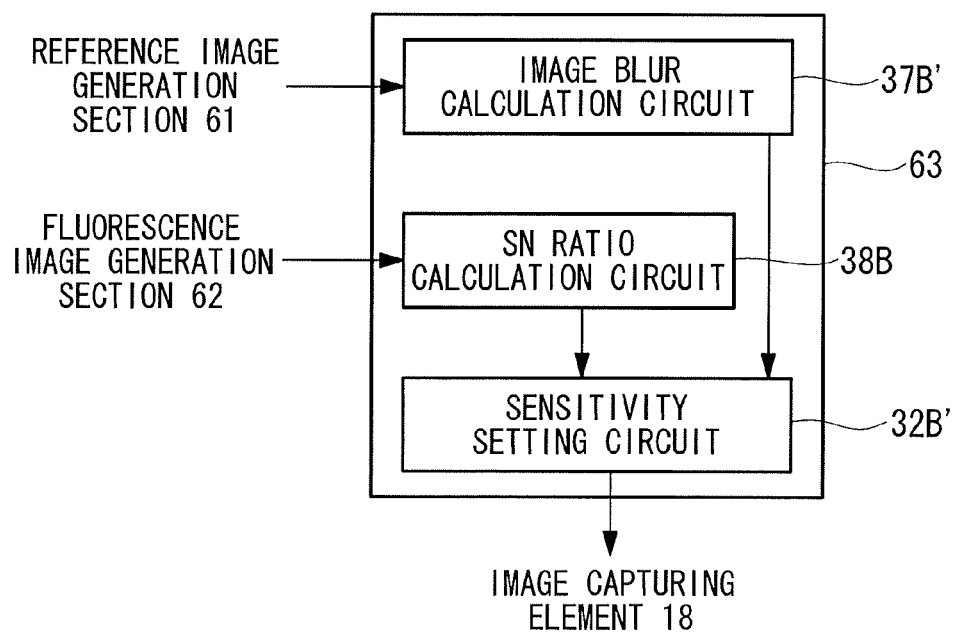
FIG. 43 is a diagram showing a table of a correspondence relationship between the luminance of the reference image and the threshold of the SN ratio stored in the sensitivity setting circuit of the preprocessing section of FIG. 42.
FIG. 44 is a block diagram showing a fourth modification of the preprocessing section of FIG. 35.

In the table, as shown in FIG. 43, it is preferable to set a higher SN threshold $S_3$ of the SN ratio SNR to improve the visibility of the observation target A in an application in which the observation distance is large, that is, when the luminance D/t of the reference image is low. In an application in which the observation distance is small, that is, when the luminance D/t of the reference image is high, a lower SN threshold $S_3$ of the SN ratio SNR can be set in the table.

In contrast, since the observation site is largely displayed when the observation distance is small, the reduction in the resolution and the generation of image blur are tolerated to some extent. In this case, a higher SN threshold $S_3$ of the SN ratio SNR may be set to increase the number of pixels B for binning summing.

Note that the values of the luminance D/t in FIG. 43 are examples of values when the luminance value is expressed in 12-bit gradation, and the exposure time is expressed in seconds. More specifically, with D/t=100000, the gradation value is 2400 when the exposure time is 24 msec.

In addition, since the observation site is displayed small when the observation distance is large, the influence of the reduction in the resolution and the image blur is large. In this case, a lower SN threshold $S_3$ of the SN ratio SNR may be set to prevent the exposure time t from becoming too long and to prevent the number of pixels B for binning summing from becoming too large.

In addition, as shown in FIG. 44, an image blur calculation circuit 37B' that calculates the image blur M from the reference image generated by the reference image generation section 61 may be arranged, and the sensitivity setting circuit 32B' may set the exposure time t and the number of pixels B for binning summing according to the size of the calculated image blur M. The image blur M can be calculated by using a known technique to calculate the magnitude of the image blur and using the magnitude of the blur to convert the magnitude into a numeric value.

Figure 45:
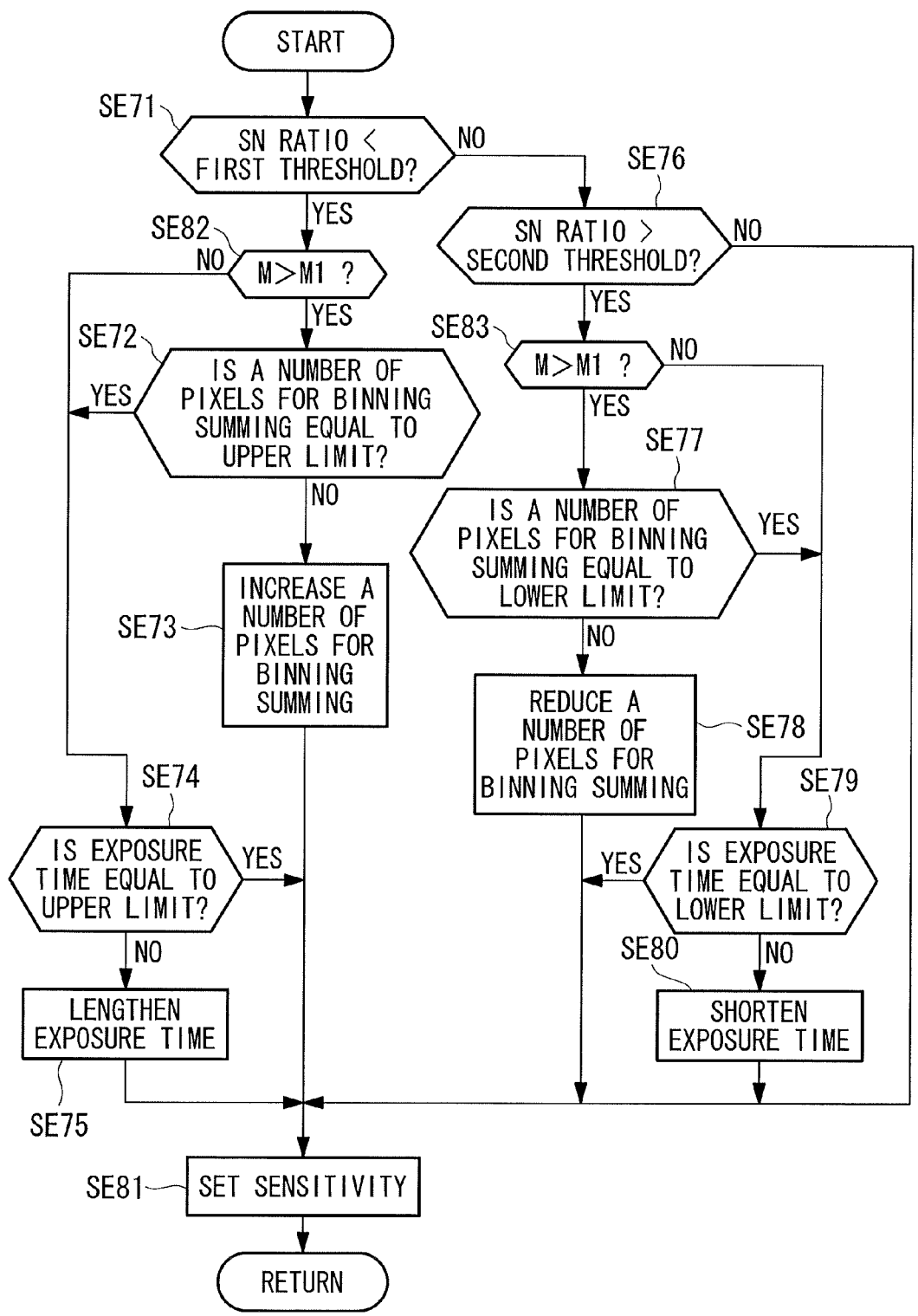
FIG. 45 is a flowchart describing a process of the sensitivity setting circuit of the preprocessing section of FIG. 44.

In this case, as shown in FIG. 45, the sensitivity setting circuit 32B' determines whether the SN ratio SNR is smaller than the predetermined first SN threshold (step SE71). Then, if the SN ratio SNR is smaller than the first SN threshold, the image blur M transmitted from the image blur calculation circuit 37B' is compared with the predetermined threshold M1 to determine whether M>M1 (step SE82). If the image blur M is larger than the threshold M1, the process advances to step SE72. If the image blur M is equal to or lower than the threshold M1, the process advances to step SE74.

In addition, if the SN ratio SNR is equal to or higher than the predetermined first SN threshold, whether the SN ratio SNR is larger than the predetermined second SN threshold is determined (step SE76). Then, if the SN ratio SNR is larger than the second SN threshold, the image blur M transmitted from the image blur calculation circuit 37B' is compared with the predetermined threshold M1 to determine whether M>M1 (step SE83). If the image blur M is larger than the threshold M1, the process advances to step SE77. If the image blur M is equal to or lower than the threshold M1, the process advances to step SE79.

By doing so, shortening the exposure time t is prioritized when the image blur M is large, and lengthening the exposure time t is prioritized when the image blur M is small. There is an advantage that the number of pixels B for binning summing can be reduced to perform the fluorescence observation at a high resolution. By doing so, sensitivity adjustment more appropriate for the circumstances can be performed.

Furthermore, in place of the image blur calculation circuit 29, a luminance calculation section 36B' that calculates the luminance I of the reference image generated by the reference image generation section 61 may be arranged as shown in FIG. 42, and the sensitivity setting circuit 32B' may set the exposure time t and the number of pixels B for binning summing according to the size of the calculated luminance I of the reference image.

Figure 46:
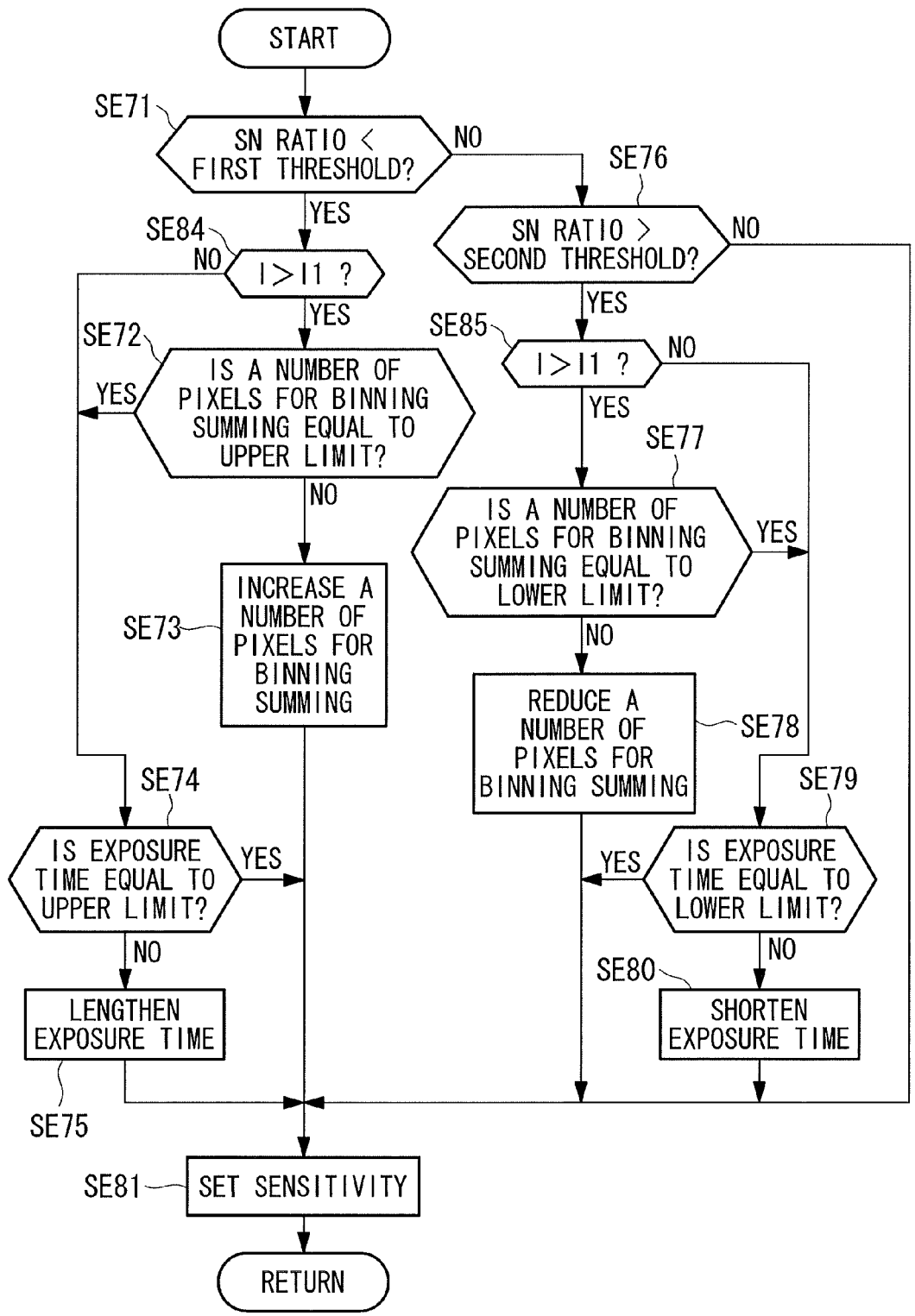
FIG. 46 is a flowchart describing a process of the sensitivity setting circuit of the preprocessing section of FIG. 42.

In this case, the sensitivity setting circuit 32B' determines whether the SN ratio SNR is smaller than the predetermined first SN threshold as shown in FIG. 46 (step SE71). Then, if the SN ratio SNR is smaller than the first SN threshold, the luminance I transmitted from the luminance calculation section 36B' is compared with the predetermined threshold I1, and whether I>I1 is determined (step SE84). If the luminance I is larger than the threshold I1, the process advances to step SE72. If the luminance I is equal to or lower than the threshold I1, the process advances to step SE74.

In addition, if the SN ratio SNR is equal to or higher than the predetermined first SN threshold, whether the SN ratio SNR is larger than the predetermined second SN threshold is determined (step SE76). Then if the SN ratio SNR is larger than the second SN threshold, the luminance I transmitted from the luminance calculation section is compared with the predetermined threshold I1, and whether I>I1 is determined (step SE85). If the luminance I is larger than the threshold I1, the process advances to step SE77. If the luminance I is equal to or lower than the threshold I1, the process advances to step SE79.

Since the observation site is relatively largely displayed on the image when the luminance I is high, that is, when the observation distance is relatively short, the observation site is sufficiently visible even if the resolution is slightly reduced. Therefore, in this case, the number of pixels B for binning summing is set higher, and conversely, the exposure time t can be short. Therefore, there is an advantage that the image blur can be suppressed.

On the other hand, since the observation distance is relatively short when the luminance I is low, the observation site is displayed on the screen relatively small. In such a case, the resolution needs to be kept high, and the number of pixels B for binning summing is set smaller.

The configuration allows more suitable sensitivity adjustment. Particularly, this is an effective method for usage that requires a high resolution, such as in the usage in which the observation distance is relatively large as in an abdominal cavity endoscope or in an observation of the stomach, or when a small diseased region such as peritoneal dissemination metastasis foci is observed.

The second modification of the first preprocessing mode can be further modified as follows.

Figure 47:
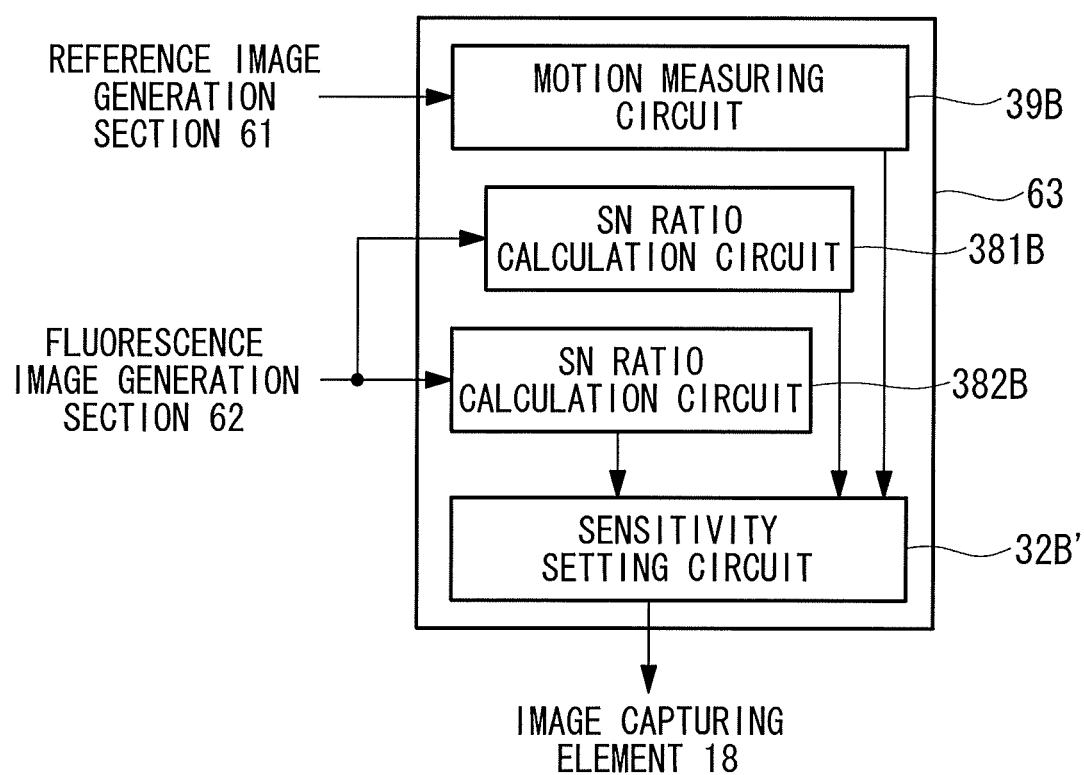
FIG. 47 is a block diagram showing a fifth modification of the preprocessing section of FIG. 35.

More specifically, as shown in FIG. 47, the preprocessing section 63 includes: a motion measuring circuit 39B that measures a motion speed of the insertion portion 2 based on the reference image generated by the reference image generation section 61; an SN ratio calculation circuit 381B that calculates the SN ratio SNR from the temporal average values and fluctuations based on the fluorescence images generated by the fluorescence image generation section 62; and an SN ratio calculation circuit 382B that calculates the SN ratio SNR from the spatial average values and fluctuations.

Then, the sensitivity setting circuit 32B' is configured to select which one of the SN ratios SNR output by the SN ratio calculation circuits 381B and 382B will be used according to the motion speed N measured by the motion measuring circuit 39B. Specifically, if the motion speed N is larger than a predetermined threshold N1, the SN ratio SNR calculated from the spatial average values and fluctuations output from the SN ratio calculation circuit 382B is used. If the motion speed N is equal to or lower than the threshold N1, the SN ratio SNR calculated from the temporal average values and fluctuations output from the SN ratio calculation circuit 381B is used.

When the motion of the insertion portion 2 is fast, the SN ratio SNR using the spatial average values and fluctuations that can be calculated by a single fluorescence image is more preferable than the SN ratio SNR using the temporal fluctuations that requires a plurality of fluorescence images, because more accurate calculation is possible. When the motion is slow, substantially the same site is observed. Therefore, the SN ratio SNR using the temporal average values and fluctuations that is hardly influenced by variations due to individual differences between the image capturing elements 18 is more preferable, because more accurate calculation is possible.

When the fluorescence observation apparatus 500 according to the fifth embodiment shown in FIG. 5 is provided with the present preprocessing mode, a suitable SN threshold may be stored in the sensitivity setting circuit 32B', for each piece of identification information of the insertion portion 2.

By doing so, when the insertion portion 2 is exchanged, the IC reader 74 reads the identification information in the IC chip 73 arranged on the insertion portion 2 and transmits the identification information to the correction condition setting sections 66, 66', 66" or the sensitivity setting circuit 32B'. Since the correction condition setting sections 66, 66', 66" or the sensitivity setting circuit 32B' automatically selects the SN threshold corresponding to the identification information of the insertion portion 2, observation is possible at a sensitivity appropriate for the observation conditions.

{Second Preprocessing Mode}

Next, the second preprocessing mode by the preprocessing section 63 included in the fluorescence observation apparatuses 100, 200, 300, 400, and 500 according to the first to fifth embodiments will be described. The second preprocessing mode is a processing mode of raising at least one of the reference image and the fluorescence image to the power of a value based on the observation distance.

The second preprocessing mode is suitable for removing the dependency of observation distance and observation angle remained in the division image due to the observation distance from the image capturing elements 17 and 18 to the observation target A. More specifically, the correction condition setting sections 66 and 66' of the fluorescence observation apparatuses 100 and 200 according to the first and second embodiments set the preprocessing parameters of the second preprocessing mode when "local view" or "overhead view" is input or determined as the observation condition. The correction condition setting section 66" of the fluorescence observation apparatuses 300, 400, and 500 according to the third to fifth embodiments sets the preprocessing parameters of the second preprocessing mode when "Douglas' pouch" or the like for local observation or "greater omentum", "subphrenic area", "intestinal membrane", or the like for overhead observation is input or determined.

The second preprocessing mode is a mode in which the luminance value of the fluorescence image is raised to the power of a reciprocal of a first exponent (preprocessing parameter) obtained by power approximation of the distance characteristics from the illumination unit 4 to the observation target of the luminance of the fluorescence image generated when excitation light at a predetermined intensity is radiated on the observation target, and the luminance value of the reference image is raised to the power of a reciprocal of a second exponent (preprocessing parameter) obtained by power approximation of the distance characteristics from the illumination unit to the observation target of the luminance of the reference image generated when illumination light at a predetermined intensity is radiated on the observation target. In this case, the correction condition setting sections 62, 62', and 62" command the preprocessing section 63 to increase at least one of the first and second exponents when the observation condition corresponds to "local view" and command the preprocessing section 63 to reduce at least one of the first and second exponents when the observation condition corresponds to "overhead view".

Figure 48:
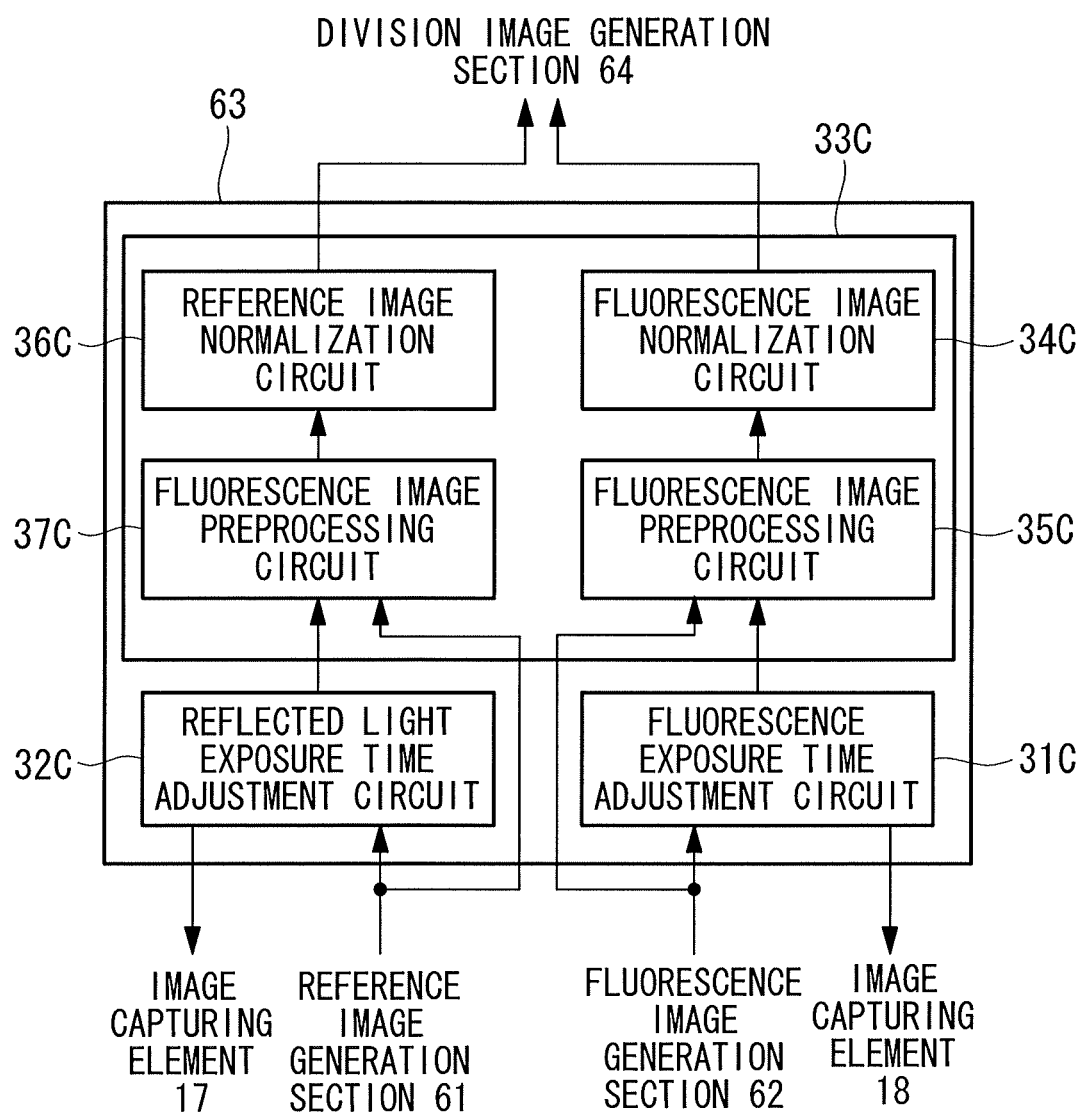
FIG. 48 is a block diagram showing a configuration of the preprocessing section that executes a second preprocessing mode.

As shown in FIG. 48, a fluorescence exposure time adjustment circuit 31C, a reflected light exposure time adjustment circuit 32C, and an image correction circuit 33C included in the preprocessing section 63 execute the second preprocessing mode. The fluorescence exposure time adjustment circuit 31C adjusts the exposure time (image capturing condition) of the image capturing element 18 for fluorescence image. The reflected light exposure time adjustment circuit 32C adjusts the exposure time (image capturing condition) of the image capturing element 17 for reference image. The image correction circuit 33C uses the reference image generated by the reference image generation section 61 to correct the fluorescence image generated by the fluorescence image generation section 62.

The fluorescence exposure time adjustment circuit 31C is configured to adjust the exposure time of the image capturing element 18 based on the luminance value of the fluorescence image generated by the fluorescence image generation section 62.

Similarly, the reflected light exposure time adjustment circuit 32C is configured to adjust the exposure time of the image capturing element 17 based on the luminance value of the reference image generated by the reference image generation section 61.

An average value of luminance values of a predetermined area (hereinafter, called "area of interest") of the fluorescence image and the reference image obtained by radiating the excitation light and the illumination light to the observation target A from the illumination unit 20 while changing a distance (hereinafter, referred to as "observation distance") Dn from the tip 2a of the insertion portion 2 to the observation target A is used as the luminance value of the fluorescence image and the luminance value of the reference image.

Here, the following reference example will be illustrated to describe a method of obtaining the luminance value.

Figure 49:
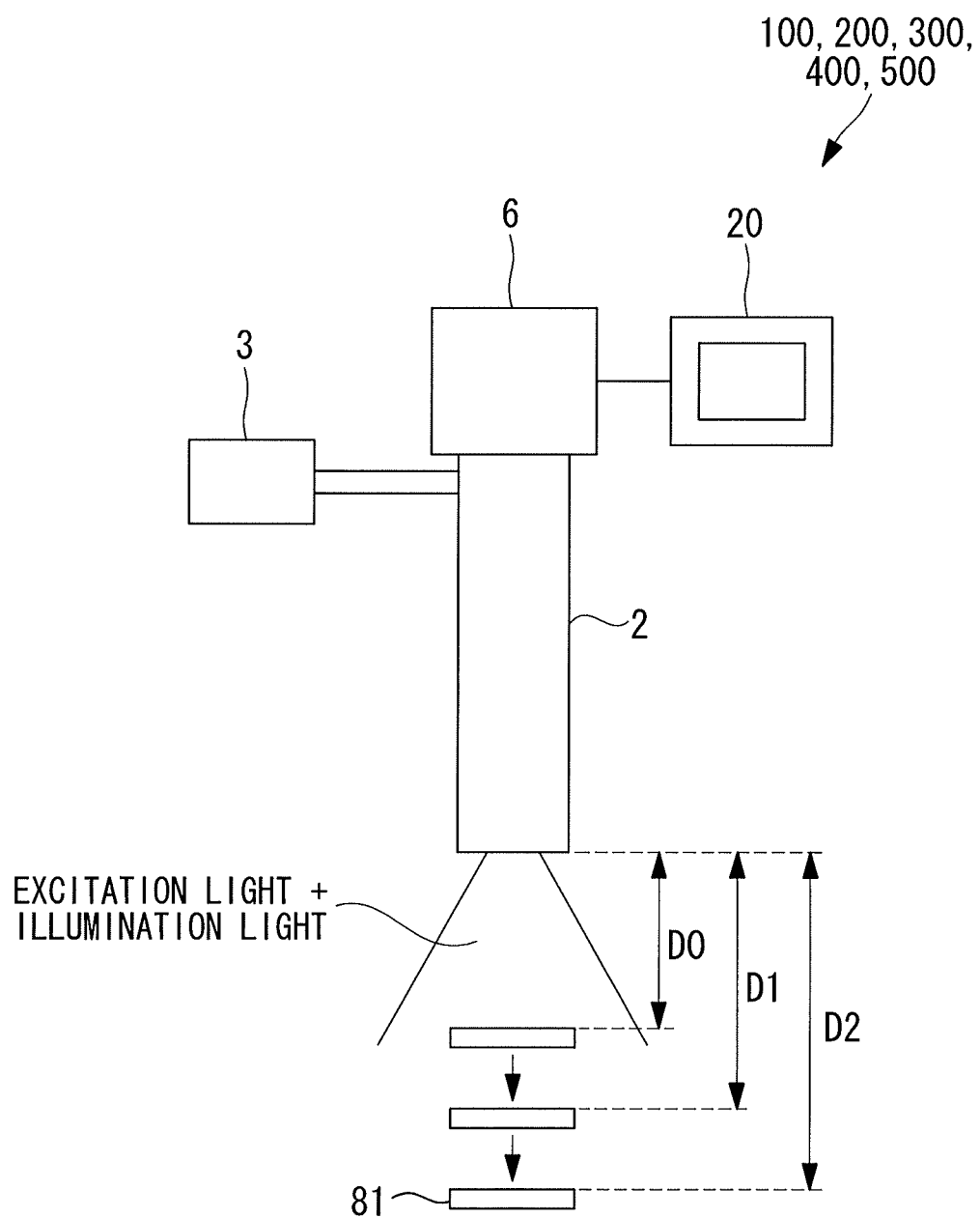
FIG. 49 is a diagram showing a state of changing the observation distance between an insertion portion of the fluorescence observation apparatus including the preprocessing section of FIG. 48 and a standard sample.

For example, as shown in FIG. 49, illumination light is radiated to a standard sample 81 with optical characteristics close to a living body, such as colon tissue of a pig injected with a fluorescent dye, while changing the observation distance Dn to D0, D1, and D2 (D0<D1<D2), and fluorescence images as shown in FIGS. 50A to 50C and FIGS. 51A to 51C are acquired. In the drawings, reference sign 83 denotes a field of view of the image capturing element 18, and reference sign 85 denotes an area of interest.

Figure 50A:
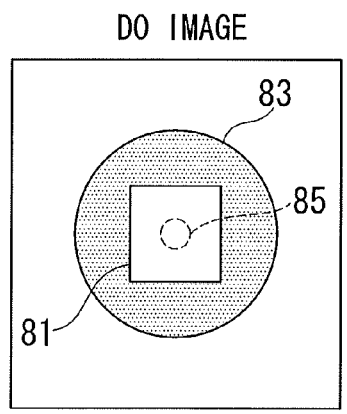
FIG. 50A is a diagram showing an image in a state of an observation distance D0 when the size of the area of interest is not changed.
Figure 50B:
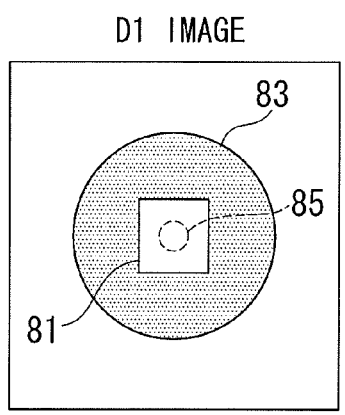
FIG. 50B is a diagram showing an image in a state of an observation distance D1.
Figure 50C:
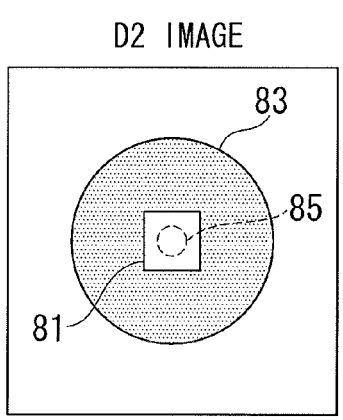
FIG. 50C is a diagram showing an image in a state of an observation distance D2.
Figure 51A:
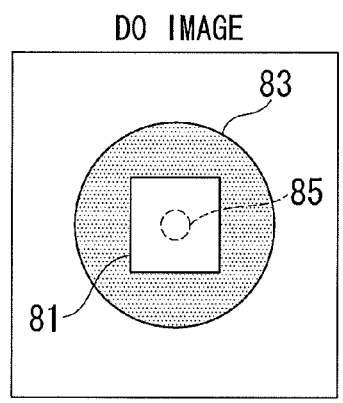
FIG. 51A is a diagram showing an image in the state of the observation distance D0 when the size of the area of interest is changed.
Figure 51B:
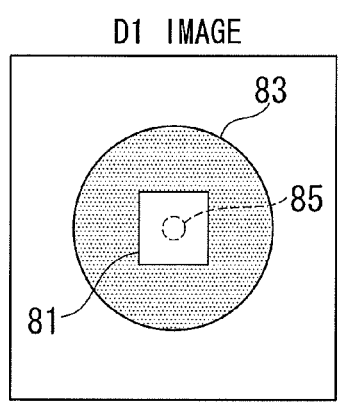
FIG. 51B is a diagram showing an image in the state of the observation distance D1.
Figure 51C:
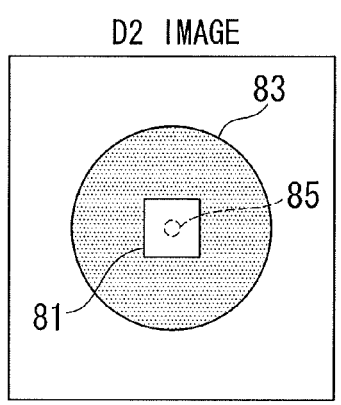
FIG. 51C is a diagram showing an image in the state of the observation distance D2.

If the fluorescence intensity of the standard sample 81 is constant, such as when the surface of the observation target A as a subject is substantially flat, the size of the area of interest 85 is maintained constant regardless of the observation distance Dn as shown in FIGS. 50A to 50C to calculate the luminance values. On the other hand, if the fluorescence intensity in the standard sample 81 is not constant, such as when the surface of the observation target A has irregularities or when the fluorescence distribution in the observation target A has nonuniformities, the size of the area of interest 85 is changed according to the observation distance Dn as shown in FIGS. 51A to 51C to calculate the luminance values. By changing the size of the area of interest, the luminance values of the same site can be obtained even if the observation distance Dn is changed.

The image correction circuit 33C includes: a fluorescence image normalization circuit 34C that normalizes the luminance of the fluorescence image generated by the fluorescence image generation section 62; a fluorescence image preprocessing circuit 35C that applies arithmetic processing to the fluorescence image with the normalized luminance; a reference image normalization circuit 36C that normalizes the luminance of the reference image acquired by the reference image generation section 61; and a reference image preprocessing circuit 37C that applies arithmetic processing to the reference image with the normalized luminance. The division reference image acquired by the reference image preprocessing circuit 37C and the division fluorescence image acquired by the fluorescence image preprocessing circuit 35C are output to the division image generation section 64.

The fluorescence image normalization circuit 34C is configured to read the luminance value of the fluorescence image from the fluorescence image generation section 62 and divide the luminance value by the exposure time of the image capturing element 18 set by the fluorescence exposure time adjustment circuit 31C.

The fluorescence image preprocessing circuit 35C is configured to acquire the division fluorescence image by raising the luminance value of the normalized fluorescence image to the power of a reciprocal $1/\alpha$ (or $-1/\alpha$) of a first component $\alpha$ obtained by power approximation of the distance characteristics at the observation distance Dn of the luminance of the fluorescence image that is acquired by the image capturing element 18 radiating the excitation light at a predetermined intensity to the observation target A and that is normalized by the fluorescence image normalization circuit 34C. Specifically, the following power computation is performed.

$$FL_{after} = A \times FL_{before}^{x} \quad (9)$$

Here, $FL_{after}$ denotes the luminance value of the division fluorescence image, $FL_{before}$ denotes the luminance value of the fluorescence image, x denotes $1/\alpha$ or $-1/\alpha$ that is the first exponent, and A denotes a constant.

As a result of the power consumption, a division fluorescence image, in which the luminance is proportional to the change in the distance, is acquired.

Similarly, the reference image normalization circuit 36C is configured to read the luminance information of the reference image from the reference image generation section 61 and divide the luminance information by the exposure time of the image capturing element 17 set by the reflected light exposure time adjustment circuit 32C.

Furthermore, the reference image preprocessing circuit 37C is configured to acquire the division reference image by raising the luminance value of the normalized reference image to the power of a reciprocal $1/\beta$ (or $-1/\beta$) of a second component $\beta$ obtained by power approximation of the distance characteristics at the observation distance Dn of the luminance of the reference image that is acquired by the image capturing element 17 radiating the reflected light at a predetermined intensity to the observation target A and that is normalized by the reference image normalization circuit 36C. Specifically, the following power computation is performed.

$$RL_{after} = B \times FL_{before}^{y} \quad (10)$$

Here, $RL_{after}$ denotes the luminance value of the division reference image, $RL_{before}$ denotes the luminance value of the reference image, y denotes $1/\beta$ or $-1/\beta$, $\beta$ denotes the second exponent, and B denotes a constant.

As a result of the power consumption, a division reference image, in which the luminance is proportional to the change in the distance, is acquired.

Figure 52:
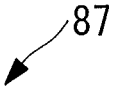
FIG. 52 is a diagram showing an example of a concentration conversion table included in an image processing section including the preprocessing section of FIG. 48.

When the preprocessing section 63 provided with the second preprocessing mode is included, it is preferable that the image combining section 67 include a concentration conversion table 87 associating the luminance value of a division image K and the amount of fluorescent agent present (more specifically, concentration of fluorescent agent) as shown in FIG. 52 and that the fluorescence concentration of a specific area be displayed on the monitor 20.

According to the second preprocessing mode by the preprocessing section 63 with the configuration, the fluorescence image information acquired by the image capturing element 18 and the reference image information acquired by the image capturing element 17 are input to the image processing section 6 and subjected to image processing. Hereinafter, the image processing in the image processing section 6 will be described with reference to a flowchart of FIG. 53.

The fluorescence image information from the image capturing element 18 is input to the fluorescence image generation section 62, and a two-dimensional fluorescence image is generated. In this case, the fluorescence exposure time adjustment circuit 31C sets the exposure time of the image capturing element 18 based on the luminance value of the fluorescence image generated by the fluorescence image generation section 62 (step SF1). By doing so, the fluorescence image generation section 62 acquires a fluorescence image with an appropriate brightness, regardless of the luminance of the fluorescence generated in the observation target A (step SF2).

Similarly, the reference image information is input to the reference image generation section 61, and a two-dimensional reference image is generated. In this case, the reflected light exposure time adjustment circuit 32C adjusts the exposure time of the image capturing element 17 based on the luminance value of the reference image generated by the reference image generation section 61 (step SG1). By doing so, the reference image generation section 61 acquires a reference image with an appropriate brightness, regardless of the luminance of the reflected light returned from the observation target A (step SG2).

The fluorescence image generated by the fluorescence image generation section 62 and the reference image generated by the reference image generation section 61 are transmitted to the image correction circuit 33C.

In this case, the fluorescence image acquired by the image capturing element 18 includes information of the exponentiation of the distance of the fluorescence at the observation distance Dn, and the reference image acquired by the image capturing element 17 includes information of the exponentiation of the distance of the illumination light at the observation distance D. In addition, since the properties of the fluorescence and the reflected light are different due to the influence of internal scattering, surface reflection, or the like, the distance characteristics of the luminance of the fluorescence image at the observation distance Dn and the distance characteristics of the luminance of the reference image at the observation distance Dn are different. Furthermore, when the exposure time of the image capturing element 18 and the exposure time of the image capturing element 17 are different, the luminance value of the fluorescence image and the luminance value of the reference image are different.

In the image correction circuit 33C, the fluorescence image normalization circuit 34C first divides the luminance value of the fluorescence image by the exposure time of the image capturing element 18 (step SF3). By doing so, the difference of the exposure time in the fluorescence image is normalized, and the fluorescence image is standardized to the luminance value per unit time. In addition, the reference image normalization circuit 36C divides the luminance value of the reference image by the exposure time of the image capturing element 17 (step SG3). By doing so, the influence of the exposure time in the reference image is normalized, and the reference image is standardized to the luminance value per unit time.

The fluorescence image with the luminance normalized by the fluorescence image normalization circuit 34C is transmitted to the fluorescence image preprocessing circuit 35C, and the reference image with the luminance normalized by the reference image normalization circuit 36C is transmitted to the reference image preprocessing circuit 37C.

Figure 54A:
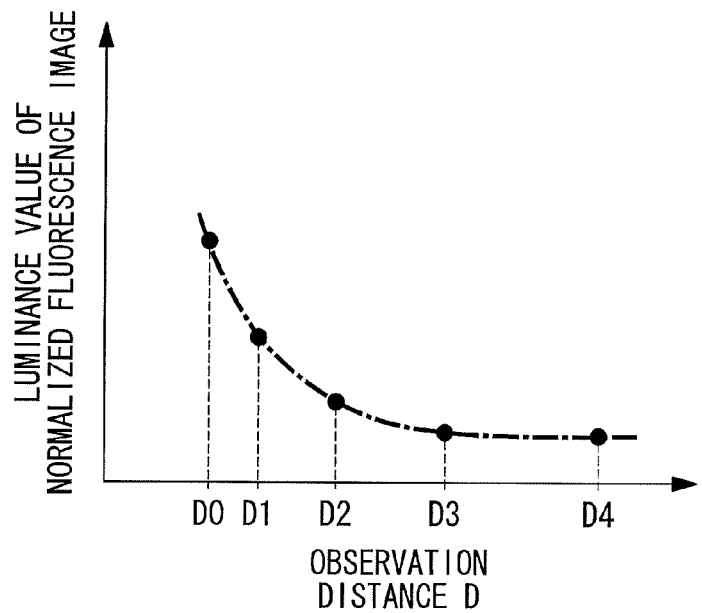
FIG. 54A is a graph plotting luminance values of the fluorescence image relative to the observation distance.
Figure 54B:
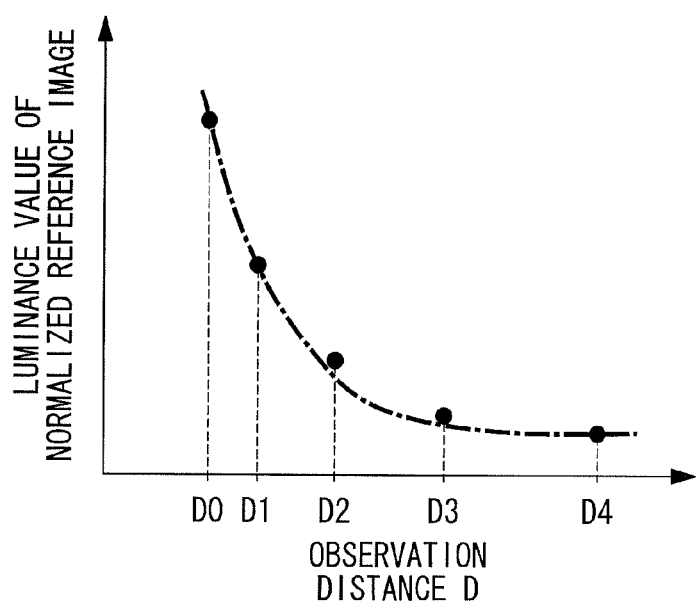
FIG. 54B is a graph plotting luminance values of the reference image relative to the observation distance.
Figure 55A:
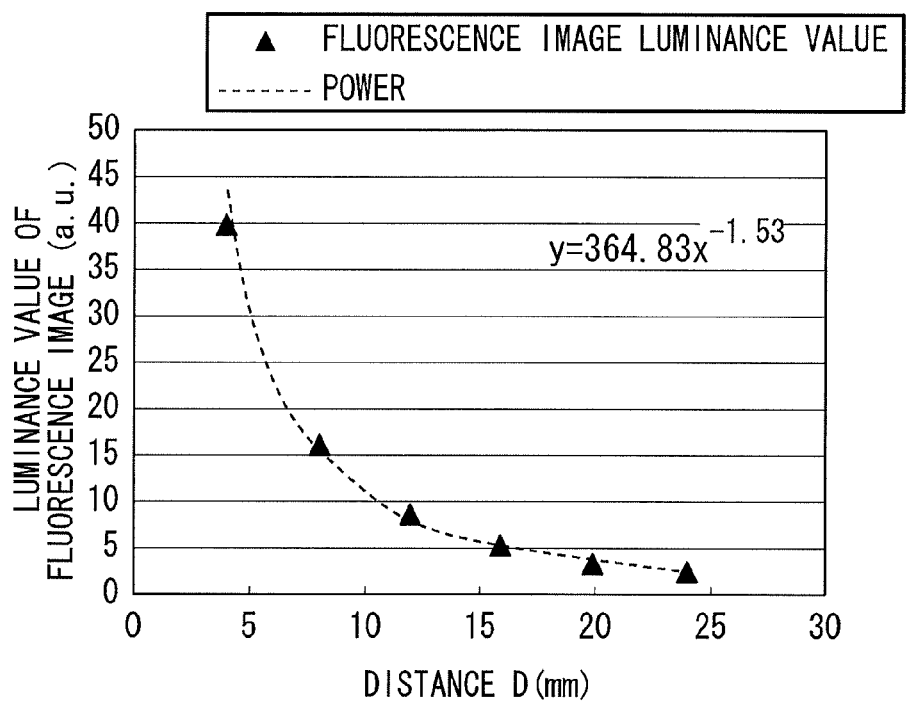
FIG. 55A is a graph showing a regression curve of FIG. 54A.
Figure 55B:
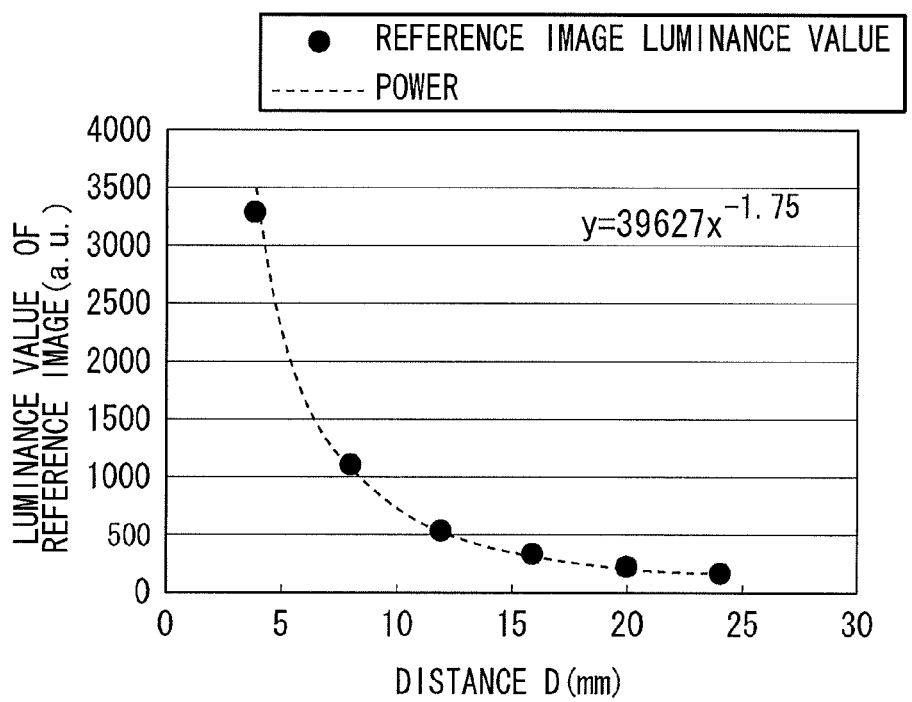
FIG. 55B is a graph showing a regression curve of FIG. 54E.

The fluorescence image preprocessing circuit 35C and the reference image reprocessing circuit 37C plot, relative to the observation distance Dn, the luminance values when the excitation light or the reflected light at a predetermined intensity is radiated to the observation target A, as shown in FIGS. 54A and 54B. For example, the observation distance Dn is changed to D0, D1, D2, D3, and D4 (D0<D1<D2<D3<D4), and regression curves as shown in FIGS. 55A and 55B are obtained by power approximation of the obtained distance characteristics, that is, by performing regression to power functions $D^\alpha$, and $D^\beta$. By doing so, the first exponent α and the second exponent β indicating the dependency on the observation distance Dn are obtained. In FIGS. 54A, 54B, 55A, and 55B, the vertical axis denotes the luminance value of the fluorescence image or the reference image, and the horizontal axis denotes the observation distance Dn.

Next, the fluorescence image preprocessing circuit 35C raises the luminance value of each pixel of the fluorescence image to the power of the reciprocal 1/α of the first exponent α based on the correction arithmetic expression (9) (step SF4). By doing so, the information of the exponentiation of the distance is removed, and a division fluorescence image with the luminance proportional to the change in the distance is acquired. In addition, the reference image reprocessing circuit 37C raises the luminance value of each pixel of the reference image to the power of the reciprocal 1/β of the second exponent β based on the correction arithmetic expression (10) (step SG4). By doing so, the information of the exponentiation of the distance is removed, and a division reference image with the luminance proportional to the change in the distance is acquired.

Figure 56A:
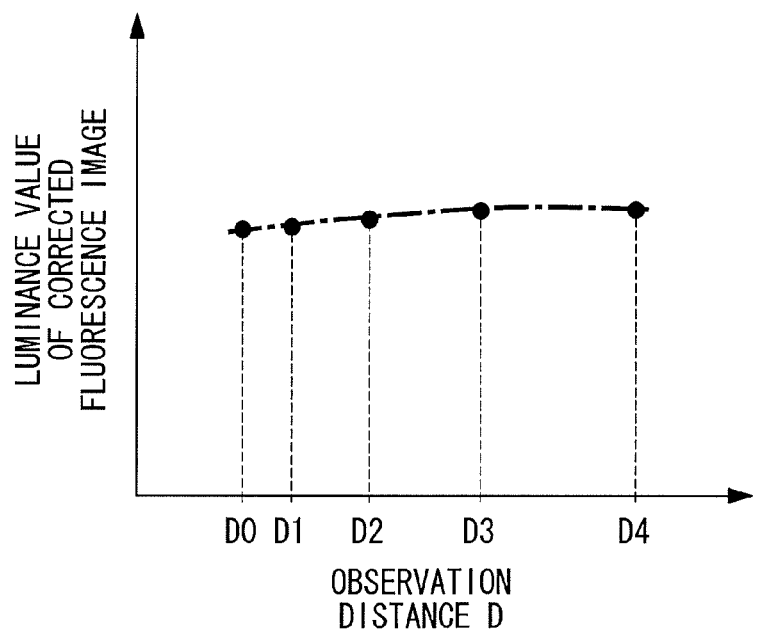
FIG. 56A is a graph showing a relationship between the luminance value of a corrected fluorescence image and the observation distance.

The division fluorescence image and the division reference image are transmitted to the division image generation section 64, and the division fluorescence image is divided by the division reference image (step SFG5). Since the division fluorescence image and the division reference image are related such that the luminance is proportional to the change in the distance as a result of the power arithmetic processing, dividing the division fluorescence image by the reference image can acquire a precisely corrected quantitative division image K in which the distance dependency is canceled as shown in FIG. 56A.

As described, according to the second preprocessing mode, the fluorescence image is corrected after making the information of the exponentiation of the distance included in the fluorescence image and the reference image uniform. In this way, a highly quantitative division fluorescence image can be acquired in which the distance dependency of the fluorescence image and the reference image is canceled. By doing so, the diseased portion can be accurately diagnosed based on the luminance value of the division fluorescence image.

Figure 56B:
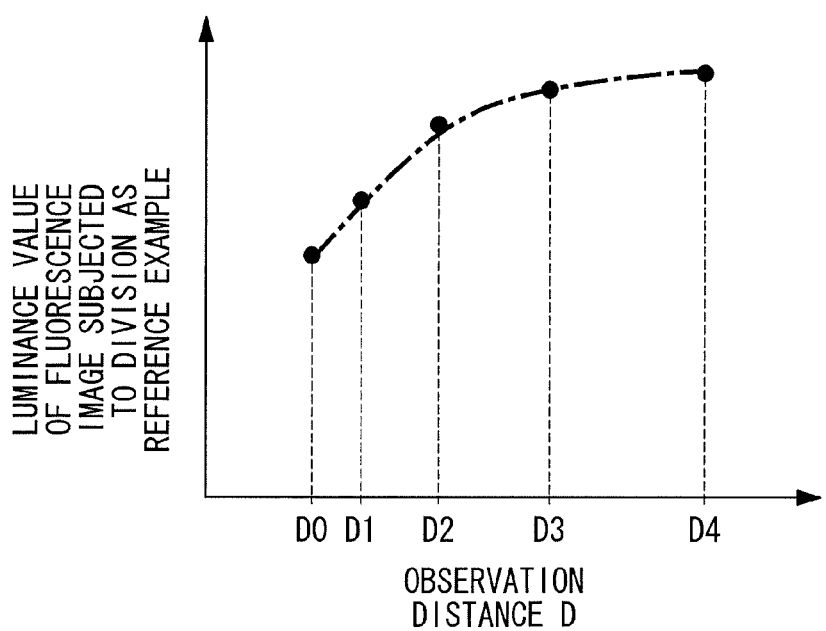
FIG. 56B is a graph showing a relationship between the luminance value of a corrected reference image and the observation distance.
Figure 57:
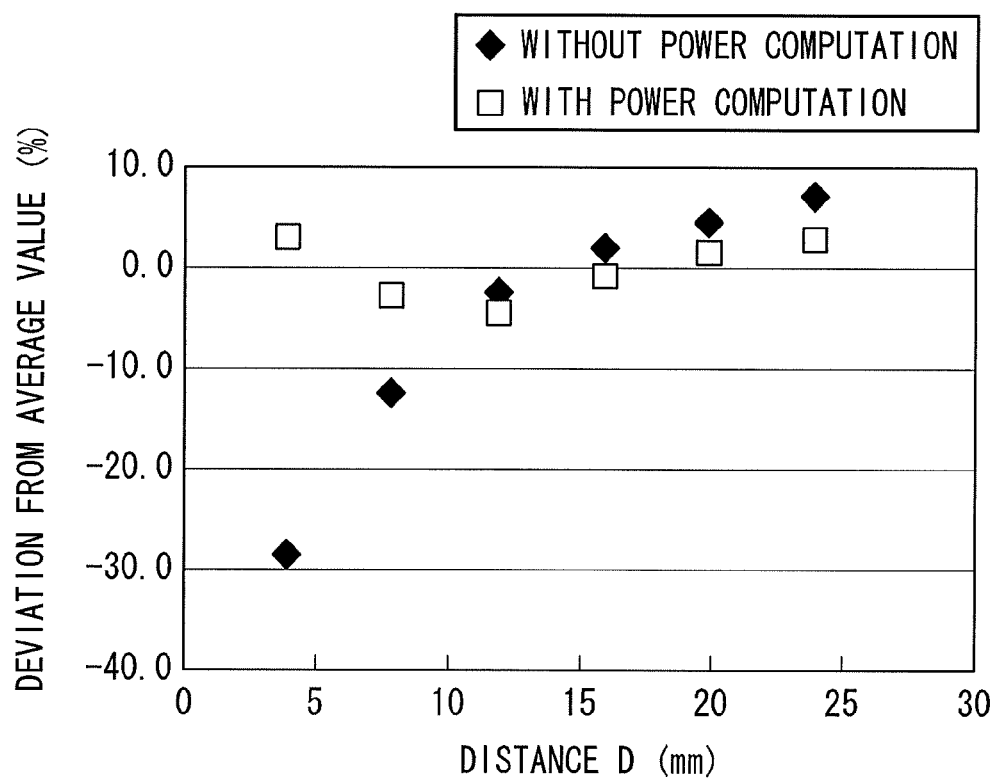
FIG. 57 is a graph comparing deviation of the luminance values of the fluorescence image when power arithmetic processing is applied and deviation of the luminance values of the fluorescence image when the power arithmetic processing is not applied.

As a reference example of the second preprocessing mode, FIG. 56B shows a relationship between the luminance value of the fluorescence image and the observation distance Dn when the fluorescence image is divided by the reference image without executing the power arithmetic processing. Since the fluorescence image and the reference image without the power arithmetic processing include information of the exponentiation of the distance, the distance dependency cannot be completely canceled just by simply dividing the fluorescence image by the reference image, and the influence of the distance remains in the divided fluorescence image. FIG. 57 shows a relationship between the observation distance Dn of the fluorescence image and the deviation from the average value of the luminance values when the power computation is performed and when the power computation is not performed. In FIG. 57, the vertical axis denotes the deviation (%) from the average value of the luminance values, and the horizontal axis denotes the observation distance Dn.

The second preprocessing mode can be modified as follows.

Figure 58:
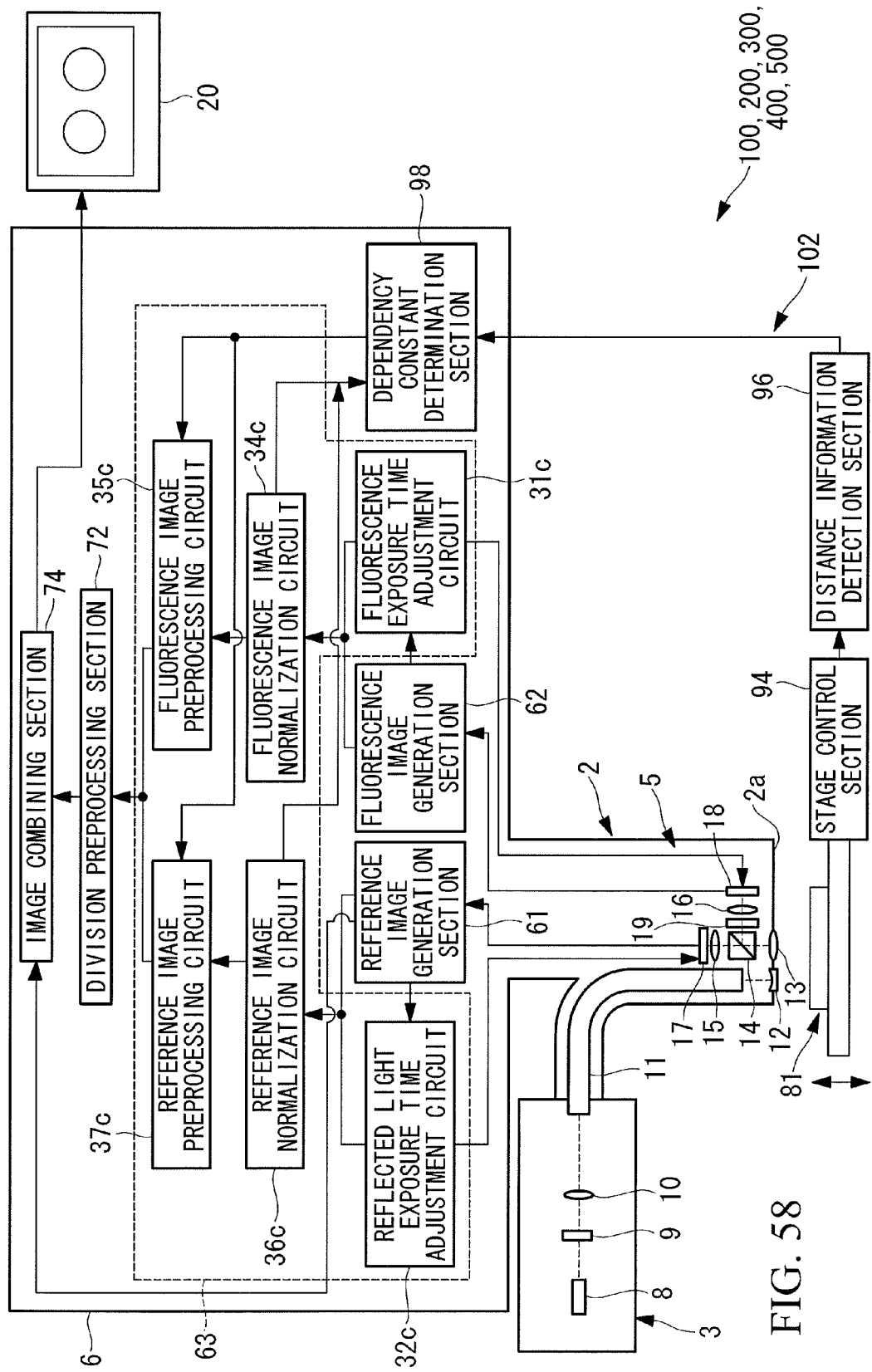
FIG. 58 is a block diagram showing a schematic configuration of a fluorescence observation apparatus including a modification of the preprocessing section of FIG. 48.

For example, in a first modification, the fluorescence observation apparatuses 100, 200, 300, 400, and 500 including the preprocessing section 63 provided with the second preprocessing mode may be combined with a calibration device 102 to form a fluorescence observation system as shown in FIG. 58. Note that part of the configuration is not illustrated in FIG. 58.

The calibration device 102 includes: a translation stage (observation state setting mechanism) 92 for arranging the standard sample 81 to face the tip 2a of the insertion portion 2 to change the observation distance Dn between the tip 2a of the insertion portion 2 and the standard sample 81; a stage control section 94 that controls the position of the translation stage 92; a distance information detection section 96 that detects the distance information of the observation distance Dn; and a dependency constant determination section (exponent calculation section) 98 that calculates the first exponent α and the second exponent β. The dependency constant determination section 98 is configured to calculate the first exponent α and the second exponent β based on the normalized fluorescence image and reference image transmitted from the fluorescence image normalization circuit 34C and the reference image normalization circuit 36C and based on the distance information detected by the distance information detection section 96.

Hereinafter, a calculation method of the first exponent α and the second exponent β by the dependency constant determination section 98 will be described with reference to a flowchart of FIG. 59.

The observation distance Dn is set by the operation of the stage control section 94 (step SH1), and the observation distance Dn at this time is detected by the distance information detection section 96 and transmitted to the dependency constant determination section 98. In this state, the illumination unit 20 radiates the reflected light including the excitation light to the standard sample 81, and the fluorescence and the reflected light are captured to acquire the fluorescence image and the reference image (step SH2). After the luminance values of the fluorescence image and the reference image are normalized by dividing the luminance values by the exposure time (steps SH3 and SH4), the fluorescence image and the reference image are transmitted to the dependency constant determination section 98, and the luminance values are plotted in association with the distance information (step SH5).

The stage control section 94 repeats steps SH1 to C6 multiple times for a predetermined number of times a (a is at least 2 or more) (step SH6). By doing so, for example, the observation distance Dn is changed to D0 and D1, and a regression curve is obtained by power approximation of the obtained distance characteristics, that is, by performing regression to power functions $D^\alpha$ and $D^\beta$ (step SH7). The first exponent α and the second exponent β indicating the dependency for the observation distance Dn are calculated (step SH8). By doing so, the dependency constant determination section 98 can determine the observation distance Dn and accurate exponents of the fluorescence image and the reference image corresponding to the observation distance Dn.

Note that in the present modification, the distance information detection section 96 may be omitted, and the distance information of the observation distance Dn may be manually input to the dependency constant determination section 98.

Figure 59:
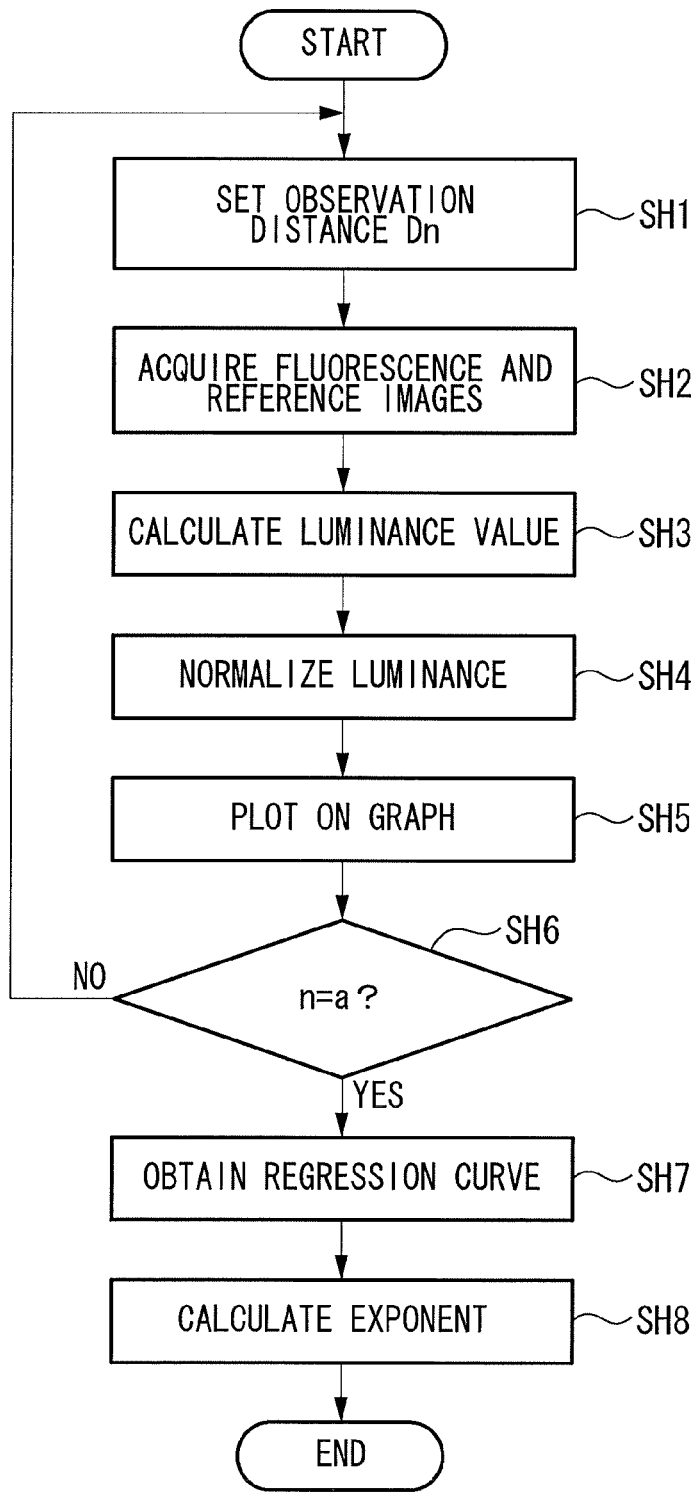
FIG. 59 is a flowchart showing a calculation method of an exponent of the fluorescence observation apparatus of FIG. 58.
Figure 60:
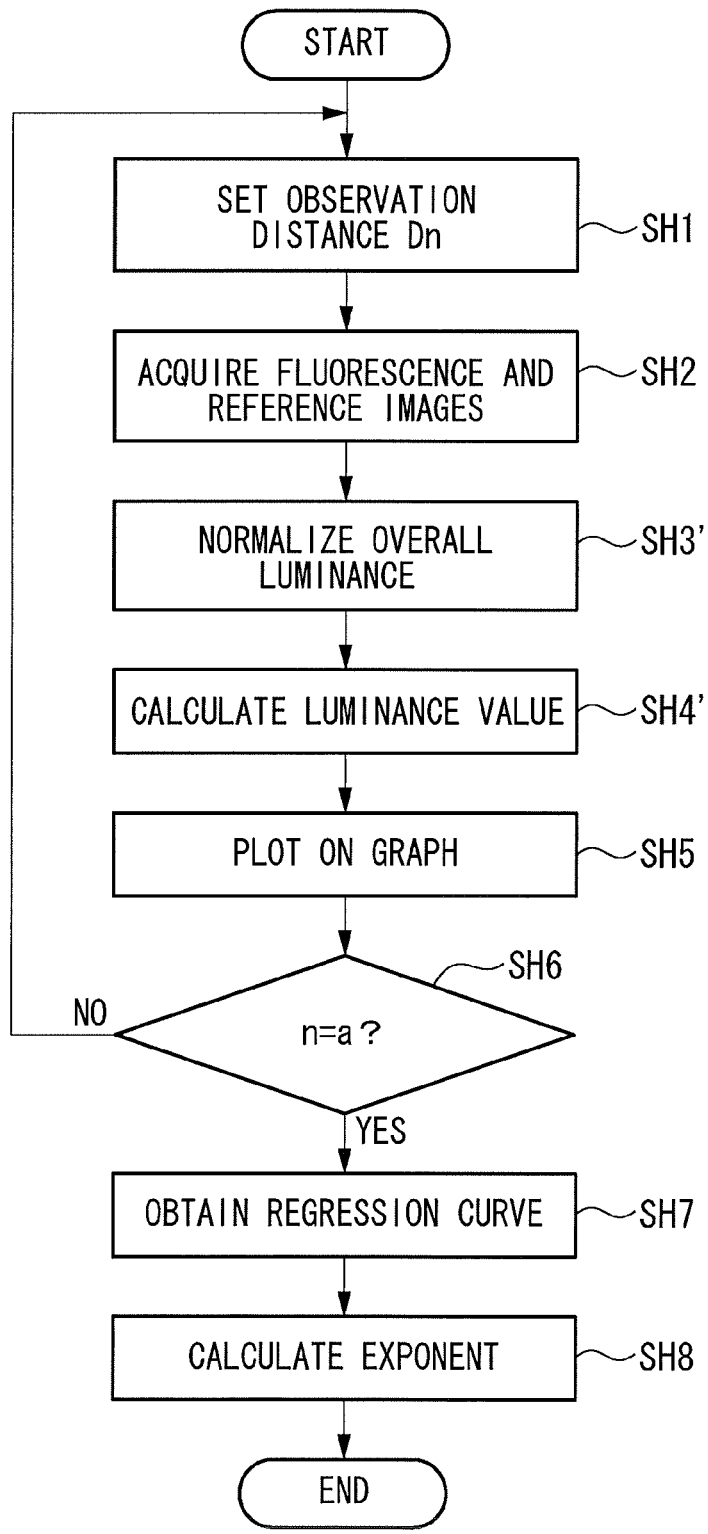
FIG. 60 is a flowchart showing image processing according to a modification of the second preprocessing mode.

Furthermore, in the second preprocessing mode, after the average values of the luminance values of the areas of interest of the fluorescence image and the reference image before the normalization are calculated (see step SH3 of FIG. 59), the average values are treated as the luminance values to divide the luminance values by the exposure time for the normalization (see SH14 of FIG. 59). Instead of this, for example, as shown in a flowchart of FIG. 60, after dividing the luminance of the entire fluorescence image and the luminance of the entire reference image by the exposure time for normalization (step SH3'), the average values of the luminance values of the areas of interest of the normalized fluorescence image and reference image may be calculated (step SH4').

Figure 61:
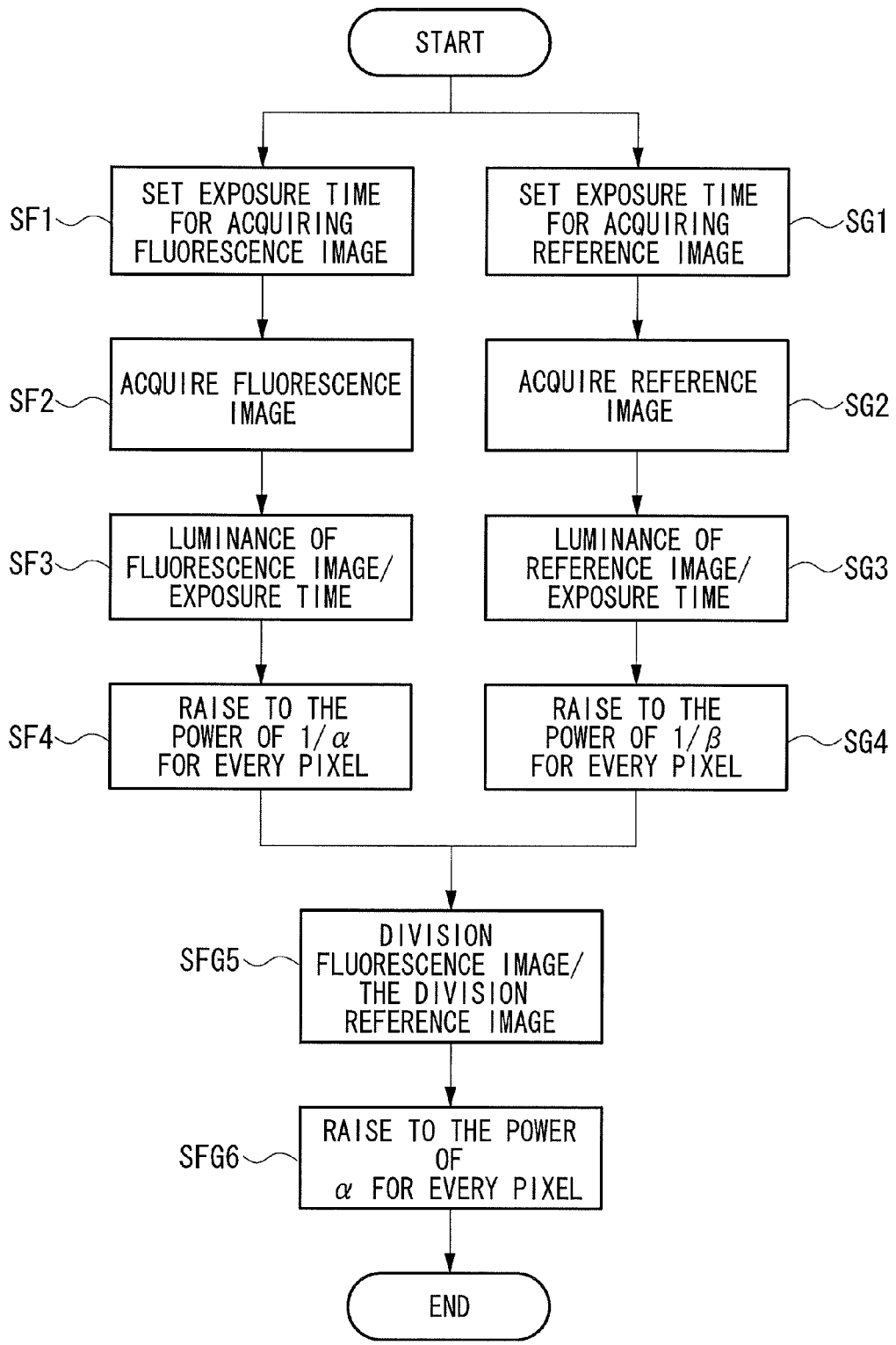
FIG. 61 is a flowchart of image processing according to a modification of the second preprocessing mode.
Figure 62:
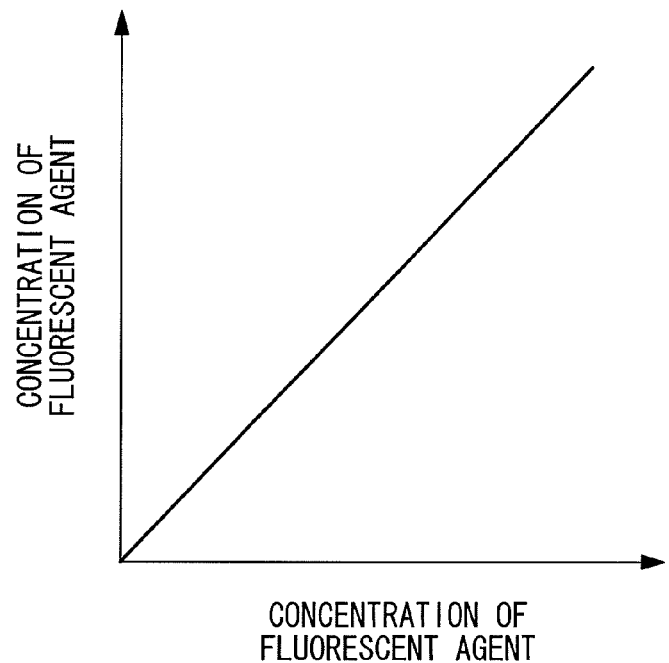
FIG. 62 is a graph showing a relationship between the luminance value and an amount of fluorescent agent present according to another modification of the second preprocessing mode.
Figure 63:
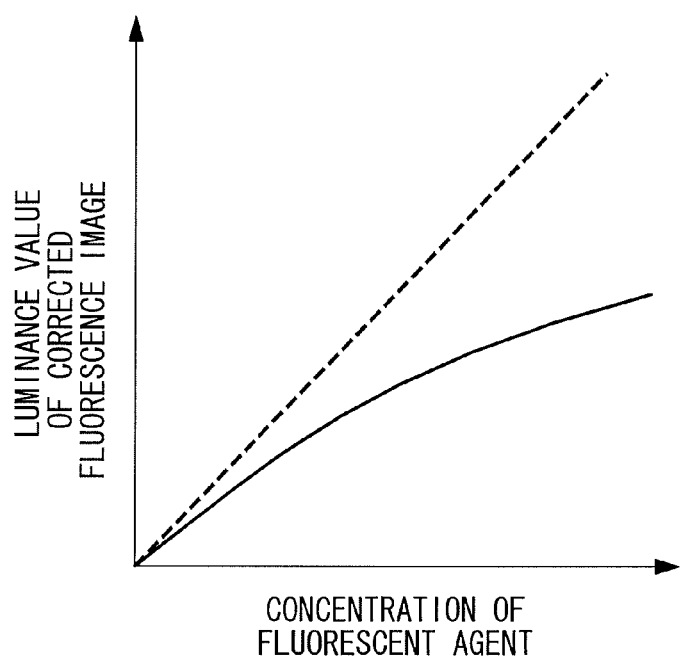
FIG. 63 is a graph showing a relationship between the luminance value and the amount of fluorescent agent present in a reference example of the fluorescence observation apparatus of FIG. 62.

In a modification of the second preprocessing mode, for example, the post-processing section 65 may further raise the luminance value of each pixel of the division image K acquired by the division image generation section 64 to the power of the first exponent α, in the image correction circuit 33C as shown in a flowchart of FIG. 61 (step SFG6). By doing so, the post-processing section 65 can reduce the distance dependency while maintaining the proportional relationship between the luminance value of the division image K and the amount of fluorescent agent present (that is, concentration of fluorescent agent) as shown in FIG. 62. Note that FIG. 63 illustrates a reference example indicating a relationship between the luminance value of the division image K and the concentration of the fluorescent agent when the post-processing section 65 does not raise the values to the power of the first exponent α.

Furthermore, in the preprocessing section 63 that executes the second preprocessing mode, the image correction circuit 33C includes the fluorescence image preprocessing circuit 35C. In another embodiment, for example, the fluorescence image preprocessing circuit 35C may be omitted, and the reference image preprocessing circuit 37C may raise the luminance values of the reference image to the power of a third exponent α/β (or −α/β), which is obtained by dividing the first exponent α by the second exponent β, to acquire the division reference image.

Figure 64:
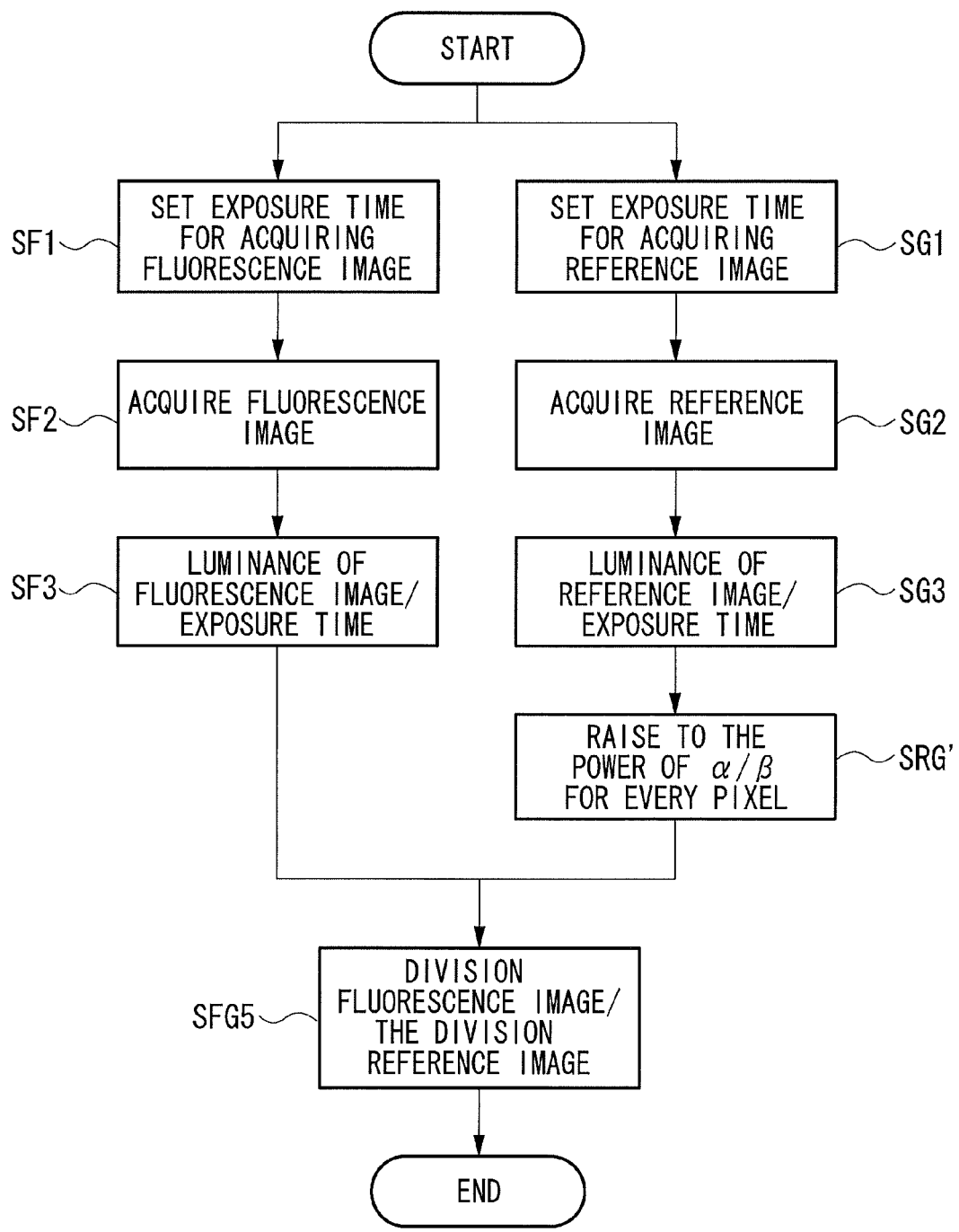
FIG. 64 is a flowchart of image processing according to another modification of the second preprocessing mode.

In this case, as shown in a flowchart of FIG. 64, the fluorescence image normalized by the fluorescence image normalization circuit 34C can be transmitted to the division image generation section 64, and the reference image preprocessing circuit 37C can perform the following power computation (step SG4').

$$RL_{after} = B \times RL_{before}^{z} \quad (11)$$

Here, $RL_{after}$ denotes the luminance value of the division reference image, $RL_{before}$ denotes the luminance value of the reference image, z denotes the third exponent (α/β or −α/β), α denotes the first exponent, β denotes the second exponent, and B denotes a constant.

By doing so, the image correction circuit 33C can accurately correct the influence of the distance just by performing the power computation once and can acquire the division image K in which the luminance value and the amount of fluorescent agent present are in a directly proportional relationship.

The second preprocessing mode can also be executed by another modification illustrated below.

Figures 65, 66:
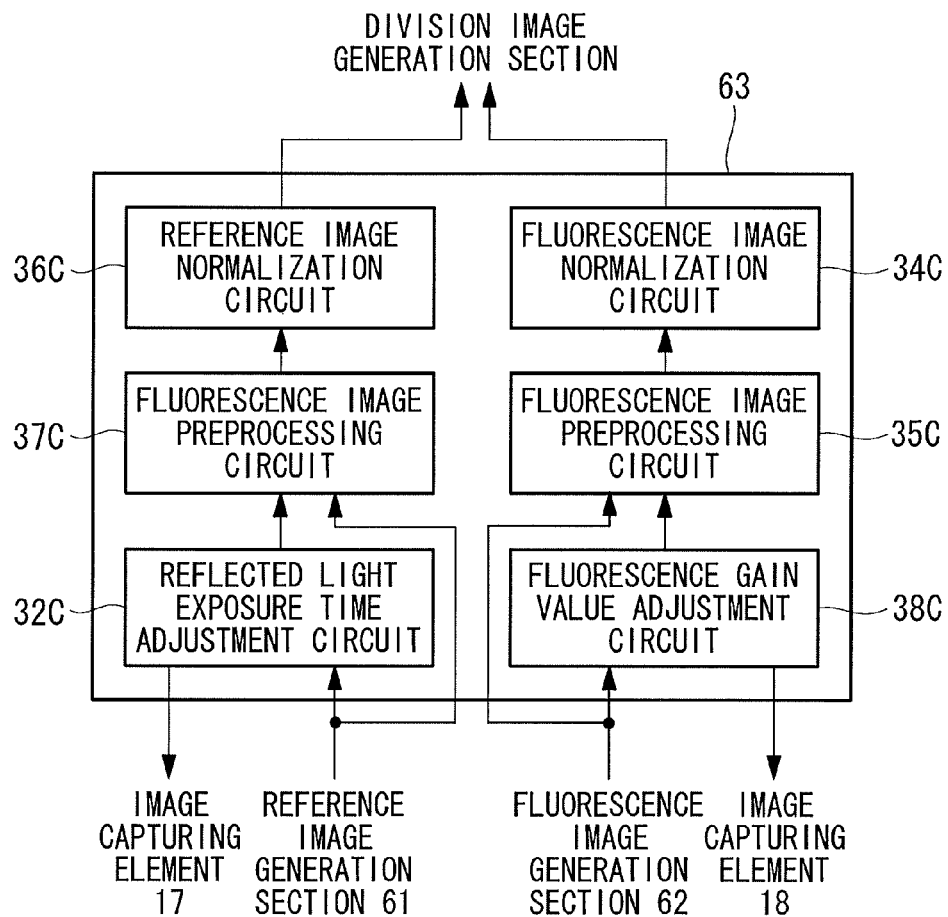
FIG. 65 is a block diagram showing a configuration of the preprocessing section according to the other modification of the second preprocessing mode.
FIG. 66 is a diagram showing an example of a gain conversion table included in a fluorescence image normalization circuit of the preprocessing section of FIG. 65.

As shown in FIG. 65, instead of the fluorescence exposure time adjustment circuit 31C, the preprocessing section 63 including a fluorescence gain value adjustment circuit 38C that adjusts a gain value (image capturing condition, gain factor) for amplifying the fluorescence image information acquired by the image capturing element 18 executes the other modification of the second preprocessing mode.

The fluorescence gain value adjustment circuit 38C is configured to adjust the gain value of the image capturing element 18 based on the luminance value of the fluorescence image generated by the fluorescence image generation section 62.

The gain value of the image capturing element 18 set by the fluorescence gain value adjustment circuit 38C is input to the fluorescence image normalization circuit 34C. In addition, the fluorescence image normalization circuit 34C includes a gain factor conversion table 287 associating the gain values and gain multiplication factors as shown in FIG. 66.

Figure 67:
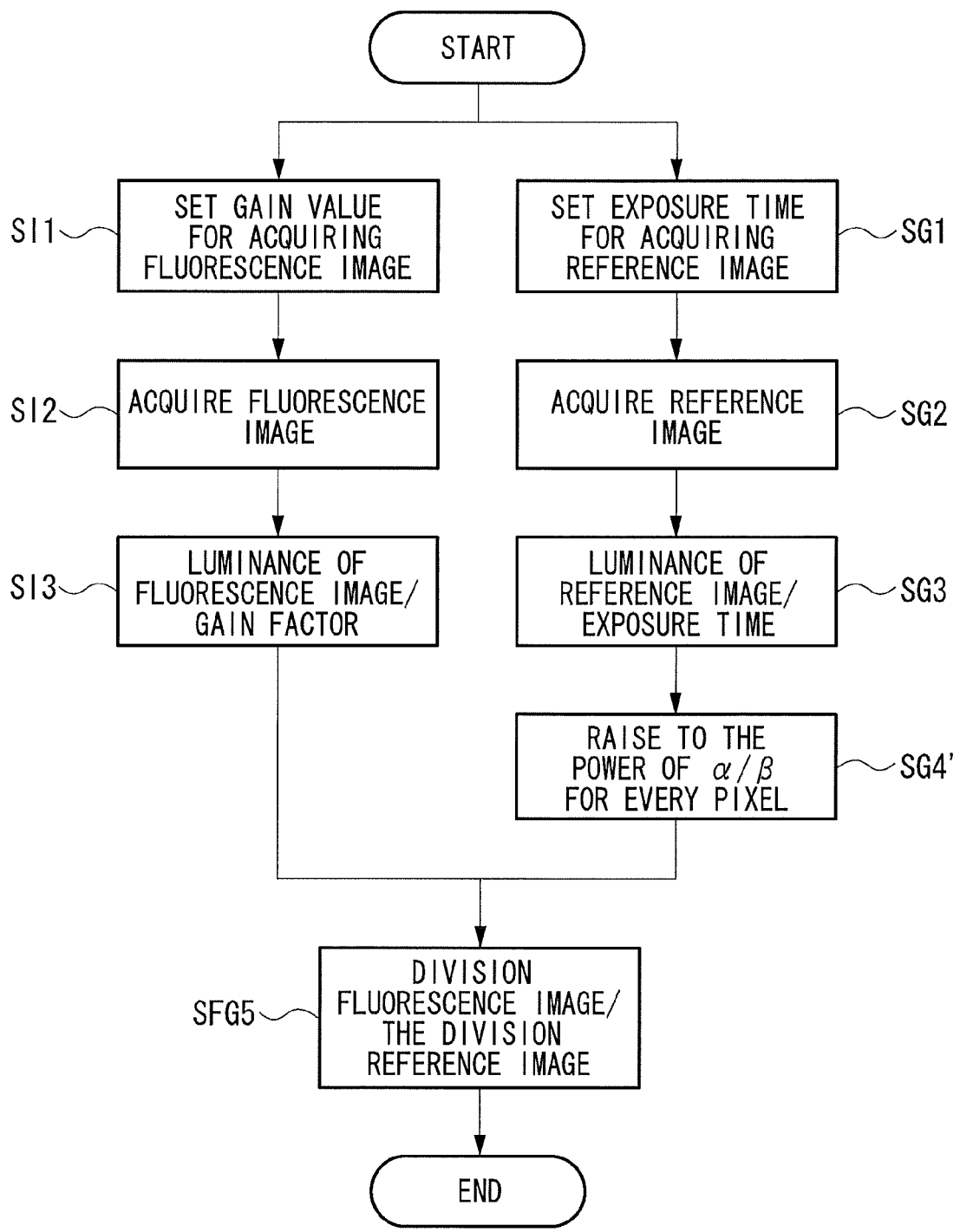
FIG. 67 is a flowchart of image processing in the preprocessing section of FIG. 65.

According to the first modification of the second preprocessing mode by the preprocessing section 63 with the configuration, as shown in a flowchart of FIG. 67, the fluorescence gain value adjustment circuit 38C sets the gain value of the image capturing element 18 based on the luminance value of the fluorescence image generated by the fluorescence image generation section 62 (step SI1). By doing so, the fluorescence image generation section 62 obtains a fluorescence image with an appropriate brightness, regardless of the incident light level of the fluorescence generated in the observation target A (step SI2).

The fluorescence image normalization circuit 34C divides the luminance value of the fluorescence image read from the fluorescence image generation section 62 by the gain multiplication factor corresponding to the gain value at the acquisition of the fluorescence image by the image capturing element 18 (step SI3). By doing so, the influence of the gain value in the fluorescence image is normalized, and the fluorescence image can be standardized at a constant luminance value per multiplication value.

Figure 68:
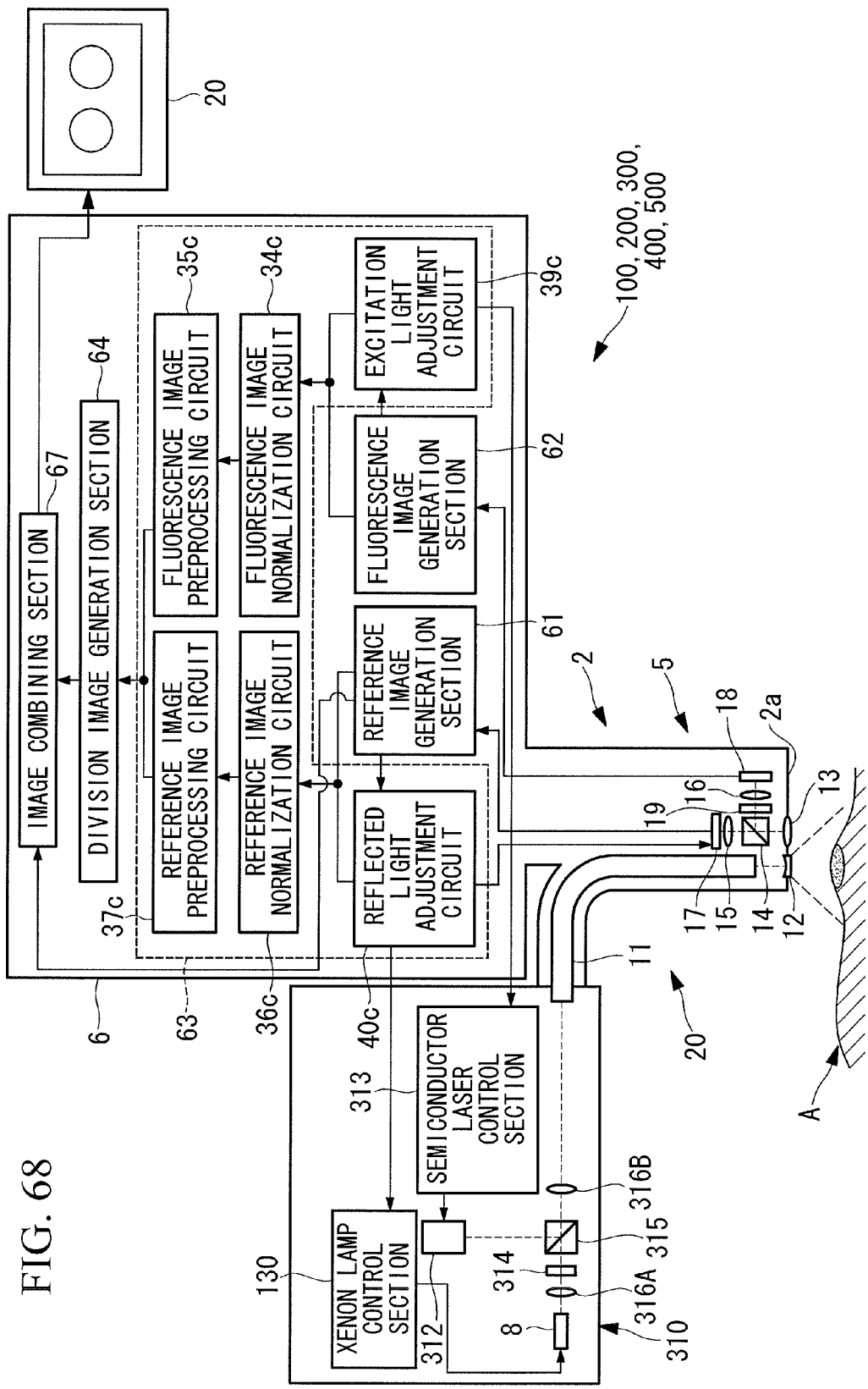
FIG. 68 is a block diagram showing a schematic configuration of a fluorescence observation apparatus according to another modification of the second preprocessing mode.

As shown in FIG. 68, another modification of the second preprocessing mode is executed by the fluorescence observation apparatuses 100, 200, 300, 400, and 500 including: a light source 310 further including a semiconductor laser 312; and the preprocessing section 63 including, in place of the fluorescence exposure time adjustment circuit 31C and the reflected light exposure time adjustment circuit 32C: an excitation light adjustment circuit (image capturing condition adjustment section) 354 that adjusts the light adjustment level of the excitation light emitted from the illumination unit 20; and a reflected light adjustment circuit (image capturing condition adjustment section) 358 that adjusts the light adjustment level of the illumination light.

The light source 310 includes: the xenon lamp 8; a xenon lamp control section 130; an infrared cut filter 314 that blocks the infrared light in the illumination light emitted from the xenon lamp 8 and that transmits only the reflected light; a semiconductor laser 312 that emits excitation light in the wavelength band of 740 nm; a semiconductor laser control section 313; and a light source dichroic mirror 315 that transmits the reflected light transmitted through the infrared cut filter 314 and that reflects the excitation light emitted from the semiconductor laser 312 to guide the reflected light and the excitation light to the same optical path. The infrared cut filter 14 can transmit only the reflected light in the wavelength band of 400 nm to 680 nm, for example. Note that reference sign 316A denotes a first coupling lens that focuses the reflected light transmitted through the infrared cut filter 314, and reference sign 316B denotes a second coupling lens that focuses the reflected light and the excitation light guided to the same optical path by the light source dichroic mirror 315.

The excitation light adjustment circuit 39C is configured to adjust the light adjustment level of the semiconductor laser 312 by the semiconductor laser control section 313 based on the luminance value of the fluorescence image generated by the fluorescence image generation section 62.

Similarly, the reflected light adjustment circuit 40C is configured to adjust the light adjustment level of the xenon lamp 8 by the xenon lamp control section 130 based on the luminance value of the reference image generated by the reference image generation section 61.

Figure 69:
FIG. 69 is a diagram showing an example of an excitation light intensity conversion table included in the fluorescence image normalization circuit of the fluorescence observation apparatus of FIG. 68.

A light adjustment level of the semiconductor laser control section 313 set by the excitation light adjustment circuit 39C is input to the fluorescence image normalization circuit 34C. In addition, the fluorescence image normalization circuit 34C includes an excitation light intensity conversion table 387 associating the light adjustment level and the excitation light intensity as shown in FIG. 69.

Similarly, a light adjustment level of the xenon lamp control section 130 set by the reflected light adjustment circuit 40C is input to the reference image normalization circuit 36C. In addition, the reference image normalization circuit 36C includes a reflected light intensity conversion table (not shown) associating the light adjustment level and the reflected light intensity (illumination light intensity). Note that the excitation light intensity and the reflected light intensity can be determined by intensity ratios based on minimum values.

In the fluorescence observation apparatuses 100, 200, 300, 400, and 500 with the configuration, the reflected light that is emitted from the xenon lamp 8, transmitted through the infrared cut filter 314, and focused by the first coupling lens 316A transmits through the light source dichroic mirror 315. The excitation light emitted from the semiconductor laser 312 is reflected by the light source dichroic mirror 315. The reflected light and the excitation light pass through the same optical path and enter a light guide fiber 22 after being focused by the second coupling lens 316B.

Figure 70:
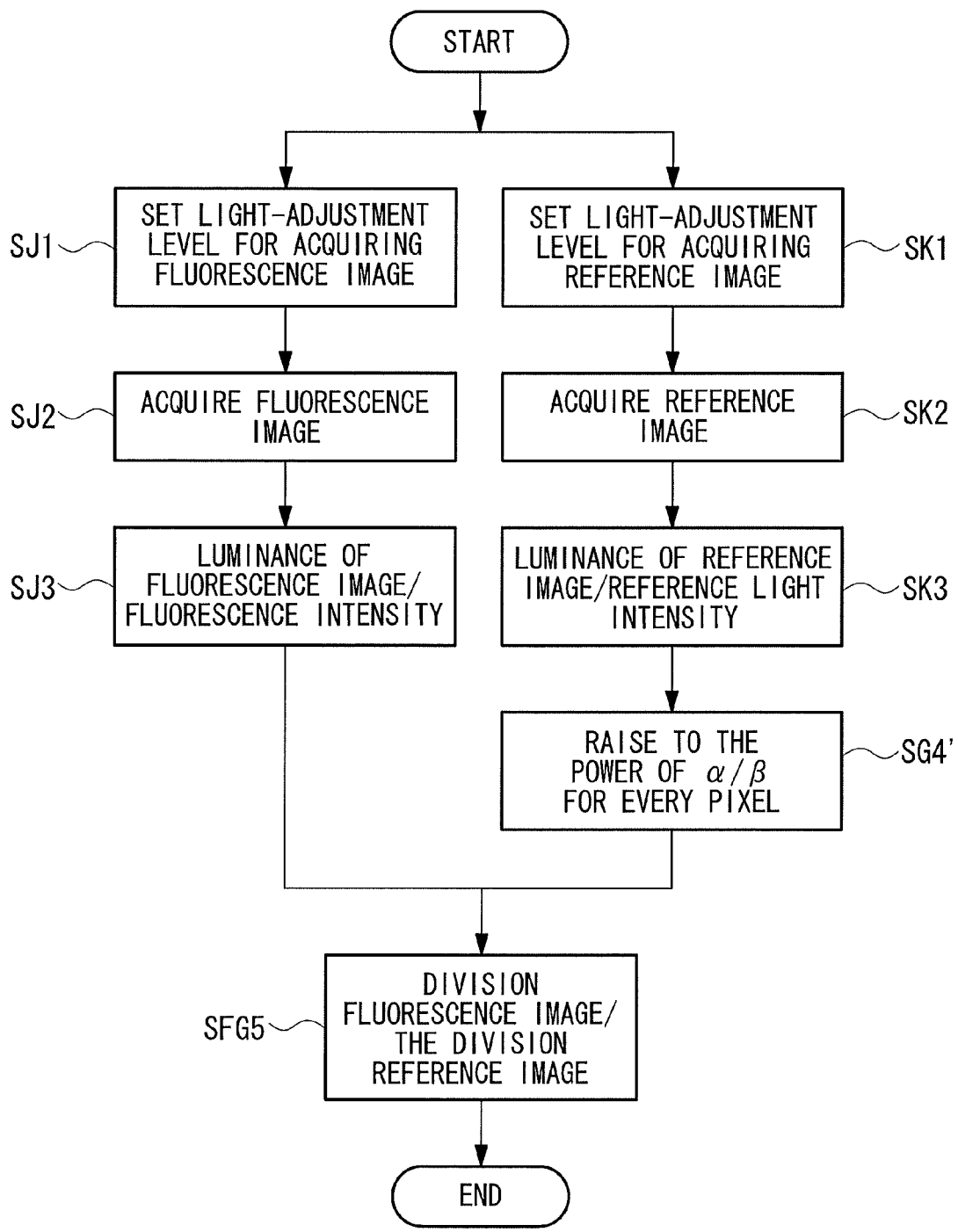
FIG. 70 is a flowchart of image processing in the image processing section of FIG. 68.

In the preprocessing section 63, as shown in a flowchart of FIG. 70, the excitation light adjustment circuit 39C sets the light adjustment level of the semiconductor laser control section 313 based on the luminance value of the fluorescence image generated by the fluorescence image generation section 62 (step SJ1). By doing so, the fluorescence image generation section 62 changes the intensity of the fluorescence generated in the observation target A to acquire a fluorescence image with an appropriate brightness (step SJ2).

Similarly, the reflected light adjustment circuit 40C sets the light adjustment level of the xenon lamp control section 130 based on the luminance value of the reference image generated by the reference image generation section 61 (step SK1). By doing so, the reference image generation section 61 changes the intensity of the reflected light returned from the observation target A to acquire a reference image with an appropriate brightness (step SK2).

Then, the fluorescence image normalization circuit 34C divides the luminance value of the fluorescence image read from the fluorescence image generation section 62 by the excitation light intensity corresponding to the light adjustment level of the semiconductor laser control section 313 (step SJ3). By doing so, the influence of the light adjustment level of the excitation light is normalized, and the fluorescence image can be standardized at a constant luminance value per excitation light intensity.

In addition, the reference image normalization circuit 36C divides the luminance value of the reference image read from the reference image generation section 61 by the reflected light intensity corresponding to the light adjustment level of the xenon lamp control section 130 (step SK3). By doing so, the influence of the light adjustment level of the illumination light is normalized, and the reference image can be standardized at a constant luminance value per reflected light intensity.

In the second preprocessing mode and the modification, the fluorescence image preprocessing circuit 35C and the reference image preprocessing circuit 37C may perform the power computation after subtracting noise components of the image capturing element 18 and the image capturing element 17. By doing so, the accuracy of the power computation can be improved.

Next, a first modification of the second preprocessing mode will be described.

Figure 71:
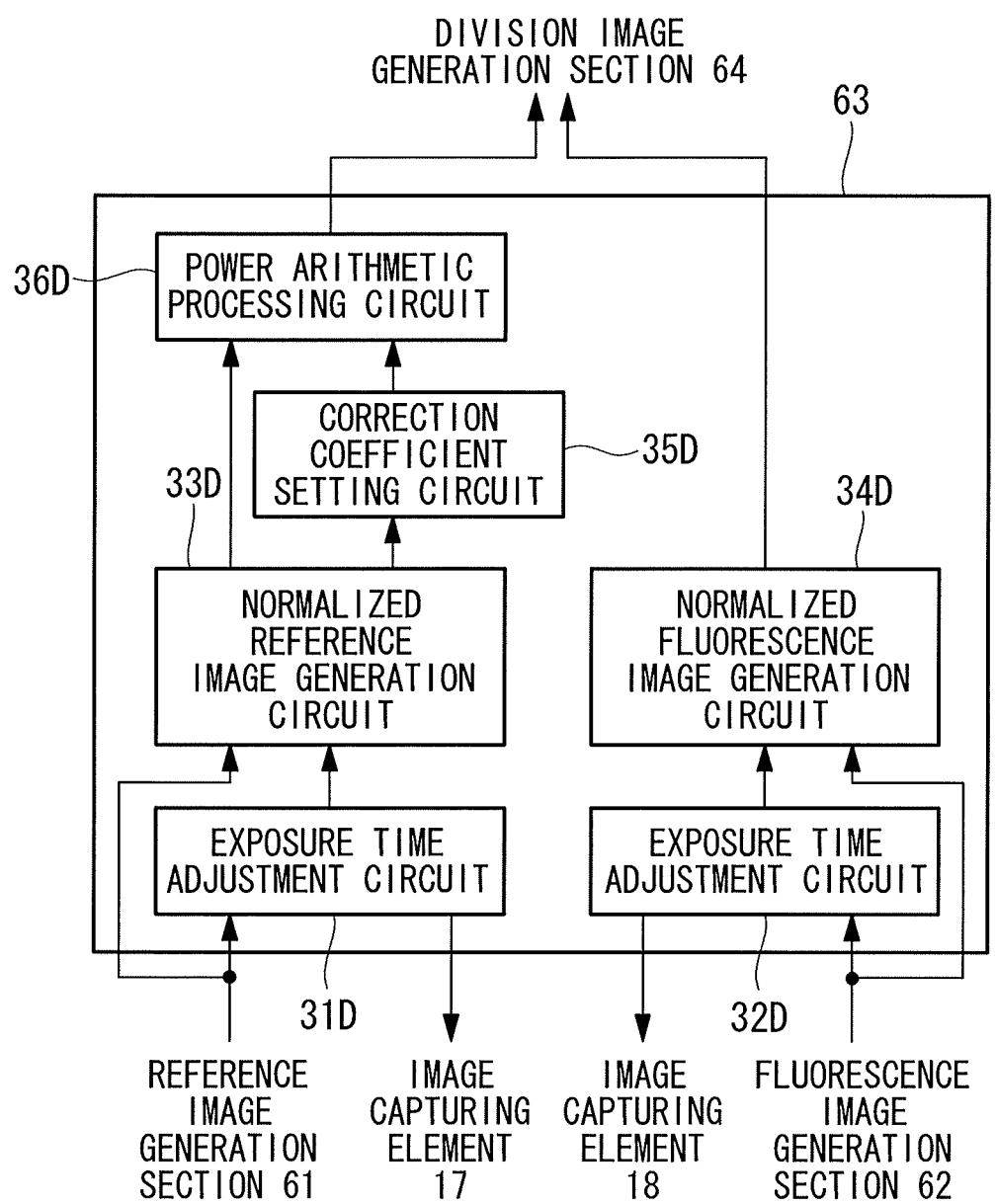
FIG. 71 is a block diagram showing a configuration of the preprocessing section that executes a first modification of the second preprocessing mode.

The first modification of the second preprocessing mode is a mode in which a correction coefficient that is set based on distance information between the image capturing element for reference image and the observation target is used as an index, and power computation is applied to the light intensity information of at least one of the reference image and the fluorescence image. As shown in FIG. 71, exposure time adjustment circuits 31D and 32D, a normalized reference image generation circuit 33D, a normalized fluorescence image generation circuit 34D, and a correction coefficient setting circuit 35D included in the preprocessing section 63 execute the first modification of the second preprocessing mode.

The exposure time adjustment circuits 31D and 32D calculate exposure times $S_3$ and $S_4$ of the image capturing elements 17 and 18 based on the reference image and the fluorescence image generated by the reference image generation section 61 and the fluorescence image generation section 22. The normalized reference image generation circuit 33D and the normalized fluorescence image generation circuit 34D generate a normalized reference image and a normalized fluorescence image from the reference image and the fluorescence image, respectively. The correction coefficient setting circuit 35D sets correction coefficients $\alpha$ and $\beta$ based on the normalized reference image generated by the normalized reference image generation circuit 33D. The power arithmetic processing circuit 36D uses the correction coefficients $\alpha$ and $\beta$ set by the correction coefficient setting circuit 35D as indices to perform power computation of the normalized reference image. The normalized fluorescence image generated by the normalized fluorescence image generation circuit 34D and the normalized reference image subjected to the power computation in the power arithmetic processing circuit 36D are input to the division image generation section 64 as a division reference image or a division fluorescence image.

The normalized reference image generation circuit 33D and the normalized fluorescence image generation circuit 34D are configured to divide the reference image and the fluorescence image by the exposure times $S_3$ and $S_4$ of the image capturing elements 17 and 18 adjusted by the exposure time adjustment circuits 31D and 32D to generate the normalized reference image and the normalized fluorescence image, respectively. By doing so, overall variations of the signal intensity of the reference image and the fluorescence image dependent on the exposure times $S_3$ and $S_4$ of the image capturing elements 17 and 18 are removed, and a normalized reference image and a normalized fluorescence image can be obtained.

The correction coefficient setting circuit 35D stores the indices $\alpha$ and $\beta$ as correction coefficients in association with distance information (hereinafter, called "observation distance information") from the tip surface 2a of the insertion portion 2 to the surface of the observation target A, for example. Specifically, since the signal intensity and the observation distance D in each pixel of the normalized reference image correspond on a one-to-one basis, the indices α and β are stored in association with the signal intensity.

Furthermore, in the present modification, a predetermined boundary value D(n) of the signal intensity is set, and two different correction coefficients $α_1$ and $α_2$ and two correction coefficients $β_1$ and $β_2$ around the boundary value D(n) are stored. Then, the correction coefficient setting circuit 35D compares the signal intensity and the boundary value D(n) of each pixel of the normalized reference image transmitted from the normalized reference image generation circuit 33D to set the first correction coefficients $α_1$ and $β_1$ if the signal intensity is smaller than the boundary value D(n) and to set the second correction coefficients $α_2$ and $β_2$ if the signal intensity is equal to or higher than the boundary value D(n).

In this case, the two correction coefficients α and β and the boundary value D(n) are determined as follows, through measurement prior to the fluorescence observation.

Figure 72:
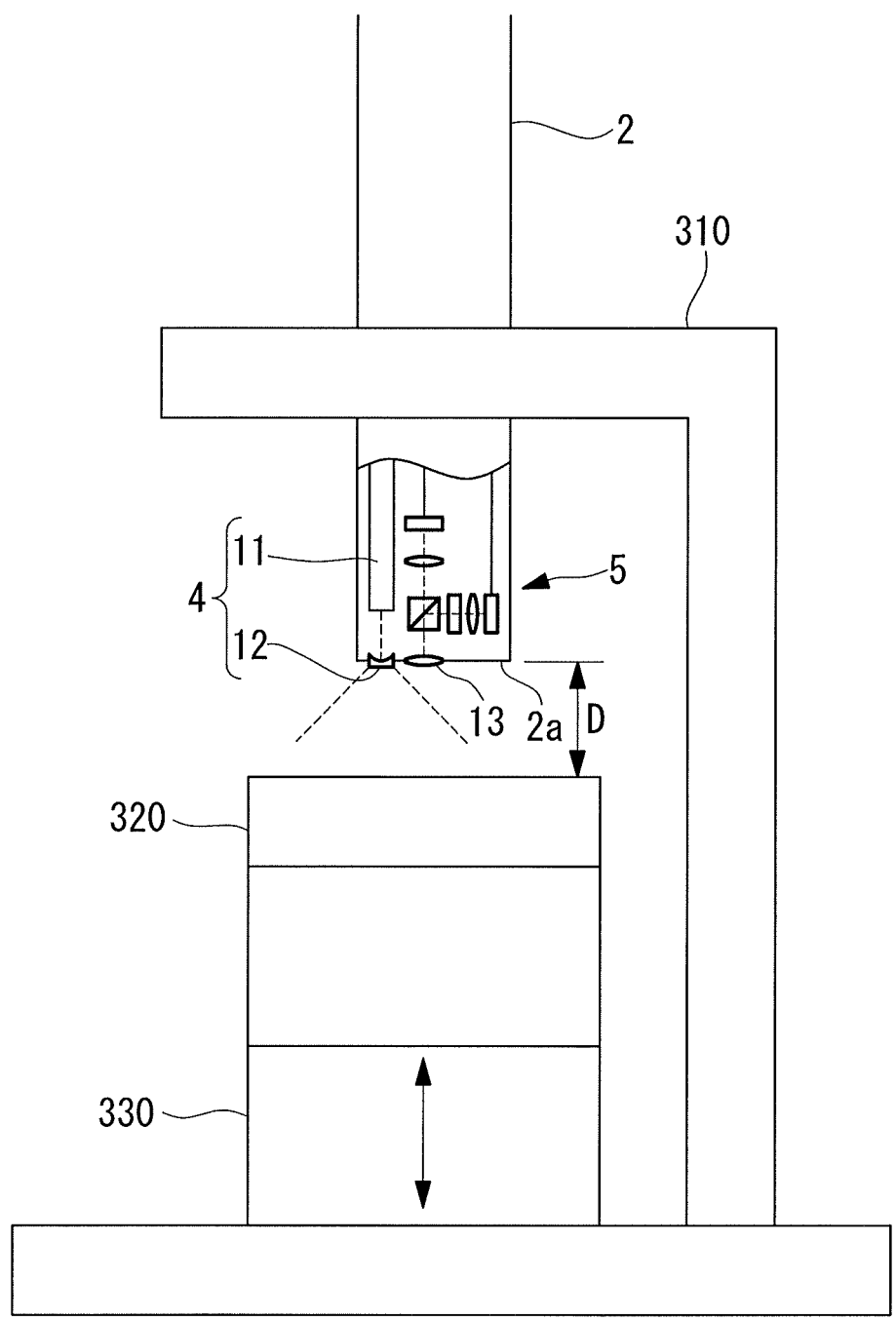
FIG. 72 is a diagram describing a process of setting correction coefficients and a boundary value in the preprocessing section of FIG. 71.

More specifically, to determine the correction coefficients α and β and the boundary value D(n), a holder 310 for fixing the insertion portion 2, a standard sample 320 facing, at the observation distance D, the tip surface 2a of the insertion portion 2 fixed to the holder 310, and a translation stage 330 for changing the observation distance D between the tip surface 2a of the insertion portion 2 and the standard sample 320 are prepared as shown in FIG. 72. A displacement sensor not shown, such as an encoder, is arranged on the translation stage 330.

A phantom with the same scattering or absorption characteristics as those of the living body to be observed may be used as the standard sample 320, or excised tissue of a human or an animal (such as a pig and a mouse) may be used as the standard sample 320.

Figure 73:
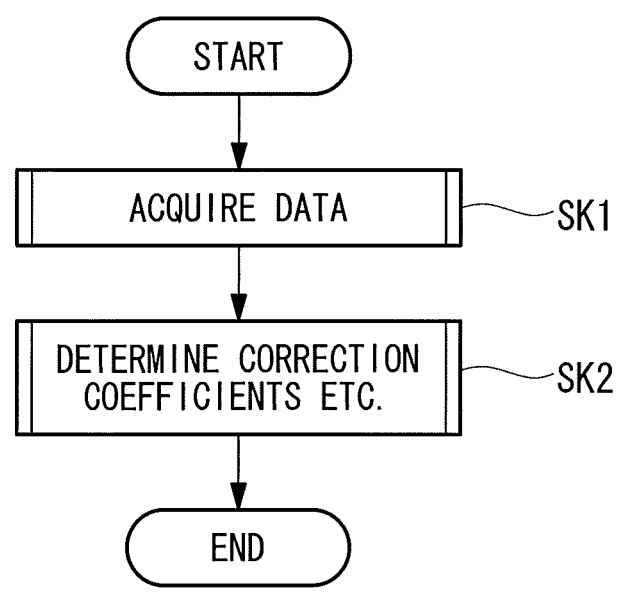
FIG. 73 is a flowchart showing the process of FIG. 72.
Figure 74:
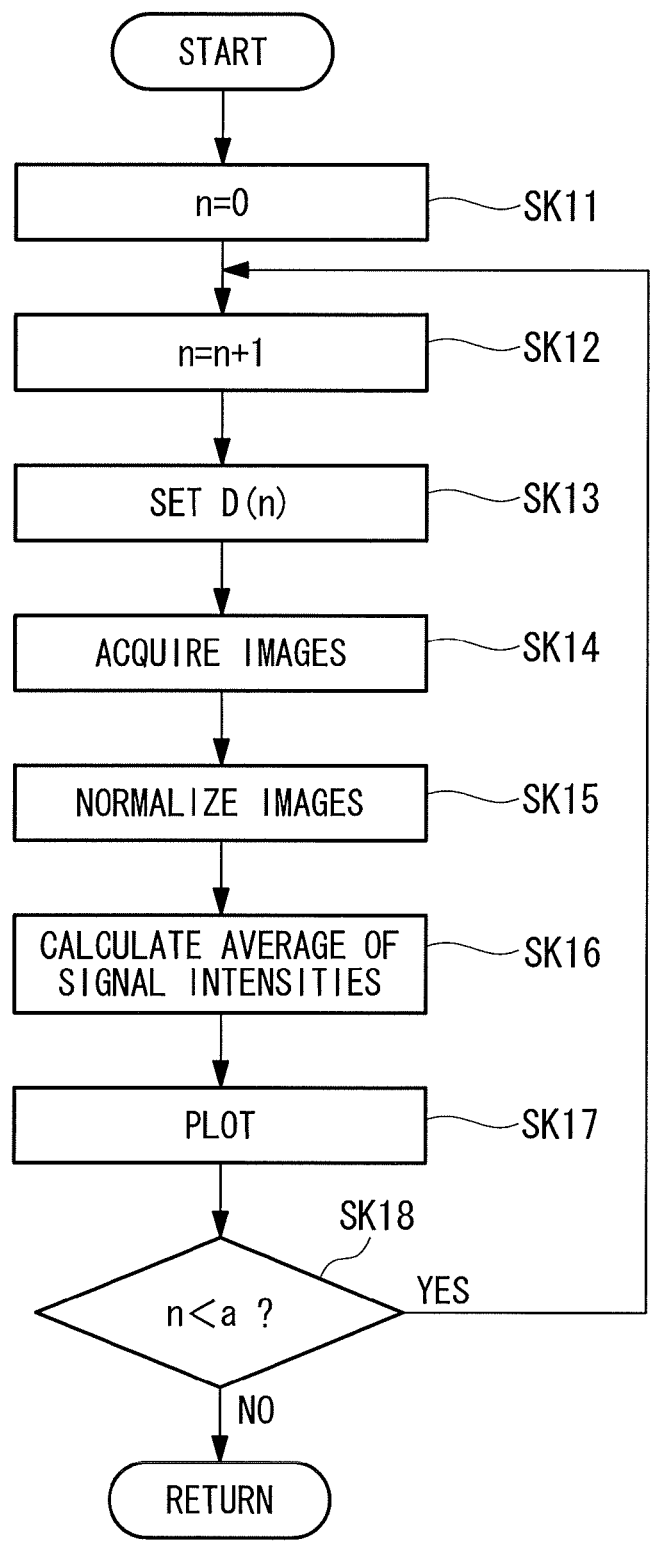
FIG. 74 is a flowchart showing a data acquisition step in the process of FIG. 73.
Figure 75:
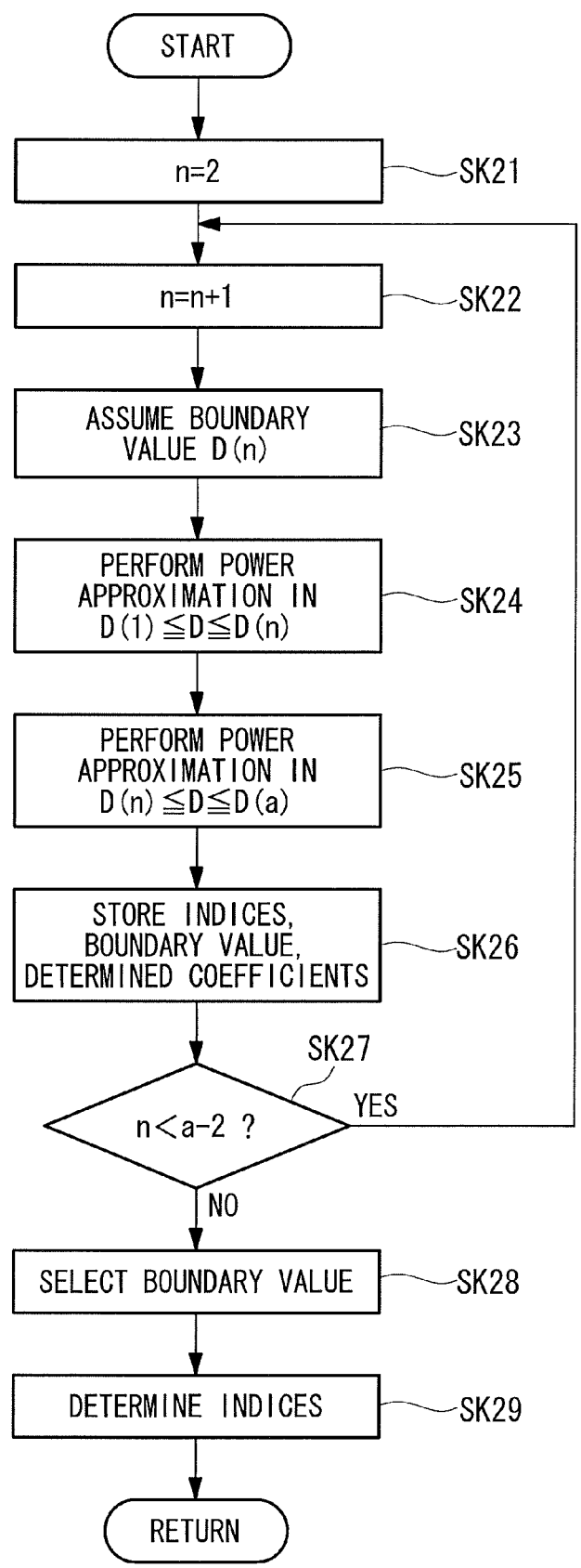
FIG. 75 is a flowchart showing a correction coefficient determination step in the process of FIG. 73.

A data acquisition step SK1 and a correction coefficient determination step SK2 are executed in accordance with flowcharts shown in FIGS. 73, 74, and 75.

Figure 76:
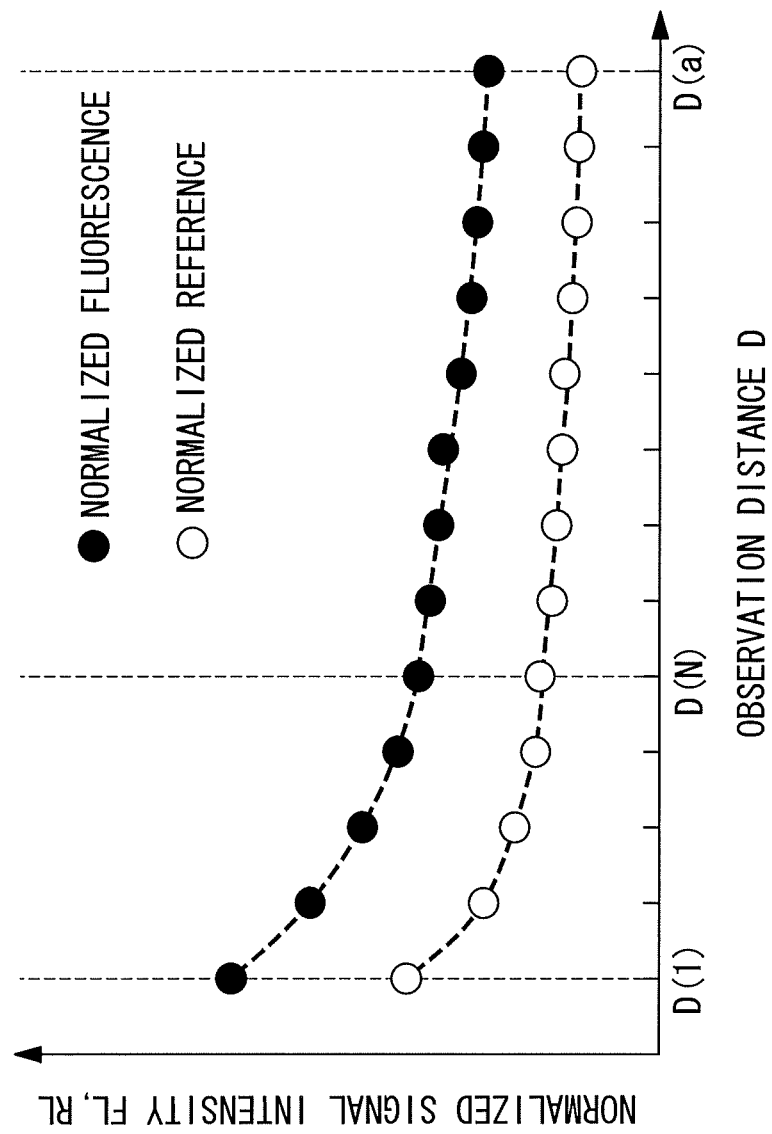
FIG. 76 is a plot diagram showing a relationship between observation distance and signal intensity acquired in the process of FIG. 73.

First, in the data acquisition step SK1, as shown in FIG. 73, n is initialized (steps SK11 and SK12), the translation state 330 is operated to accurately set the observation distance D(n) (n is a natural number) by the displacement sensor (step SK13), the reference image and the fluorescence image at this time are acquired (step SK14), the normalized reference image and the normalized fluorescence image are calculated (step SK15), the average value of the signal intensity in the predetermined area of interest is calculated (step SK16), and the average value is plotted as a value of the signal intensity relative to the observation distance D(n) (step SK17). This operation is repeated (step SK18) to obtain a plot of a plurality of points (a points) as shown in FIG. 76.

In this case, the area of interest may be set to a certain size regardless of the observation distance D if the fluorescence intensity in the standard sample 320 is constant. When the surface of the standard sample 320 has irregularities or when the fluorescence distribution in the standard sample 310 is non-uniform, it is preferable to always acquire the signal intensity of the same area by reducing the size of the area of interest with an increase in the observation distance D.

Next, in the correction coefficient determination step SK2, n=3 is first set (steps SK21 and SK22), and the observation distance D(n) of an n-th point is set as a boundary value (step SK23), as shown in FIG. 75. The reason that D(3) is set as the first boundary value is that data of equal to or higher than three points is necessary to use the power approximation based on the least squares method or the like.

Then, power approximation is performed in an area of the observation distance D(1) to D(n) and in an area of D(n) and D(a) (steps SK24 and SK25) to calculate indices, and the indices are stored along with the determined coefficients $R^2$ and the boundary value D(n) (step SK26).

Then, n is incremented 1 by 1 (step SK22), and the operation is repeated until N=a−2 (step SK27) to obtain a data table shown in FIG. 77. Then, a combination of the boundary value D(n) and the indices α and β with which the sum of the determined coefficients $R^2$ is closest to 4 is selected from the data table (step SK28), and the combination is stored in the correction coefficient setting circuit 35D (step SK29).

In the present modification, the index α obtained for the fluorescence image is divided by the index β obtained for the reference image, and an index α/β is stored as a correction coefficient.

The power arithmetic processing circuit 36D is configured to use the correction coefficient α/β set in the correction coefficient setting circuit 35D as an index to apply power arithmetic processing to the intensity signal (light intensity information) in each pixel of the normalized reference image to generate a division reference image. The division reference image generated in the power arithmetic processing circuit 36D is input to the division image generation section 64. On the other hand, as for the fluorescence image, the normalized fluorescence image is input to the division image generation section 64 as a division fluorescence image.

Note that in the description of the present preprocessing mode, when the normalized fluorescence image is input to the division image generation section 64 as a division fluorescence image without the power arithmetic processing, the input normalized fluorescence image will be called a division fluorescence image. Similarly, when the normalized reference image is input to the division image generation section 64 as a division reference image without the power arithmetic processing, the input normalized reference image will be called a division reference image.

According to the second preprocessing mode by the preprocessing section 63 with the configuration, when the image capturing elements 17 and 18 generate the reference image and the fluorescence image, the exposure time adjustment circuits 31D and 32D calculate the exposure times $S_3$ and $S_4$ of the image capturing elements 17 and 18 based on the generated reference image and fluorescence image to automatically adjust the exposure of the image capturing elements 17 and 18. The reference image, the fluorescence image, and the exposure times $S_3$ and $S_4$ of the image capturing elements 17 and 18 in capturing the images are transmitted to the image correction section 64.

In the preprocessing section 63, the normalized reference image generation circuit 33D divides the reference image by the exposure time $S_3$ of the image capturing element 17 to generate a normalized reference image, and the normalized fluorescence image generation circuit 34D divides the fluorescence image by the exposure time $S_4$ of the image capturing element 18 to generate a normalized fluorescence image.

Then, based on the signal intensity of each pixel of the normalized reference image, the correction coefficient setting circuit 35D sets the correction coefficients α and β, and the power arithmetic processing circuit 36D uses the correction coefficient an set for each pixel as an index to perform power computation of the signal intensity of each pixel based on the index to generate a division reference image.

Subsequently, the division reference image and the normalized fluorescence image as a division fluorescence image output from the normalized fluorescence image generation circuit 34D are input to the division image generation section 64, and the division fluorescence image is divided by the division reference image to generate a division image.

In this way, according to the first modification of the second preprocessing mode, the predetermined observation distance D is set as the boundary value D(n), and the division reference image subjected to the power computation using, as the indexes, the correction coefficients $\alpha_1$, $\beta_1$, $\alpha_2$, and $\beta_2$ that are different before and after the boundary value D(n) is used to divide the division fluorescence image. As a result, there is an advantage that a highly quantitative division image can be obtained even if the observation distance D largely fluctuates.

Figure 78:
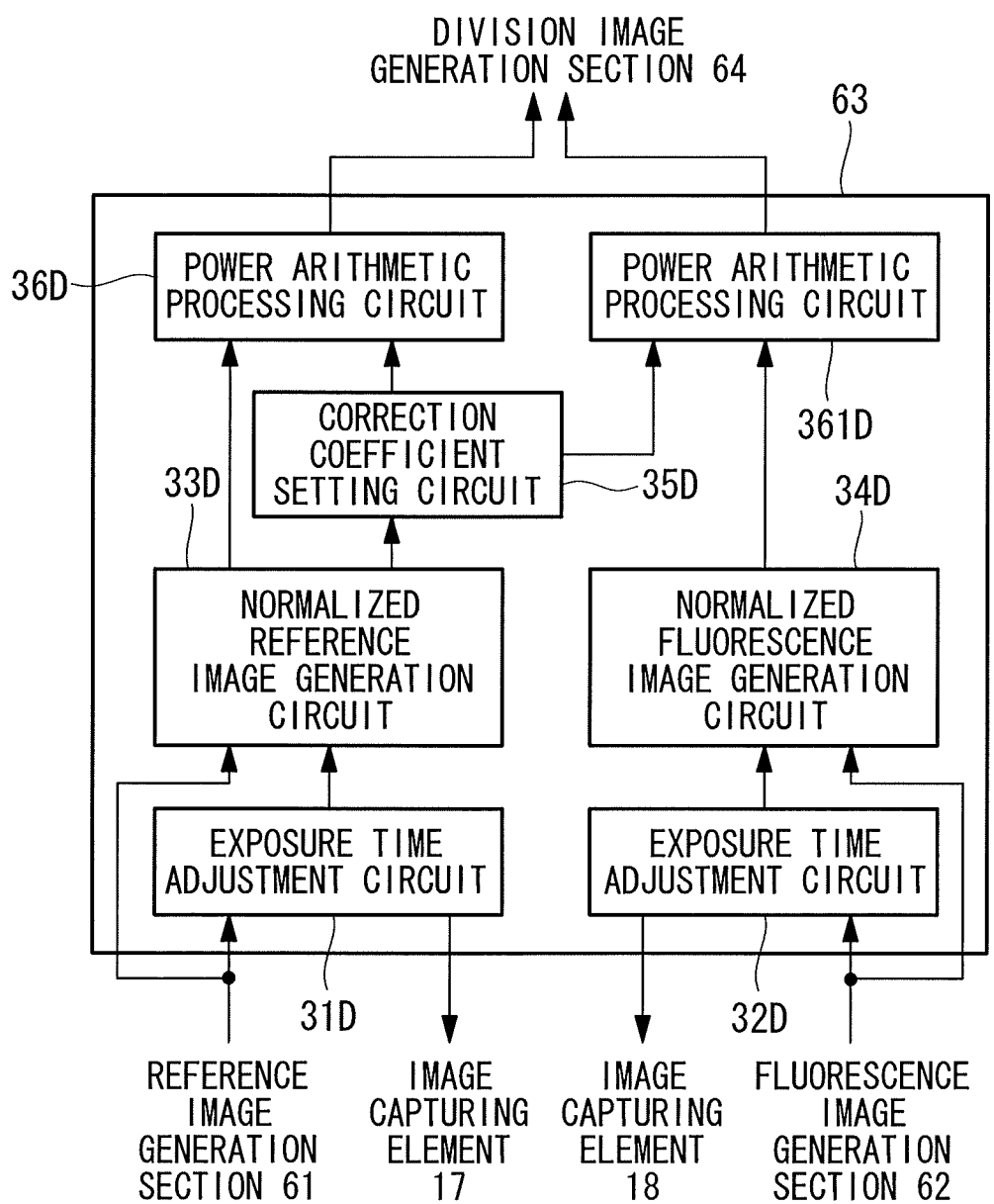
FIG. 78 is a block diagram showing a modification of the preprocessing section of FIG. 71.

Furthermore, in the first modification of the second preprocessing mode, the indexes $\alpha$ and $\beta$ calculated for both of the signal intensity of the normalized fluorescence image and the signal intensity of the normalized reference image are used to perform the power computation of only the signal intensity of the normalized reference image. Therefore, compared to when the power computation is performed for both of the normalized fluorescence image and the normalized reference image, the amount of calculation is reduced, and there is an advantage that rapid calculation can be performed. Instead of this, as shown in FIG. 78, a power arithmetic processing circuit 361D may also be arranged for the normalized fluorescence image, and the indexes $\alpha$ and $\beta$ set in the correction coefficient setting circuit 35D may be used to apply power computation of $1/\beta$ to the normalized reference image and to apply power computation of $1/\alpha$ to the normalized fluorescence image to obtain the division fluorescence image.

Furthermore, in combination with the first modification of the second preprocessing mode, the post-processing section 65 may perform power computation of raising the normalized fluorescence image to the power of the obtained index $\alpha$ for each pixel of the division image obtained by dividing the division fluorescence image by the division reference image in the division image generation section 64. By doing so, the signal intensity of each pixel and the amount of fluorescence present in the observation target A can be proportional, and further quantitative observation can be performed.

Instead of this, a correspondence table (conversion table) of the signal intensity of the division image and the fluorescence concentration may be included, and the fluorescence concentration of a specific area may be displayed on the image.

Figure 79:
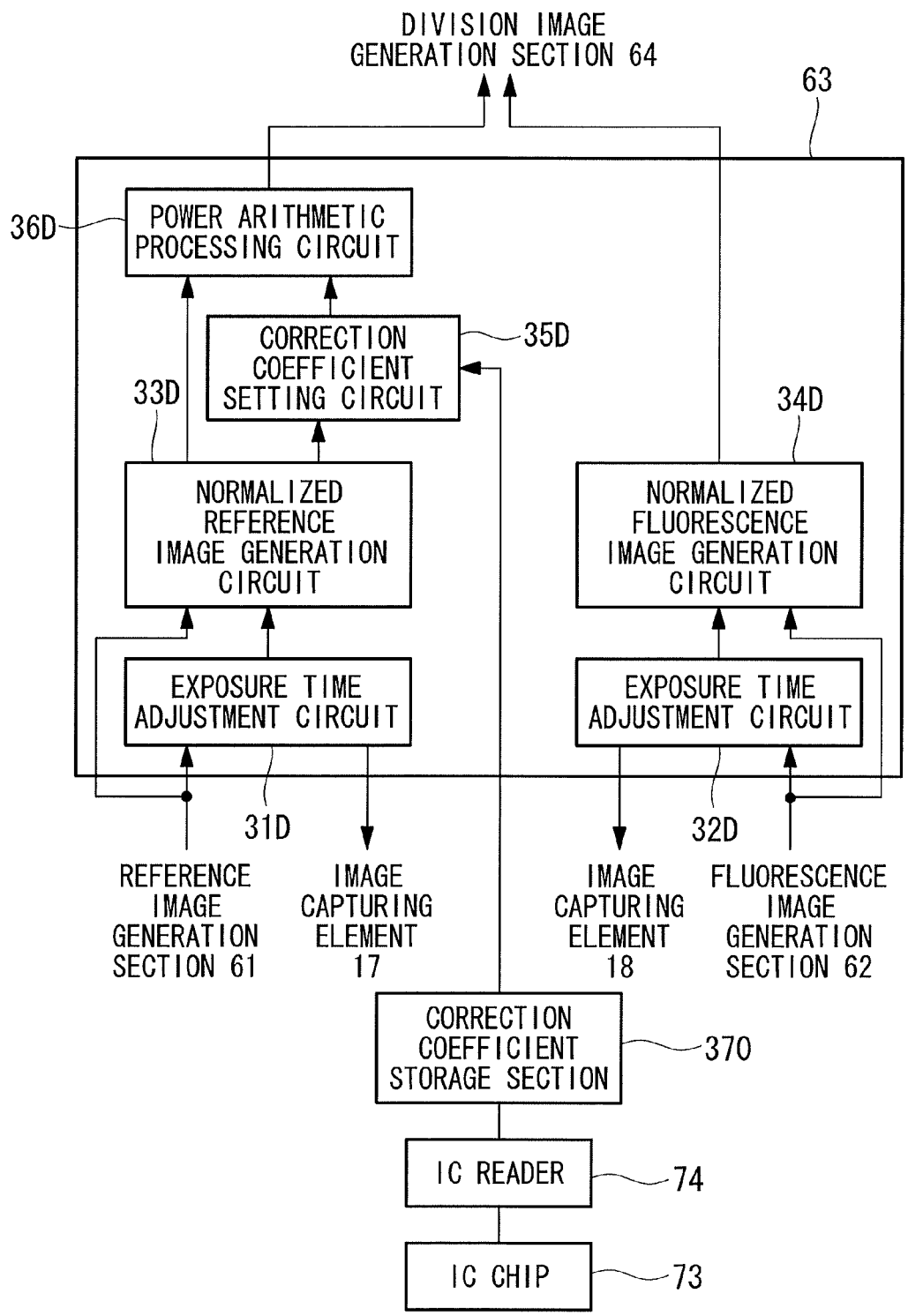
FIG. 79 is a partial block diagram showing a modification of the fluorescence observation apparatus according to the fifth embodiment including the preprocessing section of FIG. 71.

In addition, when the fluorescence observation apparatus 500 according to the fifth embodiment shown in FIG. 5 is provided with the first modification of the second preprocessing mode, the image processing section 6 may include a correction coefficient storage section 370 that stores the correction coefficients $\alpha$ and $\beta$ and the boundary value D(n) in association with the identification information of the insertion portion 2 as shown in FIG. 79. By doing so, when the insertion portion 2 is exchanged, the IC reader 74 reads out the identification information stored in the IC chip 73 of the insertion portion 2, and the correction coefficients $\alpha$ and $\beta$ and the boundary value D(n) stored in the correction coefficient storage section 370 in association with the identification information of the insertion portion 2 are read out and stored in the correction coefficient setting circuit 35D. In this case, the correction coefficient storage section 370 may be included in the correction condition setting sections 66, 66', and 66".

By doing so, there is an advantage that the variations in the correction coefficient due to the individual differences of the insertion portion 2 can be calibrated with high precision.

Figure 80:
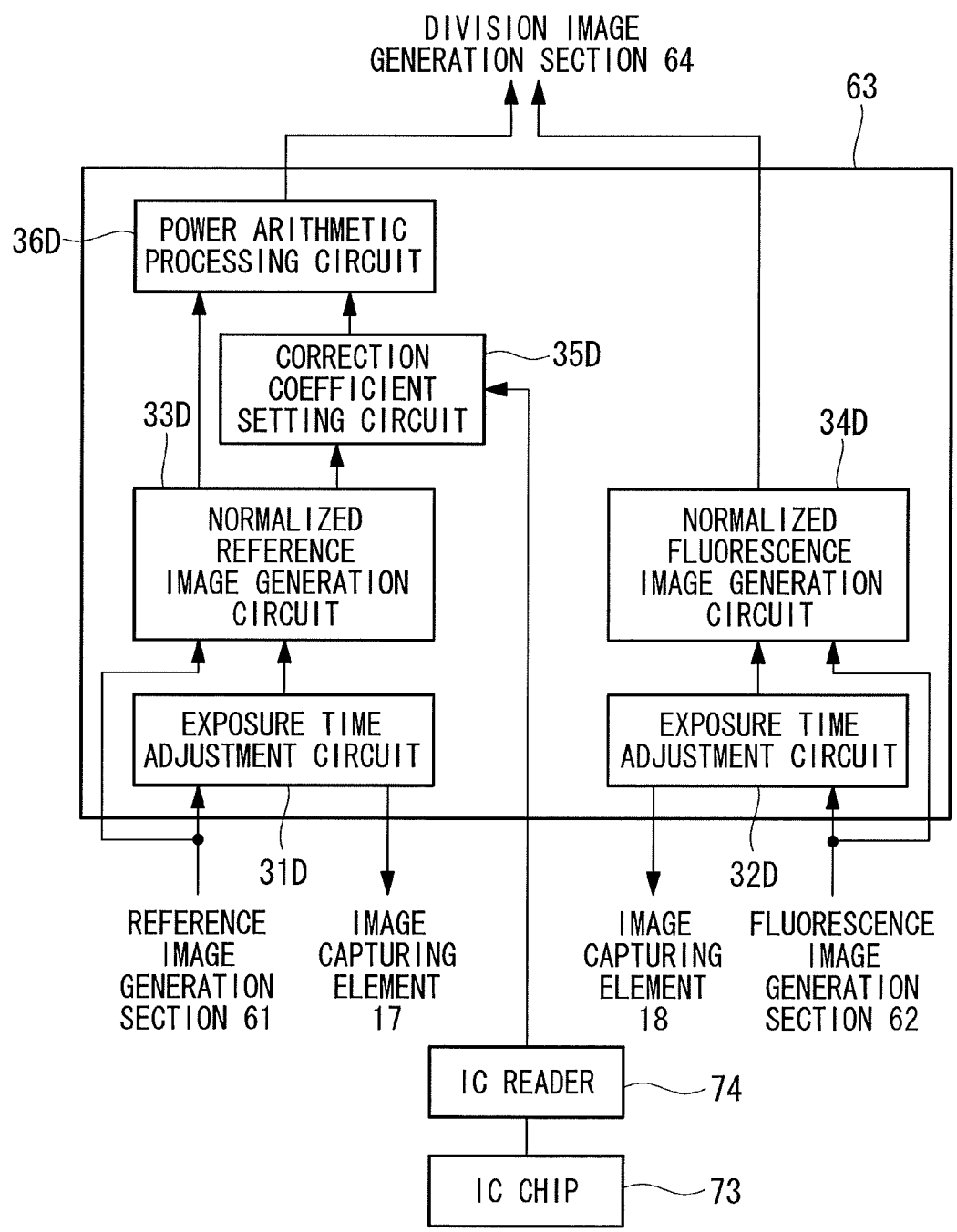
FIG. 80 is a partial block diagram showing another modification of the fluorescence observation apparatus according to the fifth embodiment including the preprocessing section of FIG. 71.

Furthermore, instead of retaining the identification information of the insertion portion 2 in the IC chip 73 and storing the correction coefficients $\alpha$, $\beta$, and the like in the correction coefficient storage section 370, the IC chip 73 may directly store the correction coefficients $\alpha$ and $\beta$ and the boundary value D(n) as shown in FIG. 80, and the correction coefficients $\alpha$ and $\beta$ and the boundary value D(n) read by the IC reader 74 may be transmitted to the correction coefficient setting circuit 35D.

In addition, although the single boundary value D(n) is set to set different correction coefficients around the boundary value D(n) in the first modification of the second preprocessing mode, instead of this, two or more boundary values D(n) may be set to set three or more correction coefficients. When there are two or more boundary values D(n), the setting method of the correction coefficients can follow the flowcharts of FIGS. 73 to 75.

For example, when three or more correction coefficients are set, two boundary values D1 and D2 are selected in a range of observation distance $D(3) \leq D \leq D(a-2)$. The power approximation is performed in areas of $D(1) \leq D \leq D1$, $D1 \leq D \leq D2$, and $D2 \leq D \leq D(a-2)$, and the indices, the boundary values, and determined coefficients are stored for all combinations of the boundary values D1 and D2. By doing so, the indices and the boundary values D1 and D2, in which the sum of the determined coefficients is closest to 6, can be adopted from the obtained database.

In addition, when more boundary values are used for the division, for example, the power approximation may be performed for each of three or more continuous observation distances D in a range of observation distance $D(1) \leq D \leq D(a)$ to obtain correction coefficients.

In addition, although the reference image and the fluorescence image are normalized by the exposure times $S_3$ and $S_4$ of the image capturing elements 17 and 18 respectively in the first modification of the second preprocessing mode, instead of this, the gains of the image capturing elements 17 and 18 may be adjusted based on the signal intensities of the reference image and the fluorescence image, and the reference image and the fluorescence image may be divided by gain multiplication factors corresponding to the gains to obtain the normalized reference image and the normalized fluorescence image.

Figure 81:
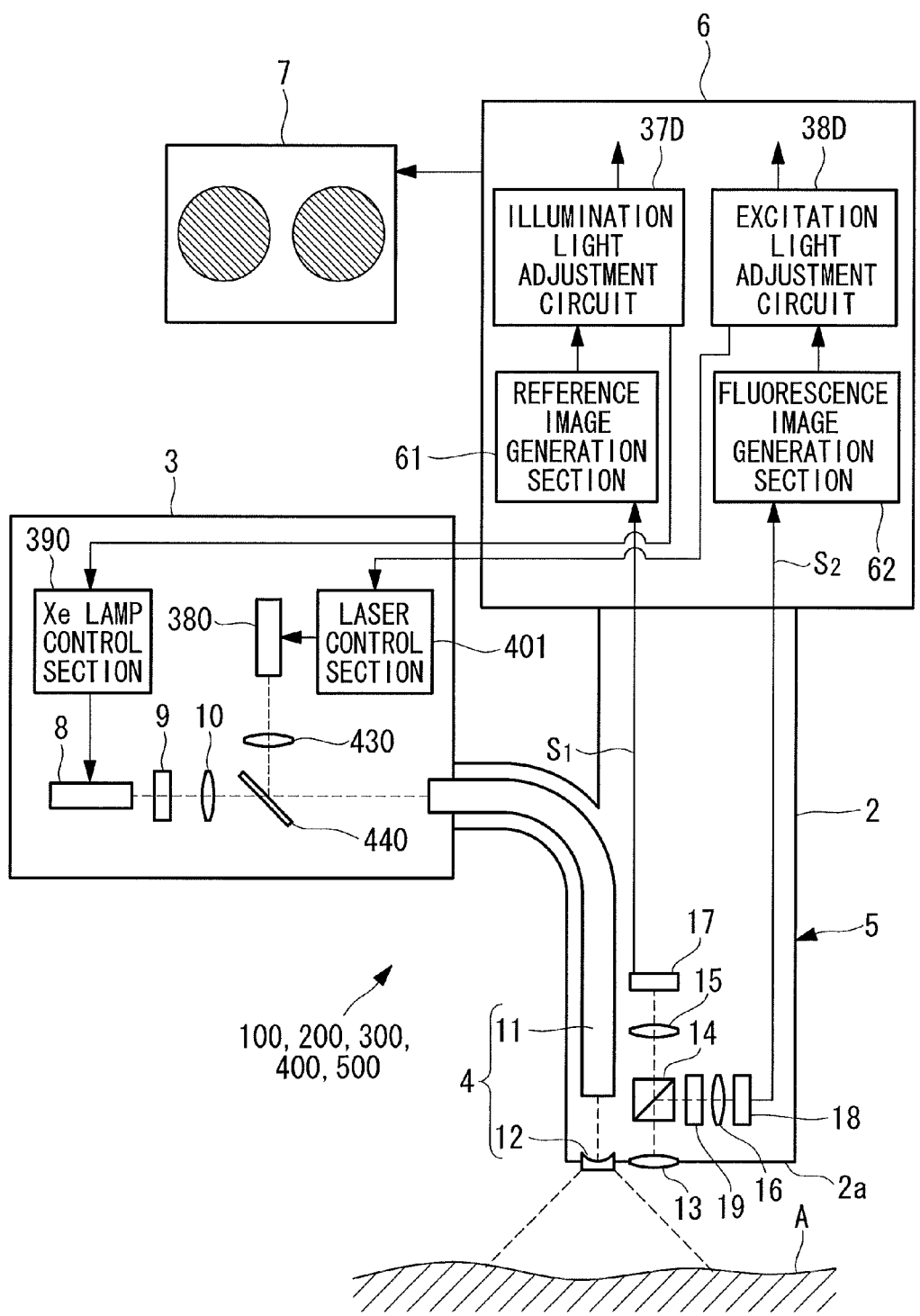
FIG. 81 is a partial configuration diagram showing a modification of the fluorescence observation apparatus including the preprocessing section of FIG. 71.

In addition, as shown in FIG. 81, the light source 3 may include the Xe lamp 8 and a laser light source 380, and a Xe lamp control section 390 and a laser control section 401 may control the output. When light adjustment can be performed, an illumination light adjustment circuit 37D and an excitation light adjustment circuit 38D may divide the reference image and the fluorescence image by the intensity $S_3$ of the illumination light and the intensity $S_4$ of the excitation light calculated based on the signal intensities of the reference image and the fluorescence image to obtain the normalized reference image and the normalized fluorescence image. Reference sign 430 denotes a focusing lens, and reference sign 440 denotes a dichroic mirror. Part of the configuration is not illustrated in FIG. 81.

In addition, before the normalization of the reference image and the fluorescence image, the noise components of the image capturing elements 17 and 18 may be subtracted. By doing so, there is an advantage that the operational precision can be improved.

{Third Preprocessing Mode}

Next, the third preprocessing mode by the preprocessing section 63 included in the fluorescence observation apparatuses 100, 200, 300, 400, and 500 according to the first to fifth embodiments will be described.

The third preprocessing mode is a processing mode in which the gradation values of the reference image and the fluorescence image are adjusted according to a reference table (LUT; Look up Table) that is set based on the distance characteristics of the reflected light and the fluorescence to match the dependencies of observation distance in the reference image and the fluorescence image.

The third preprocessing mode is suitable for removing the dependency of observation distance and observation angle remained in the division image caused by the difference in the distance characteristics between the wavelengths. More specifically, the correction condition setting sections 66 and 66' of the fluorescence observation apparatuses 100 and 200 according to the first and second embodiments set the preprocessing parameters of the third preprocessing mode when "multi-color" is input or determined as the observation condition. The correction condition setting section 66" of the fluorescence observation apparatuses 300, 400, and 500 according to the third to fifth embodiments sets the preprocessing parameters of the third preprocessing mode when "greater omentum", "stomach", or the like, in which tissues or organs with different hues are mixed in the field of view, is input or determined.

In this case, in the third preprocessing mode described below, the correction condition setting sections 66, 66', and 66" measure in advance the distance characteristics of each wavelength (hue) for each observation site corresponding to the observation conditions with a plurality of mixed hues and store coefficients for the gradation values that are preprocessing parameters calculated based on the measurement values.

The third preprocessing mode is a processing mode of generating the division fluorescence image and the division reference image by multiplying at least one of the fluorescence image and the reference image by the coefficients set by the correction condition setting sections 66, 66', and 66". The coefficients are predetermined so that the distance characteristics of the fluorescence intensity and the distance characteristics of the reflected light intensity acquired in advance for the standard sample are directly proportional to each other. The third preprocessing mode and the second preprocessing mode are alternatively used. Which one of the second processing mode and the third processing mode will be used may be arbitrarily selected by the user before the observation or may be automatically selected according to the observation condition.

Figure 82:
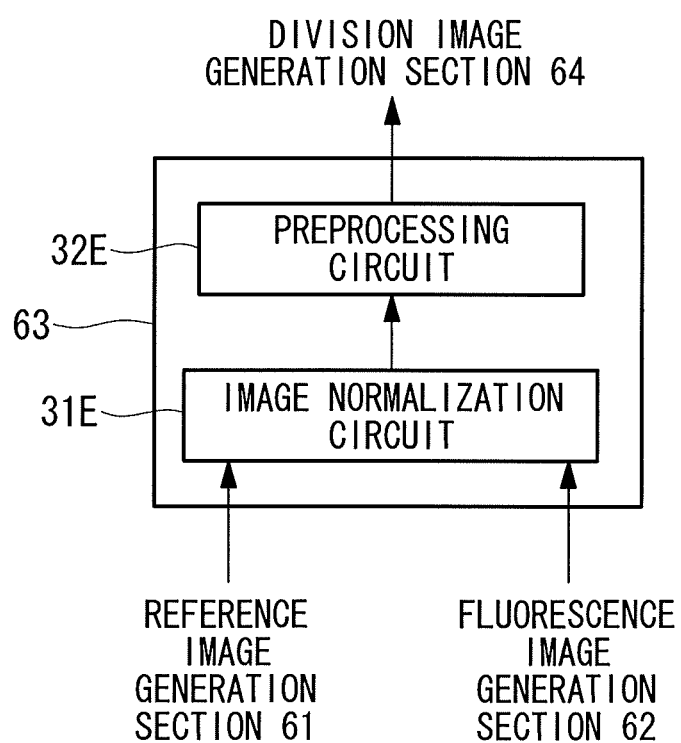
FIG. 82 is a block diagram showing a configuration of the preprocessing section that executes a third preprocessing mode.

The third preprocessing mode is executed by an image normalization circuit 31E and a preprocessing circuit 32E included in the preprocessing section 63 as shown in FIG. 82.

The image normalization circuit 31E normalizes the reference image and the fluorescence image generated by the reference image generation section 61 and the fluorescence image generation section 62 to generate the normalized reference image and the normalized fluorescence image.

The preprocessing circuit 32E generates the division reference image and the division fluorescence image from the normalized reference image and the normalized fluorescence image generated by the image normalization circuit 31E.

In this case, the fluorescence image can be, for example, a fluorescence image from a fluorescent dye Cy7. Particularly, a tumor-specific fluorescent agent, such as a fluorescent agent with a combination of an antibody for a cancer-specific molecule CEA (Anti-CEA antibody) and Cy7, can be provided in advance to the observation target A to obtain a tumor-specific fluorescence image. In addition, the reference image can be an image based on, for example, the reflected light of the illumination light reflected on the surface of the observation target A and the reflected light formed by scattering in the observation target A.

The image normalization circuit 31E is configured to normalize the reference image and the fluorescence image by using a relational expression shown in Equation 7.

$$\text{Normalized gradation value} = \frac{\text{Acquired image gradation value}}{\text{Exposure time}} \times \frac{\text{Specified gain}}{\text{Observation gain}} \quad \{\text{Equation 7}\}$$

More specifically, when the image capturing elements 17 and 18 acquire the reference image and the fluorescence image of 16-bit gradation, the exposure time and the gain are adjusted so that the gradation values of the pixels fall within the range, and the normalization is performed to make the observation conditions constant. The predetermined gain in Equation 1 is, for example, a gain set to 1 at the time of the reflected light observation and set to 100 at the time of the fluorescence observation.

In the third preprocessing mode, the correction condition setting sections 66, 66', and 66" include a storage section (not shown) that stores coefficients, which cause the distance characteristics of the fluorescence intensity with respect to the standard sample and the distance characteristics of the reflected light intensity with respect to the same standard sample to be directly proportional to each other, in association with the reflected light intensity. The correction condition setting sections 66, 66', and 66" measure the hue of each pixel of the reference image and outputs the coefficients (preprocessing parameters) corresponding to the gradation values of the pixels stored according to the hue to the preprocessing circuit 32E.

The preprocessing circuit 32E is configured to multiply each pixel of the reference image input from the reference image generation section 61 by the coefficient corresponding to the gradation value of each pixel set by the correction condition setting sections 66, 66', and 66" to generate the division reference image. In this case, the preprocessing circuit 32E is configured to output the input fluorescence image as the division fluorescence image.

Here, FIGS. 83 and 84 illustrate an example of the coefficients calculated based on the gradation values of the reference image and the fluorescence image when the observation distance is changed, for example, from 10 mm to 200 mm, and a phantom or an organ of a pig or the like is observed as a standard sample.

More specifically, when the gradation value (reflected light intensity) of a pixel in the acquired reference image is 16.6, the gradation value of the pixel is multiplied by a coefficient 2.024. This is repeated for all pixels to obtain the division reference image. When the gradation value of one of the pixels is a value between two gradation values shown in FIG. 84, a coefficient obtained by linear interpolation of two coefficients corresponding to the gradation values of FIG. 83 is multiplied.

According to the third preprocessing mode by the preprocessing section 63 with the configuration, the reference image and the fluorescence image generated in the image generation sections 61 and 62 are input to the image normalization circuit 31E and normalized by Equation 7, and the preprocessing circuit 32E converts the normalized reference image and the normalized fluorescence image to the division reference image and the division fluorescence image (preprocessing step). In the third preprocessing mode, the normalized reference image is multiplied by the coefficients to form the division reference image, and the normalized fluorescence image becomes the division fluorescence image.

The coefficients for the multiplication of the normalized reference image by the preprocessing circuit 32E are a ratio of the normalized fluorescence image and the normalized reference image acquired by using the standard sample, and the coefficients are selected so that the distance characteristics of the fluorescence intensity of the normalized fluorescence image in the standard sample match the distance characteristics of the reflected light intensity of the normalized reference image of the same standard sample. Therefore, the division image generation section 64 can divide the division fluorescence image by the division reference image obtained by multiplying the normalized reference image of the observation target A by the coefficients to obtain a corrected fluorescence image in which the dependency of observation distance is sufficiently reduced. More specifically, there is an advantage that highly quantitative fluorescence observation can be performed.

In this case, a plurality of types of standard samples with different hues can be used to calculate the coefficients, and the correction condition setting sections 66, 66', and 66" can store the coefficients according to the hues. In this way, a suitable coefficient can be set for each pixel according to the hues of the reference image, and the coefficient can be transmitted to the preprocessing section 63.

Note that in the third preprocessing mode, the fluorescence image and the reference image acquired by the image capturing elements 18 and 19 include noise derived from dark current of the image capturing elements 18 and 19 and reading operation. In addition, when the reference image includes a pixel, in which the luminance value is zero, in the division process, the divided result becomes infinite, and appropriate correction is hindered.

Accordingly, the preprocessing circuit 32E may provide the fluorescence image with an offset for removing the noise components derived from the dark current or the reading operation and provide the reference image with an offset for removing the noise components derived from the dark current or the reading operation and for preventing the luminance values of all pixels from becoming zero.

Figure 85:
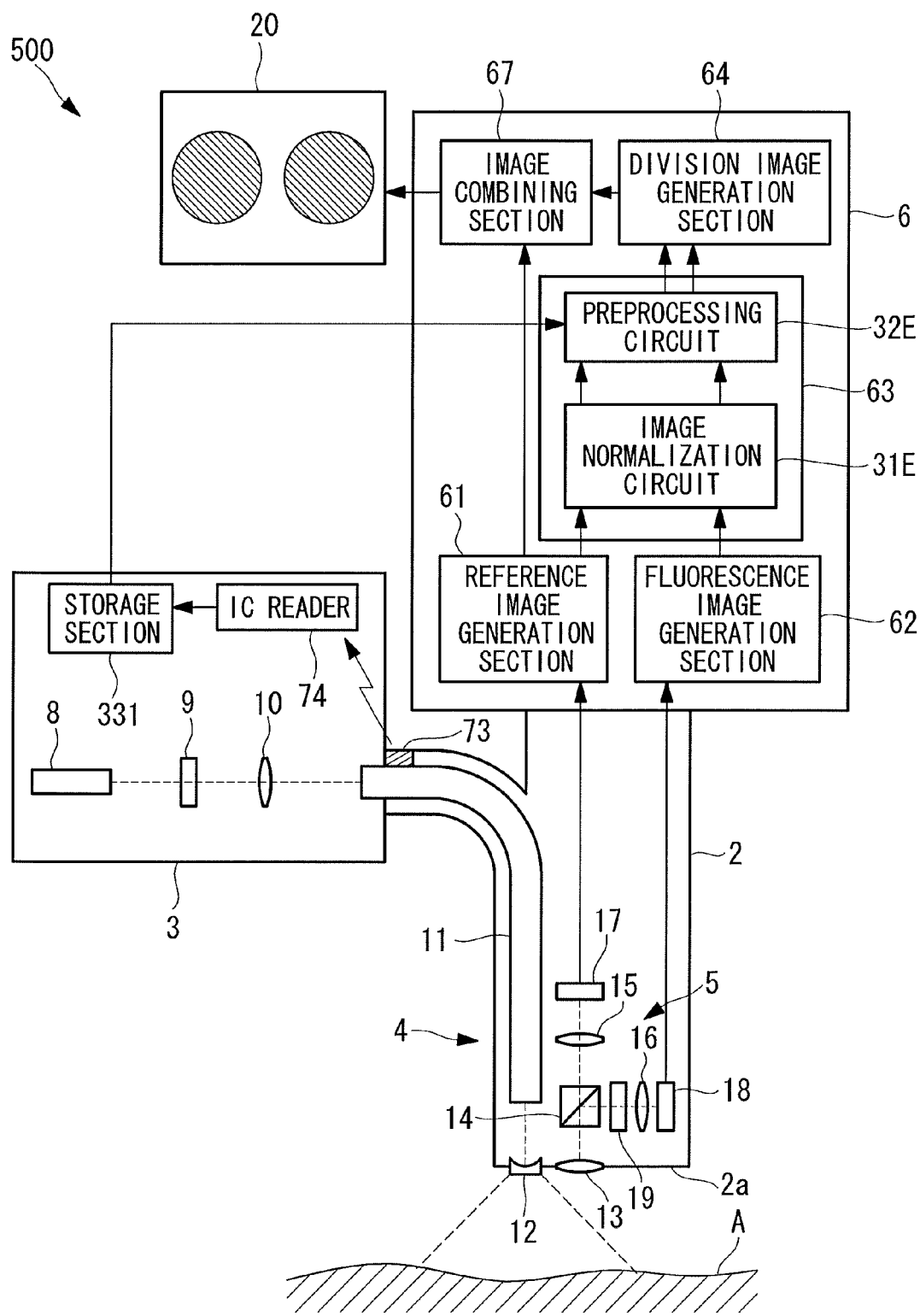
FIG. 85 is an overall configuration diagram showing a modification of the fluorescence observation apparatus of FIG. 82.

In addition, when the fluorescence observation apparatus 500 according to the fifth embodiment shown in FIG. 5 is provided with the third preprocessing mode, it is preferable to include a storage section 331 that associates and stores the identification information and the coefficients appropriate for each insertion portion 2 as shown in FIG. 85. When the insertion portion 2 is detached and exchanged to another insertion portion 2, various optical systems included in the insertion portion 2, such as the objective lens 13, are changed. Therefore, the coefficients are changed due to a change in the numerical aperture (NA), the pupil diameter, or the like of the objective lens 13 or due to a change in the wavelength of the fluorescence to be detected, the observation target site (such as stomach tissue and color tissue), or the like.

The preprocessing circuit 32E receives the coefficients corresponding to the identification information of the insertion portion 2 output from the storage section 331 to perform the computation.

By doing so, even if the insertion portion 2 is exchanged with respect to the light source 3, optimal coefficients are set to the insertion portion 2, and there is an advantage that a highly quantitative fluorescence image can be always acquired.

In addition, although the coefficients for matching the distance characteristics of the reflected light intensity with respect to the standard sample with the distance characteristics of the fluorescence intensity are employed in the third preprocessing mode, the coefficients are not limited to these, and the coefficients may make the characteristics directly proportional.

In addition, coefficients for multiplication with the normalized fluorescence image may be stored in place of the coefficients for multiplication with the normalized reference image, or coefficients for multiplication with the normalized reference image and the normalized fluorescence image may be stored.

In addition, although the configuration for performing the highly quantitative fluorescence observation by reducing the dependency of observation dependency is employed in the third preprocessing mode, instead of this, a configuration of reducing the dependency of observation angle may be employed. Specifically, the preprocessing circuit 32E multiplies the normalized reference image of the observation target A by coefficients that are a ratio of the normalized fluorescence image and the normalized reference image acquired while changing the observation angle by using the standard sample and that are selected to cause the angle characteristics of the fluorescence intensity of the normalized fluorescence image in the standard sample to be directly proportional to the angle characteristics of the reflected light intensity of the normalized reference image in the same standard sample. Then, the division image generation section 64 can divide the division fluorescence image by the obtained division reference image to obtain a corrected fluorescence image in which the dependency of observation angle is sufficiently reduced. More specifically, there is an advantage that highly quantitative fluorescence observation can be performed.

Next, a fluorescence observation system 600 including a fluorescence observation apparatus provided with the third preprocessing mode will be described.

Figure 86:
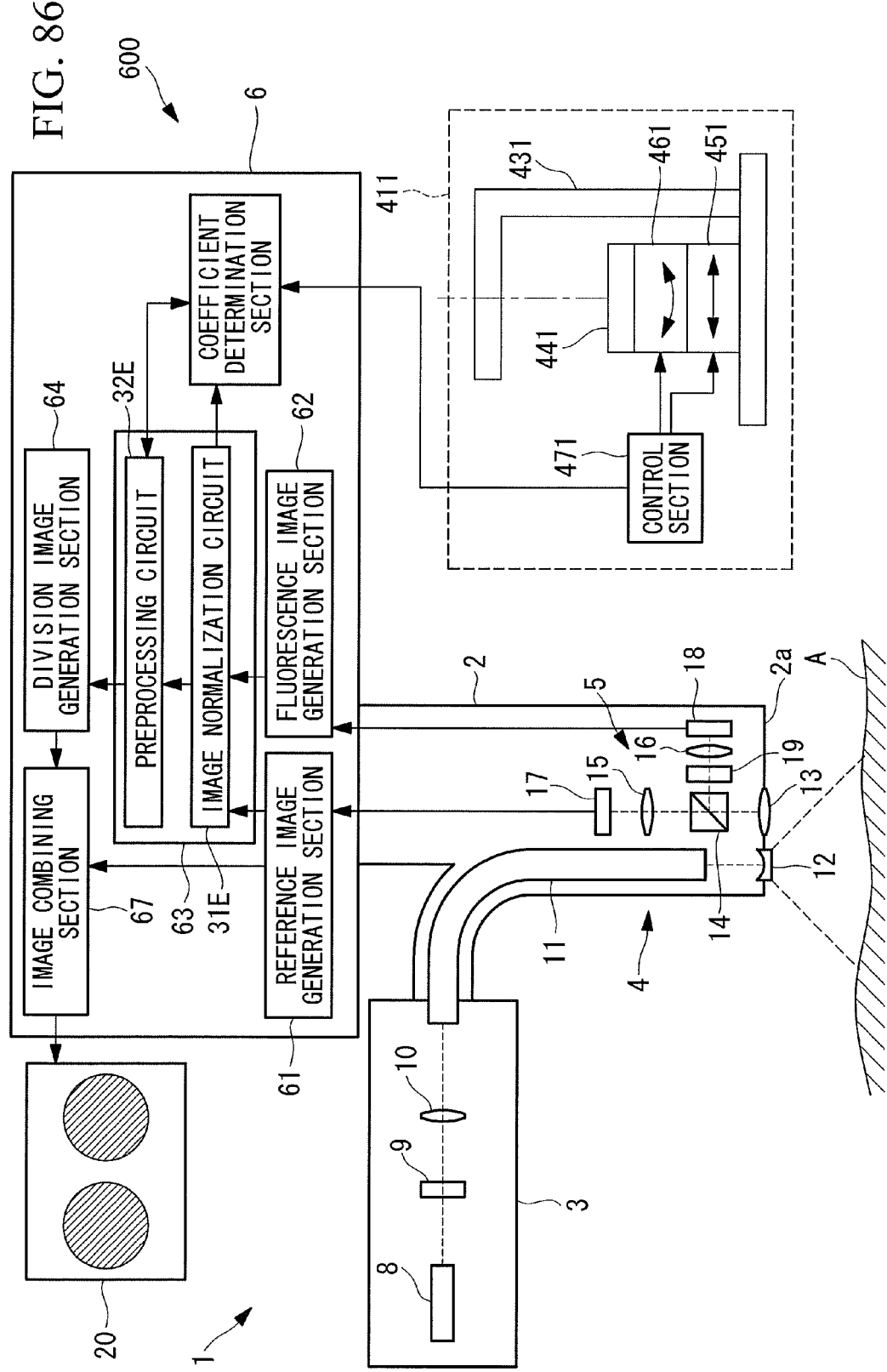
FIG. 86 is a partial configuration diagram showing a fluorescence observation system including the fluorescence observation apparatus provided with the preprocessing section of FIG. 85.

As shown in FIG. 86, the fluorescence observation system 600 includes the fluorescence observation apparatuses 100, 200, 300, 400, and 500 (hereinafter, these will be collectively called a fluorescence apparatus 1) and a calibration device 411 equipped with the fluorescence observation apparatus 1.

In this configuration, the fluorescence observation apparatus 1 includes a coefficient determination section 421 that calculates a coefficient.

Figure 87:
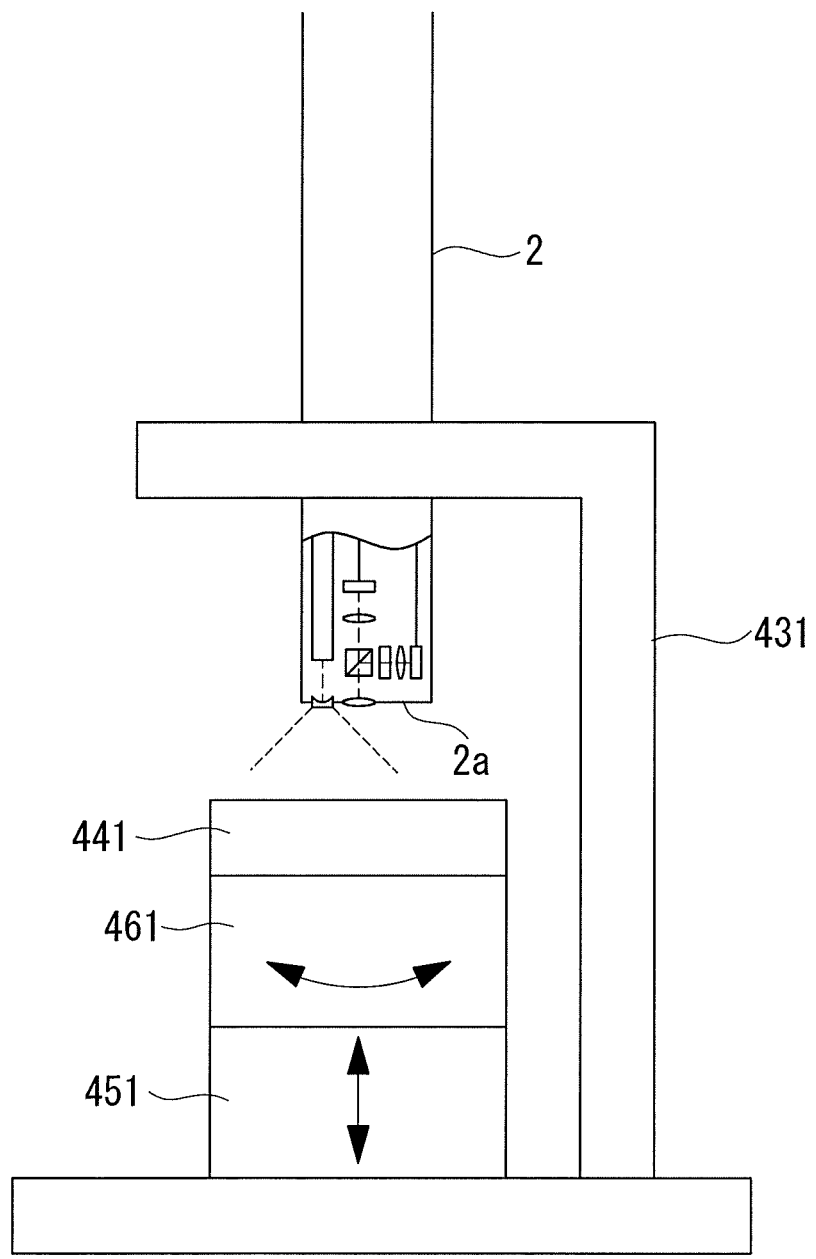
FIG. 87 is a diagram showing a calibration device of the fluorescence observation system of FIG. 82.

As shown in FIGS. 86 and 87, the calibration device 411 includes: a holder 431 for fixing the insertion portion 2; a standard sample 441 with already-known hue that faces, at an observation distance, the tip surface 2a of the insertion portion 2 fixed to the holder 431; a translation stage 451 that changes the observation distance between the tip surface 2a of the insertion portion 2 and the standard sample 441; a tilt stage 461 that changes the angle (observation angle) of the surface of the standard sample 441 relative to the optical axis of the objective lens 13; and a control section 471 that controls the stages 451 and 461.

The control section 471 is configured to drive the stages 451 and 461 to change the observation distance or the observation angle and to output a trigger signal at a predetermined timing.

In addition, the coefficient determination section 421 is configured to receive the normalized fluorescence image and the normalized reference image transmitted from the image normalization circuit 31E, retain the luminance value of the normalized fluorescence image and the luminance value of the normalized reference image at the reception of a trigger signal S from the control section 471, calculate a coefficient by dividing the luminance value of the normalized fluorescence image by the luminance value of the normalized reference image, and store the calculated coefficient in association with the luminance value and the hue of the normalized reference image.

To acquire coefficients when the observation distance is changed, the control section 471 first drives the translation stage 451 so that the tip surface 2a of the insertion portion 2 is at an observation start distance from the surface of the standard sample 441 as shown in FIG. 87. Next, the unit 4 radiates the illumination light and the excitation light to the standard sample 441 to enable capturing an image of the reflected light and the fluorescence. The control section 471 moves the stage 45 by a predetermined distance at a time and outputs the trigger signal S every time the stage 45 is moved. By doing so, a plurality of coefficients acquired at a plurality of different observation distances are associated with the luminance values of the normalized reference image and stored in the coefficient determination section 421.

Meanwhile, to acquire coefficients when the observation angle is changed, the control section 471 first drives the translation stage 451 and the tilt stage 461 so that the tip surface 2a of the insertion portion 2 is at an observation start distance and at an angle relative to the surface of the standard sample 441 as shown in FIG. 87. Next, the unit 4 radiates the illumination light and the excitation light to the standard sample 441 to enable capturing an image of the reflected light and the fluorescence. The control section 471 moves the tilt stage 461 at a predetermined distance at a time and outputs the trigger signal S every time the tilt stage 461 is moved. By doing so, a plurality of coefficients acquired at a plurality of different observation angles are associated with the luminance values of the normalized reference image and stored in the coefficient determination section 421.

The coefficients when the observation distance is changed and the coefficients when the observation angle is changed can be appropriately selected according to the observation conditions.

In addition, when a luminance value of the normalized reference image is input from the preprocessing circuit 32E, the coefficient determination section 421 is configured to calculate a coefficient corresponding to the luminance and output the coefficient to the preprocessing circuit 32E. More specifically, since the coefficient determination section 421 stores a plurality of coefficients associated with the luminance values of a plurality of normalized reference images at intervals, when a luminance value between the luminance values is input, the coefficients are interpolated between the luminance values before and after the input luminance value to calculate a new coefficient, and the coefficient is output to the preprocessing circuit 32E.

In this way, according to the fluorescence observation system 600, even if the observation target A or the observation conditions, such as the optical systems and the fluorescence wavelength used for the observation, are changed, coefficients according to the change can be set every time, and there is an advantage that the observation can be performed based on highly quantitative fluorescence images in various observation targets A and observation conditions.

For example, when the fluorescence observation apparatus 1 is applied to an endoscope, optimal coefficients can be set accordingly even if there is a difference in the type, such as a rigid scope and a flexible scope, or a difference in the observation site, such as an upper digestive endoscope and a lower digestive endoscope. Furthermore, in the same type of fluorescence observation apparatus 1, coefficients can be set to individual apparatuses regardless of the individual differences.

In addition, a suitable coefficient can be set according to the hue to set a suitable coefficient for each pixel even if subjects with different hues (for example, organs with different colors such as liver and stomach) are observed at the same time in one screen, and a more accurate image can be presented.

Note that a phantom with the same scattering or absorption characteristics as those of the living body to be observed may be used as the standard sample 441, or excised tissue of a human or an animal (such as a pig and a mouse) may be used.

Note that in the first to third preprocessing modes, a preprocessing mode that is not selected as a preprocessing mode for setting the preprocessing parameters may also be used in a state in which constant preprocessing parameters (initial values) are set. For example, the preprocessing parameters of the first preprocessing mode are set when the observation condition corresponds to "high fat". At the same time, in the third preprocessing mode, the initial values of the preprocessing parameters may be used as it is.

{Post-Processing Modes}

Next, first to third post-processing modes by the post-processing section 65 included in the fluorescence observation apparatuses 100, 200, 300, 400, and 500 according to the first to fifth embodiments will be described in detail.

{First Post-Processing Mode}

The first post-processing mode by the post-processing section 65 included in the fluorescence observation apparatuses 100, 200, 300, 400, and 500 according to the first to fifth embodiments will be described. The first post-processing mode is a mode of executing a process of emphasizing a relatively high-luminance area common to the division image and the fluorescence image.

The first post-processing mode is suitable for removing the dependency of observation distance and observation angle remained in the division image due to a deviation in the light levels of the reflected light and the fluorescence caused by a large difference in the observation distance in the field of view and due to a partial reduction in the light level caused by shade. More specifically, the correction condition setting sections 66 and 66' of the fluorescence observation apparatuses 100 and 200 according to the first and second embodiments set post-processing parameters of the first post-processing mode when "perspective large", "perspective small", "irregular", or "flat" is input or determined as the observation condition. The correction condition setting section 66" of the fluorescence observation apparatuses 300, 400, and 500 according to the third to fifth embodiments sets post-processing parameters of the first post-processing modes when "Douglas' pouch", "stomach", or the like with a structure deep in the depth direction of the field view, "greater omentum", "intestinal membrane", or the like with a structure relatively flat with respect to the field of view, "greater omentum", "intestinal membrane", or the like in an irregular surface shape, or "subphrenic area" or the like in a smooth surface shape is input or determined.

In this case, in the first post-processing mode described below, the correction condition setting sections 66, 66', and 66" set indices A and B (described later), which are post-processing parameters, to increase the weight of the division image when the observation conditions indicate a large length of perspective in the field of view and a smooth surface of the observation target. On the other hand, the correction condition setting sections 66, 66', and 66" set the indices A and B (described later), which are post-processing parameters, to increase the weight of the fluorescence image when the observation conditions indicate a small length of perspective in the field of view and an irregular surface of the observation target.

Figure 88:
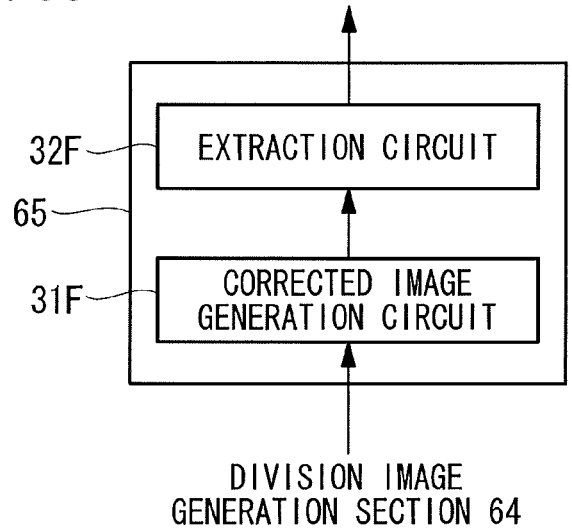
FIG. 88 is a block diagram showing a configuration of a post-processing section that executes a first post-processing mode.

The first post-processing mode is a mode of generating a corrected fluorescence image by multiplying or adding the division image and the fluorescence image. As shown in FIG. 88, a corrected image generation circuit 31F and an extraction circuit 32F included in the post-processing section 65 execute the first post-processing mode.

The corrected image generation circuit 31F generates a corrected image by multiplying the division image generated by the division image generation section 64 by the fluorescence image. The extraction circuit 32F extracts areas with the gradation values greater than a predetermined threshold in the corrected image.

The fluorescence image generation section 62 generates a two-dimensional fluorescence image from the fluorescence image information acquired by the image capturing element 18 and outputs the generated fluorescence image to the division image generation section 64 and the corrected image generation circuit 31F. In this case, the fluorescent agent is actually accumulated not only on the diseased portion, but also on a normal portion in a small amount. The fluorescence is also emitted from the normal portion, although weaker than the fluorescence from the diseased portion. Therefore, the generated fluorescence image is an image with a background as a whole (FIG. 89A).

Figure 89A:
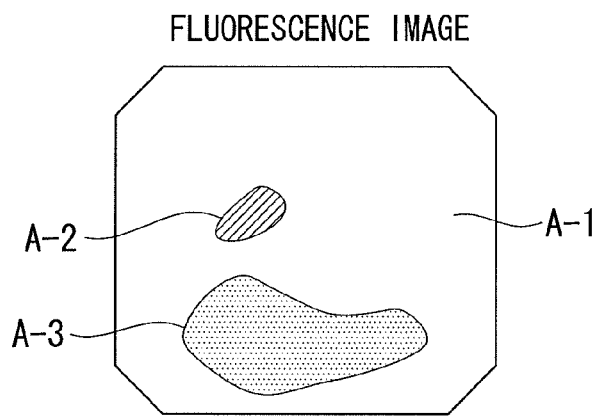
FIG. 89A is an explanatory diagram of a fluorescence image generated in the fluorescence observation apparatus including the post-processing section of FIG. 87.

Thus, the fluorescence image includes a low-luminance area of the background (A-1 of FIG. 89A), a relatively high-luminance area compared to the low-luminance area because of the fluorescence emitted from the diseased portion (A-2 of FIG. 89A), and a relatively high-luminance area because of a close distance to the examination target (A-3 of FIG. 89A).

The reference image generation section 61 generates a two-dimensional reference image G1 from the reference image information acquired by the image capturing element 17 and outputs the generated reference image G1 to the division image generation section 64 and the image combining section 67. In this case, the reference image G1 is an image affected by the color characteristics of the examination target, that is, the absorption characteristics of the illumination light (FIG. 89B).

Figure 89B:
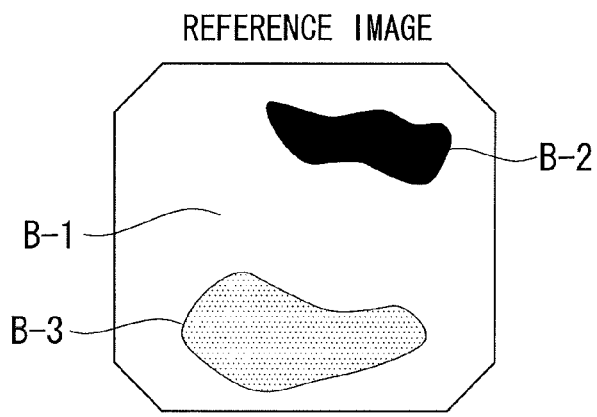
FIG. 89B is an explanatory diagram of a reference image generated in the fluorescence observation apparatus including the post-processing section of FIG. 87.

Therefore, the generated reference image G1 includes a low-luminance area of the background based on the overall distribution of the reflected light (B-1 of FIG. 89B), a low-luminance area caused by the color characteristics of the examination target (B-2 of FIG. 89B), and a relatively high-luminance area compared to the low-luminance areas because of a close distance to the examination target (B-3 of FIG. 89B).

Figure 89C:
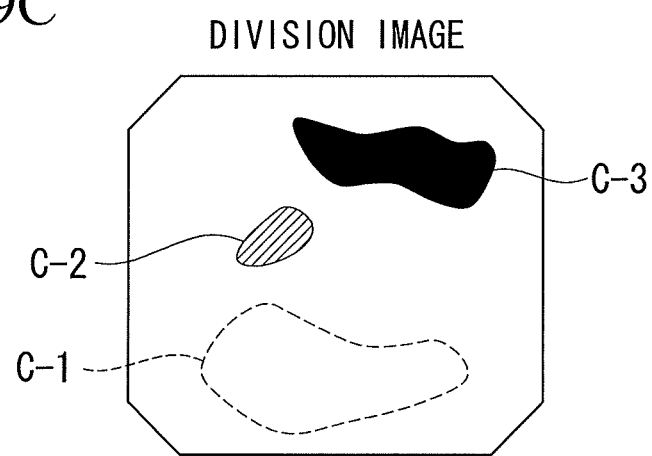
FIG. 89C is an explanatory diagram of a division image generated in the fluorescence observation apparatus including the post-processing section of FIG. 87.

The division image generation section 64 divides the fluorescence image of the same observation target A by the reference image to generate a division image (FIG. 89C). By doing so, an image (division image) including an area (C-1 of FIG. 89C) in which the influence of the observation distance and the observation angle is reduced can be generated.

In this case, the division image includes a relatively high-luminance area (C-2 of FIG. 89C) due to the fluorescence generated from the diseased portion. Furthermore, when the reference image includes a low-luminance area caused by the color characteristics of the examination target, the luminance of the area corresponding to the low-luminance are is amplified in the division image, and a high-luminance area (C-3 of FIG. 89C) is included.

Figure 89D:
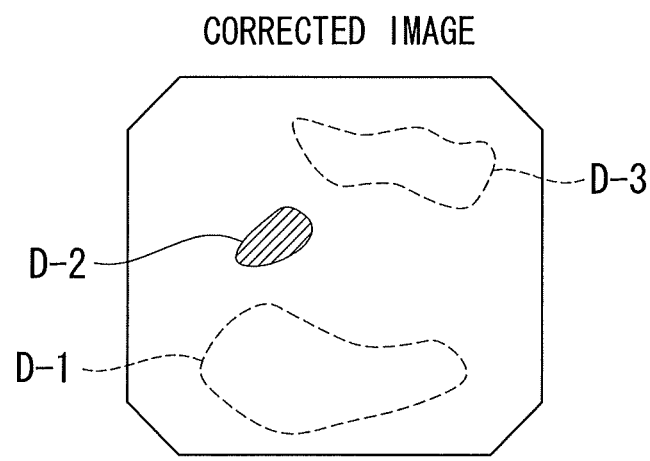
FIG. 89D is an explanatory diagram of a corrected image generated in the fluorescence observation apparatus including the post-processing section of FIG. 87.

The corrected image generation circuit 31F multiplies the division image by the fluorescence image after raising the division image and the fluorescence image to the power of indices A and B (post-processing parameters), such as (division image)^A×(fluorescence image)^B, to correct the division image to generate a corrected image (FIG. 89D). In this case, the corrected image includes an area (D-1 of FIG. 89D) that reflects the result of reducing the influence due to the observation distance and the observation angle in the division image. In the corrected image, an area common to the relatively high-luminance area in the fluorescence image and the relatively high-luminance area in the division image is emphasized, or more specifically, a high-luminance area (D-2 of FIG. 89D) due to the fluorescence emitted from the diseased portion is emphasized. As a result, an image (corrected image) including an area (D-3 of FIG. 89D) in which the change in the intensity of the illumination light caused by the difference in the absorption characteristics of the illumination light in the examination target is reduced can be generated.

In this case, the correction condition setting sections 66, 66', and 66" command the post-processing section 65 to set a large index A when the observation conditions correspond to "perspective large" and "flat" and to set a large index B when the observation conditions correspond to "perspective small" and "irregular".

Based on a predetermined threshold, the extraction circuit 32F extracts, as feature areas, pixels with gradation values larger than the threshold among all pixels of the corrected image.

In the present post-processing mode, the image combining section 67 generates a combined image by superimposing the feature areas extracted by the extraction circuit 32F on the reference image G1.

Figure 90:
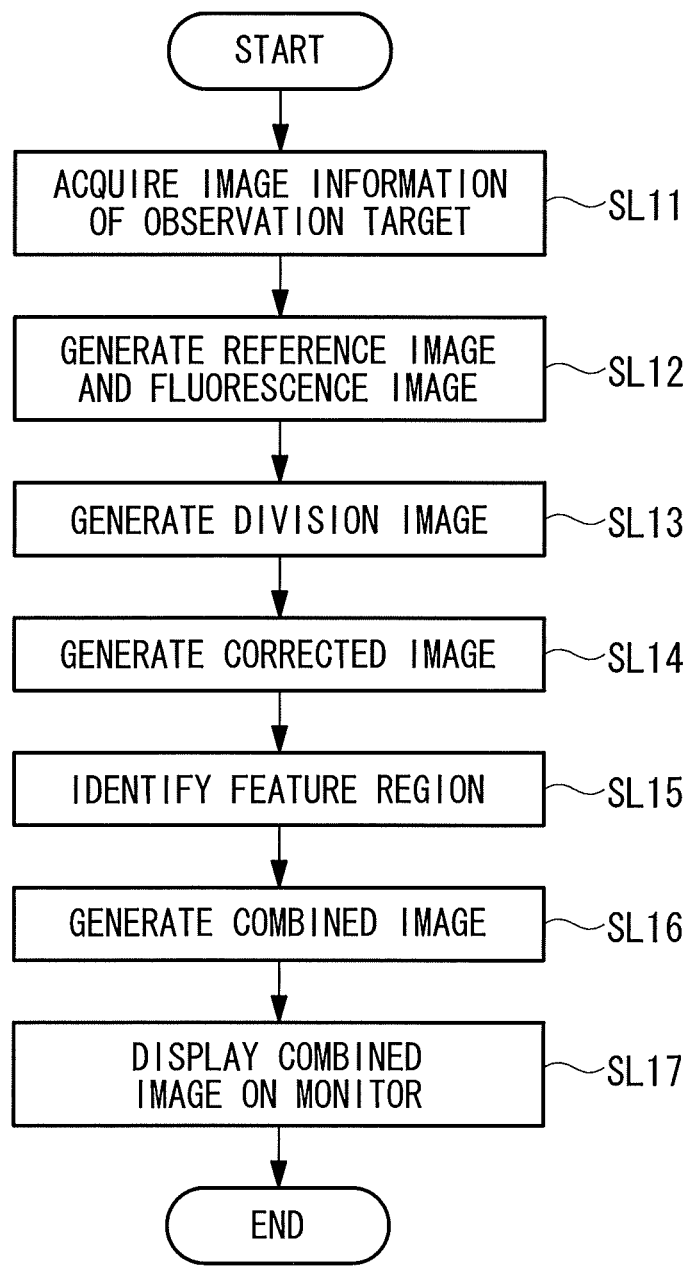
FIG. 90 is a flowchart showing a processing method by the post-processing section of FIG. 88.

According to the first post-processing mode by the post-processing section 65 with the setting, image information of the observation target A is acquired (step SL11), and a reference image and a fluorescence image are generated from the image information (step SL12), as shown in FIG. 90. The fluorescence image is output to the division image generation section 64 and the corrected image generation circuit 31F.

Note that the fluorescent agent is actually accumulated not only on the diseased portion, but also on a normal portion in a small amount, and weak fluorescence due to the site (background) other than the diseased portion is emitted. In addition, for example, relatively strong fluorescence is emitted even from the normal site because of the distance or angle between the tip 2a of the insertion portion 2 and the observation target A, and it may be difficult to determine whether the site is a diseased portion or a normal portion in the obtained fluorescence image.

Therefore, in the next step SL13, the division image generation section 64 generates a division image by dividing the fluorescence image by the reference image. By doing so, the change in the fluorescence intensity depending on the observation distance or the observation angle can be reduced in the division image. More specifically, since the intensity of the reference image largely depends on the observation distance or the observation angle, the influence of the observation distance or the observation angle can be reduced by normalizing the fluorescence image by the reference image. The generated division image is output to the corrected image generation circuit 31F.

In this case, inherent intensity of the reflected light may not be obtained in the reference image because of the difference in the absorption characteristics of the reference light in the examination target in addition to the difference in the dependency for the observation distance or the observation angle between the fluorescence and the reflected light. Therefore, when the division image is generated based on the reference image, although the influence of the change in the fluorescence intensity caused by the observation distance or the observation angle can be suppressed in the division image, the division image may be affected by the change in the intensity of the reflected light caused by the difference in the absorption characteristics of the reference light in the examination target.

Accordingly, in the next step SL14, the corrected image generation circuit 31F multiplies the division image by the fluorescence image to generate a corrected image in which the change in the intensity of the division image caused by the difference in the absorption characteristics of the reflected light in the observation target A is corrected. More specifically, the division image may be multiplied by the fluorescence image not related to the absorption in the observation target A to reduce the change in the fluorescence intensity caused by the observation distance or the observation angle and to generate the corrected image in which the influence of the absorption is reduced. More specifically, the area common to the relatively high-luminance area in the fluorescence image and the relatively high-luminance area in the reference image, that is, the area with the generation of fluorescence from the diseased portion, is emphasized in the corrected image. The generated corrected image is output to the extraction circuit 32F.

In the next step SL15, from the corrected image input from the corrected image generation circuit 31F, the extraction circuit 32F extracts, as feature areas, pixels with the gradation values larger than a predetermined threshold among all pixels of the corrected image based on the threshold, and the process advances to the next step SL16. In the first post-processing mode, the image displaying the extracted areas is equivalent to the corrected fluorescence image. In step SL16, the image combining section 67 generates a combined image. By doing so, in the combined image, the contrast between the diseased portion and the background is increased on the basis of the predetermined threshold. The image combining section 67 outputs the generated combined image to the monitor 20. In the next step SL17, the combined image received from the image combining section 67 is displayed on the monitor 20.

As described, according to the first post-processing mode, the corrected image generation circuit 31F can perform the multiplication of the division image generated by the division image generation section 64 based on (division image)$^A \times$(fluorescence image)$^B$ to suppress the influence of the observation distance or the observation angle and to correct the change in the intensity of the reflected light caused by the difference in the absorption characteristics of the reference light in the examination target that affects the division image to thereby generate, as a corrected fluorescence image, a corrected image in which the contrast between the fluorescence (background) from the normal portion and the diseased portion is increased.

Furthermore, the extraction circuit 32F extracts, as feature areas, areas with higher gradation values than the threshold, in which the fluorescence from the diseased portion is mainly displayed. Therefore, the feature areas are superimposed on the reference image to generate an image, and the contrast between the diseased portion and the background is further increased on the basis of the threshold in the generated image. Thus, the diseased portion can be more accurately and precisely extracted from the corrected image in which the influence of the background on the division image depending on the change in the reference light intensity due to the absorption characteristics of the examination target is suppressed.

Note that in the generation of the corrected image in the first post-processing mode, the division image is first generated, and then the division image is multiplied by the fluorescence image. However, the order of calculation is not limited to this, and an example of a possible order of calculation includes an order in which the fluorescence image is multiplied by the fluorescence image, and this is divided by the reference image.

In addition, based on the division image and the fluorescence image, coefficients A and B may be set as post-processing parameters, and $$A \times \text{(division image)} + B \times \text{(fluorescence image)}$$

may be used to sum the division image and the fluorescence image to generate the corrected image.

The first post-processing mode can be modified as follows.

Figure 91:
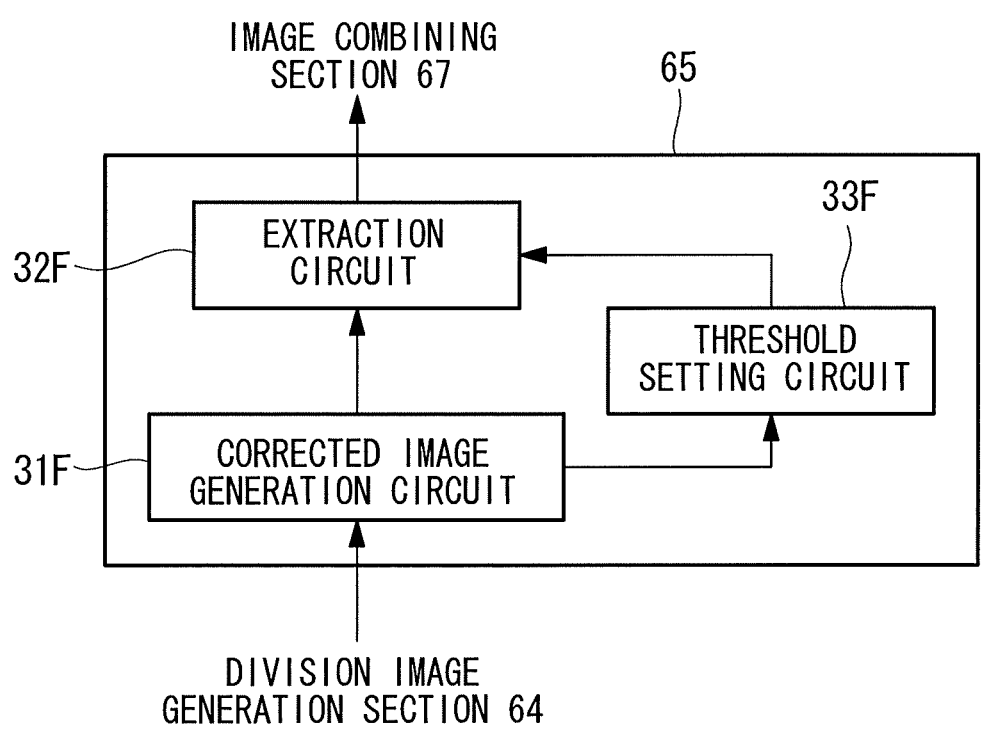
FIG. 91 is a block diagram showing a modification of the post-processing section of FIG. 1.

In the first post-processing mode, although the extraction circuit 32F extracts, from the corrected image, the areas in the corrected image with the gradation values larger than the threshold set by the correction condition setting sections 66, 66', and 66", the process is not limited to this, and the configuration of the post-processing section 65 that executes the first post-processing mode can be modified as in FIG. 91. More specifically, the post-processing section 65 of FIG. 9 can include a threshold setting circuit 33F that acquires the information of the corrected image from the corrected image generation circuit 31F to compute and set a threshold based on the corrected image. Hereinafter, a processing method based on the first post-processing mode according to the present modification will be described.

The post-processing section 65 includes the threshold setting circuit 33F that computes and sets the threshold as a reference for the extraction of the feature areas by the extraction circuit 32F. The threshold setting circuit 33F acquires the information of the corrected image from the corrected image generation circuit 31F and computes and sets the threshold based on the average value of the gradation values of the pixels in the corrected image. More specifically, as shown in the following Expression (12), the threshold setting circuit 33F sets, as a threshold S, a value obtained by multiplying an average gradation value m of the entire corrected image by a predetermined coefficient a and outputs the set threshold S to the extraction circuit 32F.

$$S = am \tag{12}$$

Figure 92:
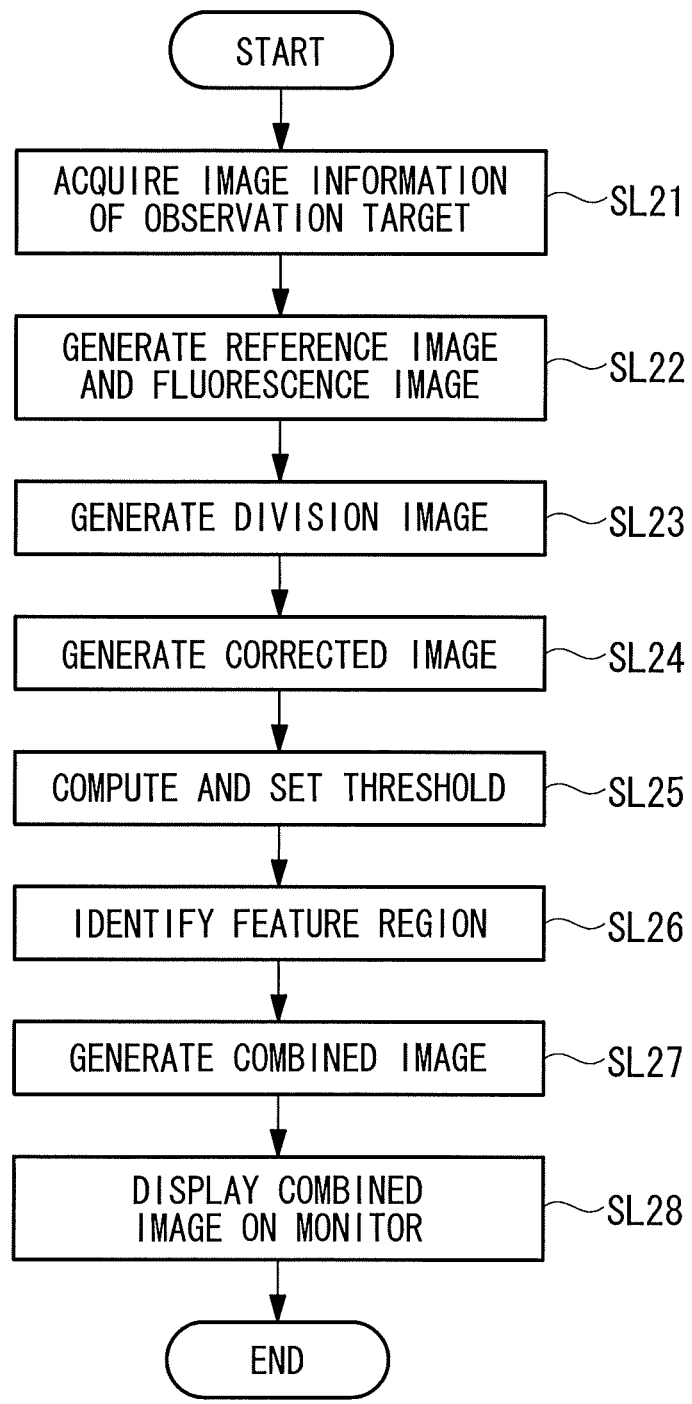
FIG. 92 is a flowchart showing a processing method based on the post-processing mode executed by the post-processing section of FIG. 91.

A modification of the first post-processing mode by the post-processing section 65 according to the present modification with the configuration will be described with reference to a flowchart of FIG. 92.

According to the post-processing section 65 of the present modification, after the division image and the corrected image are generated based on the fluorescence image and the reference image (step SL21 to step SL24), the generated corrected image is output to the threshold setting circuit 33F and output to the extraction circuit 32F, and the process advances to the next step SL25.

In step SL25, the threshold setting circuit 33F determines the coefficient a of Expression (12) and calculates the threshold S based on Expression (12) by calculating the average gradation value m of the entire image of the corrected image output from the division image generation section 64 and using the set coefficient a and the calculated average gradation value m of the entire image. By doing so, the threshold S of the gradation value in the division image is set, and the set threshold S is output to the extraction circuit 32F.

In the next step SL26, based on the threshold S set in step SL25, the extraction circuit 32F extracts, as feature areas, pixels with the gradation values larger than the threshold S among all pixels of the corrected image from the corrected image, and the process advances to the next step SL27. In step SL27, the image combining section 67 generates a combined image by superimposing the feature areas extracted by the extraction circuit 32F on the reference image. By doing so, the contrast between the diseased portion and the background is increased in the combined image based on the predetermined threshold. The image combining section 67 outputs the generated combined image to the monitor 20. In the next step SL28, the combined image received from the image combining section 67 is displayed on the monitor 20.

As described, according to the first post-processing mode of the present modification, the extraction circuit 32F further extracts, as features areas, the areas mainly displaying the fluorescence from the diseased portion with the gradation values higher than the threshold, in addition to the effect of the first post-processing mode. Therefore, by generating an image by superimposing the feature areas on the reference image, the contrast between the diseased portion and the background is further increased in the generated image based on the threshold. Particularly, since the threshold setting circuit 33F sets the threshold based on the average gradation value of the entire corrected image, the diseased portion can be extracted with high precision by updating the threshold in accordance with the variations of the gradation values in the corrected image and reducing the influence of the individual differences and temporal changes of the examination target in the acquired corrected image.

Therefore, the information of the observation target A can be acquired by suppressing the influence of the background, and the diseased portion can be extracted more accurately with high precision.

Note that although the threshold is set based on the average gradation value m in the present modification, the setting is not limited to this. For example, as shown in the following Expression (13), the threshold S can also be set based on a sum of the average gradation value m of the entire image and a standard deviation σ.

$$S = am + b\sigma \quad (13)$$

σ: standard deviation of gradation value of each pixel in corrected image

In this case, even when there are variations in the gradation values of the pixels in the corrected image, a more precise threshold can be set compared to when the threshold is set based only on the average gradation value.

In addition, the threshold setting circuit 33F may set the threshold for each division image of the subsequent frames or may set the threshold when the average value of the gradation values of the pixels of the subsequent frames fluctuates in excess of a certain proportion.

Note that, the observation target A can also be specified based on the identification information of the insertion portion 2. More specifically, in the fluorescence observation apparatus 500 according to the fifth embodiment, the IC chip 73 stores, as the identification information, information and the like of the observation target site corresponding to each insertion portion 2.

In this case, when the insertion portion 2 is connected to the light source 3, the IC reader 74 reads out the identification information stored in the IC chip 73 and transmits the identification information to the input section 75 to specify the observation target site based on the identification information. Then, the information regarding the specified observation target is output to the correction condition setting sections 66, 66', and 66".

Although the color characteristics of the observation target A have been mentioned in the description of the first post-processing mode, there are the same effects even when the intensity of the reflected light is reduced by factors other than the distance (for example, shape such as irregularities).

{Second Post-Processing Mode}

Next, the second post-processing mode by the post-processing section 65 included in the fluorescence observation apparatuses 100, 200, 300, 400, and 500 according to the first to fifth embodiments will be described. The second post-processing mode is a processing mode of executing a process of increasing the contrast in a division image of an area with the gradation value equal to or larger than the gradation value threshold and an area with the gradation value smaller than the gradation value threshold.

The second post-processing mode is suitable for removing the dependency of observation distance and observation angle remained in the division image due to the observation distance from the tip surface 2a of the insertion portion 2 to the observation target A. More specifically, the correction condition setting sections 66 and 66' of the fluorescence observation apparatuses 100 and 200 according to the first and second embodiments set the post-processing parameters of the second post-processing mode when "local view" or "overhead view" is input or determined as the observation condition. The correction condition setting section 66" of the fluorescence observation apparatuses 300, 400, and 500 according to the third to fifth embodiments sets the post-processing parameters of the second post-processing mode when "Douglas' pouch" or the like for local observation or "greater omentum", "subphrenic area", "intestinal membrane", or the like for overhead observation is input or determined.

In this case, in the second post-processing mode described later, the correction condition setting sections 66, 66', and 66" set a larger weighting coefficient a (post-processing parameter) described later to increase the gradation value threshold when the observation condition corresponds to "local observation" in which the light levels of the reflected light and the fluorescence tend to be high. On the other hand, the correction condition setting sections 66, 66', and 66" set a smaller weighting coefficient a to reduce the gradation value threshold when the observation condition corresponds to "overhead observation" in which the light levels of the reflected light and the fluorescence tend to be low.

Figure 93:
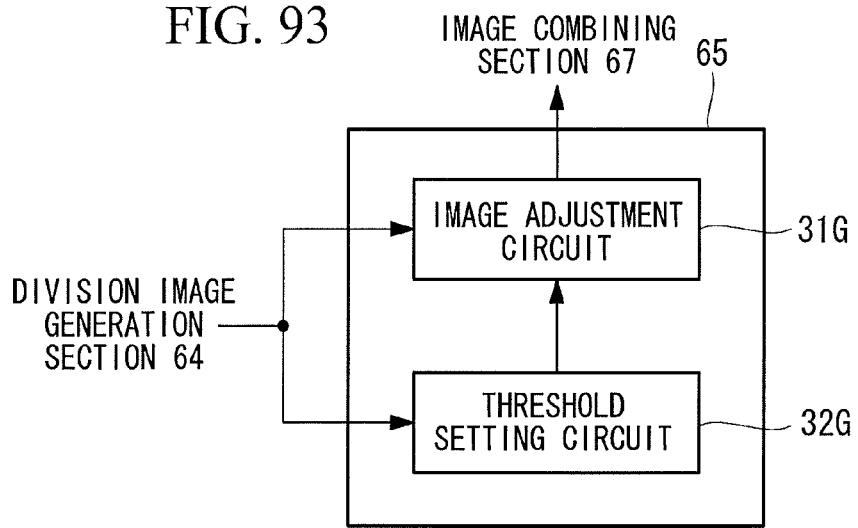
FIG. 93 is a block diagram showing a configuration of the post-processing section and a correction condition setting section that execute a second post-processing mode.

As shown in FIG. 93, an image adjustment circuit 31G and a threshold setting circuit 32G included in the post-processing section 65 execute the second post-processing mode.

The threshold setting circuit 32G sets a gradation value threshold of the gradation value in the division image generated by the division image generation section 64. Specifically, as indicated by the following Equation 8, the threshold setting circuit 32G is configured to set, as a gradation value threshold, a value obtained by multiplying the average value m of the gradation values of the pixels in the division image (average gradation value of the entire image) by the weighting coefficient a set by the correction condition setting sections 66, 66', and 66".

$$S = a \times m \quad \{\text{Equation 8}\}$$

The image adjustment circuit 31G adjusts the gradation values in the division image. Specifically, the image adjustment circuit 31G is configured to display the pixels by replacing, with a gradation value of 0, the pixels having gradation values less than the gradation value threshold S set by the threshold setting circuit 32G to increase the contrast in the division image between the areas of the pixels with the gradation values equal to or larger than the gradation value threshold S and the areas of the pixels with small gradation values.

Figure 94A:
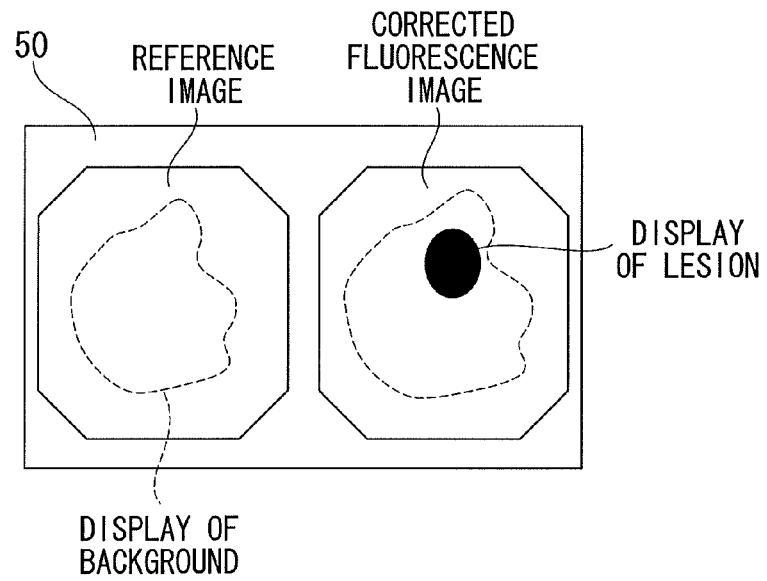
FIG. 94A shows an example of a reference image and a corrected fluorescence image displayed on a monitor of FIG. 93.

According to the second post-processing mode executed by the post-processing section 65 with the configuration, the division image generated by the division image generation section 64 is transmitted to the threshold setting circuit 32G and transmitted and displayed on the monitor 20 together with the reference image after the application of the post-processing by the image adjustment circuit 31 as shown in FIG. 94A.

Figure 94B:
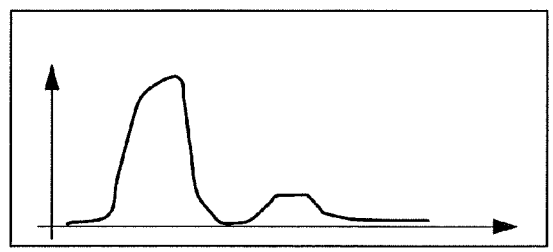
FIG. 94B is a histogram showing a relationship between gradation values of pixels in the corrected fluorescence image of FIG. 94A and the frequency of each of the gradation values occupying the entire image.

As shown in FIG. 94B, the division image mainly includes an area displaying weak fluorescence from the background and an area displaying strong fluorescence from the diseased portion. In FIG. 94B, the horizontal axis denotes the gradation values, and the vertical axis denotes the frequency of each of the gradation values occupying the entire division image (the same applies to FIGS. 96B, 97A, and 98A). Note that a histogram as shown in FIG. 94B may be displayed on the monitor 20.

In this case, since the dependency on the observation distance or the observation angle is different between the fluorescence and the reflected light, the influence of the observation distance or the observation angle cannot be completely corrected in the division image, and constant errors may occur.

Figure 95:
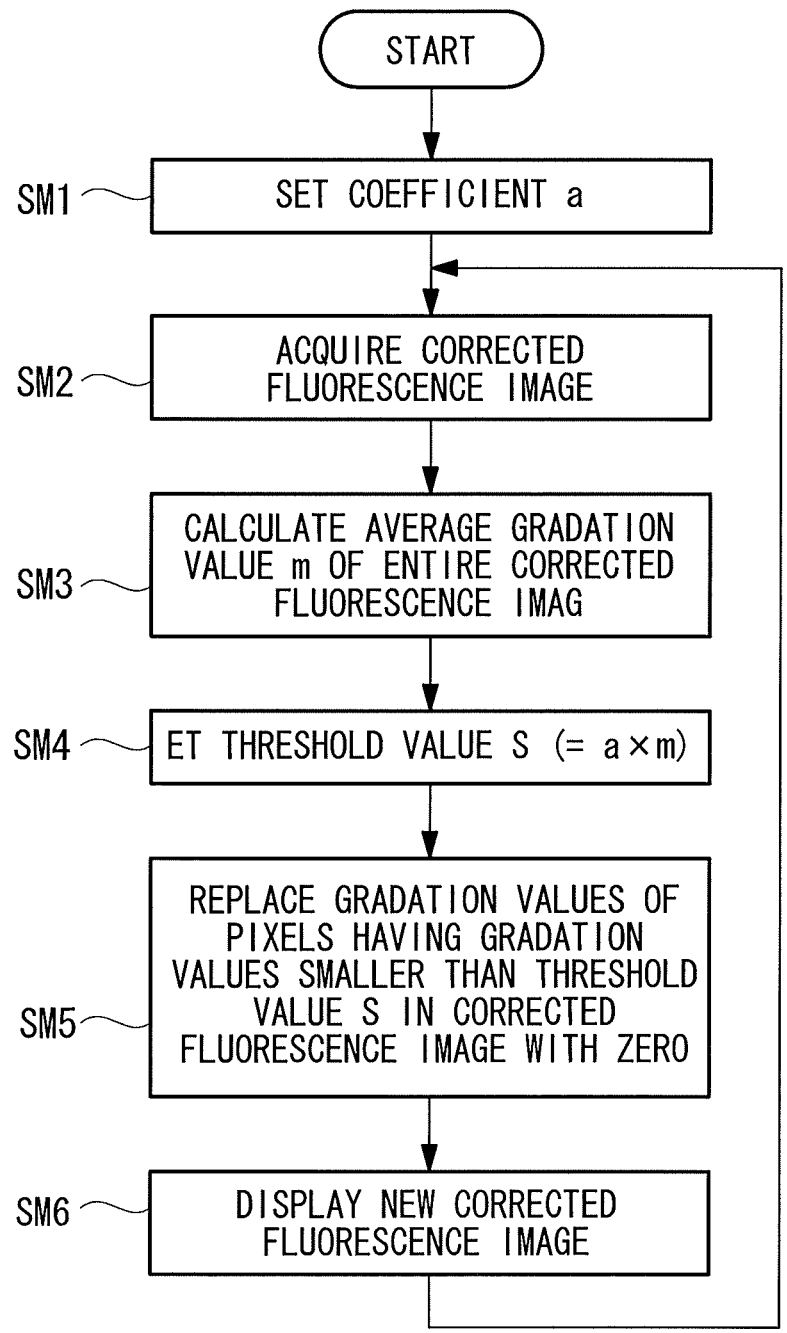
FIG. 95 is a flowchart showing a processing method based on the second post-processing mode.

Hereinafter, setting of the gradation value threshold by the threshold setting circuit 32G and adjustment of the division image by the image adjustment circuit 31G performed to acquire quantitative information of the observation target A will be described with reference to a flowchart shown in FIG. 95.

The threshold setting circuit 32G sets the weighting coefficient a (for example, a=1.5) of Equation 8 according to a command from the correction condition setting sections 66, 66', and 66" (step SM1). Next, when the division image transmitted from the division image generation section 64 is acquired (step SM2), the threshold setting circuit 32G calculates the average gradation value m of the entire image (step SM3).

The average gradation value m of the entire image is calculated by, for example, the following Equation 9.

$$m = \frac{n_1 \times \overline{m_1} + n_2 \times \overline{m_2}}{n_1 + n_2} \quad \{\text{Equation 9}\}$$

In this case, $\overline{m}_1$ denotes an average value of gradation values of pixels displaying the background, $\overline{m}_2$ denotes an average value of gradation values of pixels displaying the lesion, $n_1$ denotes the total number of pixels displaying the background, and $n_2$ denotes the total number of pixels displaying the lesion.

In this case, when the number of all pixels of the division image is 1,000,000, it is assumed that 950,000 pixels display the fluorescence from the background (total number of pixels of background $n_1$=950,000) and that 50,000 pixels display the fluorescence from the diseased portion (total number of pixels of diseased portion $n_2$=50,000). In addition, when the contrast of the fluorescent agent is 1:2, it is assumed that an average gradation value of background $m_1$=1000 and an average gradation value of diseased portion $m_2$=2000.

Based on this assumption, the average gradation value of entire image m=1050 is calculated by calculation expression (2).

Next, the threshold setting circuit 32G uses the set weighting coefficient a and the calculated average gradation value m of the entire image to calculate the gradation value threshold S=1575 based on equation 8. By doing so, the gradation value threshold S of the gradation value in the division image is set (step SM4) and transmitted to the image adjustment circuit 31G.

Among all pixels of the division image, the image adjustment circuit 31G replaces the pixels having the gradation values less than the gradation value threshold S=1575 with a gradation value of 0 (step SM5). In this case, assuming that the distribution of the gradation values of the pixels displaying the background and the gradation values of the pixels displaying the diseased portion is in accordance with a normal distribution and that the standard deviation is ten times the square root of the average value of the gradation values of the pixels displaying the background and the gradation values of the pixels displaying the diseased portion, 96.5% of the display of the background is eliminated, and 82.9% of the display of the diseased portion is maintained.

Figure 96A:
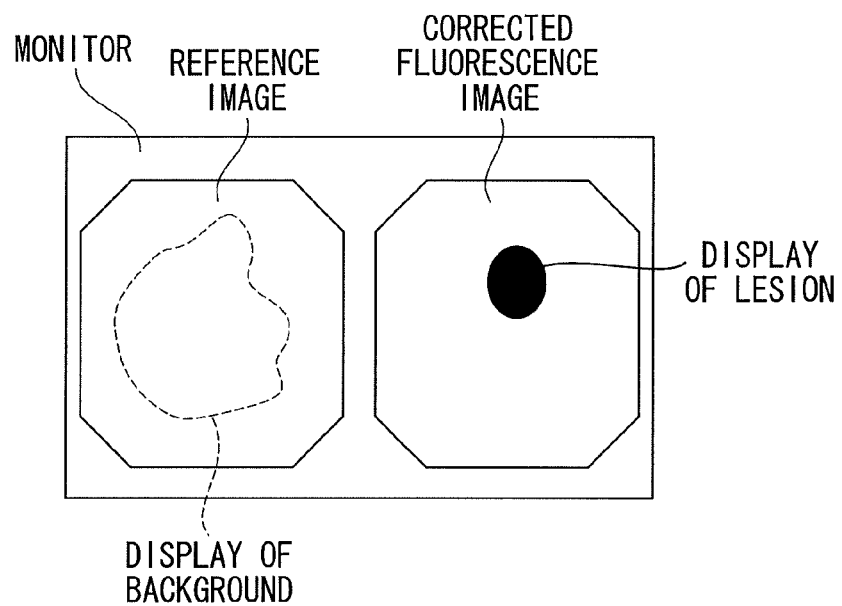
FIG. 96A shows an example of the reference image and the corrected fluorescence image displayed on the monitor.
Figure 96B:
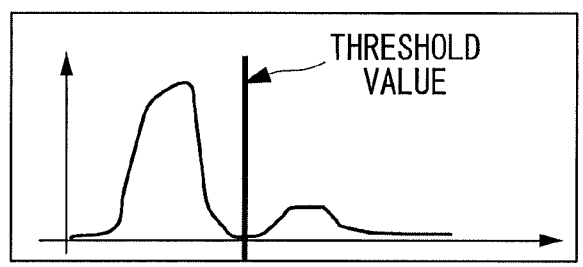
FIG. 96B is a histogram showing a relationship between the gradation values of the pixels in the corrected fluorescence image of FIG. 96A and the frequency of each of the gradation values occupying the entire image.

By doing so, a corrected fluorescence image with an increased contrast between the area displaying the diseased portion and the area displaying the background is displayed on the monitor 20 as shown in FIG. 96A (step SM6). As shown in FIG. 96B, the corrected fluorescence image includes an area mainly displaying the fluorescence from the diseased portion, in which the gradation value is equal to or higher than the gradation value threshold S.

Figure 97A:
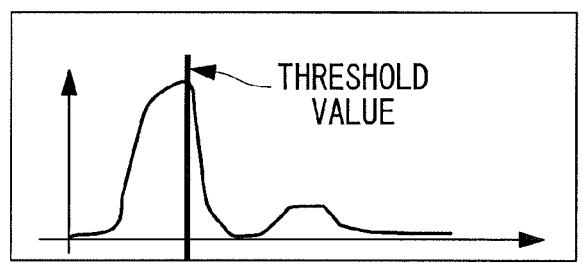
FIG. 97A is a histogram showing a relationship between the gradation values of the pixels in the division image and the frequency of each of the gradation values occupying the entire image after a change in the gradation values.

Next, it is assumed that the observation distance and the observation angle fluctuate and that the average value of the gradation values of the pixels in the division image of the subsequent frames fluctuates to increase as shown in FIG. 97A due to an error factor. Here, it is assumed that the average value of the gradation values of the pixels displaying the background and the average value of the gradation values of the pixels displaying the diseased portion fluctuate to increase by 50%, that is, $m_1$=1500 and $m_2$=3000.

Figure 97B:
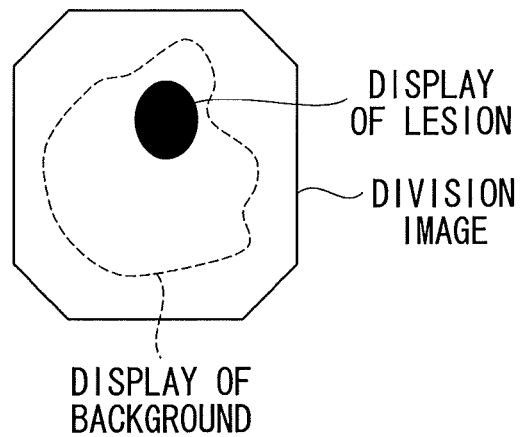
FIG. 97B is a diagram showing an example of the division image of FIG. 97A.

In this case, if the gradation value threshold S=1575 is maintained without changing the current gradation value threshold after the fluctuation of the gradation values, although 99.5% of the display of the diseased portion is maintained, only 57.7% of the display of the background is eliminated as shown in FIG. 97B due to an increase in the areas with the gradation values exceeding the gradation value threshold S, and the sharpness of the division image is reduced.

In the second post-processing mode, since the threshold setting circuit 32G sets the gradation value threshold S based on the average gradation value m of the entire image, steps SM2 to SM6 are repeated.

Figure 98A:
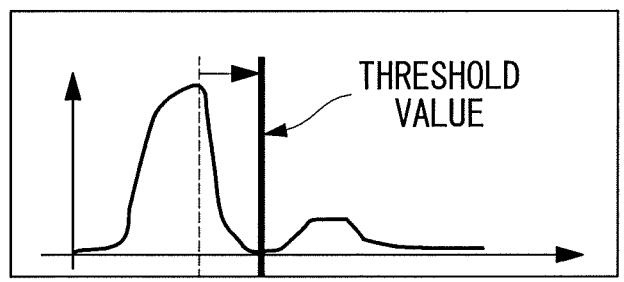
FIG. 98A is a histogram showing a relationship between the gradation values of the pixels in the division after the image adjustment and the frequency of each of the gradation values occupying the entire image.

When a division image of the subsequent frame is acquired (step SM2), the threshold setting circuit 32G calculates the average gradation value m of the entire image of the subsequent frame based on Equation 9 (step SM3), and as shown in FIG. 98A, sets a new gradation value threshold S=2363 larger than the gradation value threshold S=1575 in the previous frame (step SM4).

Figure 98B:
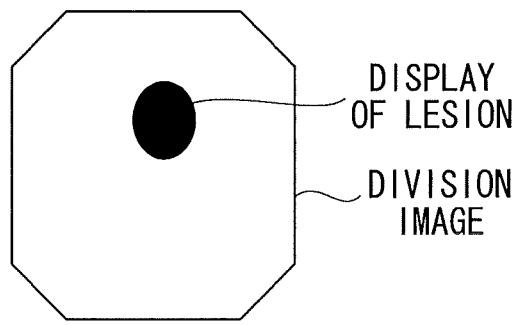
FIG. 98B is a diagram showing an example of the division image of FIG. 98A.

By doing so, the image adjustment circuit 31G adjusts the gradation values in the division image (step SM5). As shown in FIG. 98B, a new corrected fluorescence image is displayed, in which 98.7% of the display of the background is eliminated, and 87.8% of the display of the diseased portion is maintained (step SM6).

In this way, steps SM2 to SM6 are repeated, and the division image of the subsequent frame is generated. The gradation value threshold S is updated based on the average gradation value m of the entire image, and the new corrected fluorescence image with adjusted gradation values is displayed on the monitor 20.

As described, according to the second post-processing mode, the image adjustment circuit 31G adjusts the gradation values of the division image to increase the contrast between the diseased portion and the background based on the predetermined gradation value threshold, and a sharp corrected fluorescence image can be generated in which the influence of the weak fluorescence generated from the background is suppressed.

In addition, since the threshold setting circuit 32G sets the gradation value threshold based on the average gradation value of the division image, the gradation value threshold can be updated in accordance with the fluctuation of the gradation values in the division image, and the sharpness of each of the acquired division images can be maintained. By doing so, quantitative information of the observation target A can be acquired.

Although the weighting coefficient a=1.5 is illustrated in the description, the correction condition setting sections 66, 66', and 66" appropriately change the value of the weighting coefficient a according to the observation situation as described above.

The second post-processing mode can be modified as follows.

For example, although the gradation value threshold is set based on the average gradation value m of the entire division image in the second post-processing mode, the threshold setting circuit 32G may set the gradation value threshold S based on the average gradation value m of the entire image, the standard deviation, and weighting coefficients a and b (post-processing parameters) in a first modification as indicated by the following Equation 10. In this case, the correction condition setting sections 66, 66', and 66" command the post-processing section 65 to set large weighting coefficients a and b when the observation condition corresponds to "local observation" and to set small weighting coefficients a and b when the observation condition corresponds to "overhead observation".

$$S = a \times m + b \times \sigma \quad \{\text{Equation 10}\}$$

In this case, $\sigma$ denotes a standard deviation of gradation values of pixels in division image In addition, the standard deviation $\sigma$ of the entire image can be calculated by the following Equation 11.

$$\sigma^2 = \overline{x^2} - m^2 \quad \{\text{Equation 11}\}$$
$$= \frac{n_1 \times \overline{x_1^2} + n_2 \times \overline{x_2^2}}{n_1 + n_2} - m^2$$
$$= \frac{n_1(\sigma_1^2 + m_1^2) + n_2(\sigma_2^2 + m_2^2)}{n_1 + n_2} - m^2$$

In this case, $\overline{x}^2$ denotes a square mean value of the gradation values of the entire image, $\overline{x}_1^2$ denotes a square mean value of the gradation values of the background, $\overline{x}_2^2$ denotes a square mean value of the gradation values of the lesion, $\sigma_1$ denotes a standard deviation of the gradation values of the pixels displaying the background, and $\sigma_2$ denotes a standard deviation of the gradation values of the pixels displaying the lesion.

In this case, although a standard deviation $\sigma_1$ of the background and a standard deviation $\sigma_2$ of the diseased portion are ideally values close to the square root of the average gradation value, the fluctuation increases due to the influence of the fluctuation of the distribution of illuminated light, irregularities on the surface of the observation target A, and the like. Accordingly, it is assumed that the standard deviations $\sigma_1$ and $\sigma_2$ are ten times the ideal values (square root of average gradation value), wherein standard deviation of background $\sigma_1$ of background=316 and standard deviation $\sigma_2$ of diseased portion=447. Hereinafter, it is assumed that a=b=1 in the description.

Figure 99:
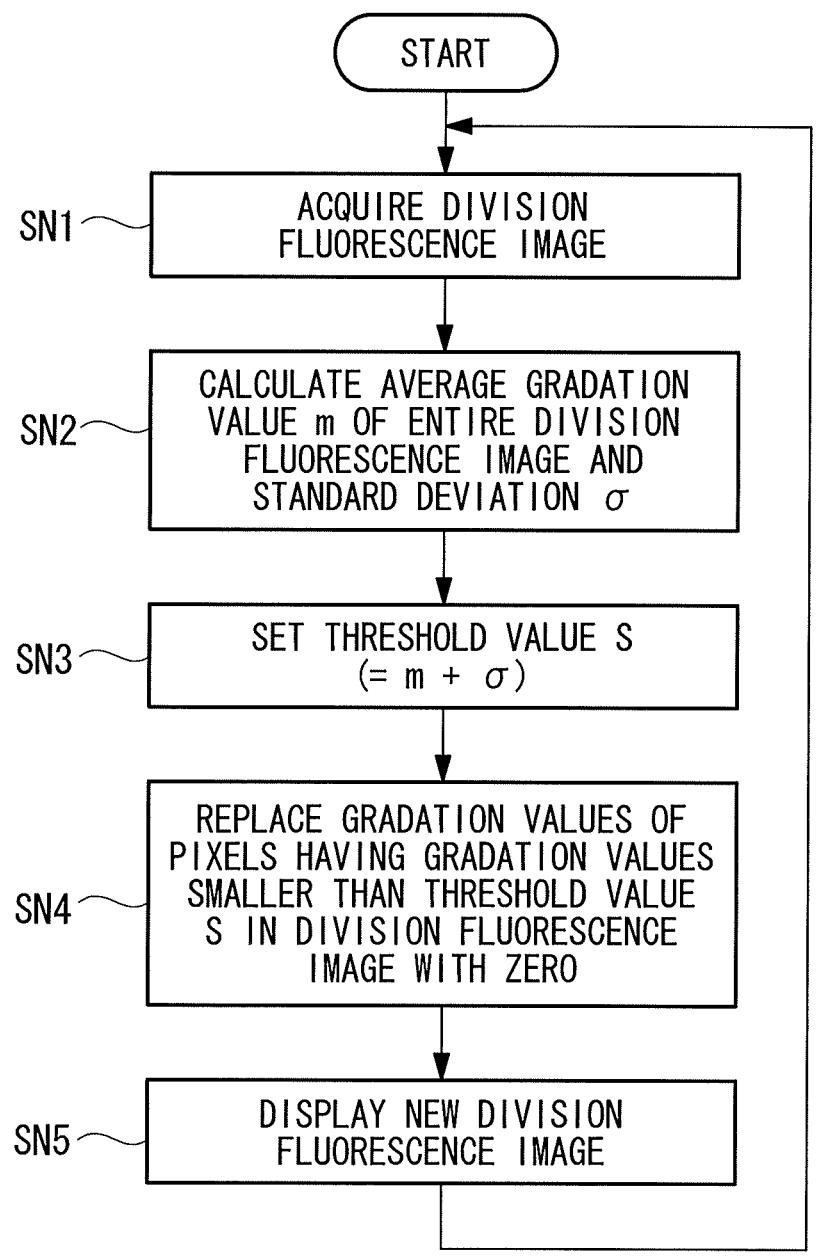
FIG. 99 is a flowchart showing a first modification of the second post-processing mode.

Based on this assumption, as shown in a flowchart of FIG. 99, when the threshold setting circuit 32G acquires the division image (step SN1), the average gradation value m of entire image=1050 and the standard deviation $\sigma$=391 are calculated by Equations 9 and 11 (step SN2). In addition, the threshold setting circuit 32G uses the calculated average gradation value m of entire image and standard deviation $\sigma$ to calculate and set the gradation value threshold S=1441 based on Equation 10 (step SN3).

The image adjustment circuit 31G replaces, with a gradation value of 0, the pixels with the gradation values less than the gradation value threshold S=1441 among all pixels of the division image (step SN4). By doing so, a corrected fluorescence image is displayed on the monitor 20, in which 91.8% of the display of the background is eliminated, and 89.5% of the display of the diseased portion is maintained (step SN5).

Next, when the average value of the gradation values of the pixels in the division image of the subsequent frame fluctuates to increase due to an error factor after fluctuation of the observation distance or the observation angle, if the gradation value threshold S=1441 is maintained without changing the gradation value threshold, although 98.8% of the display of the diseased portion is maintained after the fluctuation of the gradation value, only 65.2% of the display of the background is eliminated, and the sharpness of the division image is reduced.

In the present modification, since the threshold setting circuit 32G sets the gradation value threshold S based on the sum of the average gradation value m of the entire image and the standard deviation $\sigma$, steps SN1 to SN5 are repeated.

For example, if the average value of the gradation values of the pixels fluctuates by 30%, it can be assumed that the average gradation value $m_1$ of background=1300, the standard deviation $\sigma_1$=361, the average gradation value $m_2$ of diseased portion=2600, and the standard deviation $\sigma_2$=510.

When the threshold setting circuit 32G acquires the division image of the subsequent frame (step SN1), the average gradation value m=1365 of the entire image of the subsequent frame and the standard deviation $\sigma$=466 calculated based on Equations 9 and 11 are used (step SN2) to set a new gradation value threshold S=1831 based on Equation 10 (step SN3). By doing so, the image adjustment circuit 31G adjusts the gradation values of the division image (step SN4), and a new corrected fluorescence image is displayed in which 92.9% of the display of the background is eliminated, and 93.4% of the display of the diseased portion is maintained (step SN5).

As described, according to the present modification, since the gradation value threshold S is set based on the sum of the average gradation value m of the entire image and the standard deviation $\sigma$, a sharp corrected fluorescence image can be always acquired even if an error factor with respective to the observation distance or the observation angle remains in the division image. In addition, even if there are variations in the gradation values of the pixels in the division image, a more precise gradation value threshold can be set compared to when the gradation value threshold is set based only on the average gradation value.

Here, a comparative example of the present modification will be described below.

For example, it is assumed that the average value of the gradation values of the pixels fluctuates 30%, the average gradation value of background $m_1$=700, the standard deviation $\sigma_1$=265, the average gradation value of diseased portion $m_2$=1400, and the standard deviation $\sigma_2$=374. In this case, if the gradation value threshold S is calculated based only on the average gradation value m of the entire image in the comparative example, the gradation value threshold S=1103. Although 93% of the display of the background is eliminated, only 78% of the display of the diseased portion is maintained.

On the other hand, if the gradation value threshold S is calculated based on the sum of the average gradation value m of the entire image and the standard deviation $\sigma$ as in the present modification, the gradation value threshold S=1046. 90% of the display of the background is eliminated, and 83% of the display of the diseased portion is maintained. Therefore, the gradation value threshold that maintains more display of the diseased portion can be set, and this is particularly effective in placing higher priority on the sensitivity over the specificity.

Figure 100:
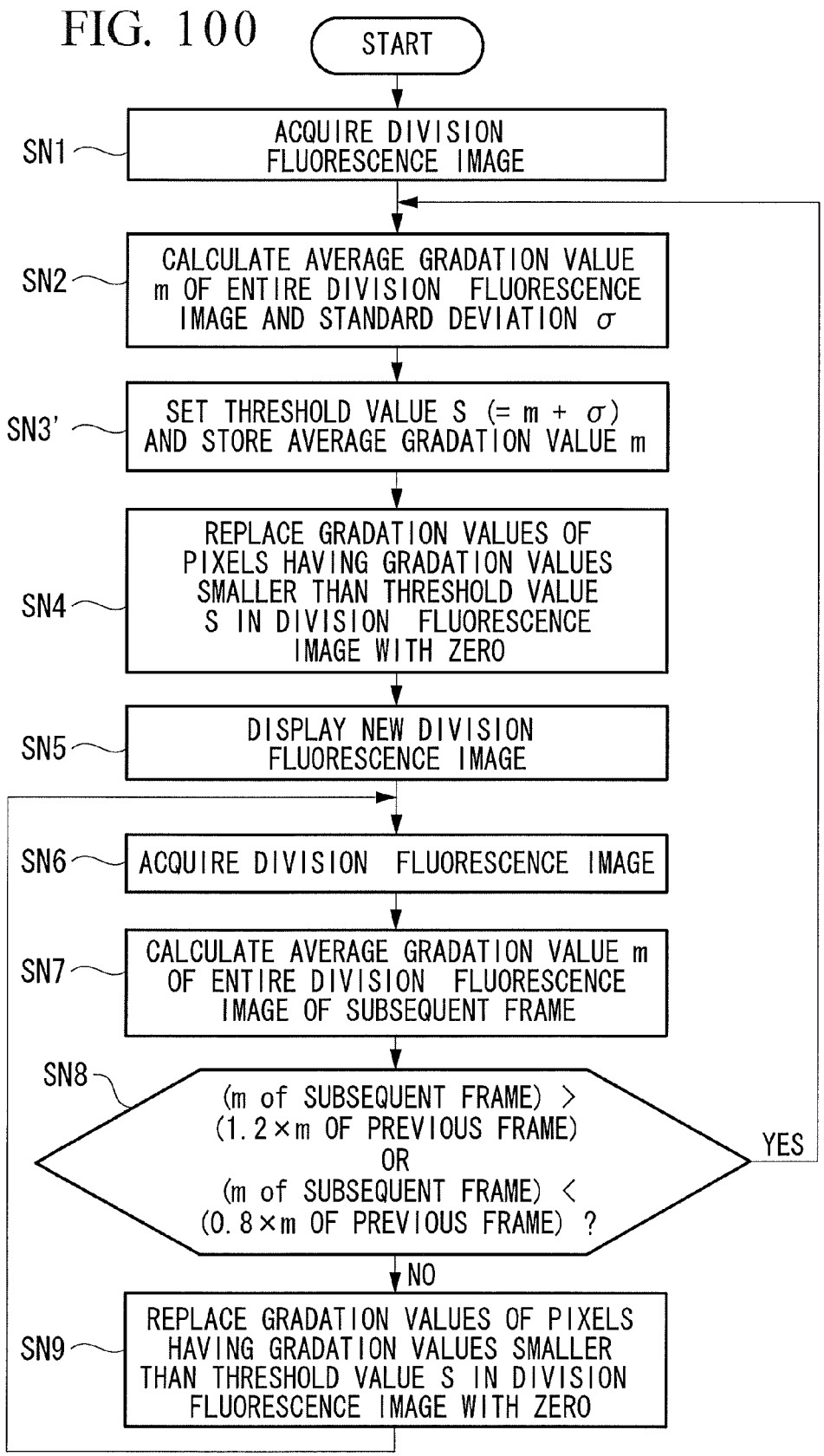
FIG. 100 is a flowchart showing a second modification of the second post-processing mode.

In addition, although the gradation value threshold S is set for each deviation image of the subsequent frame in the second post-processing mode and the present modification, the gradation value threshold may be set when the average value of the gradation values of the pixels of the subsequent frames fluctuate in excess of a certain proportion in the second modification. In this case, as shown in a flowchart of FIG. 100, the threshold setting circuit 32G sets the gradation value threshold S of the gradation values in the division image and stores the average gradation value m of the entire image at this point (step SN3'), and a new division image is displayed through steps SN4 and SN5.

Next, when a division image of the subsequent frame is acquired (step SN6), the threshold setting circuit 32G calculates the average gradation value m of the entire image (step SN7) and compares the average gradation value m with the stored average gradation value m of the entire image of the previous frame (step SN8).

As a result, for example, if the average gradation value m of the entire image of the subsequent frame is equal to or higher than 1.2 times or equal to or lower than 0.8 times the average gradation value m of the entire image of the previous frame, steps SN2 to SN8 are repeated. By doing so, the standard deviation $\sigma$ of the entire image of the subsequent frame is calculated (step SN2). A new gradation value threshold S is set, and a new average gradation value m is stored (step SN3').

On the other hand, in step SN8, if the average gradation value m of the entire image of the subsequent frame is equal to or higher than 0.8 times and equal to or lower than 1.2 times the average gradation value m of the entire image of the previous frame, the division image of the subsequent frame is adjusted without changing the gradation value threshold, and the corrected fluorescence image is displayed (step SN9). The process returns to step SN6.

Since the average value of the gradation values of the pixels and the standard deviation do not largely fluctuate in a state that the observation conditions are relatively stable, a corrected fluorescence image with stable sharpness can be acquired without resetting the gradation value threshold S every time the division image is generated. In addition, since the threshold S is maintained unless the average value of the gradation values of the pixels largely fluctuates, the calculation amount of the standard deviation $\sigma$ can be reduced to improve the processing speed.

Figure 101:
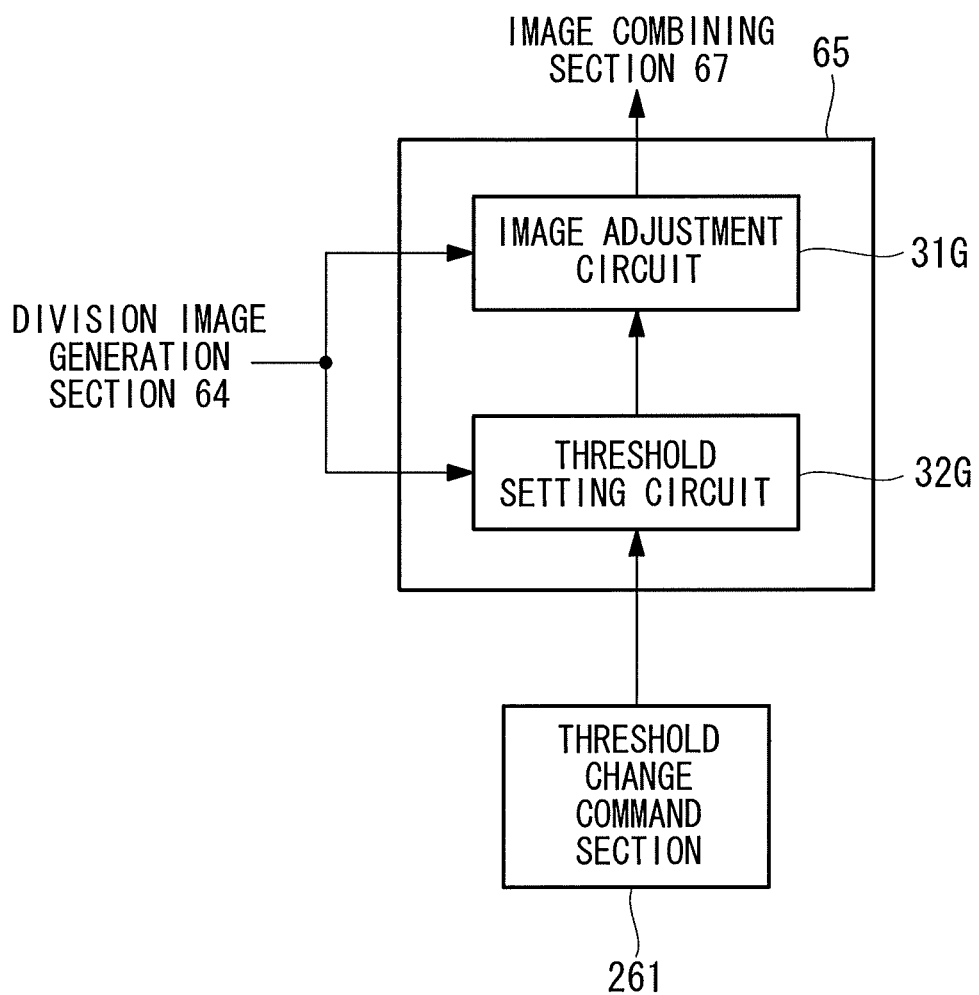
FIG. 101 is a partial block diagram of a fluorescence observation apparatus that executes a third modification of the second post-processing mode.

Furthermore, in a third modification, the fluorescence observation apparatus may include a threshold change command section 261 for inputting a change command of the gradation value threshold as shown in FIG. 101, and the operator may be able to operate the threshold change command section 261 to manually change the gradation value threshold. By doing so, instead of always setting the gradation value threshold every time the division image of the subsequent frame is generated, the division image can be adjusted when the operator determines that the gradation value threshold is not suitable during the observation.

Figure 102:
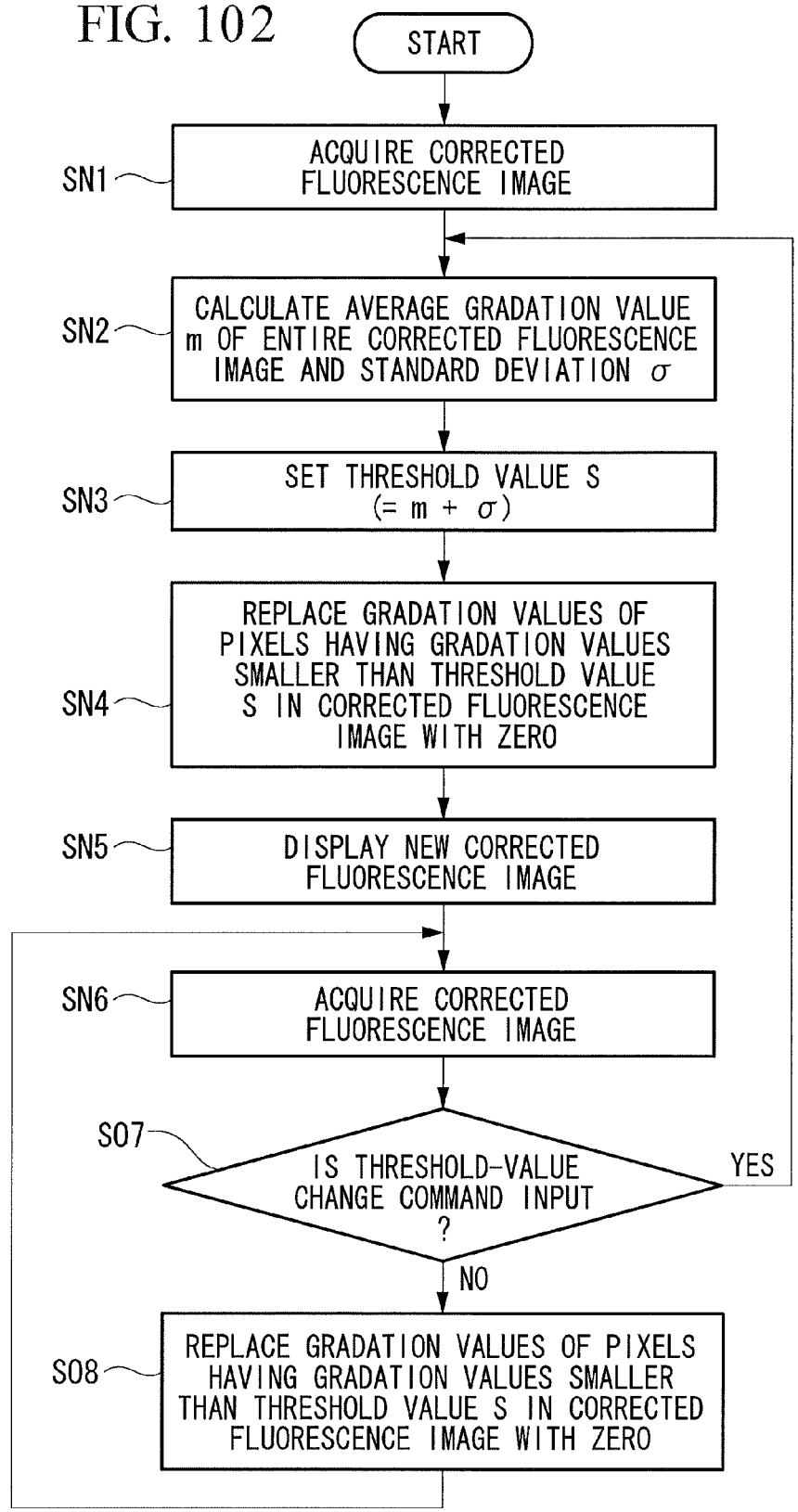
FIG. 102 is a flowchart showing operation of the fluorescence observation apparatus of FIG. 101.

In this case, as shown in a flowchart of FIG. 102, after the division image of the subsequent frame is acquired by the threshold setting circuit 32G (step SN6), when the operator inputs a change command to the threshold change command section 261 (step SO7 "YES"), steps SN1 to SO7 can be repeated. By doing so, the threshold setting circuit 32G is operated, and the gradation value threshold S is set based on the sum of the average gradation value m of the entire image of the subsequent frame and the standard deviation $\sigma$ (step SN3).

On the other hand, if the operator does not input a change command to the threshold change command section 261 (step SO7 "NO"), the image adjustment circuit 31G can adjust the gradation value of the division image based on the current gradation value threshold S (step SO8), and the process can return to step SN6.

Furthermore, in a fourth modification, the gradation value threshold may be set for every several frames, instead of always setting the gradation value threshold every time the division image of the subsequent frame is generated. In this case, for example, information n related to the frequency of changing the gradation value threshold can be individually determined for the insertion portion 2. The fluorescence observation apparatuses 100, 200, 300, 400, and 500 can include an identification information reading section (not shown) of the insertion portion 2 that reads out the information n of the connected insertion portion 2, and the threshold setting circuit 32G can change the gradation value threshold based on the read information n. In addition, the information n can mean, for example, the gradation value threshold is changed once when the number of frames i reaches n. The information n and the identification information reading section of the insertion portion 2 may correspond to the identification information and the IC reader 74 in the fluorescence observation apparatus according to the fifth embodiment, respectively.

Figure 103:
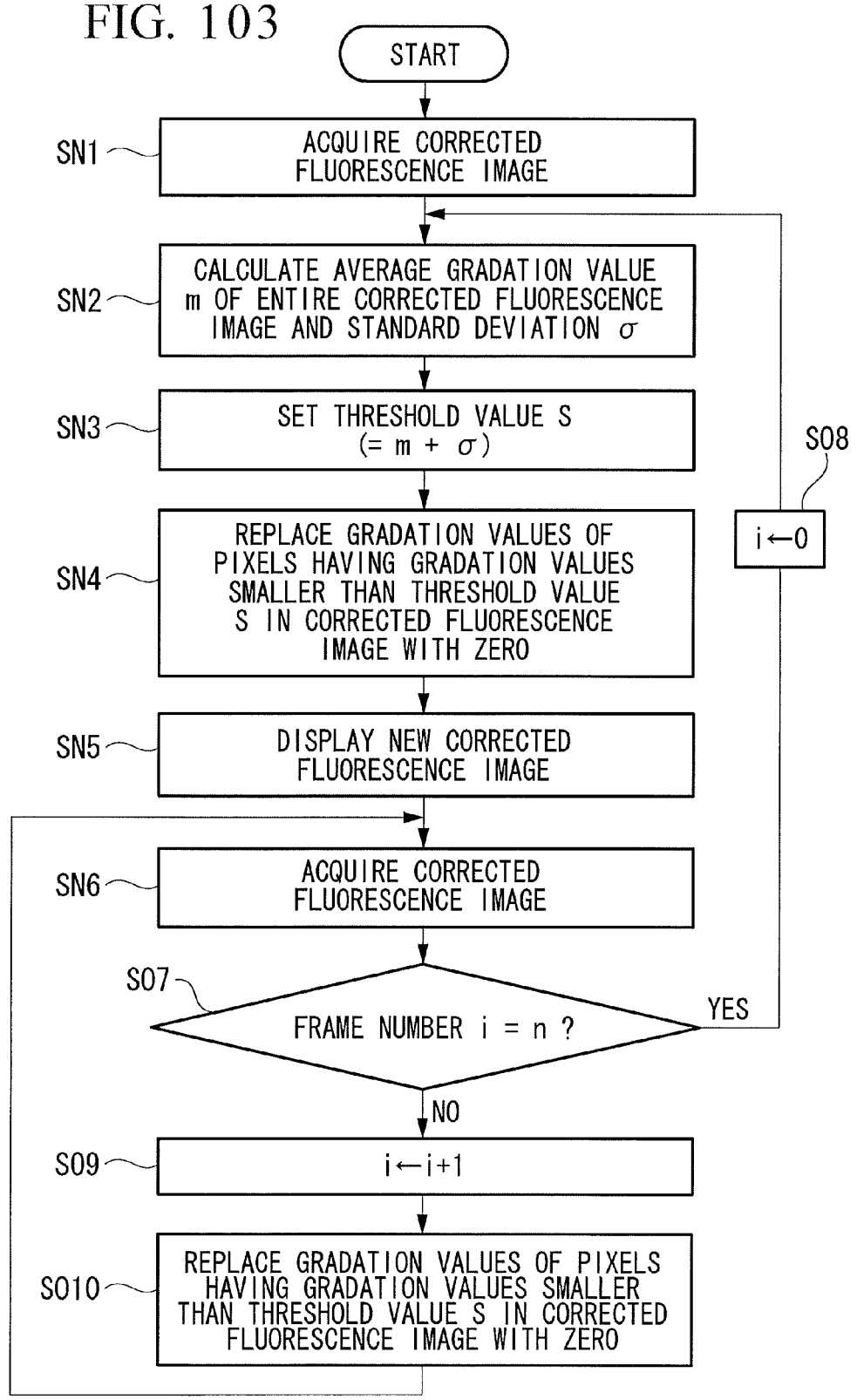
FIG. 103 is a flowchart showing a fourth embodiment of the second post-processing mode.

In this case, as shown in a flowchart of FIG. 103, when the number of subsequent frames i acquired by the threshold setting circuit 32G in step SN6 reaches n (step SP7 "YES"), the number of frames i can be reset (step SP8), and steps SN2 to SP7 can be repeated. By doing so, the gradation value threshold S is set based on the sum of the average gradation value m of the entire image of the subsequent frame and the standard deviation σ (step SN2 and step SN3).

On the other hand, if the number of subsequent frames i has not reached n (step SP7 "NO"), after 1 is added to the number of frames i (step SP9), the image adjustment circuit 31G can adjust the gradation value of the division image based on the current gradation value threshold S (step SP10). The process can return to step SN6.

By doing so, the number of times of calculating the average gradation value m of the entire image and the standard deviation σ can be reduced to increase the processing speed. For example, it is better to relatively frequently reset the gradation value threshold S under the observation condition in which the observation distance largely fluctuates according to expansion and contraction such as in the stomach, and the frequency of resetting the gradation value threshold S may be reduced under the observation condition in which the observation distance is relatively constant as the lumen diameter is fixed to some extent such as in the colon.

Furthermore, in the second post-processing mode and the modification, the image adjustment circuit 31G eliminates the display of the fluorescence of the background and maintains the display of the diseased portion. However, it is only necessary to increase the contrast between the fluorescence from the diseased portion and the fluorescence from the background. For example, the gradation values of the pixels may be reduced without eliminating the display of the background, and the gradation values of the pixels displaying the diseased portion may be increased.

{Third Post-Processing Mode}

Next, the third post-processing mode by the post-processing section 65 included in the fluorescence observation apparatuses 100, 200, 300, 400, and 500 according to the first to fifth embodiments will be described. The third post-processing mode is a mode of executing a process of extracting a first area with the gradation value higher than a first threshold of the fluorescence image, extracting a second area with the gradation value higher than a second threshold of the division image, and extracting, from the fluorescence image, an overlap area in which the first area and the second area overlap.

The third post-processing mode and the first post-processing mode are alternatively used. More specifically, the correction condition setting sections 66, 66', and 66" of the fluorescence, observation apparatuses 100, 200, 300, 400, and 500 according to the first to fifth embodiments set post-processing parameters of the third post-processing mode for the same observation conditions as those of the first post-processing mode. Which one of the first post-processing mode and the third post-processing mode will be used may be selected by the user before the observation, and only one of the modes may be mounted in the manufacturing of the apparatus.

In this case, the correction condition setting sections 66, 66', and 66" set a second threshold for division image described later (post-processing parameter) to a small value relative to a first threshold for fluorescence image (post-processing parameter) to increase the weight of the division image when the observation conditions indicate a large length of perspective in the field of view and a smooth surface of the observation target in the third post-processing mode described later. On the other hand, the correction condition setting sections 66, 66', and 66" set the first threshold for fluorescence image to a small value relative to the second threshold for division image to increase the weight of the fluorescence image when the observation conditions indicate a small length of perspective in the field of view and an irregular surface of the observation target.

Figure 104:
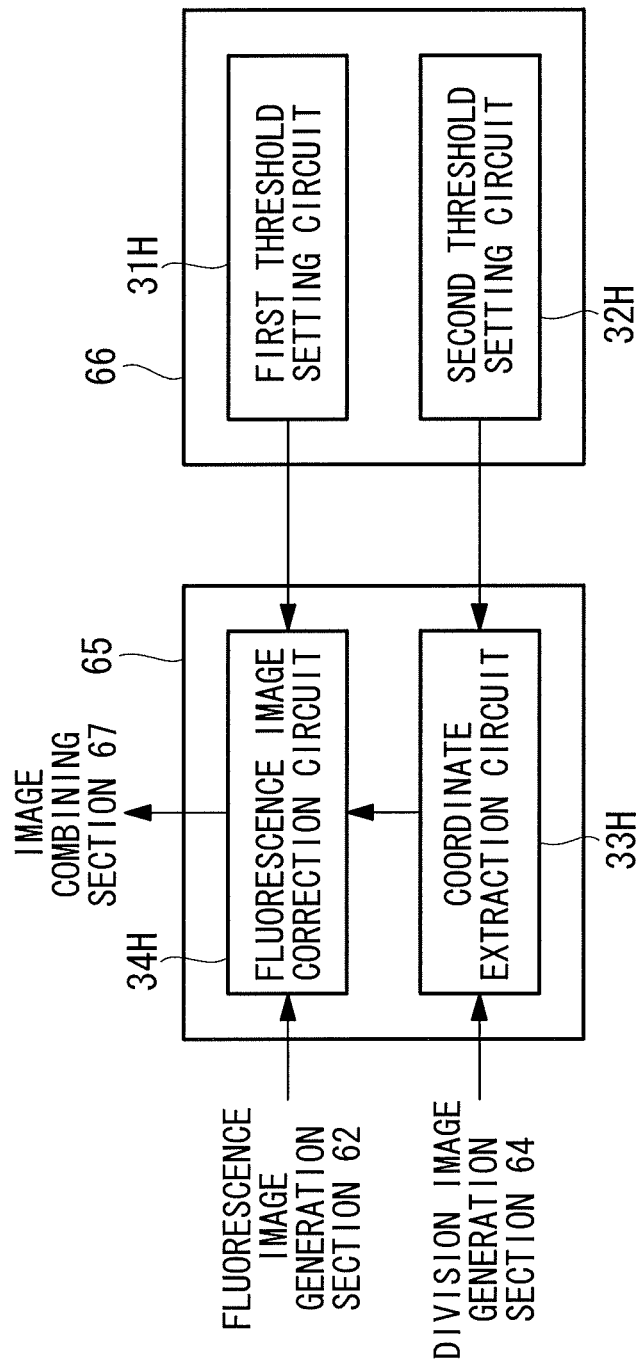

As shown in FIG. 104, a first threshold setting circuit 31H and a second threshold setting circuit 32H included in the correction condition setting sections 66, 66', and 66" and a coordinate extraction circuit (second area extraction section) 33H and a fluorescence image correction circuit (first area extraction section, corrected fluorescence image generation section) 34H included in the post-processing section 65 execute the third post-processing mode. The coordinate extraction circuit 33H extracts predetermined coordinates of the pixels in the division image. The fluorescence image correction circuit 34H corrects the fluorescence image.

The first threshold setting circuit 31H sets, as the first threshold, a threshold for removing areas with low gradation values, such as the background, due to weak fluorescence emitted from the normal portion of the observation target A in the fluorescence image. In addition, the first threshold setting circuit 31H outputs the set first threshold to the fluorescence image correction circuit 34H.

The second threshold setting circuit 32H sets, as the second threshold, a threshold for removing areas with low gradation values such as the background of the observation target A in the division image. In addition, the second threshold setting circuit 32H outputs the set second threshold to the coordinate extraction circuit 33H.

The coordinate extraction circuit 33H extracts coordinates of the pixels in the division image with the gradation values equal to or lower than the second threshold input from the second threshold setting circuit 32H. In addition, the coordinate extraction circuit 33H outputs the extracted coordinates to the fluorescence image correction circuit 34H.

The fluorescence image correction circuit 34H performs correction of replacing, with a gradation value of 0, the pixels in the fluorescence image with the gradation values lower than the first threshold input from the first threshold setting circuit 31H. Furthermore, the fluorescence image correction circuit 34H performs correction of replacing, with a gradation value of 0, the pixels of the corrected fluorescence image with the coordinates overlapping with the coordinates extracted by the coordinate extraction circuit 33H. By doing so, an image obtained by correcting the fluorescence image twice is generated as a corrected fluorescence image. In addition, the fluorescence image correction circuit 34H transmits the generated corrected fluorescence image to the image combining section 67 along with the reference image and the fluorescence image.

Figure 105:
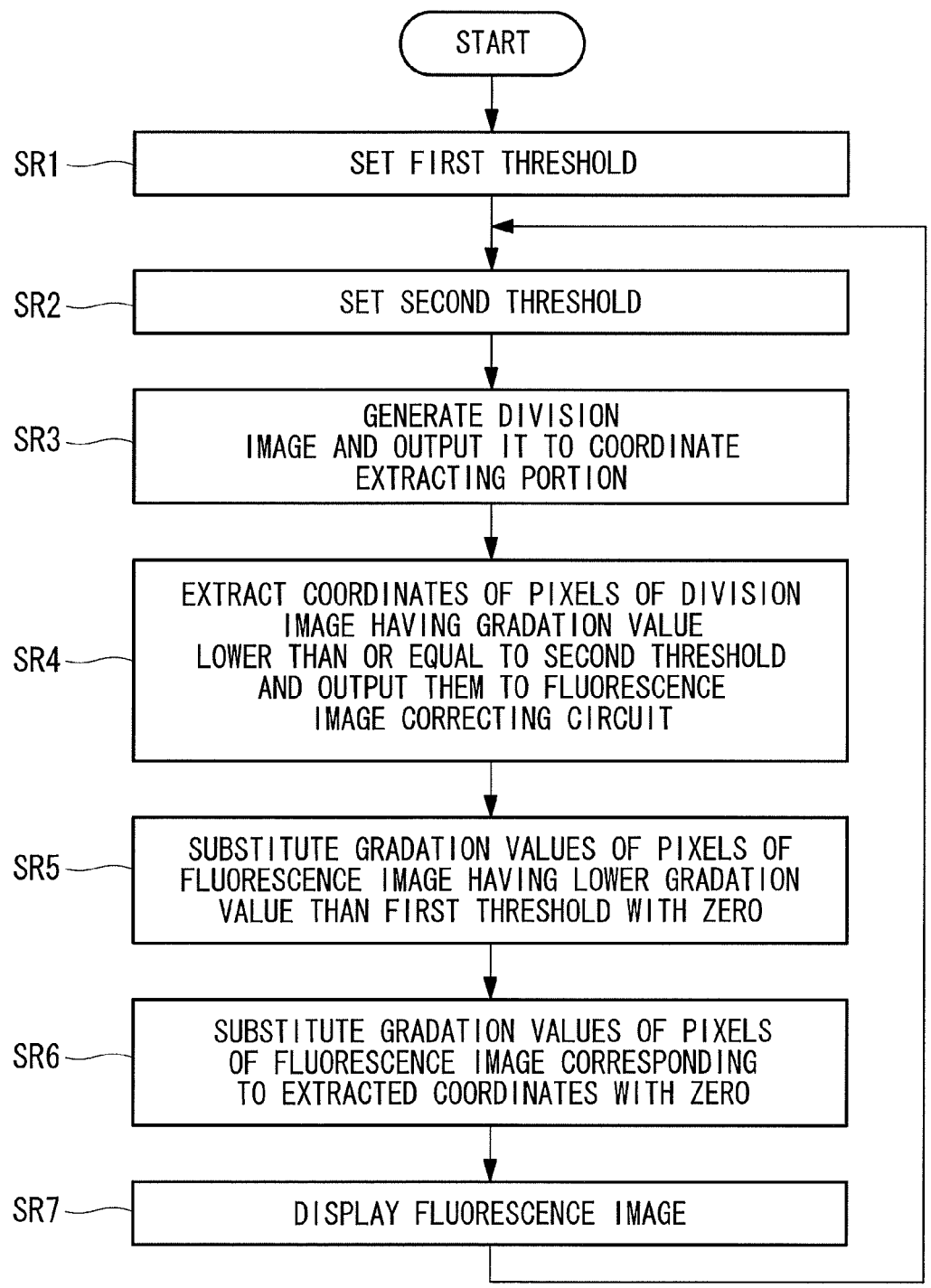

According to the third post-processing mode by the post-processing section 65 and the correction condition setting sections 66, 66', and 66" with the configuration, as shown in FIG. 105, the first threshold setting circuit 31H sets the first threshold (step SR1) and outputs the first threshold to the fluorescence image correction circuit 34H. In addition, the second threshold setting circuit 32H sets the second threshold (step SR2) and outputs the second threshold to the coordinate extraction circuit 33H.

Figure 106:
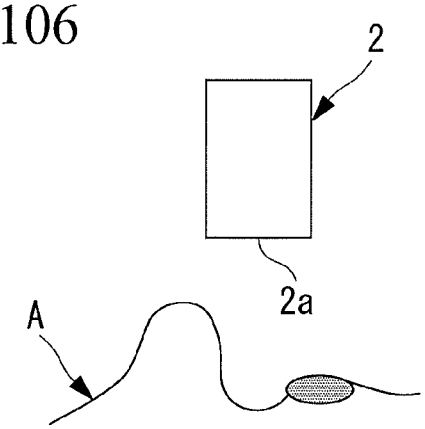

Next, the insertion portion 2 is inserted inside the body, and as shown in FIG. 106, the fluorescence image and the reference image generated based on the image information generated by the image capturing elements 17 and 18 by arranging the tip 2a to face the observation target A are transmitted and displayed on the monitor 20 through the fluorescence image correction circuit 34H.

In this case, since the fluorescence agent is actually accumulated not only on the diseased portion, but also on the normal portion in a small amount, weak fluorescence is also emitted from the sites other than the diseased portion, and the sites are displayed as a background image excluding the diseased portion and the like in the fluorescence image, that is, as the background. In addition, if the normal portion is too close to the insertion portion 2, the normal portion is identified as an area with a high gradation value although the fluorescence is weak, and the normal portion may be displayed as a diseased portion in the fluorescence image (hereinafter, such an area will be called a "false positive site").

Figure 107A:
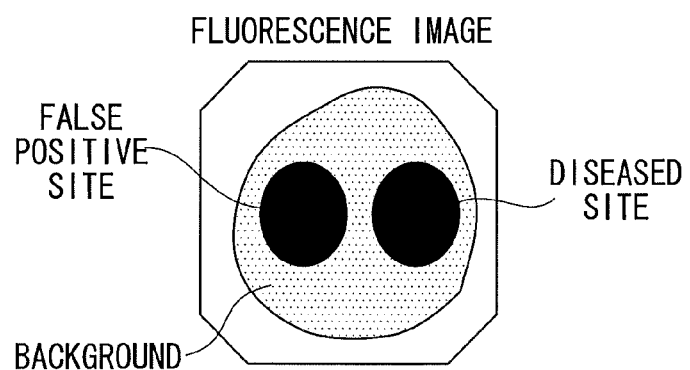
Figure 107B:
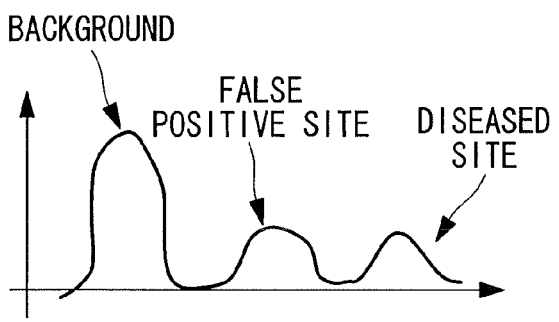

As shown in FIGS. 107A and 107B, the fluorescence image mainly includes an area of the diseased portion, an area of the false positive site, and an area of the surrounding background. In FIG. 107B, the horizontal axis denotes the gradation values, and the vertical axis denotes the frequency of each of the gradation values occupying the entire corrected fluorescence image (the same applies to FIGS. 108B and 109B). Meanwhile, the division image (FIG. 108A) generated by the division image generation section 64 is transmitted to the coordinate extraction circuit 33H (step SR3).

Figure 108A:
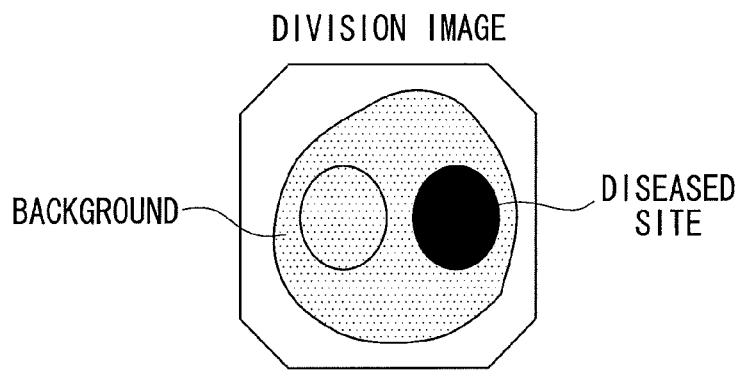
Figure 108B:
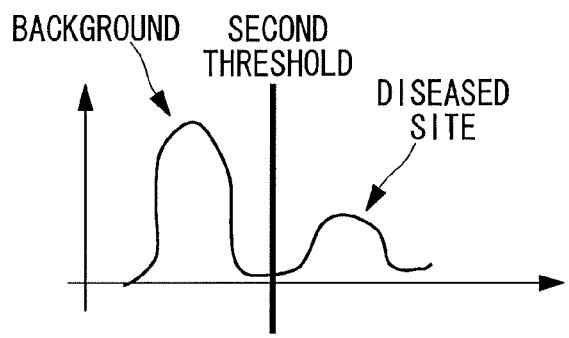

In this case, since the influence of the observation distance and the observation angle is reduced in the division image, the area of the false positive site in excess of the first threshold due to the influence of the observation distance or the observation angle in the fluorescence image does not exceed the second threshold in the division image, and the area can be identified as part of the background. As shown in FIGS. 108A and 108B, the division image mainly includes an area of the diseased portion with the gradation values higher than the second threshold and an area of the background including the false positive site with the gradation values equal to or lower than the second threshold.

The coordinate extraction circuit 33H extracts the coordinates of the pixels with the gradation values equal to or lower than the second threshold input from the second threshold setting circuit 32H in the division image transmitted from the division image generation section 64 and transmits the coordinates to the fluorescence image correction circuit 34H (step SR4). By doing so, similar to the extraction of the area (second area) with the gradation values higher than the second threshold in the division image by the coordinate extraction circuit 33H, that is, similar to the extraction of the area of the diseased portion, the second area and the area with low gradation values, such as the background, are distinguished.

Figure 109A:
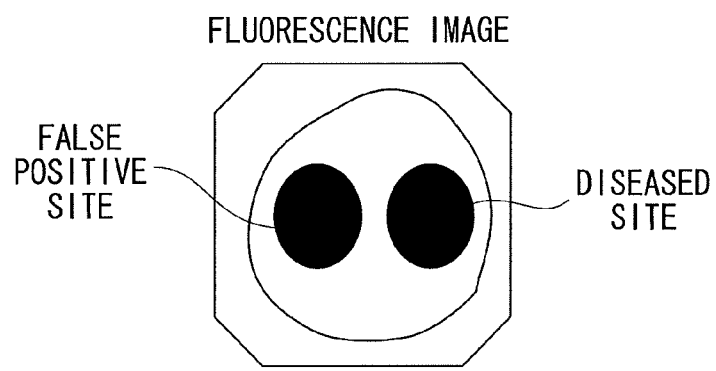
Figure 109B:
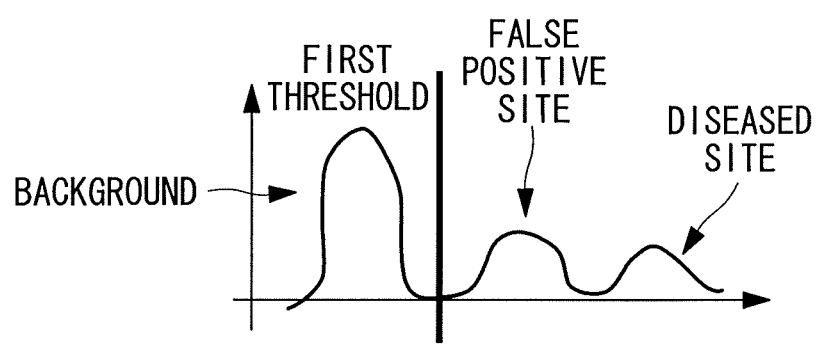

The fluorescence image correction circuit 34H replaces, with a gradation value of 0, the pixels in the fluorescence image with the gradation values lower than the first threshold input from the first threshold setting circuit 31H (step SR5). By doing so, as shown in FIGS. 109A and 109B, the background of the fluorescence image is removed, and the areas (first areas) with the gradation values higher than the first threshold, that is, the area of the diseased portion and the area of the false positive site, are extracted.

Figure 110:
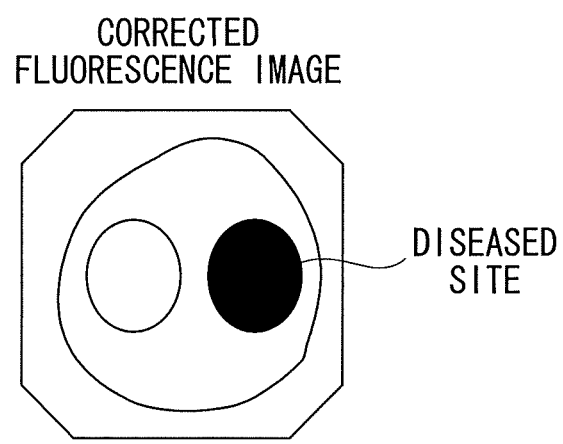

Next, the fluorescence image correction circuit 34H replaces, with a gradation value of 0, the pixels corresponding to the coordinates input from the coordinate extraction circuit 33H, in the fluorescence image in which the area of the diseased portion and the area of the false positive site are extracted (step SR6). By doing so, as shown in FIG. 110, the area of the false positive site of the fluorescence image is removed, and a corrected fluorescence image is generated, in which the area of the diseased portion that is an overlap area of the first area of the fluorescence image and the second area of the division image is extracted.

The generated corrected fluorescence image is transmitted and displayed on the monitor 20 (step SR7). In this way, when the fluorescence image and the reference image of the subsequent frame are generated, steps SR3 to SR7 are repeated, and a new corrected fluorescence image is displayed on the monitor 20.

As described, according to the third post-processing mode, the first threshold setting circuit 31H removes the background of the fluorescence image, and the second threshold setting circuit 32H and the fluorescence image correction circuit 49 further remove the false positive site of the fluorescence image. Therefore, not only the influence of the background lower than the first threshold, but also the influence of the false positive site higher than the first threshold is suppressed, and the corrected fluorescence image extracting only the diseased portion can be generated.

In addition, the generation of the corrected fluorescence image based on the fluorescence image can suppress the influence of the factors that degrade the image quality specific to the reference image reflected on the division image, such as information related to the shape of the edge portion of the observation target A, the shade portion, or the like and information related to colors different from the surrounding such as a bleeding site and a blood vessel. By doing so, a highly accurate corrected fluorescence image with few factors that degrade the image quality can be acquired.

Note that in the third post-processing mode, instead of the extraction of the coordinates of the pixels with the gradation values equal to or lower than the second threshold of the division image by the coordinate extraction circuit 33H, the coordinate extraction circuit 33H may directly extract the coordinates of the area (second area) with the gradation values higher than the second threshold of the division image. In this case, the coordinate extraction circuit 33H may output the coordinates of the second area to the fluorescence image correction circuit 34H, and the fluorescence image correction circuit 34H may generate the corrected fluorescence image by replacing, with a gradation value of 0, the pixels other than the pixels (overlap area) corresponding to the coordinates of the second area in the fluorescence image in which the first area is extracted.

Furthermore, in the third post-processing mode, although the fluorescence image correction circuit 34H replaces the pixels having the gradation values lower than the first threshold of the fluorescence image with a gradation value of 0, it is only necessary that the first area with the gradation values higher than the first threshold of the fluorescence image can be extracted, and for example, the first area of the fluorescence image and the area with the gradation values lower than the first threshold may be displayed in different colors. In addition, although the fluorescence image correction circuit 34H replaces, with a gradation value of 0, the pixels of the coordinates overlapping the coordinates in the fluorescence image extracted by the coordinate extraction circuit 33H, it is only necessary that the overlap area of the first area of the fluorescence image and the second area with the gradation values higher than the second threshold of the division image can be extracted from the fluorescence image, and for example, the overlap area and the areas other than the overlap area may be displayed in different colors.

The third post-processing mode can be modified as follows.

Figure 111:
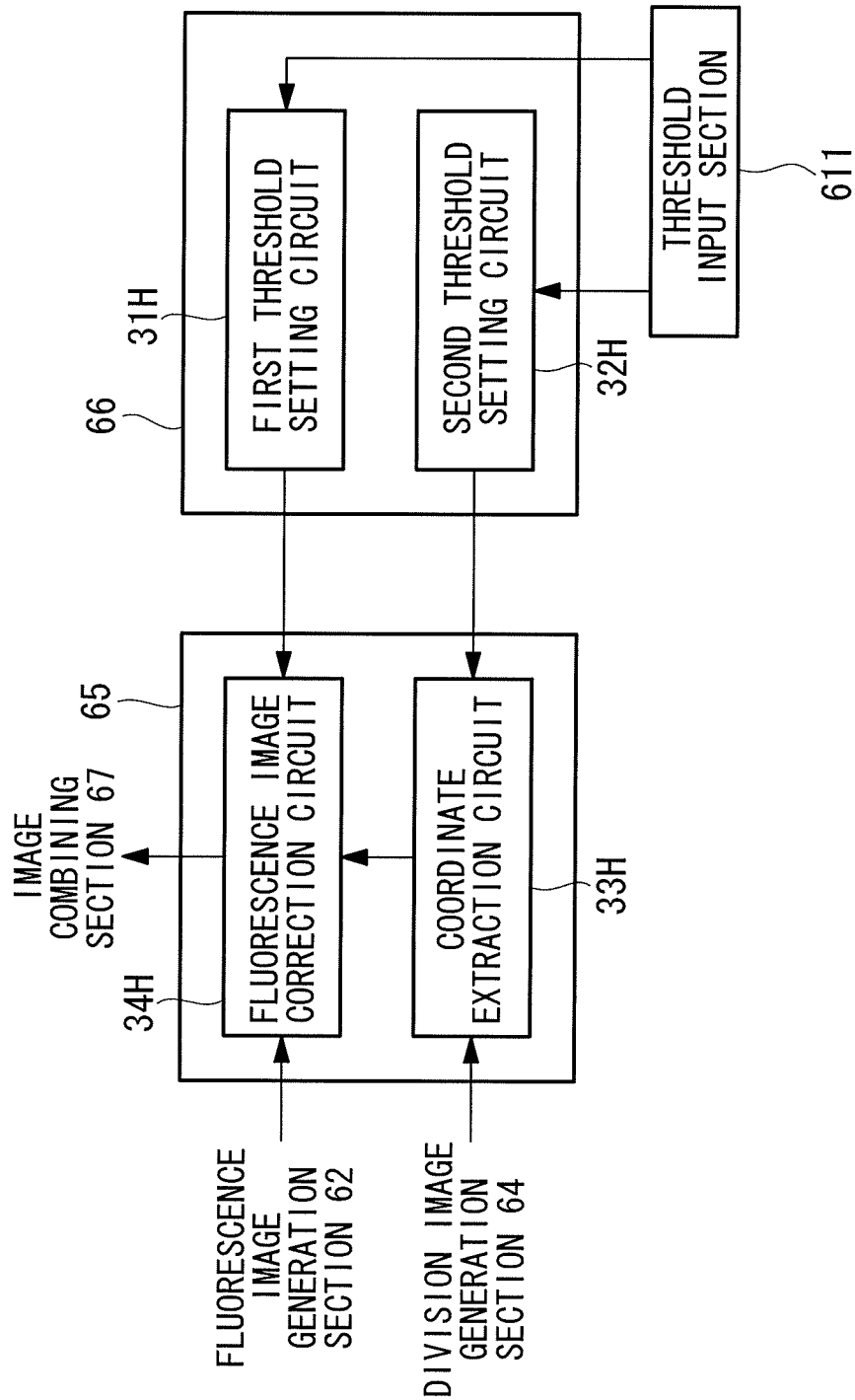

For example, although the first threshold setting circuit 31H and the second threshold setting circuit 32H set the thresholds in the third post-processing mode, the fluorescence observation apparatus may include a threshold input section 611 for inputting the thresholds as shown in FIG. 111 in a first modification, and the operator may be able to operate the threshold input section 611 to manually input the first threshold and the second threshold to the first threshold setting circuit 31H and the second threshold setting circuit 32H, respectively. By doing so, the operator can set desired thresholds according to the observation target or the observation method.

In the present modification, for example, a phantom (standard sample) Y may be observed to set the first threshold and the second threshold as shown in FIG. 112. The phantom Y can have, for example, two projections A1 and B1 on a flat-plate-like base. When the phantom Y is observed under predetermined observation conditions (distance and angle), the projection A1 may emit stronger fluorescence than the surrounding, indicating a gradation value of 2000 on the fluorescence image. The projection B1 may emit fluorescence of about the same intensity as that of the base, indicating a gradation value 1000 on the fluorescence image.

In this case, for example, as shown in a flowchart of FIG. 113, the predetermined first threshold and second threshold are reset (step SS1), and observation is started by disposing the phantom Y so that the observation distance from the insertion portion 2 to the projections A1 and B1 is about 70% of the distance from the insertion portion 2 to the base (step SS2). Since the fluorescence intensity is inversely proportional to the square of the observation distance, in the observation under the predetermined observation conditions, the fluorescence image generation section 21 generates a fluorescence image in which the base has a gradation value of 1000, the projection A1 has a gradation value of about 4000, and the projection B1 has a gradation value of about 2000. Meanwhile, since the influence of the observation distance is reduced in the division image generated by the division image generation section 64, the base and the projection B1 have a gradation value of 1000, and the projection A1 has a gradation value of about 4000.

Next, the first threshold setting circuit 31H sets the first threshold to, for example, 1500 so that only the projections A1 and B1 are displayed on the fluorescence image (step SS3). In addition, the second threshold setting circuit 32H sets the second threshold to 1500 so that the projection B1, along with the base, is identified to be equal to or lower than the second threshold (step SS4). Since the thresholds are set this way, the base of the phantom Y as the background and the projection B1 as the false positive site can be removed, and a corrected fluorescence image that displays the projection A1 can be generated. Therefore, the first threshold and the second threshold can be used to observe the observation target A inside of the body of a living body (step SS5).

Note that a plurality of phantoms in shapes corresponding to the shapes of the sites to be observed can be prepared to accurately set the thresholds for various observation targets. For example, when a colon is observed, a phantom in a tubular shape similar to the lumen of the colon can be used to set the thresholds. Furthermore, when a stomach is observed, a hollow phantom with a relatively large space can be used to set the thresholds.

In addition, in the present modification, for example, the fluorescence observation apparatus 101 may include, as shown in FIG. 114: a storage section 631 that stores the thresholds set by using a plurality of phantoms Y; and a selection section 651 that selects a threshold of each phantom stored in the storage section 631. By doing so, a threshold with high precision can be easily set in observation under the same observation conditions, and the operation can be simplified.

Furthermore, in a second modification, the IC chip 73 in the configuration of the fluorescence observation apparatus 500 according to the fifth embodiment shown in FIG. 5 may store identification information of the insertion portion 2, such as the number of radiation sections formed by the light guide fiber 11 and the illumination optical system 12 and observation angles between the radiation sections and light receiving sections formed by the objective lens 13.

In this case, when the insertion portion 2 is connected to the light source 3, the IC reader 74 can read out the identification information of the insertion portion 2 stored in the IC chip 73 and output the identification information to the first threshold setting circuit 31H and the second threshold setting circuit 32H, and the first threshold setting circuit 31H (threshold setting section circuit) and the second threshold setting circuit 32H (threshold setting circuit) can set the first threshold and the second threshold based on the identification information of the insertion portion 2. By doing so, practical first threshold and second threshold can be set for each insertion portion 2 for different usage and specifications, and a more precise corrected fluorescence image can be acquired according to the observation target and the observation method.

Note that in the present modification, the phantom Y may be observed to set the first threshold and the second threshold as in the first modification.

Furthermore, in a third modification, as shown in FIG. 115, the post-processing section 65 can include a feature value calculation circuit 35H that calculates the average value m of the gradation values of the pixels in the division image and the standard deviation σ of the gradation values, and the second threshold setting circuit 32H can set the second threshold S based on the sum of average value m of the gradation values and the standard deviation σ as indicated in the following Equation 12.

$$S = a \times m + b \times \sigma \qquad \{\text{Equation 12}\}$$

In this case, a and b denote coefficients.

To observe the observation target A inside of the body of a living body by using the fluorescence observation apparatus according to the present modification, as shown in a flowchart of FIG. 116, the feature value calculation circuit 35H can first set the coefficients a and b (for example, a=b=1) of Equation 12 (step ST1), and the division image generated by the division image generation section 64 can be output to the feature value calculation circuit 35H and the coordinate extraction circuit 33H (step ST2). In addition, the feature value calculation circuit 35H can calculate the average gradation value m of the entire division image and the standard deviation σ and output them to the second threshold setting circuit 32H (step ST3), and the second threshold setting circuit 32H can use Equation 12 to set the second threshold S to output the second threshold S to the coordinate extraction circuit 33H (step ST4). Subsequently, steps ST5 to ST8 are the same as steps SR4 to SR7 of FIG. 105.

By doing so, a precise second threshold can be set even when the second threshold is updated in accordance with the fluctuation of the gradation values of the pixels in the division image or when there are variations in the gradation values of the pixels. In addition, errors with respect to the observation distance or the observation error in the division image can be absorbed, and a precise second threshold can be set for each division image generated. Note that the coefficients a and b may be set to be inversely proportional to the proportion of the diseased portion in the assumed division image, for example. By doing so, the minimum value and the maximum value of the second threshold can be limited based on the proportion of the areas of the pixels with high gradation values in the division image.

Note that in the present modification, although the second threshold setting circuit 32H sets the second threshold S based on the sum of the average gradation value m of the entire division image and the standard deviation σ of the gradation value, for example, the first threshold setting circuit 31H may also set the first threshold based on the sum of the average gradation value of the entire fluorescence image and the standard deviation of the gradation value. In this case, similarly to the second threshold S, the feature value calculation circuit 35H can calculate the average gradation value of the entire fluorescence image and the standard deviation and output them to the first threshold setting circuit 31H.

Furthermore, in the present modification, a coefficient input section (not shown) that inputs the coefficients a and b to the feature value calculation circuit 35H may also be included.

Note that in the first to third post-processing modes, the post-processing mode not selected as a post-processing mode for setting the post-processing parameters may also be used by setting constant post-processing parameters (initial values). For example, although the post-processing parameters of the second post-processing mode are set when the observation condition corresponds to "local", the third post-processing mode may also be used at the same time by setting the post-processing parameters to the initial values.

REFERENCE SIGNS LIST 3 light source
4 illumination unit (illumination section)
5 image capturing unit
6 image processing section
7 observation condition input section (observation condition determination section)
17 image capturing element (reference image acquisition section)
18 image capturing element (fluorescence image acquisition section)
20 monitor (display section)
61 reference image generation section
62 fluorescence image generation section
63 preprocessing section (correction processing section)
64 division image generation section
65 post-processing section (correction processing section)
66, 66', 66" correction condition setting sections
67 image combining section
68 observation condition determination section (observation condition determination section)
69, 69' observation site determination sections (observation condition determination sections)
71 observation site input section (observation condition determination section)
72 observation information input section (observation condition determination section)
100, 200, 300, 400, 500 fluorescence observation apparatuses
A observation target (subject)

The invention claimed is:

1. A fluorescence observation apparatus comprising:
a processor comprising hardware, wherein the processor is configured to:
generate a fluorescence image from fluorescence image information acquired by a fluorescence image sensor capturing fluorescence generated in a subject by radiation of excitation light from a light source to the subject;
generate a reference image from reference image information acquired by a reference image sensor capturing reflected light returned from the subject by radiation of illumination light from the light source to the subject;
generate a division image by dividing an image based on the fluorescence image by an image based on the reference image;
control a display to display a corrected fluorescence image based on the division image;
apply correction processing to at least one of the reference image, the fluorescence image, and the division image, wherein the correction processing is applied prior to the generation of the division image or prior to the display of the corrected fluorescence image by the display;
determine one or more observation conditions of the subject;
set parameters regarding the correction processing according to the one or more observation conditions determined;
apply different post-processing under a plurality of post-processing modes to the division image to generate the corrected fluorescence image; and
set, as post-correction processing parameters, the parameters regarding at least one of the plurality of post-processing modes according to the one or more observation conditions.

2. The fluorescence observation apparatus according to claim 1,
wherein the processor is configured to:
set, as a post-processing parameters, weights to be provided to the division image and the fluorescence image; and
weight the division image and the fluorescence image by the weights set, and multiply or sum the weighted images.

3. The fluorescence observation apparatus according to claim 1,
wherein the processor is configured to:
calculate a gradation value threshold for gradation values of the fluorescence image based on an average value of gradation values of pixels in the division image, a standard deviation, and a weighting coefficient and increase a contrast in the corrected fluorescence image between areas with the gradation values equal to or larger than the calculated gradation value threshold and areas with the gradation values smaller than the gradation value threshold, and
set the weighting coefficient as a post-processing parameter.

4. The fluorescence observation apparatus according to claim 1,
wherein the processor is configured to:
set, as a post-processing parameters, a first threshold for the gradation values of the fluorescence image and a second threshold for the gradation values of the division image; and
extract a first area with the gradation values higher than the first threshold of the fluorescence image, extract a second area with the gradation values higher than the second threshold of the division image, and extract, from the fluorescence image, an overlap area where the extracted first area and second area overlap.

5. The fluorescence observation apparatus according to claim 1,
wherein the processor is further configured to apply a pre-correction processing to at least one of the reference image and the fluorescence image to generate a division reference image and a division fluorescence image used for the generation of the division image.

6. The fluorescence observation apparatus according to claim 5,
wherein the processor is configured to:
execute a plurality of pre-processing modes for applying different pre-correction processing to at least one of the reference image and the fluorescence image; and
set, as preprocessing parameters, the parameters regarding at least one of the plurality of preprocessing modes according to the one or more observation conditions.

7. The fluorescence observation apparatus according to claim 5,
wherein the processor is configured to:
set, as a preprocessing parameter, an SN threshold for an SN ratio in the fluorescence image according to the one or more observation conditions; and
adjust the number of pixels for binning summing and/or exposure time in the fluorescence image sensor based on luminance information of the fluorescence image acquired by the fluorescence image sensor so that the SN ratio in the fluorescence image is equal to or higher than the SN threshold.

8. The fluorescence observation apparatus according to claim 7,
wherein the processor is configured to calculate a fluctuation from the luminance information of the fluorescence image acquired by the fluorescence image sensor, calculate the SN ratio in the fluorescence image from the calculated fluctuation and luminance information, and adjust the number of pixels for binning summing and/or the exposure time in the fluorescence image sensor so that the calculated SN ratio is equal to or higher than a predetermined SN threshold.

9. The fluorescence observation apparatus according to claim 5,
wherein the processor is configured to:
set, as a preprocessing parameter, an intensity threshold for fluorescence intensity of the fluorescence image; and
adjust the number of pixels for binning summing and/or the exposure time in the fluorescence image sensor so that the fluorescence intensity in at least part of the fluorescence image acquired by the fluorescence image sensor is equal to or lower than the intensity threshold.

10. The fluorescence observation apparatus according to claim 5,
wherein the processor is configured to:
set, as preprocessing parameters, a first exponent obtained by power approximation of distance characteristics, from the light source to the subject, of the luminance of the fluorescence image when the excitation light at a predetermined intensity is radiated to the subject and a second exponent obtained by power approximation of distance characteristics, from the light source to the subject, of the luminance of the reference image when the illumination light at a predetermined intensity is radiated to the subject, and
raise a luminance value of the fluorescence image to the power of a reciprocal of the first exponent and raise a luminance value of the reference image to the power of a reciprocal of the second exponent.

11. The fluorescence observation apparatus according to claim 5,
wherein the processor is configured to:
set a correction coefficient as a preprocessing parameter based on a distance information between the reference image and the subject; and
use the correction coefficient as an index to perform power computation of light intensity information of at least one of the reference image and the fluorescence image.

12. The fluorescence observation apparatus according to claim 5,
wherein the processor is configured to:
control a memory to store, in association with the one or more observation conditions, coefficients that cause distance characteristics and/or angle characteristics of fluorescence intensity acquired in advance for a standard sample and distance characteristics and/or angle characteristics of reflected light intensity to be directly proportional to each other and multiply at least one of the fluorescence image and the reference image by the coefficients; and
select, as a preprocessing parameter, a coefficient used in the multiplication of the at least one of the fluorescence image and the reference image by the coefficients according to the one or more observation conditions.

13. The fluorescence observation apparatus according to claim 1,
wherein the processor is configured to determine the one or more observation conditions based on features of the reference image.

14. The fluorescence observation apparatus according to claim 1,
wherein the processor is configured to:
control a memory to store the one or more observation conditions in association with one or more predetermined observation sites; and
determine the one or more observation conditions based on an input by an operator of one of the one or more predetermined observation sites.

15. The fluorescence observation apparatus according to claim 1,
wherein the processor is configured to:
associate and control a memory to store one or more observation sites and information related to observation; and
determine, as the one or more observation conditions, the one or more observation sites based on the information related to the observation input by an operator and based on features of the reference image.

16. A fluorescence observation apparatus comprising:
a processor comprising hardware, wherein the processor is configured to:
  generate a fluorescence image from fluorescence image information acquired by a fluorescence image sensor capturing fluorescence generated in a subject by radiation of excitation light from a light source to the subject;
  generate a reference image from reference image information acquired by a reference image sensor capturing reflected light returned from the subject by radiation of illumination light from the light source to the subject;
  generate a division image by dividing an image based on the fluorescence image by an image based on the reference image;
  control a display to display a corrected fluorescence image based on the division image;
  apply correction processing to at least one of the reference image, the fluorescence image, and the division image, wherein the correction processing is applied prior to the generation of the division image or prior to the display of the corrected fluorescence image by the display;
  determine one or more observation conditions of the subject;
  set parameters regarding the correction processing according to the one or more observation conditions determined;
  control a memory to store the one or more observation conditions in association with one or more predetermined observation sites; and
  determine the one or more observation conditions based on an input by an operator of one of the one or more predetermined observation sites.

17. A fluorescence observation apparatus comprising:
a processor comprising hardware, wherein the processor is configured to:
  generate a fluorescence image from fluorescence image information acquired by a fluorescence image sensor capturing fluorescence generated in a subject by radiation of excitation light from a light source to the subject;
  generate a reference image from reference image information acquired by a reference image sensor capturing reflected light returned from the subject by radiation of illumination light from the light source to the subject;
  generate a division image by dividing an image based on the fluorescence image by an image based on the reference image;
  control a display to display a corrected fluorescence image based on the division image;
  apply correction processing to at least one of the reference image, the fluorescence image, and the division image, wherein the correction processing is applied prior to the generation of the division image or prior to the display of the corrected fluorescence image by the display;
  determine one or more observation conditions of the subject;
  set parameters regarding the correction processing according to the one or more observation conditions determined;
  associate and control a memory to store one or more observation sites and information related to observation; and
  determine, as the one or more observation conditions, the one or more observation sites based on the information related to the observation input by an operator and based on features of the reference image.

* * * * *